United States Patent
Zarling et al.

(10) Patent No.: US 10,654,908 B2
(45) Date of Patent: May 19, 2020

(54) ISOLATED T CELL RECEPTORS AND METHODS OF USE THEREFOR

(71) Applicant: University of Virginia Patent Foundation, Charlottesville, VA (US)

(72) Inventors: Angela Zarling, Richmond, VA (US); Victor H. Engelhard, Crozet, VA (US); Kara L. Cummings, Charlottesville, VA (US); Rebecca C. Obeng, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 289 days.

(21) Appl. No.: 15/303,677

(22) PCT Filed: Apr. 15, 2015

(86) PCT No.: PCT/US2015/025942
§ 371 (c)(1),
(2) Date: Oct. 12, 2016

(87) PCT Pub. No.: WO2015/160928
PCT Pub. Date: Oct. 22, 2015

(65) Prior Publication Data
US 2017/0029484 A1    Feb. 2, 2017

Related U.S. Application Data

(60) Provisional application No. 61/979,854, filed on Apr. 15, 2014.

(51) Int. Cl.
| | |
|---|---|
| C07K 14/725 | (2006.01) |
| A61K 38/17 | (2006.01) |
| A61K 39/00 | (2006.01) |
| G01N 33/566 | (2006.01) |
| G01N 33/574 | (2006.01) |
| A61K 38/19 | (2006.01) |
| G01N 33/50 | (2006.01) |
| G01N 33/569 | (2006.01) |
| A61K 35/17 | (2015.01) |
| A61K 47/64 | (2017.01) |
| A61K 45/06 | (2006.01) |
| C07K 16/28 | (2006.01) |

(52) U.S. Cl.
CPC .......... *C07K 14/7051* (2013.01); *A61K 35/17* (2013.01); *A61K 38/1774* (2013.01); *A61K 38/19* (2013.01); *A61K 39/0011* (2013.01); *A61K 45/06* (2013.01); *A61K 47/6425* (2017.08); *C07K 16/2809* (2013.01); *G01N 33/505* (2013.01); *G01N 33/566* (2013.01); *G01N 33/56977* (2013.01); *G01N 33/574* (2013.01); *G01N 33/57484* (2013.01); *A61K 2039/5158* (2013.01); *A61K 2039/55533* (2013.01); *C07K 2317/76* (2013.01)

(58) Field of Classification Search
None
See application file for complete search history.

(56) References Cited

U.S. PATENT DOCUMENTS

| | | |
|---|---|---|
| 7,067,110 B1 | 6/2006 | Gillies et al. |
| 7,166,573 B1 | 1/2007 | Obata |
| 7,449,548 B2 | 11/2008 | Raitano et al. |
| 8,124,741 B2 | 2/2012 | Raitano et al. |
| 8,217,144 B2 | 7/2012 | Jakobsen et al. |
| 8,283,446 B2 | 10/2012 | Jakobsen et al. |
| 8,519,100 B2 | 8/2013 | Jakobsen et al. |
| 9,345,755 B2 | 5/2016 | Slingluff, Jr. et al. |
| 2005/0277161 A1 | 12/2005 | Engelhard et al. |
| 2006/0204509 A1 | 9/2006 | Harty et al. |
| 2006/0251666 A1 | 11/2006 | Nakatsura et al. |
| 2008/0292647 A1 | 11/2008 | Kawakami et al. |
| 2009/0074800 A1 | 3/2009 | Nakatsura et al. |
| 2009/0258378 A1 | 10/2009 | Wang et al. |
| 2009/0304657 A1 | 12/2009 | Morgan et al. |
| 2011/0059463 A1 | 3/2011 | Moritz et al. |
| 2011/0293637 A1 | 12/2011 | Hacohen et al. |
| 2011/0318380 A1 | 12/2011 | Brix et al. |
| 2012/0129776 A1 | 5/2012 | Cohen et al. |
| 2012/0177669 A1 | 7/2012 | Topalian et al. |

(Continued)

FOREIGN PATENT DOCUMENTS

| | | |
|---|---|---|
| WO | WO 1996/040789 | 12/1996 |
| WO | WO 2000/073801 | 12/2000 |

(Continued)

OTHER PUBLICATIONS

Natarajan et al., 2016, Cell Reports 14, 2833-2845 (Year: 2016).*
Janeway et al., Immunobiology, 5th Ed., Garland Science, pp. 106-108 and 260-263, (2001) (Year: 2001).*
Manning et al., Immunity, vol. 8, 413-425, Apr. 1998. (Year: 1998).*
Li et al., JMB, vol. 399, 2010, pp. 596-603. (Year: 2010).*
Garcia et al., Cell, vol. 122, 333-336, Aug. 12, 2005. (Year: 2005).*
Portolano et al., J Immunol. Feb. 1, 1993;150(3):880-7. (Year: 1993).*

(Continued)

*Primary Examiner* — Zachary S Skelding
(74) *Attorney, Agent, or Firm* — Jenkins, Wilson, Taylor & Hunt, P.A.

(57) ABSTRACT

Provided are isolated TCRs, TCR-like molecules, and portions thereof that bind to phosphopeptide-HLA-A2 complexes. The isolated TCRs, TCR-like molecules, or portions are optionally soluble TCRs, TCR-like molecules, or portions. Also provided are isolated nucleic acids encoding the disclosed TCRs, TCR-like molecules, or portions; host cells that contain the disclosed TCRs, TCR-like molecules, or portions; pharmaceutical compositions that include the disclosed TCRs, TCR-like molecules, portions, nucleic acids, and/or T cells; kits; and methods of using the same.

20 Claims, 14 Drawing Sheets

Specification includes a Sequence Listing.

(56) References Cited

U.S. PATENT DOCUMENTS

| | | |
|---|---|---|
| 2013/0021432 A1 | 1/2013 | Kalipatnapu et al. |
| 2013/0259883 A1 | 10/2013 | Hunt et al. |
| 2015/0224182 A1 | 8/2015 | Hunt et al. |
| 2015/0328297 A1 | 11/2015 | Hunt et al. |
| 2016/0000893 A1 | 1/2016 | Hunt et al. |
| 2019/0015494 A1 | 1/2019 | Hunt et al. |

FOREIGN PATENT DOCUMENTS

| | | | |
|---|---|---|---|
| WO | WO-2007017201 A1 * | 2/2007 | ........... C12N 5/0636 |
| WO | WO 2007/127335 | 11/2007 | |
| WO | WO 2009/134883 | 11/2009 | |
| WO | WO 2010/129537 | 11/2010 | |
| WO | WO 2011/149909 A2 | 12/2011 | |
| WO | WO 2013/177593 | 11/2013 | |
| WO | WO 2015/160928 | 10/2015 | |
| WO | WO 2017/192969 A1 | 11/2017 | |

OTHER PUBLICATIONS

Woodsworth et al., Genome Medicine 2013, 5:98. (Year: 2013).*
Robins et al., Blood. 2009;114:4099-4107. (Year: 2009).*
Subbramanian et al. (Nat Biotechnol. Nov. 2004;22(11):1429-34. (Year: 2004).*
"CUL4A Antibody" Cell Signaling Technology, Inc. http://www.cellsignal.com/pdf/2699.pdf, (1 page) (Sep. 16, 2010).
Altschul et al., "Basic local alignment search tool," J Mol Biol, vol. 215, pp. 403-410 (1990).
Andersen et al. (2001) Induction of Systemic CTL Responses in Melanoma Patients by Dendritic Cell Vaccination; Cessation of CTL Responses is Associated with Disease Progression. Int. J. Cancer, vol. 94 pp. 820-824 (2001).
Bins et al., "Phase I clinical study with multiple peptide vaccines in combination with tetanus toxoid and GM-CSF in advanced-stage HLA-A*0201-positive melanoma patients," J. Immunther, vol. 30, No. 2, pp. 234-239 (2007).
Bullock et al. "Manipulation of avidity to improve effectiveness of adoptively transferred CD8(+) T cells for melanoma immunotherapy in human MHC class I-transgenic mice," J Immunol 167:5824-5831 (2001).
Bystryn et al. "Double-blind trial of a polyvalent, shed-antigen, melanoma vaccine" Clin Cancer Res 7:1882-1887 (2001).
Castelli et al., "T-Cell Recognition of Melanoma-Associated Antigens," J Cell Physiol, vol. 182, pp. 323-331 (2000).
Chianese-Bullock et al., "Multi-peptide vaccines vialed as peptide mixtures can be stable reagents for use in peptide-based immune therapies," Vaccine, vol. 27, No. 11, pp. 1764-1770 (Mar. 2009).
Cobbold et al., "Adoptive transfer of cytomegalovirus-specific CTL to stem cell transplant patients after selection by HLA-peptide tetramers," J Exp Med, vol. 202, No. 3, pp. 379-386 (Aug. 1, 2005).
Cobbold et al., MHC Class I-Associated Phosphopepetides are the Targets of Memory-like Immunity in Leukemia. Science Translational Medicine, vol. 5, No. 203:203ra125, pp. 1-10 (12 pages) (Sep. 18, 2013).
Communication pursuant to Rule 164(1) EPC for European Patent Application No. 13835570.6 dated Jul. 4, 2016.
Communication of the extended European search report for European Patent Application No. 13862491.1 dated Sep. 19, 2016.
Cottine et al., "Identification of Novel Class I MHC-Restricted Phosphopeptides for Use as Cancer Immunotherapeutics," 58th Annual ASMS Conference on Mass Spectrometry and Allied Topics, Presentation, Salt Lake City, Utah (May 23-27, 2010).
Depontieu et al. Supplemental Information for "Identification of tumor-associated, MHC class II-restricted phosphopeptides as targets for immunotherapy." Natl Acad Sci U.S.A., vol. 106, No. 29 DOI:10.1073/pnas.10903852106 , pp. 1-7 (7 pages) (2009).
Depontieu et al., "Identification of tumor-associated, MHC class II-restricted phosphopeptides as targets for immunotherapy," Proc Natl Acad Sci U.S.A., vol. 106, No. 29, pp. 12073-12078 (Jul. 21, 2009).
Dudley et al., "Adoptive cell therapy for patients with metastatic melanoma: evaluation of intensive myeloablative chemoradiation preparative regimens," J Clin Oncol, vol. 26, No. 32, pp. 5233-5239 (Nov. 10, 2008).
DuPage et al., "Expression of tumour-specific antigens underlies cancer immunoediting," Nature, vol. 482, No. 7385, pp. 405-409 (2012).
Engelhard, Current Opinion in Immunology vol. 6 p. 13 (1994).
Engelhard, "The contributions of mass spectrometry to understanding of immune recognition by T lymphocytes," Int J Mass Spectrom, vol. 259, No. 1-3, pp. 32-39 (Jan. 1, 2007).
Engelhard, "Identification of phosphorylated peptide antigens displayed on cancer cells and prospects for their use as immunotherapeutics," Powerpoint Presentation, Eleventh International Conference on Progress Vaccination Against Cancer (PIVAC-11),, Copenhagen, Denmark (27 pages) (Oct. 10-13, 2011).
European Search Report corresponding to European Patent Application No. 13832812.5-1403/2897631 dated Apr. 28, 2016.
Evans et al., "Differential Comparison of Phosphorylated MHC Class I HLA-A2.1 Peptides from Three Different Cancer Call Lines," Poster, 50th Annual ASMS Conference on Mass Spectrometry and Allied Topics, Orlando, Florida (2 pages) (Jun. 2-6, 2002).
Examination Report No. 1 for standard patent application corresponding to Australian Patent Application No. 2013312529 dated May 22, 2017.
Ferguson et al. "Strategies and challenges in eliciting immunity to melanoma," Immunol Rev, vol. 222, pp. 28-42 (Apr. 2008).
Ficarro et al., "Identification of Phosphorylated Peptides Associated with Class I MHC Molecules and Implications for Immunotherapy," Poster, 48th Annual ASMS Conference on Mass Spectrometry and Allied Topics, Long Beach, California (Jun. 11-15, 2000).
Goldman et al., "The cancer vaccine roller coaster," Nat Biotech, vol. 27, No. 2, pp. 129-139 (Corrected online: Jun. 7, 2010 | doi:10.1038/nbt0209-129) (Feb. 2009).
Guo et al., "Different length peptides bind to HLA-Ax68 similarly at their ends but bulge out in the middle," Nature, vol. 360, pp. 364-366 (Nov. 26, 1992).
Hawkins et al., "Identification of Breast Cancer Peptide Epitopes Presented by HLA-A*0201," Journal of Proteome Research, vol. 7, pp. 1445-1457 (2008).
Hogan et al., "The peptide recognized by HLA-A68.2-restricted, squamous cell carcinoma of the lung-specific cytotoxic T lymphocytes is derived from a mutated elongation factor 2 gene," Cancer Res, vol. 58, pp. 5144-5150 (Nov. 15, 1998).
Hojlund et al., "In vivo phosphoproteome of human skeletal muscle revealed by phosphopeptide enrichment and HPLC-ESI-MS/MS," J Proteome Res., vol. 8, No. 11, pp. 4954-4965 (Nov. 2009).
Hopkins, "Sequence analysis of HLA-B7 peptides by ETD mass spectrometry: Comparative analysis of phosphopeptides on cancer and non-cancer cells," Poster, 53rd Annual ASMS Conference on Mass Spectrometry and Allied Topics, San Antonio, Texas (1 page) (Jun. 5-9, 2005).
Hung et al., "Cul4A is an oncogene in malignant pleural mesothelioma," J. Cell Mol Med., vol. 15, No. 2, pp. 350-358 (Feb. 2011).
Hunt et al. "Characterization of peptides bound to the class I MHC molecule HLA-A2.1 by mass spectrometry," Science, vol. 255, pp. 2669-2671 (1992).
Interview Summary for U.S. Appl. No. 14/425,946 dated Sep. 15, 2016.
Interview Summary for U.S. Appl. No. 14/424,702 dated Sep. 15, 2016.
James et al., "Analysis of HLA-A2 MHC Phosphopeptides with Titanium Dioxide, IMAC, Peptide Derivatization and Electron Transfer Dissociation," Poster, 58th Annual ASMS Conference on Mass Spectrometry and Allied Topics, Salt Lake City, Utah (1 page) (May 23-27, 2010).
Jia et al., "SCF E3 ubiquitin ligases as anticancer targets," Curr Cancer Drug Targets, vol. 11, No. 3, pp. 347-356 (Mar. 2011).
Kielhorn et al., "Tissue microarray-based analysis shows phospho-beta-catenin expression in malignant melanoma is associated with poor outcome," Int J Cancer, vol. 103, pp. 652-656 (2003).
Lee et al., "Pathogenic Role of the CRL4 Ubiquitin Ligase in Human Disease," Front Oncol., vol. 2, pp. 1-7 (Mar. 2012).

(56) References Cited

OTHER PUBLICATIONS

Lie et al., "CUL4A abrogation augments DNA damage response and protection against skin carcinogenesis," Mol Cell, vol. 34, No. 4, pp. 451-60 (May 2009).
Meyer et al., "Identification of natural MHC class II presented phosphopeptides and tumor-derived MHC class I phospholigands". J Proteome Res, vol. 8, pp. 3666-3674 (2009).
Mohammed et al., "Phosphorylation-dependent interaction between antigenic peptides and MHC class I: a molecular basis for the presentation of transformed self," Nat Immunol, vol. 9, No. 11, pp. 1236-1243 (Nov. 2008).
Morin et al., "Activation of beta-catenin-TCF signaling in colon cancer by mutations in beta-catenin or APC," Science, vol. 275, pp. 1787-1790 (Mar. 21, 1997).
Noguchi et al. "Personalized peptide vaccination: a new approach for advanced cancer as therapeutic cancer vaccine," Cancer Immunol Immunother, vol. 62, pp. 919-929, Epub 2012 Nov. 30, 2013.
Norris et al., "The Identification of MHC Class II Peptides Expressed in vivo by B-Cell Leukemias and Lymphomas," Poster, 56th Annual ASMS Conference on Mass Spectrometry and Allied Topics, Denver, Colorado (1 page) (Jun. 1-8, 2008).
Norris et al., "Utilizing secreted MHC molecules (sHLA) to investigate the phosphor-immuno-peptidome of breast cancer," Poster, 57th Annual ASMS Conference on Mass Spectrometry and Allied Topics, Philadelphia, Pennsylvania (1 page) (May 31-Jun. 4, 2009).
Norris, A., "Identification of MHC Class I Phospho-peptide Antigens from Breast Cancer Utilizing sHLA Technology and Complementary Enrichment Strategies," Poster, 58th Annual ASMS Conference on Mass Spectrometry and Allied Topics, Salt Lake City, Utah (1 page) (May 23-27, 2010).
Notice of Allowance and Fee(s) due corresponding to U.S. Appl. No. 14/424,702 dated Oct. 13, 2016.
Notification Concerning Transmittal of International Preliminary Report on Patentability (Chapter 1 of the Patent Cooperation Treaty) corresponding to PCT/US2013/057856 dated Mar. 12, 2015.
Notification Concerning Transmittal of International Preliminary Report on Patentability (Chapter 1 of the Patent Cooperation Treaty) corresponding to PCT/US2013/058255 dated Apr. 30, 2015.
Notification Concerning Transmittal of International Preliminary Report on Patentability (Chapter 1 of the Patent Cooperation Treaty) corresponding to PCT/US2013/075073 dated Jun. 25, 2015.
Notification of Transmittal of the International Search Report and the Written Opinion of the International Searching Authority, or the Declaration, corresponding to PCT/US2013/058477 dated Dec. 20, 2013.
Notification of Transmittal of the International Search Report and the Written Opinion of the International Searching Authority, or the Declaration, corresponding to PCT/US2013/058255 dated Feb. 21, 2014.
Notification of Transmittal of the International Search Report and the Written Opinion of the International Searching Authority, or the Declaration, corresponding to PCT/US2013/057856 dated Feb. 28, 2014.
Notification of Transmittal of the International Search Report and the Written Opinion of the International Searching Authority, or the Declaration, corresponding to PCT/US2013/075073 dated May 20, 2014.
Notification of Transmittal of the International Search Report and the Written Opinion of the International Searching Authority, or the Declaration corresponding to International Application No. PCT/US2011/037699 dated Feb. 9, 2012.
Office Action (Restriction Requirement) corresponding to U.S. Appl. No. 14/425,946 dated Nov. 25, 2015.
Office Action (Restriction Requirement) corresponding to U.S. Appl. No. 14/424,702 dated Nov. 20, 2015.
Office Action corresponding to U.S. Appl. No. 14/425,946 dated Mar. 17, 2016.
Office Action corresponding to U.S. Appl. No. 14/424,702 dated Mar. 14, 2016.
Office Action corresponding to U.S. Appl. No. 14/425,946 dated Jun. 24, 2016.
Office Action corresponding to U.S. Appl. No. 14/424,702 dated Jun. 24, 2016.
Office Action corresponding to U.S. Appl. No. 14/425,946 (dated Nov. 25, 2016).
Office Action corresponding to U.S. Appl. No. 13/699,563 dated Oct. 11, 2016.
Ostankovitch et al. "N-glycosylation enhances presentation of a MHC class I-restricted epitope from tyrosinase," J Immunol, vol. 182, pp. 4830-4835 (2009).
Petersen et al., "Phosphorylated self-peptides alter human leukocyte antigen class I-restricted antigen presentation and generate tumor-specific epitopes," Proc Natl Acad Sci U.S.A., vol. 106, No. 8, pp. 2776-2781 (Feb. 24, 2009).
Polefrone et al., "Differential Expression of Class I, HLA-A2 Phosphopeptides on Tumor Cells: Characterization of Potential Candidates for Immunotherapy or a Cancer Vaccine," Poster, 53rd Annual ASMS Conference on Mass Spectrometry and Allied Topics, San Antonio, Texas (2 pages) (Jun. 5-9, 2005).
Qian et al., "Analysis of HLA-DR4 restricted peptides by electron transfer dissociation tandem mass spectrometry," Poster, 54th Annual ASMS Conference on Mass Spectrometry and Allied Topics, Seattle, Washington (1 page) (May 28-Jun. 1, 2006).
Qian et al., "Class I and II MHC restricted phosphopeptides as cancer immunotherapeutics or diagnostics," Poster, 55th Annual ASMS Conference on Mass Spectrometry and Allied Topics, Indianapolis, Indiana (Jun. 3-7, 2007).
Rammensee et al, "MHC ligands and peptide motifs: first listing," Immunogenetics, vol. 41, pp. 178-228 (1995).
Ren et al., "Oncogenic CUL4A determines the response to thalidomide treatment in prostate cancer," J Mol Med (Berl), vol. 90, No. 10, pp. 1121-1132 (Oct. 2012).
Restriction Requirement corresponding to U.S. Appl. No. 13/699,563 dated Mar. 16, 2016.
Rock et al., "Degradation of Cell Proteins and the Generation of MHC Class I-Presented Peptides," Annu Rev Immunol, vol. 17, pp. 739-779 (1999).
Schwartzentruber et al. "gp100 peptide vaccine and interleukin-2 in patients with advanced melanoma," N Engl J Med, vol. 364, No. 22, pp. 2119-2127 (Jun. 2, 2011).
Shastri et al, Presentation of Endogenous Peptide/MHC Class I Complexes is Profoundly Influenced by Specific C-Terminal Flanking Residues,: J. Immunol. vol. 155, pp. 4339-4346 (1995).
Slingluff et al., "Clinical and immunologic results of a randomized phase II trial of vaccination using four melanoma peptides either administered in granulocyte-macrophage colony-stimulating factor in adjuvant or pulsed on dendritic cells," J Clin Oncol, vol. 21, No. 21, pp. 4016-4026 (Nov. 1, 2003).
Slingluff, "Peptide approaches to melanoma vaccines: innovations and challenges," iSTBc/CVC workshop, Alexandria, VA (30 pages) (Nov. 10, 2005).
Slingluff et al., "Immunity to melanoma antigens: from self-tolerance to immunotherapy," Adv Immunol, vol. 90, pp. 243-295 (2006).
Slingluff et al., "The present and future of peptide vaccines for cancer: single or multiple, long or short, alone or in combination?" Cancer J., vol. 17, No. 5, pp. 343-350 (Sep. 2011).
Slingluff et al., "Randomized multicenter trial of the effects of melanoma-associated helper peptides and cyclophosphamide on the immunogenicity of a multipeptide melanoma vaccine," J Clin Oncol, vol. 29, No. 21, pp. 2924-2932 (Jul. 20, 2011).
Storkus et al., "Reversal of natural killing susceptibility in target cells expressing transfected class 1 HLA genes," PNAS USA, vol. 86, No. 7, pp. 2361-2364 (Apr. 1989).
The UniProt Consortium, "The Universal Protein Resource (UniProt) in 2010", Nucleic Acids Research, vol. 38, pp. D142-D148 (Oct. 20, 2009).
Tyagi et al., "MAGRIT: the largest-ever phase III lung cancer trial aims to establish a novel tumor-specific approach to therapy," Clin Lung Cancer, vol. 10, pp. 371-374 (Sep. 2009).

(56) References Cited

OTHER PUBLICATIONS

Utz et al., "Proteins phosphorylated during stress-induced apoptosis are common targets for autoantibody production in patients with systemic lupus erythematosus," J Exp Med, vol. 185, No. 5, pp. 843-854 (Mar. 3, 1997).
Wang et al., "Extensive Crosstalk Between O-GlcNAcylation and Phosphorylation Regulates Cytokinesis," Sci Signal, vol. 3, No. 104:ra2, including Supplemental Materials, pp. 1-22 (2010).
Watts, "Capture and Processing of Exogenous Antigens for Presentation on MHC Molecules," Annu Rev Immunol, vol. 15, pp. 821-850 (1997).
Zarling et al., "Phosphorylated peptides are naturally processed and presented by MHC class I molecules in vivo,". J Exp Med, vol. 192, No. 12, pp. 1755-1762 (Dec. 18, 2000).
Zarling et al., "Identification of class I MHC associated phosphopeptides as targets for cancer immunotherapy," Proc Natl Acad Sci U.S.A., vol. 103, No. 40, pp. 14889-14894 (Oct. 3, 2006).
Zarling et al., "Abstract 1584: MHC-restricted phosphopeptides as broad-based immunotherapeutic targets for cancer," Poster Presentations—Tumor Vaccine Development, Proceedings: AACR 103rd Annual Meeting 2012, ; Chicago, IL, Cancer Research, 72(8):Supplement 1 (Mar. 31-Apr. 4, 2012).
Clay et al. (1999) Efficient transfer of a tumor antigen-5 reactive TCR to human peripheral blood lymphocytes confers anti-tumor reactivity. J Immunol 163:507-513.
Johnson et al. (2006) Gene Transfer of Tumor-Reactive TCR Confers Both High Avidity and Tumor Reactivity to Nonreactive Peripheral Blood Mononuclear Cells and 15 Tumor-Infiltrating Lymphocytes. J Immunol 177:6548-6559
Jorritsma et al. (2007) Selecting highly affine and well-expressed TCRs for gene therapy of melanoma. Blood 110:3564-572.
Notification of Transmittal of International Preliminary Report on Patentability (Chapter 1 of the Patent Cooperation Treaty) corresponding to PCT/US2015/025942 dated Oct. 16, 2015.
Notification of Transmittal of the International Search Report and the Written Opinion of the International Searching Authority, or the Declaration, corresponding to PCT/US2016/045852 dated Nov. 26, 2016.
Notification of Transmittal of the International Search Report and the Written Opinion of the International Searching Authority, or the Declaration, corresponding to PCT/US2015/025942 dated Oct. 19, 2015.
Office Action corresponding to Australian Patent Application No. 2013359001 dated Jul. 28, 2017.
Office Action corresponding to European Patent Application Serial No. 13 832 812.5 dated Jul. 11, 2017.
Office Action corresponding to Australian Patent Application No. 2013308409 dated May 17, 2017.
Office Action corresponding to U.S. Appl. No. 14/425,946 dated Jun. 8, 2017.
Office Action corresponding to U.S. Appl. No. 14/651,932 dated Jun. 23, 2017.
Weihrauch et al. (2005) Phase I/II Combined Chemoimmunotherapy With Carcinoembryonic Antigen-Derived HLA-A2-restricted CAP-1 Peptide and Irinotecan, 5-Fluorouracil, and Leucovorin in Patients With Primary Metastatic Colorectal Cancer. Clin Cancer Res 11(16):5993-6001.
Zarling et al. (2014) MHC-Restricted Phosphopeptides from Insulin Receptor Substrate-2 and CDC25b Offer Broad-Based Immunotherapeutic Agents for Cancer. Cancer Res 74(23):6784-6795.
Notification of Transmittal of the International Search Report and the Written Opinion of the International Searching Authority, or the Declaration corresponding to International Application No. PCT/US2017/031266 dated Aug. 24, 2017.
Pages et al. (2009) In situ cytotoxic and memory T cells predict outcome in the patients with early-stage colorectal cancer. Journal of clinical oncology 27(35):5944-5951.

Communication of the extended European search report corresponding to European Patent Application No. 15780107.7 dated Oct. 23, 2017.
Blaydes et al. (2000) Methods in Molecular Biology, Stress Response Methods and Protocols. Humana Press. vol. 99, Chapter 14 "The Development and Use of Phospho-Specific Antibodies to Study Protein Phosphorylation", pp. 177-189.
Boon (Adv. Can. Res. 1992 58:177-210) (Year: 1992).
De Queiroz et al. (2014)O-GlcNAcylation the sweet side of the cancer. Front Oncol 4(132)1-10.
Examination Report corresponding to Australian Patent Application No. 2018203355 dated Apr. 7, 2019.
Examination Report corresponding to Australian Patent Application No. 2018203542 dated Mar. 29, 2019.
Examination Report corresponding to Australian Patent Application No. 2018208738 dated Jul. 12, 2019.
Ezzell (J. NIH Res. 1995 7:46) (Year: 1995).
Extended European Search Report correspondin to European Patent Application No. 16835708.5 dated Feb. 21, 2019.
Hart et al. (2011) Cross talk between O-GlcNAcylation and phosphorylation: roles in signaling, transcription, and chronic disease. Annu Rev Biochem 80:825-858.
Haurum et al. (1994) Recognition of carbohydrate by major histocompatibility complex class I-restricted, glycopeptide-specific cytotoxic T lymphocytes. J Exp Med 180(2): 739-744.
Haurum et al. (1995) Peptide anchor residue glycosylation: effect on class I major histocompatibility complex binding and cytotoxic T lymphocyte recognition. Eur J Immunol 25(12):3270-3276.
Haurum et al. (1999) Presentation of cytosolic glycosylated peptides by human class I major histocompatibility complex molecules in vivo. J Exp Med 190(1): 145-150.
Kastrup et al. (2000) Lectin purified human class I MHC-derived peptides: evidence for presentation of glycopeptides in vivo. Tissue Antigens 56(2): 129-135.
Klebanoff et al, Immunol Rev vol. 239(1): 27-44 (Jan. 2011) (Year: 2011).
Office Action corresponding to U.S. Appl. No. 14/425,946 dated Jan. 16, 2018.
Office Action corresponding to U.S. Appl. No. 14/425,946 dated Apr. 30, 2018.
Office Action corresponding to U.S. Appl. No. 14/425,946 dated Dec. 17, 2018.
Office Action corresponding to U.S. Appl. No. 14/651,932 dated Feb. 6, 2018.
Office Action corresponding to U.S. Appl. No. 14/651,932 dated Oct. 10, 2018.
Office Action corresponding to U.S. Appl. No. 14/651,932 dated Apr. 19, 2019.
Office Action corresponding to European Patent Application No. 13835570.6 dated May 9, 2019.
Office Action corresponding to European Patent Application Serial No. 13 862 491.1 dated Dec. 13, 2017.
Office Action corresponding to U.S. Appl. No. 14/425,946 dated Mar. 26, 2019.
Office Action corresponding to U.S. Appl. No. 14/425,946 dated Aug. 9, 2019.
Office Action (Restriction Requirement) corresponding to U.S. Appl. No. 15/388,896 dated Jun. 6, 2018.
Office Action corresponding to U.S. Appl. No. 15/388,896 dated Dec. 3, 2018.
Office Action corresponding to U.S. Appl. No. 15/388,896 dated Dec. 17, 2018.
Office Action corresponding to U.S. Appl. No. 15/388,896 dated Jul. 1, 2019.
Office Action corresponding to European Patent Application No. 13 385 570.6 dated Feb. 21, 2018.
Slawson and Hart (2011) O-GlcNAc signaling: implications for cancer biology. Nat Rev Cancer 11:678-684.
Spitler (Cancer Biotherapy, 1995, 10:1-3) (Year: 1995).
Summons to Attend Oral Proceedings corresponding to European Patent Application No. 13862491.1 dated Mar. 6, 2019.
Wang et al. (2010a) Enrichment and site-mapping of O-linked N-acetylglucosamine by a combination of chemical/enzymatic tag-

(56) References Cited

OTHER PUBLICATIONS ging, photochemical cleavage, and electron transfer dissociation (ETD) mass spectrometry. Mol Cell Proteomics 9(1):153-160.
Wells et al. (2004) O-GlcNAc transferase is in a functional complex with protein phosphatase 1 catalytic subunits. J Biol Chem 279(37):38466-38470.
Wolfert and Boons (2013) Adaptive immune activation: glycosylation does matter. Nature Chem Biol 9:776-784.

* cited by examiner

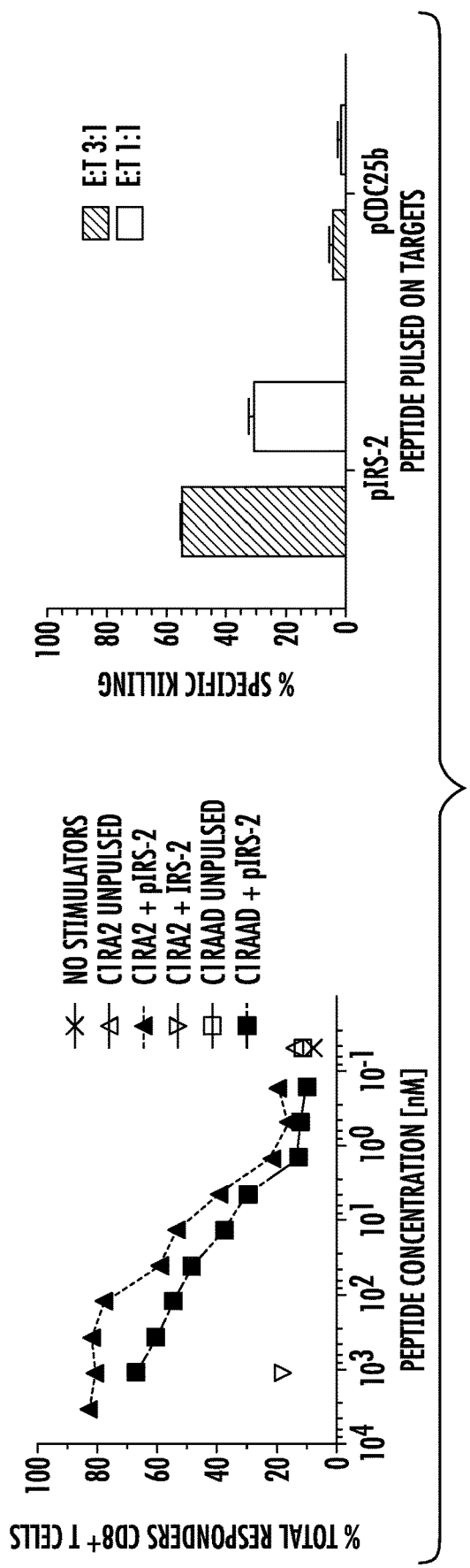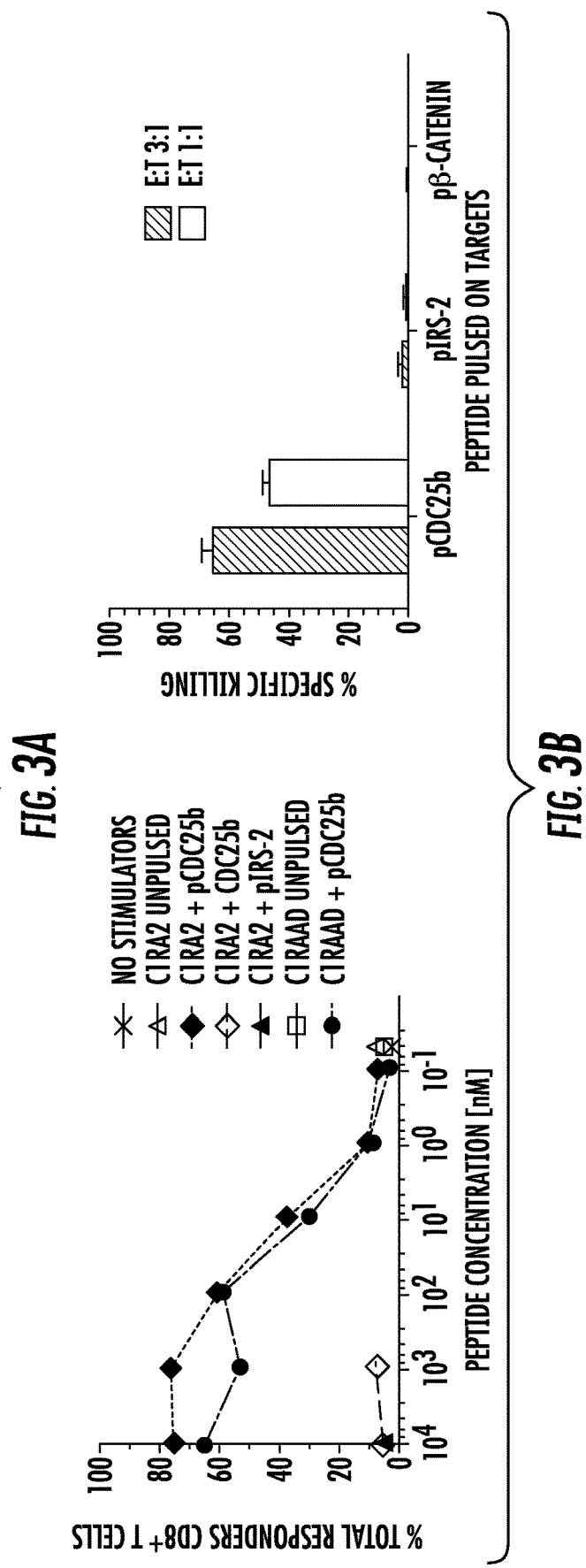
FIG. 3A
FIG. 3B

ISOLATED T CELL RECEPTORS AND METHODS OF USE THEREFOR

CROSS REFERENCE TO RELATED APPLICATIONS

The presently disclosed subject matter claims the benefit of U.S. Provisional Patent Application Ser. No. 61/979,854, filed Apr. 15, 2014, the entire disclosure of which is incorporated herein by reference in its entirety.

GRANT STATEMENT

This invention was made with government support under grant numbers AI020963, CA134060, and CA044579 awarded by the National Institutes of Health. The government has certain rights in the invention.

REFERENCE TO SEQUENCE LISTING

The Sequence Listing associated with the instant disclosure has been electronically submitted to the United States Patent and Trademark Office as a 146 kilobyte ASCII text file created on Apr. 2, 2015 and entitled "3062_9PCT_ST25.txt". The Sequence Listing submitted via EFS-Web is identical with respect to the sequences disclosure to the Sequence Listing submitted to the United States Patent and Trademark Office on Apr. 15, 2014 as a 146 kilobyte ASCII text file created on Mar. 18, 2014 and entitled "3062_9_ST25.txt". Both Sequence Listings are hereby incorporated by reference in their entireties.

TECHNICAL FIELD

The presently disclosed subject matter relates to the area of diagnostics and therapeutics. In particular, it relates to immunotherapies and diagnostics in the context of proliferative diseases such as but not limited to cancer.

BACKGROUND

The mammalian immune system has evolved a variety of mechanisms to protect the host from cancerous cells. An important component of this response is mediated by cells referred to as T cells. Cytotoxic T lymphocytes (CTL) are specialized T cells that primarily function by recognizing and killing cancerous cells or infected cells, but they can also function by secreting soluble molecules referred to as cytokines that can mediate a variety of effects on the immune system. T helper cells primarily function by recognizing antigen on specialized antigen presenting cells, and in turn secreting cytokines that activate B cells, T cells, and macrophages. A variety of evidence suggests that immunotherapy designed to stimulate a tumor-specific CTL response would be effective in controlling cancer. For example, it has been shown that human CTL recognize sarcomas (Slovin et al., 1986), renal cell carcinomas (Schendel et al., 1993), colorectal carcinomas (Jacob et al., 1997), ovarian carcinomas (Peoples et al., 1993), pancreatic carcinomas (Peiper et al., 1997), squamous tumors of the head and neck (Yasumura et al., 1993), and squamous carcinomas of the lung (Slingluff et al., 1994; Yoshino et al., 1994). The largest number of reports of human tumor-reactive CTLs, however, has concerned melanomas (Boon et al., 1994). The ability of tumor-specific CTL to mediate tumor regression, in both human (Parmiani et al., 2002; Weber, 2002) and animal models, suggests that methods directed at increasing CTL activity would likely have a beneficial effect with respect to tumor treatment.

Clinical trials using adoptive cellular therapy and active vaccination have demonstrated the importance of CD8 T-cells in controlling cancer (Morgan et al., 2006; Rosenberg, 2008; Hiugano et al., 2009; Schwartzentruber et al., 2011). A large number of tumor-associated antigens (TAA) recognized by CD8 T-cells have been identified in the last 20 years, and clinical tumor regressions have been associated with immunotherapies based on some of them (Slingluff et al., 2004; Rosenberg, 2008). However, cancer vaccines targeting a range of TAA have induced disappointing clinical response rates of 3-6% (Rosenberg et al., 2004). The repertoire of TAA include: i) neoantigens formed by mutations in cellular proteins; ii) antigens induced by oncogenic viruses; iii) cancer-testis antigens normally expressed only in germ-line cells; and iv) tissue-specific differentiation antigens (Williamson et al., 2006). Only a small number of TAA source proteins have been linked to either initial cellular transformation processes or later tumorigenic processes such as angiogenesis and metastasis (Hogan et al., 1998; Simpson et al., 2005). Targeting TAA derived from proteins that are vital for a cancer cell's survival and metastatic potential is attractive, since down-regulation and/or mutation of genes encoding these proteins as a means of immune evasion could compromise cellular malignancy (Dunn et al., 2004; Hirohashi et al., 2009).

As such, TCRs can be employed for various purposes for which how antibody molecules have been utilized. One challenge with respect to TCRs as opposed to antibodies, however, is that the former are not secreted from the cells in which they are made. This can limit the utility of TCRs as therapeutic and/or diagnostic agents. These challenges have been met to varying degrees of success by the production of soluble TCRs.

Several methods for producing soluble TCRs and TCR-like molecules have recent been reported. For example, U.S. Patent Application Publication No. 2008/0015139 of Lichterfeld et al. describes the production and use of soluble TCRs for the detection and treatment of viral infections. PCT International Patent Application Publication No. WO 2013/057586 of Walseng et al. describes various additional methods for producing soluble TCRs, such as isolation of α and β chains from bacterial inclusion bodies (see also Richman & Kranz, 2007) and STAR™ technology (Altor Bioscience Corporation, Miramar, Fla., United States of America), in which hybrid soluble TcR-Ig molecules are connected via a flexible linker (see also Mosquera et al., 2005).

Thus, soluble TCRs are useful as diagnostic and/or therapeutic tools. They can be employed to detect cells that express TAAs such as, but not limited to peptides derived from TAAs complexed with MHC molecules. Additionally, soluble TCRs can be used to deliver a therapeutic agent, including but not limited to a cytotoxic compound or an immunostimulating compound, to cells presenting a particular TAA-derived peptide.

The interaction of a TCR with HLA-bound antigens including, but not limited to a peptide derived from a TAA, results in cytotoxic T lymphocytes (CTLs) killing cells that express the antigen (e.g., a cancer cell) and/or secreting cytokines in response to a cancer cell. This process involves the interaction of the T cell receptor, located on the surface of the CTL, with what is generically referred to as an MHC-peptide complex which is located on the surface of the cancerous cell. Major histocompatibility complex (MHC)- encoded molecules have been subdivided into two types, and are referred to as class I and class II MHC-encoded molecules. In the human immune system, MHC molecules are referred to as human leukocyte antigens (HLA). Within the MHC complex, located on chromosome six, are three different loci that encode for class I MHC molecules. MHC molecules encoded at these loci are referred to as HLA-A, HLA-B, and HLA-C. The genes that can be encoded at each of these loci are extremely polymorphic, and thus, different individuals within the population express different class I MHC molecules on the surface of their cells. HLA-A1, HLA-A2, HLA-A3, HLA-B7, HLA-B14, HLA-B27, and HLA-B44 are examples of different class I MHC molecules that can be expressed from these loci.

The peptides which associate with the MHC molecules can either be derived from proteins made within the cell, in which case they typically associate with class I MHC molecules (Rock & Goldberg, 1999); or they can be derived from proteins which are acquired from outside of the cell, in which case they typically associate with class II MHC molecules (Watts, 1997). The peptides that evoke a cancer-specific CTL response most typically associate with class I MHC molecules. The peptides themselves are typically nine amino acids in length, but can vary from a minimum length of eight amino acids to a maximum of fourteen amino acids in length. Tumor antigens may also bind to class II MHC molecules on antigen presenting cells and provoke a T helper cell response. The peptides that bind to class II MHC molecules are generally twelve to nineteen amino acids in length, but can be as short as ten amino acids and as long as thirty amino acids.

The process by which intact proteins are degraded into peptides is referred to as antigen processing. Two major pathways of antigen processing occur within cells (Rock & Goldberg, 1999). One pathway, which is largely restricted to professional antigen presenting cells such as dendritic cells, macrophages, and B cells, degrades proteins that are typically phagocytosed or endocytosed into the cell. Peptides derived from this pathway can be presented on either class I or to class II MHC molecules. A second pathway of antigen processing is present in essentially all cells of the body. This second pathway primarily degrades proteins that are made within the cells, and the peptides derived from this pathway primarily bind to class I MHC molecules. Antigen processing by this latter pathway involves polypeptide synthesis and proteolysis in the cytoplasm, followed by transport of peptides to the plasma membrane for presentation. These peptides, initially being transported into the endoplasmic reticulum of the cell, become associated with newly synthesized class I MHC molecules and the resulting complexes are then transported to the cell surface. Peptides derived from membrane and secreted proteins have also been identified. In some cases these peptides correspond to the signal sequence of the proteins which is cleaved from the protein by the signal peptidase. In other cases, it is thought that some fraction of the membrane and secreted proteins are transported from the endoplasmic reticulum into the cytoplasm where processing subsequently occurs. Once bound to the class I MHC molecule, the peptides are recognized by antigen-specific receptors on CTL. Several methods have been developed to identify the peptides recognized by CTL, each method of which relies on the ability of a CTL to recognize and kill only those cells expressing the appropriate class I MHC molecule with the peptide bound to it. Mere expression of the class I MHC molecule is insufficient to trigger the CTL to kill the target cell if the antigenic peptide is not bound to the class I MHC molecule. Such peptides can be derived from a non-self source, such as a pathogen (for example, following the infection of a cell by a bacterium or a virus) or from a self-derived protein within a cell, such as a cancerous cell. The tumor antigens from which the peptides are derived can broadly be categorized as differentiation antigens, cancer/testis antigens, mutated gene products, widely expressed proteins, viral antigens and most recently, phosphopeptides derived from dysregulated signal transduction pathways. (Zarling et al., 2006).

Immunization with cancer-derived, class I or class II MHC-encoded molecule associated peptides, or with a precursor polypeptide or protein that contains the peptide, or with a gene that encodes a polypeptide or protein containing the peptide, are forms of immunotherapy that can be employed in the treatment of colorectal cancer. Identification of the immunogens is a necessary first step in the formulation of the appropriate immunotherapeutic agent or agents. Although a large number of tumor-associated peptide antigens recognized by tumor reactive CTL have been identified, there are few examples of antigens that are derived from proteins that are selectively expressed on a broad array of tumors, as well as associated with cellular proliferation and/or transformation.

Attractive candidates for this type of antigen are peptides derived from proteins that are differentially phosphorylated on serine (Ser), threonine (Thr), and/or tyrosine (Tyr; Zarling et al., 2000). Due to the increased and dysregulated phosphorylation of cellular proteins in transformed cells as compared to normal cells, tumors are likely to present a unique subset of phosphorylated peptides on the cell surface that are available for recognition by cytotoxic T-lymphocytes (CTL). Presently, there is no way to predict which protein phosphorylation sites in a cell will be unique to tumors, survive the antigen processing pathway, and be presented to the immune system in the context of 8-14 residue phosphopeptides bound to class I MHC molecules. However, thirty-six phosphopeptides were disclosed as presented in association with HLA-A*0201 on cancer cells (see Table 1 of Zarling et al., 2006).

SUMMARY

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

In some embodiments, the presently disclosed subject matter provides isolated T cell receptors (TCRs), TCR-like molecules, and portions thereof that bind to phosphopeptide/MHC complexes (optionally, phosphopeptide/HLA-A2 complexes). In some embodiments, the phosphopeptide is RVApSPTSGV (SEQ ID NO: 2). In some embodiments, the isolated TCR, TCR-like molecule, or portion thereof comprises an alpha chain comprising a CDR3 region comprising AVSEGADRLT (amino acids 111-120 of SEQ ID NO: 4) and a beta chain comprising a CDR3 region comprising ASSLLDSSYEQY (amino acids 112-123 of SEQ ID NO: 6), and in some embodiments the isolated TCR, TCR-like molecule, or portion thereof comprises an alpha chain comprising a CDR3 region comprising AVSAGSGGKLT (amino acids 111-122 of SEQ ID NO: 8) and a beta chain comprising a CDR3 region comprising ASSDRDNYAEQF (amino acids 110-122 of SEQ ID NO: 10). In some embodiments, the isolated TCR, TCR-like molecule, or portion thereof comprises an alpha chain comprising a TRAV9D-4*04 V region, a TRAJ45*01 J region, and a TRAC*01 constant region, and a beta chain comprising a TRBV14*01 V region, a TRBJ2-7*01 J region, a TRBD1*01 D region, and a TRBC2*03 constant region. In some embodiments, the alpha chain comprises a TRAV9D-4*04 V region, a TRAJ44*01 J region, and a TRAC*01 constant region, and the beta chain comprises a TRBV13-3*01 V region, a TRBJ2-1*01 J region, a TRBD1*01 D region, and a TRBC2*03 constant region. In some embodiments, the isolated TCR, TCR-like molecule, or portion thereof comprises an alpha chain comprising an amino acid sequence at least 90% or 95% identical to SEQ ID NO: 4 and a beta chain comprising an amino acid sequence at least 90% or 95% identical to SEQ ID NO: 6; or an alpha chain comprising an amino acid sequence at least 90% or 95% identical to SEQ ID NO: 8 and a beta chain comprising an amino acid sequence at least 90% or 95% identical to SEQ ID NO: 10. In some embodiments, the isolated TCR, TCR-like molecule, or portion thereof comprises an alpha chain comprising a CDR1 region comprising YSGTPY (amino acids 46-51 of SEQ ID NO: 4) and/or a CDR2 region comprising YYSGDPVV (amino acids 69-76 of SEQ ID NO: 4), and a beta chain comprising a CDR1 region comprising SGHDT (amino acids 46-50 of SEQ ID NO: 6) and/or a CDR2 region comprising FRDEAV (amino acids 68-73 of SEQ ID NO: 6). In some embodiments, the alpha chain comprises a CDR1 region comprising YSGTPY (amino acids 46-50 of SEQ ID NO: 8) and/or a CDR2 region comprising YYSGDPVV (amino acids 69-76 of SEQ ID NO: 8), and the beta chain comprises a CDR1 region comprising NNHDY (amino acids 45-49 of SEQ ID NO: 10) and/or a CDR2 region comprising SYVADS (amino acids 67-72 of SEQ ID NO: 10). In some embodiments, the isolated TCR, TCR-like molecule, or portion thereof is a soluble TCR, TCR-like molecule, or portion thereof comprising an alpha chain comprising a CDR1 region comprising YSGTPY (amino acids 46-51 of SEQ ID NO: 4), a CDR2 region comprising YYSGDPVV (amino acids 69-76 of SEQ ID NO: 4), and a CDR3 region comprising AVSEGADRLT (amino acids 111-120 of SEQ ID NO: 4); and a beta chain comprising a CDR1 region comprising SGHDT (amino acids 46-50 of SEQ ID NO: 6), a CDR2 region comprising FRDEAV (amino acids 68-73 of SEQ ID NO: 6), and a CDR3 region comprising ASSLLDSSYEQY (amino acids 112-123 of SEQ ID NO: 6). In some embodiments, the alpha chain comprises a CDR1 region comprising YSGTPY (amino acids 46-50 of SEQ ID NO: 8), a CDR2 region comprising YYSGDPVV (amino acids 69-76 of SEQ ID NO: 8), and a CDR3 region comprising AVSAGSGGKLT (amino acids 111-122 of SEQ ID NO: 8); and the beta chain comprises a CDR1 region comprising NNHDY (amino acids 45-49 of SEQ ID NO: 10), a CDR2 region comprising SYVADS (amino acids 67-72 of SEQ ID NO: 10), and a CDR3 region comprising ASSDRDNYAEQF (amino acids 110-122 of SEQ ID NO: 10).

In some embodiments, the phosphopeptide is GLL-GpSPVRA (SEQ ID NO: 12). In some embodiments, the isolated TCR, TCR-like molecule, or portion thereof comprises an alpha chain comprising a CDR3 region comprising AVKPGGYKVV (amino acids 112-121 of SEQ ID NO: 14) and a beta chain comprising a CDR3 region comprising ASGGDTQY (amino acids 121-129 of SEQ ID NO: 16). In some embodiments, the isolated TCR, TCR-like molecule, or portion thereof comprises an alpha chain comprising a TRAV3-3*02 V region, a TRAJ12*01 J region, and a TRAC*01 constant region, and a beta chain comprising a TRBV13-2*01 V region, a TRBJ2-5*01 J region, a TRBD2*01 D region, and a TRBC2*03 constant region. In some embodiments, the isolated TCR, TCR-like molecule, or portion thereof comprises an alpha chain comprising an amino acid sequence at least 90% or 95% identical to SEQ ID NO: 14 and a beta chain comprising an amino acid sequence at least 90% or 95% identical to SEQ ID NO: 16. In some embodiments, the isolated TCR, TCR-like molecule, or portion thereof comprises an alpha chain comprising a CDR1 region comprising DPNSYY (amino acids 48-53 of SEQ ID NO: 14) and/or a CDR2 region comprising VFSSTEI (amino acids 71-77 of SEQ ID NO: 14), and a beta chain comprising a CDR1 region comprising NNHNN (amino acids 56-60 of SEQ ID NO: 16) and/or a CDR2 region comprising SYGAGS (amino acids 78-83 of SEQ ID NO: 16). In some embodiments, the isolated TCR, TCR-like molecule, or portion thereof is a soluble TCR, TCR-like molecule, or portion thereof comprising an alpha chain comprising a CDR1 region comprising DPNSYY (amino acids 48-53 of SEQ ID NO: 14), a CDR2 region comprising VFSSTEI (amino acids 71-77 of SEQ ID NO: 14), and a CDR3 region comprising AVKPGGYKVV (amino acids 112-121 of SEQ ID NO: 14); and a beta chain comprising a CDR1 region comprising NNHNN (amino acids 56-60 of SEQ ID NO: 16), a CDR2 region comprising SYGAGS (amino acids 78-83 of SEQ ID NO: 16), and a CDR3 region comprising ASGGDTQY (amino acids 121-129 of SEQ ID NO: 16).

In some embodiments, the phosphopeptide is RTFpSPTYGL (SEQ ID NO: 19). In some embodiments, the isolated TCR, TCR-like molecule, or portion thereof comprises an alpha chain comprising a CDR3 region comprising VLSYSNNRIF (amino acids 111-120 of SEQ ID NO: 21) and a beta chain comprising a CDR3 region comprising ASSLGG-GEVF (amino acids 121-130 of SEQ ID NO: 23), and in some embodiments the isolated TCR, TCR-like molecule, or portion thereof comprises an alpha chain comprising a CDR3 region comprising VLRYGGNNKLT (amino acids 111-121 of SEQ ID NO: 25) and beta chain comprising a CDR3 region comprising ASRYRDTQY (amino acids 110-118 of SEQ ID NO: 27). In some embodiments, the isolated TCR, TCR-like molecule, or portion thereof comprises an alpha chain comprising a TRAV9D-4*02 V region, a TRAJ31*01 J region, and a TRAC*01 constant region, and a beta chain comprising a TRBV12-1*01 V region, a TRBJ1-1*01/J1-1*02 J region, a TRBD1*01 D region, and a TRBC1*01 constant region. In some embodiments, the alpha chain comprises a TRAV9D-4*02 V region, a TRAJ56*01 J region, and a TRAC*01 constant region, and the beta chain comprises a TRBV13-3*01 V region, a TRBJ2-5*01 J region, a TRBD1*01 D region, and a TRBC2*03 constant region. In some embodiments, the isolated TCR, TCR-like molecule, or portion thereof comprises an alpha chain comprising an amino acid sequence at least 90% or 95% identical to SEQ ID NO: 21 and a beta chain comprising an amino acid sequence at least 90% or 95% identical to SEQ ID NO: 23; or an alpha chain comprising an amino acid sequence at least 90% or 95% identical to SEQ ID NO: 25 and a beta chain comprising an amino acid sequence at least 90% or 95% identical to SEQ ID NO: 27. In some embodiments, the isolated TCR, TCR-like molecule, or portion thereof comprises an alpha chain comprising a CDR1 region comprising YSGTPY (amino acids 46-51 of SEQ ID NO: 21) and/or a CDR2 region comprising YYSGDPVV (amino acids 69-76 of SEQ ID NO: 21), and a beta chain comprising a CDR1 region comprising SGHSN (amino acids 56-60 of SEQ ID NO: 23) and/or a CDR2 region comprising HYEKVE (amino acids 78-83 of SEQ ID NO: 23). In some embodiments, the alpha chain comprises a CDR1 region comprising YSGTPY (amino acids 46-51 of SEQ ID NO: 25) and/or a CDR2 region comprising YYSGDPVV (amino acids 69-76 of SEQ ID NO: 25), and the beta chain comprises a CDR1 region comprising NNHDY (amino acids 45-49 of SEQ ID NO: 27) and/or a CDR2 region comprising SYVADS (amino acids 67-72 of SEQ ID NO: 27). In some embodiments, the isolated TCR, TCR-like molecule, or portion thereof is a soluble TCR, TCR-like molecule, or portion thereof comprising alpha chain comprising a CDR1 region comprising YSGTPY (amino acids 46-51 of SEQ ID NO: 21), a CDR2 region comprising YYSGDPVV (amino acids 69-76 of SEQ ID NO: 21), and a CDR3 region comprising VLSYSNNRIF (amino acids 111-120 of SEQ ID NO: 21); and a beta chain comprising a CDR1 region comprising SGHSN (amino acids 56-60 of SEQ ID NO: 23), a CDR2 region comprising HYEKVE (amino acids 78-83 of SEQ ID NO: 23), and a CDR3 region comprising ASSLGGGEVF (amino acids 121-130 of SEQ ID NO: 23). In some embodiments, the alpha chain comprises a CDR1 region comprising YSGTPY (amino acids 46-51 of SEQ ID NO: 25), a CDR2 region comprising YYSGDPVV (amino acids 69-76 of SEQ ID NO: 25), and a CDR3 region comprising VLRYGGNNKLT (amino acids 111-121 of SEQ ID NO: 25); and the beta chain comprises a CDR1 region comprising NNHDY (amino acids 45-49 of SEQ ID NO: 27), a CDR2 region comprising SYVADS (amino acids 67-72 of SEQ ID NO: 27), and a CDR3 region comprising ASRYRDTQY (amino acids 110-118 of SEQ ID NO: 27).

In some embodiments, the phosphopeptide is YLDpSGIHSGV (SEQ ID NO: 29). In some embodiments, the isolated TCR, TCR-like molecule, or portion thereof comprises an alpha chain comprising a CDR3 region comprising AIPPGTGSKLS (amino acids 108-118 of SEQ ID NO: 32) and a beta chain comprising a CDR3 region comprising ASSQGQKGY (amino acids 110-118 of SEQ ID NO: 34). In some embodiments, the isolated TCR, TCR-like molecule, or portion thereof comprises an alpha chain comprising a TRAV13*02 V region, a TRAJ58*01 J region, and a TRAC*01 constant region, and a beta chain comprising a TRBV5*01 V region, a TRBJ2-7*01 J region, a TRBD1*01 D region, and a TRBC2*03 constant region. In some embodiments, the isolated TCR, TCR-like molecule, or portion thereof comprises an alpha chain comprising an amino acid sequence at least 90% or 95% identical to SEQ ID NO: 32 and a beta chain comprising an amino acid sequence at least 90% or 95% identical to SEQ ID NO: 34. In some embodiments, the isolated TCR, TCR-like molecule, or portion thereof comprises an alpha chain comprising a CDR1 region comprising STATR (amino acids 47-51 of SEQ ID NO: 32) and/or a CDR2 region comprising NPSGT (amino acids 69-73 of SEQ ID NO: 32), and a beta chain comprising a CDR1 region comprising LGHNA (amino acids 45-49 of SEQ ID NO: 34) and/or a CDR2 region comprising YNLKQL (amino acids 67-72 of SEQ ID NO: 34). In some embodiments, the isolated TCR, TCR-like molecule, or portion thereof is a soluble TCR, TCR-like molecule, or portion thereof comprising an alpha chain comprising a CDR1 region comprising STATR (amino acids 47-51 of SEQ ID NO: 32), a CDR2 region comprising NPSGT (amino acids 69-73 of SEQ ID NO: 32), and a CDR3 region comprising AIPPGTGSKLS (amino acids 108-118 of SEQ ID NO: 32); and a beta chain comprising a CDR1 region comprising LGHNA (amino acids 45-49 of SEQ ID NO: 34), a CDR2 region comprising YNLKQL (amino acids 67-72 of SEQ ID NO: 34), and a CDR3 region comprising ASSQGQKGY (amino acids 110-118 of SEQ ID NO: 34).

In some embodiments, the phosphopeptide is YLDpSGIHSGA (SEQ ID NO: 30). In some embodiments, the isolated TCR, TCR-like molecule, or portion thereof comprises an alpha chain comprising a CDR3 region comprising ATGPNTNKVV (amino acids 110-119 of SEQ ID NO: 36) and a beta chain comprising a CDR3 region comprising ASSQGGAEQF (amino acids 110-119 of SEQ ID NO: 38). In some embodiments, the isolated TCR, TCR-like molecule, or portion thereof comprises an alpha chain comprising a TRAV8D-2*02 V region, a TRAJ34*02 J region, and a TRAC*01 constant region, and a beta chain comprising a TRBV5*01 V region, a TRBJ2-1*01 J region, a TRBD2*01 D region, and a TRBC2*03 constant region. In some embodiments, the isolated TCR, TCR-like molecule, or portion thereof comprises an alpha chain comprising an amino acid sequence at least 90% or 95% identical to SEQ ID NO: 36 and a beta chain comprising an amino acid sequence at least 90% or 95% identical to SEQ ID NO: 38. In some embodiments, the isolated TCR, TCR-like molecule, or portion thereof comprises an alpha chain comprising a CDR1 region comprising TYTTV (amino acids 47-51 of SEQ ID NO: 36) and/or a CDR2 region comprising IRSNERE (amino acids 69-75 of SEQ ID NO: 36), and a beta chain comprising a CDR1 region comprising LGHKA (amino acids 45-49 of SEQ ID NO: 38) and/or a CDR2 region comprising YNLKQL (amino acids 67-72 of SEQ ID NO: 38). In some embodiments, the isolated TCR, TCR-like molecule, or portion thereof is a soluble TCR, TCR-like molecule, or portion thereof comprising an alpha chain comprising a CDR1 region comprising TYTTV (amino acids 47-51 of SEQ ID NO: 36), a CDR2 region comprising IRSNERE (amino acids 69-75 of SEQ ID NO: 36), and a CDR3 region comprising ATGPNTNKVV (amino acids 110-119 of SEQ ID NO: 36); and a beta chain comprising a CDR1 region comprising LGHKA (amino acids 45-49 of SEQ ID NO: 38), a CDR2 region comprising YNLKQL (amino acids 67-72 of SEQ ID NO: 38), and a CDR3 region comprising ASSQGGAEQF (amino acids 110-119 of SEQ ID NO: 38).

In some embodiments, the isolated and/or soluble TCR, TCR-like molecule, or portion thereof is conjugated to an active agent. In some embodiments, the active agent is selected from the group consisting of a detectable label, an immunostimulatory molecule, and a therapeutic agent. In some embodiments, the detectable label is selected from the group consisting of biotin, streptavidin, an enzyme or catalytically active fragment thereof, a radionuclide, a nanoparticle, a paramagnetic metal ion, or a fluorescent, phosphorescent, or chemiluminescent molecule. In some embodiments, the immunostimulatory molecule is a CD3 agonist, optionally an anti-CD3 antibody. In some embodiments, the therapeutic agent is selected from the group consisting of an alkylating agent, an antimetabolite, a natural product having pharmacological activity, a mitotic inhibitor, an antibiotic, a cytotoxic agent, and a chemotherapeutic agent.

In some embodiments, the isolated and/or soluble TCR, TCR-like molecule, or portion thereof is humanized, comprises a human constant domain, or both.

The presently disclosed subject matter also provides isolated nucleic acids encoding the isolated and/or soluble TCRs, TCR-like molecules, or portions thereof disclosed herein. In some embodiments, the nucleic acids are present in vectors, optionally expression vectors. In some embodiments, the nucleic acids are present in expression vectors under transcriptional and optionally translational control of regulatory sequences sufficient to express the nucleic acids in cells, optionally prokaryotic cells and optionally eukaryotic cells. In some embodiments, the cells are mammalian cells, and in some embodiments the mammalian cells are human cells. In some embodiments, an isolated nucleic acid of the presently disclosed subject matter is a complementary DNA (cDNA) encoding any one of SEQ ID NOs: 4, 6, 8, 10, 14, 16, 21, 23, 25, 27, 32, 34, 36, or 38, or an extracellular portion thereof, optionally comprises any of the CDR1/CDR2/CDR3 combinations disclosed herein. In some embodiments, when a cDNA of the presently disclosed subject matter encodes both an alpha chain and a beta chain, the cDNA includes an internal ribosome entry site (IRES) such that translation of the cDNA in a host cell produces both the alpha chain and the beta chain encoded thereby.

The presently disclosed subject matter also provides host cells. In some embodiments, a host cell of the presently disclosed subject matter comprises an isolated and/or soluble TCR, TCR-like molecule, or portion thereof as disclosed herein, an isolated nucleic acid as disclosed herein, or both.

The presently disclosed subject matter also provides isolated T cells comprising one or more isolated and/or soluble TCRs, TCR-like molecules, and/or portions thereof disclosed herein, one or more isolated nucleic acids disclosed herein, or any combination thereof.

The presently disclosed subject matter also provides pharmaceutical compositions. In some embodiments, a pharmaceutical composition of the presently disclosed subject matter comprises an isolated and/or soluble TCR, TCR-like molecule, or portion thereof as disclosed herein; an isolated nucleic acid as disclosed herein; an isolated T cell as disclosed herein; or any combination thereof. In some embodiments, administration of a therapeutically effective amount of a pharmaceutical composition as disclosed herein to a patient who has a tumor and/or a cancer is capable of increasing the 5-year survival rate of the patient by at least 20 percent relative to average 5-year survival rates that could have been expected without treatment with the pharmaceutical composition. In some embodiments, administration of a therapeutically effective amount of a pharmaceutical composition as disclosed herein to a patient who has a tumor and/or a cancer is capable of increasing the survival rate of the patient by at least 20 percent relative to a survival rate that could have been expected without treatment with the pharmaceutical composition. In some embodiments, administration of a therapeutically effective amount of a pharmaceutical composition as disclosed herein to a patient who has a tumor and/or a cancer is capable of increasing the treatment response rate of the patient to the tumor and/or the cancer by at least 20 percent relative to a treatment rate that could have been expected without treatment with the pharmaceutical composition. In some embodiments, administration of a therapeutically effective amount of a pharmaceutical composition as disclosed herein to a patient who has a tumor and/or a cancer is capable of increasing the overall median survival of the patient by at least two months relative to an overall median survival that could have been expected without treatment with the pharmaceutical composition. In some embodiments, the pharmaceutical composition further comprises at least one peptide derived from MelanA (MART-I), gp100 (Pmel 17), tyrosinase, TRP-1, TRP-2, MAGE-1, MAGE-3, BAGE, GAGE-1, GAGE-2, p15(58), CEA, RAGE, NY-ESO (LAGE), SCP-1, Hom/Mel-40, PRAME, p53, H-Ras, HER-2/neu, BCR-ABL, E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, β-Catenin, CDK4, Mum-1, p16, TAGE, PSMA, PSCA, CT7, telomerase, 43-9F, 5T4, 791Tgp72, α-fetoprotein, β-HCG, BCA225, BTAA, CA 125, CA 15-3 (CA 27.29\BCAA), CA 195, CA 242, CA-50, CAM43, CD68\KP1, CO-029, FGF-5, G250, Ga733 (EpCAM), HTgp-175, M344, MA-50, MG7-Ag, MOV18, NB/70K, NY-CO-1, RCAS1, SDCCAG16, TA-90 (Mac-2 binding protein\cyclophilin C-associated protein), TAAL6, TAG72, TLP and TPS. In some embodiments, the pharmaceutical composition further comprises an adjuvant selected from the group consisting of montanide ISA-51 (Seppic, Inc.), QS-21 (Aquila Pharmaceuticals, Inc), tetanus helper peptides, GM-CSF, cyclophosamide, bacillus Calmette-Guérin (BCG), corynbacterium parvum, levamisole, azimezone, isoprinisone, dinitrochlorobenezene (DNCB), keyhole limpet hemocyanins (KLH), Freund's adjuvant (complete and incomplete), mineral gels, aluminum hydroxide (Alum), lysolecithin, pluronic polyols, polyanions, peptides, oil emulsions, dinitrophenol, diphtheria toxin (DT).

The presently disclosed subject matter also provides methods for adoptive T cell therapy. In some embodiments, the methods comprise administering to a subject in need thereof an isolated T cell as disclosed herein and/or a pharmaceutical composition as disclosed herein. In some embodiments, the presently disclosed methods further comprise administering to the subject an effective amount of CD4+ T helper cells before, after, or concomitantly with the isolated T cell and/or the pharmaceutical composition. In some embodiments, the presently disclosed methods further comprise exposing the subject to a treatment that creates a lymphopenic environment in the subject, thereby enhancing engraftment and/or expansion of the isolated T cell. In some embodiments of the presently disclosed methods, the subject has a tumor and/or a cancer, optionally a tumor and/or a cancer selected from the group consisting of pancreatic cancer, hepatocellular carcinoma, neuroblastoma, breast cancer, glioblastoma, and colorectal cancer, and the administered isolated T cell and/or a component of the administered pharmaceutical composition specifically binds to a tumor-associated antigen expressed by cells of the tumor and/or the cancer.

The presently disclosed subject matter also provides methods for treating tumors and/or cancers in patients, wherein said tumors and/or cancers bear one or more immunologically reactive tumor-specific antigens. In some embodiments, the methods comprise transforming peripheral blood lymphocytes isolated from a patient, optionally T cells, further optionally cytotoxic CD8+ T cells, with an expression vector, wherein the expression vector comprises a nucleotide sequence encoding an isolated and/or soluble TCR, TCR-like molecule, or portion thereof as disclosed herein; and administering the transformed cells to the patient, the transformed cells being targeted to the tumor, thereby treating the tumor.

The presently disclosed subject matter also provides methods for directing the immune response of a patient toward a predefined target antigen. In some embodiments, the methods comprise transfecting a lymphocyte with a recombinant DNA encoding an isolated and/or soluble TCR, TCR-like molecule, or portion thereof as disclosed herein; and administering the transfected lymphocyte to the patient. In some embodiments, the patient is given a pre-treatment that partially or completely destroys or otherwise inactivates the patient's T cell compartment. In some embodiments, the amount of transfected lymphocytes administered to the patient is sufficient to engraft in the patient and optionally partially or completely reconstitute the T cell compartment of the patient. In some embodiments, the patient has a tumor and/or a cancer, optionally a tumor and/or a cancer selected from the group consisting of pancreatic cancer, hepatocellular carcinoma, neuroblastoma, breast cancer, glioblastoma, and colorectal cancer. In some embodiments, the predefined target antigen comprises a phosphopeptide comprising an amino acid sequence selected from the group consisting of RVApSPTSGV (SEQ ID NO: 2), GLLGpSPVRA (SEQ ID NO: 12), RTFpSPTYGL (SEQ ID NO: 19), YLDpSGIHSGV (SEQ ID NO: 29), and YLDpSGIHSGA (SEQ ID NO: 30).

In some embodiments, the presently disclosed subject matter also provides methods for generating antigen-specific T cells. In some embodiments, the methods comprise providing a nucleic acid encoding an isolated and/or soluble TCR, TCR-like molecule, or portion thereof as disclosed herein; introducing the nucleic acid into a T cell; and optionally selecting a T cell that expresses the TCR, the TCR-like molecule, or the portion thereof. In some embodiments, the presently disclosed methods further comprise identifying an antigen-specific T cell that recognizes a complex of an MHC molecule and a phosphopeptide, wherein the phosphopeptide comprises an amino acid sequence selected from the group consisting of RVApSPTSGV (SEQ ID NO: 2), GLLGpSPVRA (SEQ ID NO: 12), RTFpSPTYGL (SEQ ID NO: 19), YLDpSGIHSGV (SEQ ID NO: 29), and YLDpSGIHSGA (SEQ ID NO: 30).

The presently disclosed subject matter also provides in some embodiments in vitro populations of T cells transfected with a nucleic acid (e.g., mRNA, cDNA, or genomic DNA) encoding an isolated and/or soluble TCR, TCR-like molecule, or portion thereof of the presently disclosed subject matter.

The presently disclosed subject matter also provides methods for treating and/or preventing cancer, said methods comprising administering to a patient in need thereof a dose of a pharmaceutical composition as disclosed herein.

The presently disclosed subject matter also provides in some embodiments methods for treating and/or preventing cancer comprising administering to a patient in need thereof one or more doses of the isolated T cells disclosed herein, optionally isolated CD8+ T cells, wherein the administered T cells are administered in combination with a pharmaceutically acceptable carrier.

The presently disclosed subject matter also provides in some embodiments methods for making cancer vaccines. In some embodiments, the presently disclosed methods comprise combining a composition comprising a plurality of the isolated T cells of the presently disclosed subject matter with an adjuvant and/or a pharmaceutically acceptable carrier and placing the composition comprising the plurality of isolated T cells and the adjuvant and/or the pharmaceutical carrier into a syringe.

The presently disclosed subject matter also provides in some embodiments kits. In some embodiments, the kits comprise a cytokine and/or an adjuvant; and at least one composition comprising an isolated and/or soluble T cell comprising a TCR, TCR-like molecule, or portion thereof as disclosed herein, an isolated T cell as disclosed herein, a pharmaceutical composition as disclosed herein, or any combination thereof. In some embodiments, a presently disclosed kit comprises a plurality of T cells that together comprise at least 1, 2, 3, 4, 5, 6, 7, or more different isolated and/or soluble TCRs, TCR-like molecules, or portions thereof as disclosed herein. In some embodiments, the cytokine is selected from the group consisting of transforming growth factors (TGFs) such as TGF-α and TGF-β; insulin-like growth factor-I and insulin-like growth factor-II; erythropoietin (EPO); osteoinductive factors; interferons such as IFNα, IFNβ, and IFNγ; colony stimulating factors (CSFs) such as macrophage-CSF (M-CSF); granulocyte-macrophage-CSF (GM-CSF); and granulocyte-CSF (G-CSF). In some embodiments, the cytokine is selected from the group consisting of nerve growth factors such as NGF-β; platelet-growth factor; transforming growth factors (TGFs) such as TGF-α and TGF-β; insulin-like growth factor-I and insulin-like growth factor-II; erythropoietin (EPO); osteoinductive factors; interferons such as IFNα, IFNβ, and IFNγ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-10, IL-11, IL-12; IL-13, IL-14, IL-15, IL-16, IL-17, IL-18, LIF, G-CSF, GM-CSF, M-CSF, EPO, kit-ligand or FLT-3, angiostatin, thrombospondin, endostatin, tumor necrosis factor, and LT. In some embodiments, the adjuvant is selected from the group consisting of montanide ISA-51 (Seppic, Inc), QS-21 (Aquila Pharmaceuticals, Inc), tetanus helper peptides, GM-CSF, cyclophosamide, bacillus Calmette-Guérin (BCG), corynbacterium parvum, levamisole, azimezone, isoprinisone, dinitrochlorobenezene (DNCB), keyhole limpet hemocyanins (KLH), Freund's adjuvant (complete and incomplete), mineral gels, aluminum hydroxide (Alum), lysolecithin, pluronic polyols, polyanions, peptides, oil emulsions, dinitrophenol, diphtheria toxin (DT). In some embodiments, the presently disclosed kit further comprises at least one peptide derived from MelanA (MART-I), gp100 (Pmel 17), tyrosinase, TRP-1, TRP-2, MAGE-1, MAGE-3, BAGE, GAGE-1, GAGE-2, p15(58), CEA, RAGE, NY-ESO (LAGE), SCP-1, Hom/Mel-40, PRAME, p53, H-Ras, HER-2/neu, BCR-ABL, E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, β-Catenin, CDK4, Mum-1, p16, TAGE, PSMA, PSCA, CT7, telomerase, 43-9F, 5T4, 791Tgp72, α-fetoprotein, β-HCG, BCA225, BTAA, CA 125, CA 15-3 (CA 27.29\BCAA), CA 195, CA 242, CA-50, CAM43, CD68\KP1, CO-029, FGF-5, G250, Ga733 (EpCAM), HTgp-175, M344, MA-50, MG7-Ag, MOV18, NB/70K, NY-CO-1, RCAS1, SDCCAG16, TA-90 (Mac-2 binding protein\cyclophilin C-associated protein), TAAL6, TAG72, TLP and TPS. In some embodiments, the at least one target peptide comprises an amino acid sequence selected from among SEQ ID NOs: 2, 12, 19, 29, and 30, or an antigenic portion thereof.

The presently disclosed subject matter also provides in vitro populations of CD8+ T cells capable of being activated upon being brought into contact with a population of dendritic cells. In some embodiments, the in vitro population of CD8+ T cells comprise one or more TCRs that bind to a complex of an HLA molecule and a phosphopeptide selected from the group consisting of RVApSPTSGV (SEQ ID NO: 2), GLLGpSPVRA (SEQ ID NO: 12), RTFpSPTYGL (SEQ ID NO: 19), YLDpSGIHSGV (SEQ ID NO: 29), and YLDpSGIHSGA (SEQ ID NO: 30).

In some embodiments, the presently disclosed subject matter also provides methods for detecting the presence of a phosphopeptide in a biological sample suspected of containing the phosphopeptide. In some embodiments, the methods comprise contacting the biological sample with a TCR, TCR-like molecule, or portion thereof of the presently disclosed subject matter (optionally a detectably labeled TCR, TCR-like molecule, or portion thereof); and detecting the TCR, TCR-like molecule, or portion thereof either directly or indirectly. In some embodiments, the TCR, TCR-like molecule, or portion thereof comprises an alpha chain comprising a CDR3 region comprising AVSEGADRLT (amino acids 111-120 of SEQ ID NO: 4) and a beta chain comprising a CDR3 region comprising ASSLLDSSYEQY (amino acids 112-123 of SEQ ID NO: 6); an alpha chain comprising a CDR3 region comprising AVSAGSGGKLT (amino acids 111-122 of SEQ ID NO: 8); and a beta chain comprising a CDR3 region comprising ASSDRDNYAEQF (amino acids 110-122 of SEQ ID NO: 10); an alpha chain comprising a CDR3 region comprising AVKPGGYKVV (amino acids 112-121 of SEQ ID NO: 14) and a beta chain comprising a CDR3 region comprising ASGGDTQY (amino acids 121-129 of SEQ ID NO: 16); an alpha chain comprising a CDR3 region comprising VLSYSNNRIF (amino acids 111-120 of SEQ ID NO: 21) and a beta chain comprising a CDR3 region comprising ASSLGGGEVF (amino acids 121-130 of SEQ ID NO: 23); an alpha chain comprising a CDR3 region comprising VLRYGGNNKLT (amino acids 111-121 of SEQ ID NO: 25) and beta chain comprising a CDR3 region comprising ASRYRDTQY (amino acids 110-118 of SEQ ID NO: 27); an alpha chain comprising a CDR3 region comprising AIPPGTGSKLS (amino acids 108-118 of SEQ ID NO: 32) and a beta chain comprising a CDR3 region comprising ASSQGQKGY (amino acids 110-118 of SEQ ID NO: 34); or an alpha chain comprising a CDR3 region comprising ATGPNTNKVV (amino acids 110-119 of SEQ ID NO: 36) and a beta chain comprising a CDR3 region comprising ASSQGGAEQF (amino acids 110-119 of SEQ ID NO: 38). In some embodiments, the biological sample is a patient biopsy and the detecting step is diagnostic of the presence of tumor cells and/or cancer cells in the patient biopsy.

In some embodiments, the presently disclosed subject matter also provides methods for diagnosing a tumor and/or a cancer in a subject. In some embodiments, the methods comprise contacting a biological sample isolated from the subject with a TCR, TCR-like molecule, or portion thereof of the presently disclosed subject matter, optionally a detectably labeled TCR, TCR-like molecule, or portion thereof, and detecting the TCR, TCR-like molecule, or portion thereof bound to the biological sample directly or indirectly, wherein detecting the TCR, TCR-like molecule, or portion thereof bound to the biological sample is indicative of a tumor and/or a cancer in the subject. In some embodiments, the TCR, TCR-like molecule, or portion thereof comprises an alpha chain comprising a CDR1 region comprising YSGTPY (amino acids 46-51 of SEQ ID NO: 4), a CDR2 region comprising YYSGDPVV (amino acids 69-76 of SEQ ID NO: 4), a CDR3 region comprising AVSEGADRLT (amino acids 111-120 of SEQ ID NO: 4), or any combination thereof; and a beta chain comprising a CDR1 region comprising SGHDT (amino acids 46-50 of SEQ ID NO: 6), a CDR2 region comprising FRDEAV (amino acids 68-73 of SEQ ID NO: 6), a CDR3 region comprising ASSLLDSSYEQY (amino acids 112-123 of SEQ ID NO: 6), or any combination thereof. In some embodiments, the TCR, TCR-like molecule, or portion thereof comprises an alpha chain comprising a CDR1 region comprising YSGTPY (amino acids 46-50 of SEQ ID NO: 8), a CDR2 region comprising YYSGDPVV (amino acids 69-76 of SEQ ID NO: 8), a CDR3 region comprising AVSAGSGGKLT (amino acids 111-122 of SEQ ID NO: 8), or any combination thereof; and a beta chain comprising a CDR1 region comprising NNHDY (amino acids 45-49 of SEQ ID NO: 10), a CDR2 region comprising SYVADS (amino acids 67-72 of SEQ ID NO: 10), a CDR3 region comprising ASSDRDNYAEQF (amino acids 110-122 of SEQ ID NO: 10), or any combination thereof. In some embodiments, the TCR, TCR-like molecule, or portion thereof comprises an alpha chain comprising a CDR1 region comprising DPNSYY (amino acids 48-53 of SEQ ID NO: 14), a CDR2 region comprising VFSSTEI (amino acids 71-77 of SEQ ID NO: 14), a CDR3 region comprising AVKPGGYKVV (amino acids 112-121 of SEQ ID NO: 14), or any combination thereof; and a beta chain comprising a CDR1 region comprising NNHNN (amino acids 56-60 of SEQ ID NO: 16), a CDR2 region comprising SYGAGS (amino acids 78-83 of SEQ ID NO: 16), a CDR3 region comprising ASGGDTQY (amino acids 121-129 of SEQ ID NO: 16), or any combination thereof. In some embodiments, the TCR, TCR-like molecule, or portion thereof comprises an alpha chain comprising a CDR1 region comprising YSGTPY (amino acids 46-51 of SEQ ID NO: 21), a CDR2 region comprising YYSGDPVV (amino acids 69-76 of SEQ ID NO: 21), a CDR3 region comprising VLSYSNNRIF (amino acids 111-120 of SEQ ID NO: 21), or any combination thereof; and a beta chain comprising a CDR1 region comprising SGHSN (amino acids 56-60 of SEQ ID NO: 23), a CDR2 region comprising HYEKVE (amino acids 78-83 of SEQ ID NO: 23), a CDR3 region comprising ASSLGGGEVF (amino acids 121-130 of SEQ ID NO: 23), or any combination thereof. In some embodiments, the TCR, TCR-like molecule, or portion thereof comprises an alpha chain comprising a CDR1 region comprising YSGTPY (amino acids 46-51 of SEQ ID NO: 25), a CDR2 region comprising YYSGDPVV (amino acids 69-76 of SEQ ID NO: 25), a CDR3 region comprising VLRYGGNNKLT (amino acids 111-121 of SEQ ID NO: 25), or any combination thereof; and a beta chain comprising a CDR1 region comprising NNHDY (amino acids 45-49 of SEQ ID NO: 27), a CDR2 region comprising SYVADS (amino acids 67-72 of SEQ ID NO: 27), a CDR3 region comprising ASRYRDTQY (amino acids 110-118 of SEQ ID NO: 27), or any combination thereof. In some embodiments, the TCR, TCR-like molecule, or portion thereof comprises an alpha chain comprising a CDR1 region comprising STATR (amino acids 47-51 of SEQ ID NO: 32), a CDR2 region comprising NPSGT (amino acids 69-73 of SEQ ID NO: 32), a CDR3 region comprising AIPPGTGSKLS (amino acids 108-118 of SEQ ID NO: 32), or any combination thereof; and a beta chain comprising a CDR1 region comprising LGHNA (amino acids 45-49 of SEQ ID NO: 34), a CDR2 region comprising YNLKQL (amino acids 67-72 of SEQ ID NO: 34), a CDR3 region comprising ASSQGQKGY (amino acids 110-118 of SEQ ID NO: 34), or any combination thereof. In some embodiments, the TCR, TCR-like molecule, or portion thereof comprises an alpha chain comprising a CDR1 region comprising TYTTV (amino acids 47-51 of SEQ ID NO: 36), a CDR2 region comprising IRSNERE (amino acids 69-75 of SEQ ID NO: 36), a CDR3 region comprising ATGPNTNKVV (amino acids 110-119 of SEQ ID NO: 36), or any combination thereof; and a beta chain comprising a CDR1 region comprising LGHKA (amino acids 45-49 of SEQ ID NO: 38), a CDR2 region comprising YNLKQL (amino acids 67-72 of SEQ ID NO: 38), a CDR3 region comprising ASSQGGAEQF (amino acids 110-119 of SEQ ID NO: 38), or any combination thereof.

BRIEF DESCRIPTION OF THE FIGURES

A more complete understanding of the presently disclosed subject matter can be obtained by reference to the accompanying Figures, when considered in conjunction with the subsequent Detailed Description. The embodiments illustrated in the Figures are intended to be exemplary only, and should not be construed as limiting the presently disclosed subject matter to the illustrated embodiments.

FIG. 1C) CD8 T-cells from HLA-A2$^+$ donors were restimulated in vitro in 6-12 replicate microcultures with pIRS-$2_{1097-11059}$, pCDC25b$_{38-46}$, M1$_{58-66}$ Flu, or Yellow Fever NS4B$_{214-222}$ peptide-pulsed DC for 7 days. Antigen-specific T-cells were detected by ELISpot using T2 stimulators pulsed with the indicated peptide. "p" refers to the phosphorylated form. In FIGS. 1A and 1B, each data point represents an individual 7-day microculture. All donor responses were tested in three separate experiments with one representative experiment shown. FIG. 1C is a bar graph showing the mean number of IFN-γ$^+$ memory CD8 T-cells from four separate donor microcultures. Response to specific peptide is shown. FIG. 1D is a series of plots showing IFN-γ production by murine CD8 T-cell lines specific for indicated phosphopeptide following co-culture with C1R-AAD or C1R-A2 targets pulsed with either pIRS-$2_{1097-1105}$ (left panel) or pCDC25b$_{38-46}$ (right panel) for 24 hours. C1R-AAD targets pulsed with the unphosphorylated peptides are indicated with triangles. Data representative of 3-4 separate experiments. FIG. 1A: diamond—pIRS-2; Square—pCDC25b, triangle—yellow fever. FIG. 1C: Solid white boxes—donor 43; left to right hatching donor 44; right to left tight hatching—donor 54; right to left broad hatching—donor 62. FIG. 1D: solid squares (left panel) or solid diamonds (right panel)—transfectants of the B lymphoblastoid cell line C1R expressing a chimeric MHC class I molecule consisting of α1 and α2 domains of HLA-A2 and α3 domain of H-2D$^d$ (C1R-AAD); open squares (left panel) or open diamonds (right panel)—transfectants of the B lymphoblastoid cell line C1R expressing HLA-A2 (C1R-A2).

FIGS. 2B and 2C show staining of mouse TCR on gated human CD8+ T cells. The data presented are representative of eight separate experiments. FIG. 2B: - hour time point; -----: 24 hour time point; – – –: 48 hour time point; – – –: 72 hour time point, — —: 72 hour time point, no RNA. FIG. 2C: — - —: : FMO control; - - - : 5 days post-electroporation; -: 3 days post-electroporation.

FIGS. 3A-3C depict the results of experiments showing expression of phosphopeptide-specific murine TCR in human CD8 T-cells conferred recognition of HLA-A2$^+$ targets and effector function. Human CD8 T-cells were electroporated with IVT RNA encoding phosphopeptide-specific murine TCR αβ chains, and assayed 12-14 hours later. FIGS. 3A and 3B: left panels, Surface CD107a and/or intracellular IFN-γ were detected by flow cytometry on pIRS-2-specific (FIG. 3A) or pCDC25b-specific (FIG. 3B) human CD8 T-cells following co-culture with indicated C1R-AAD and C1R-A2 unpulsed or peptide-pulsed targets. Right panels, In vitro cytotoxicity assay of pIRS-2-specific (FIG. 3A) or pCDC25b-specific (FIG. 3B) CD8 T-cells was performed using phosphopeptide-pulsed (CFSE$^{hi}$) or unpulsed (CFSE$^{lo}$) C1R-A2 targets. For FIGS. 3A and 3B (left panels): x: no stimulators; open triangles: C1RA2 unpulsed; solid triangles: C1RA2+ pIRS-2; upside down open triangles: C1RA2+ IRS-2; open squares: C1RAAD unpulsed; solid squares: C1RAAD+pIRS-2. For FIGS. 3A and 3B (right panels): hatched boxes—effector (E) to target (T) ration 3:1; open boxes—E:T ratio 1:1. FIG. 3C is a series of plots showing surface CD107a and intracellular IFN-γ detected on pIRS-2-specific or pCDC25b-specific human CD8 T-cells following co-culture with the indicated human cancer cells (i.e., Mel Swift, 1102Mel, SK-Mel-28, and OV-90). No RNA controls underwent electroporation with no addition of IVT RNA. Antigen expression was determined by Western blot and is shown in FIGS. 4 and 5. For all panels, data are representative of duplicate (triplicate for In vitro cytotoxicity assay) determinations in 2-5 experiments.

FIG. 4A is a series of immunoblots showing expression of pSer$^{1100}$-IRS-2 (top), total IRS-2 (middle), and GAPDH (bottom) in extracts representing 1.5×10$^5$ cell equivalents of the indicated cell lines. pSer$^{1100}$-IRS-2 and GAPDH blots were from the same gels/blots. These blots were then stripped and reprobed with anti-IRS-2 antibody. Data are from a single experiment representative of 4. Locations of 31 kiltodalton (kD), 38 kD, 150 kD, and 225 kD markers are indicated. FIG. 4B is a series of bar graphs showing surface CD107a and intracellular IFN-γ detected by flow cytometry of pIRS-2-specific human CD8 T-cells following co-culture with indicated human cancer cells. Human cancer cell lines that were HLA-A2-negative are indicated with a *. Data is representative of 3-5 experiments, open boxes: % CD107a$^+$; left to right hatched boxes: % IFNγ$^+$; right to left hatched boxes: % CD107a$^+$/IFNγ$^+$. FIG. 4C are immunoblots of pSer$^{1100}$-IRS-2 (top) and total IRS-2 (bottom) in extracts representing 50 μg total protein of the indicated cancer cells. Location of 160 kD marker is indicated. FIG. 4D is a graph showing correlation between pSer$^{1100}$-IRS-2 protein and T-cell recognition of HLA-A2$^+$ cancer cells by pIRS-2-specific human CD8 T-cells (data in FIGS. 4A and 4B). Linear regression analyses (solid line) with 95% confidence intervals (dashed lines) are shown. Slope is significantly non-zero.

FIG. 5A is a series of immunoblots showing expression of total CDC25b (top) and GAPDH (bottom) in indicated cancer cells (30 μg total protein from cytoplasmic fraction). 1 μg of HEK293T cell lysate was loaded in order to not over-expose blot. Representative blots from two experiments shown. Locations of 30 kD, 40 kD, 60 kD, and 80 kD markers are indicated. FIG. 5B is a bar graph showing that surface CD107a and intracellular IFN-γ were detected by flow cytometry of pCDC25b-specific human CD8 T-cells following co-culture with indicated human cancer cells. HLA-A2-negative cancer cells are indicated with a * and dashed line indicates background on HLA-A2$^{neg}$ targets. Data representative of two experiments, open boxes: % CD107a$^+$; left to right hatched boxes: % IFNα$^+$; right to left hatched boxes: % CD107a$^+$/IFNγ$^+$. FIG. 5C is a plot showing lack of correlation between CDC25b protein and T-cell recognition of HLA-A2$^+$ cancer cells by pCDC25b-specific human CD8 T-cells (data in FIGS. 5A and 5B).

FIG. 9A is a plot showing enhanced tumor-free survival following adoptive transfer of pIRS-2 mTCR phosphopeptide-specific TCR-expressing human CD8 T-cells (solid triangles; p=0.0290). FIG. 9B is a plot showing enhanced tumor-free survival following adoptive transfer of pCDC25b mTCR phosphopeptide-specific TCR-expressing human CD8 T-cells (upside down solid triangles; p=0.0116). FIG. 9C is a plot showing enhanced tumor-free survival following adoptive transfer of combo TCR animals (i.e., animals that received equal amounts of pIRS-2 and pCDC25b-TCR expressing human CD8 T-cells (solid diamonds; p=0.0116). Tumor free survival is equal to the measurement day when the tumor size was >30 mm$^2$. The p values listed are for Log-rank analysis comparison of control animals to experimental group through day 25.

FIG. 10A; SEQ ID NO: 2) or pDesmuslin (A10 (right to left hatched boxes) or A11 (left to right hatched boxes) TCR chains; FIG. 10B), and assayed 12-14 hours later. TCR-expressing human CD8 T-cells were co-cultured for 18-20 hours with C1R-A2 or C1R-AAD pulsed or unpulsed target cells. Supernatants were then harvested and IFN-γ was detected by ELISA. No RNA controls underwent electroporation with no addition of IVT RNA (open squares).

FIGS. 11A and 11B: Surface CD107a and/or intracellular IFN-γ were detected by flow cytometry on pβcatenin-specific human CD8 T-cells following co-culture with indicated C1R-A2 unpulsed or peptide-pulsed targets. x: no stimulators; solid squares: pβ catenin; open squares: β catenin; solid diamond (FIG. 11A) or solid triangle (FIG. 11B): unpulsed. FIG. 11C shows the comparison of the ability of the two pβcatenin-specific TCR chains to recognize the YLDpSGIHSGA (SEQ ID NO: 30) peptide on C1R-A2 pulsed target cells. Notice the 649 pA10V TCR-expressing human CD8 T-cells (solid squares) were able to recognize much lower amounts of pulsed phosphopeptide on the target cells, suggesting it has a higher affinity than the 653 pβcatenin TCR (solid triangles). No RNA controls underwent electroporation with no addition of IVT RNA (solid circles).

DETAILED DESCRIPTION

I. Definitions

Figure 1A:
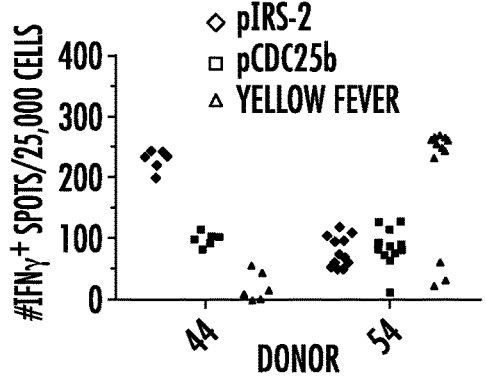
FIGS. 1A-1D are a series of graphs showing that phosphopeptides from IRS-2 and CDC25b are immunogenic in vitro for human CD8 T-cells and in vivo for AAD transgenic mice. Bulk (FIGS. 1A and 1B) and memory (CD45RO$^+$.

While the following terms are believed to be well understood by one of ordinary skill in the art, the following definitions are set forth to facilitate explanation of the presently disclosed subject matter.

All technical and scientific terms used herein, unless otherwise defined below, are intended to have the same meaning as commonly understood by one of ordinary skill in the art. Mention of techniques employed herein are intended to refer to the techniques as commonly understood in the art, including variations on those techniques or substitutions of equivalent techniques that would be apparent to one of skill in the art. While the following terms are believed to be well understood by one of ordinary skill in the art, the following definitions are set forth to facilitate explanation of the presently disclosed subject matter.

Following long-standing patent law convention, the terms "a", "an", and "the" refer to "one or more" when used in this application, including the claims. Thus, in some embodiments the phrase "a peptide" refers to one or more peptides.

The term "about", as used herein to refer to a measurable value such as an amount of weight, time, dose (e.g., therapeutic dose), etc., is meant to encompass in some embodiments variations of ±20%, in some embodiments ±10%, in some embodiments ±5%, in some embodiments ±1%, in some embodiments ±0.1%, in some embodiments ±0.5%, and in some embodiments ±0.01% from the specified amount, as such variations are appropriate to perform the disclosed methods.

As used herein, the term "and/or" when used in the context of a list of entities, refers to the entities being present singly or in any possible combination or subcombination. Thus, for example, the phrase "A, B, C, and/or D" includes A, B, C, and D individually, but also includes any and all combinations and subcombinations of A, B, C, and D.

Throughout the instant disclosure and including in the Figures, phosphorylated amino acids are depicted in lowercase "s", "t", or "y" for phosphoserine, phosphothreonine, or phosphotyrosine, respectively. Alternatively, "pS" refers to phosphoserine, "pT" refers to phosphothreonine, and "pY" refers to phosphotyrosine throughout the instant disclosure and in the Figures.

As used herein, the term "treating" and grammatical variants thereof including but not limited to "treatment" and "treat" are used herein to refer to administration of a composition of the presently disclosed subject matter in order to mitigate a condition in a patient and/or by reducing, inhibiting, and/or eliminating a particular characteristic or event associated with an undesirable condition including but not limited to a tumor or a cancer. Thus, the term "treatment" includes preventing a condition from occurring in a patient, particularly when the patient is predisposed to acquiring the condition; reducing and/or inhibiting the condition and/or its development and/or progression; and/or ameliorating and/or reversing the condition. Insofar as some embodiments of the methods of the presently disclosed subject matter are directed to preventing conditions, it is understood that the term "prevent" does not require that the condition be completely thwarted. Rather, as used herein, the term "preventing" refers to the ability of one of ordinary skill in the art to identify a population that is susceptible to condition, such that administration of the compositions of the presently disclosed subject matter might occur prior to onset of the condition. The term does not imply that the condition must be completely avoided.

As used herein, the phrase "effective amount" refers to an amount of a composition of the presently disclosed subject matter that is sufficient to exhibit a detectable therapeutic effect. The effect is detected by, for example, an improvement in clinical condition, and/or a prevention, reduction, or amelioration of at least one symptom thereof and/or at least one complication thereof. The precise effective amount for a patient can depend in some embodiments upon the patient's body weight, size, and health; the nature and extent of the condition; and the therapeutic or combination of therapeutics selected for administration. Therapeutically effective amounts for a given situation can be determined by routine experimentation that is within the skill and judgment of one of ordinary skill in the art (e.g., a clinician).

The term "phosphopeptides" includes MHC class I- and MHC class II-specific phosphopeptides. Exemplary MHC class I phosphopeptides are the pIRS2$_{1097-1105}$ phosphopeptide (SEQ ID NO: 2), the pCDC25b$_{38-46}$ phosphopeptide (SEQ ID NO: 12), the pDesmuslin$_{426-435}$ phosphopeptide (SEQ ID NO: 19), and the pβ-catenin$_{30-39}$ phosphopeptides (SEQ ID NOs: 29 and 30). SEQ ID NO: 2 corresponds to amino acids 1097-1105 of a human insulin receptor substrate 2 (IRS2) gene product presented as Accession No. NP_003740.2 in the GENBANK® biosequence database. SEQ ID NO: 12 corresponds to amino acids 38-46 of a human M-phase inducer phosphatase 2 isoform 3/CDC25B gene product presented as Accession No. NP_068658.1 in the GENBANK® biosequence database. SEQ ID NO: 19 corresponds to amino acids 426-435 of a human desmuslin/synemin isoform A gene product presented as Accession No. NP_663780.2 in the GENBANK® biosequence database, and also corresponds to amino acids 426-435 of a human desmuslin/synemin isoform B gene product presented as Accession No. NP_056101.5 in the GENBANK® biosequence database. SEQ ID NOs: 29 and 30 correspond to amino acids 30-39 of a human β-catenin gene product presented as Accession No. NP_001895.1 in the GENBANK® biosequence database, wherein in SEQ ID NO: 29, the alanine at position 39 of GENBANK® Accession No. NP_001895.1 is replaced by a valine.

Thus, in some embodiments, the phosphopeptides contain the sequences of at least one of the MHC class I binding peptides listed in SEQ ID NOs: 2, 12, 19, 29, and 30. Moreover, in some embodiments one or more of the serine residues within the recited sequences is phosphorylated. The phosphorylation can be with a natural phosphorylation ($-CH_2-O-PO_3H$) or with an enzyme non-degradable, modified phosphorylation, such as but not limited to $-CH_2-CF_2-PO_3H$ or $-CH_2-CH_2-PO_3H$. Some phosphopeptides can contain more than one of the peptides listed in SEQ ID NOs: 2, 12, 19, 29, and 30, for example, if they are overlapping, adjacent, or nearby within the native protein from which they are derived.

As used herein, the phrases "proliferative disorder" and "proliferative disease" refers to a disease, disorder, or condition associated with abnormal and/or undesirable cell proliferation. In some embodiments, a proliferative disease is a cancer, including but not limited to breast cancer, colorectal cancer, squamous carcinoma of the lung, sarcoma, renal cell carcinoma, pancreatic carcinomas, squamous tumors of the head and neck, leukemia, brain cancer, liver cancer, prostate cancer, ovarian cancer, and cervical cancer. In some embodiments, the presently disclosed compositions and methods are used to treat colorectal cancer, acute myelogenous leukemia (AML), acute lyphocytic leukemia (ALL), chronic lymphocytic lymphoma (CLL), chronic myelogenous leukemia (CML), breast cancer, renal cancer, pancreatic cancer, and/or ovarian cancer.

As used herein, the phrase "specific binding" refers to binding between a TCR, TCR-like molecule, or portion thereof and an antigen and/or an epitope thereof (including but not limited to a peptide, optionally in complex with an MHC molecule) that is indicative of the presence of the antigen and/or the epitope thereof. As such, a TCR, TCR-like molecule, or portion thereof is said to "specifically" bind an antigen and/or an epitope thereof when the dissociation constant (Kd) is in some embodiments less than about 1 µM, in some embodiments less that about 100 nM, and in some embodiments less than about 10 nM. Interactions between antibodies and antibody-like molecules and an epitope can also be characterized by an affinity constant ($K_a$). In some embodiments, a $K_a$ of less than about $10^7$/M is considered "high affinity".

As used herein, the phrase "T cell receptor" and the term "TCR" refer to a surface protein of a T cell that allows the T cell to recognize an antigen and/or an epitope thereof, typically bound to one or more major histocompatibilityi complex (MHC) molecules. A TCR functions to recognize an antigenic determinant and to initiate an immune response. Typically, TCRs are heterodimers comprising two different protein chains. In the vast majority of T cells, the TCR comprises an alpha (α) chain and a beta (β) chain. Approximately 5% of T cells have TCRs made up of gamma and delta (γ/δ) chains.

TCRs are membrane-anchored heterodimers that are found as part of a complex with a CD3 chain molecule. Each chain comprises two extracellular domains: a variable (V) region and a constant (C) region, the latter of which is membrane-proximal. The variable domains of α-chains and of β-chains consist of three hypervariable regions that are also referred to as the complementarity determining regions (CDRs). The CDRs, in particular CDR3, are primarily responsible for contacting antigens and thus define the specificity of the TCR, although CDR1 of the α-chain can interact with the N-terminal part of the antigen. CDR1 of the β-chain interacts with the C-terminal part of the peptide. TCRs are also characterized by a series of highly conserved disulfide bonds that link the two chains.

As used herein, the phrase "TCR-like polypeptide" refers to a polypeptide that behaves similarly to a T cell receptor (TCR) in that it specifically binds to an MHC-bound peptide, optionally an MHC-bound phosphopeptide as disclosed herein. In some embodiments, a "TCR-like antibody" refers to an antibody, optionally a monoclonal antibody, which specifically recognizes an MHC-bound phosphopeptide of the presently disclosed subject matter. In some embodiments, such polypeptides are members of the Ig Superfamily. In some embodiments, a TCR-like polypeptide is a single chain TCR (see e.g., U.S. Patent Application Publication No. 2012/0252742; PCT International Patent Application Publication Nos. WO 1996/013593, WO 1999/018129, and WO 2004/056845; U.S. Pat. No. 7,569,664).

As used herein, a "portion" of a TCR or TCR-like polypeptide is a subsequence of a TCR or TCR-like polypeptide that retains a desired function of the TCR or TCR-like polypeptide. In some embodiments, a portion of a TCR or TCR-like polypeptide comprises the domain of the TCR or TCR-like polypeptide that binds to a phosphopeptide/MHC complex (optionally, a phosphopeptide/HLA-A2 complex). Thus, in some embodiments the phrase "TCR, TCR-like molecule, or portion thereof" refers to TCRs, TCR-like molecules, and portions thereof that bind to phosphopeptide/MHC complexes, including but not limited to phosphopeptide/HLA-A2 complexes.

II. TCRs, TCR-like Molecules, and Portions Thereof, and Phosphopeptide Targets Thereof In some embodiments, the presently disclosed subject matter provides isolated and/or cloned TCRs, TCR-like molecules, or portions thereof that bind to post-translationally modified immunogenic therapeutic target peptides (e.g., phosphopeptides). In some embodiments, a TCR, TCR-like molecule, or portion thereof of the presently disclosed subject matter has antigen specificity for an antigen that is characteristic of a disease or disorder. The disease or disorder can be any disease or disorder involving an antigen, such as but not limited to an infectious disease, an autoimmune disease, or a tumor and/or a cancer.

In some embodiments, the phosphopeptides are fragments of tumor-associated antigens (TAAs; also referred to herein as "cancer antigens") and/or are TAAs themselves. The phrases "tumor-associated antigen" and "cancer antigen" as used herein refer to any molecule (e.g., protein, peptide, lipid, carbohydrate, etc.) solely or predominantly expressed or over-expressed by a tumor cell and/or a cancer cell, such that the antigen is associated with the tumor and/or the cancer. The TAA/cancer antigen additionally can be expressed by normal, non-tumor, or non-cancerous cells. However, in such a situation, the expression of the TAA/cancer antigen by normal, non-tumor, or non-cancerous cells is in some embodiments not as robust as the expression of the TAA/cancer antigen by tumor and/or cancer cells. Thus, in some embodiments the tumor and/or cancer cells over-express the TAA and/or express the TAA at a significantly higher level as compared to the expression of the TAA by normal, non-tumor, and/or non-cancerous cells.

The TAA can be an antigen expressed by any cell of any cancer or tumor, including the cancers and tumors described herein. The TAA can be a TAA of only one type of cancer or tumor, such that the TAA is associated with or characteristic of only one type of cancer or tumor. Alternatively, the TAA can be characteristic of more than one type of cancer or tumor. For example, the TAA can be expressed by both breast and prostate cancer cells and not expressed at all by normal, non-tumor, or non-cancer cells.

II.A. Phosphopeptides Based on IRS-2 Gene Products

In some embodiments, a phosphopeptide target is a fragment of an IRS-2 gene product. As used herein, "IRS-2" refers to the insulin receptor substrate-2 locus and its corresponding gene products. Exemplary IRS-2 gene products include the human IRS-2 gene products present in the GENBANK® biosequence database under accession numbers NM_003749.2 (cDNA nucleotide sequence) and NP_003740.2 (amino acid sequence encoded thereby; SEQ ID NO: 1).

IRS proteins are adapter proteins that link signaling from ligand-bound growth factor and cytokine receptors, including the insulin receptor, insulin-like growth factor receptor and IL-4 receptor, to multiple downstream SH2-containing signaling proteins to modulate cellular growth, metabolism, survival and differentiation (Dearth et al., 2007). IRS-2 is overexpressed at the gene or protein level in pancreatic cancer (Kornmann et al., 1998), hepatocellular carcinoma (Boissan et al., 2005), neuroblastoma (Kim et al., 2004), breast cancer (Jackson et al., 2001), glioblastoma (Knobbe & Reifenberger, 2003), and colorectal cancer (Parsons et al., 2005). IRS-2 overexpression under a mouse mammary tumor virus promoter causes mammary hyperplasia, tumorigenesis, and metastasis (Jackson et al., 2001; Nagle et al., 2004; Dearth et al., 2006; Chan & Lee, 2008).

The IRS proteins are regulated by phosphorylation of Tyr, Ser, and Thr (Dearth et al., 2007). The breadth of expression of the phosphopeptide among different cancer cells has not been investigated. It is disclosed herein that phosphorylated IRS-2 is broadly displayed on multiple cancer types and the resulting phosphopeptide is endogenously processed and presented at levels that allow strong immune responses to be generated against it. Phosphopeptide-specific CD8+ T cells can be generated from HLA-A2 transgenic mice upon immunization with pIRS-2 phosphopeptides, and these T cells are capable of recognizing and killing human melanoma and breast tumors in vitro and controlling tumor growth in a xenograft tumor model system.

In a particular embodiment, a phosphopeptide target that is derived from the human IRS-2 protein comprises the amino acid sequence RVASPTSGV (SEQ ID NO: 2; see also amino acids 1097-1105 of GENBANK® Accession No. NP_003740.2; SEQ ID NO: 1), wherein the serine at position 4 of this sequence is phosphorylated (referred to herein as "the RVApSPTSGV phosphopeptide" and the "IRS-2 phosphopeptide").

Two TCRs that bind to the IRS-2 phosphopeptide, referred to herein as "IRS-2A" and "IRS-2B", were isolated as described herein. The nucleotide sequences of the α and β chains and the amino acid sequences encoded thereby for these two IRS-2 phosphopeptide-specific TCRs were determined.

For IRS-2A, the α chain nucleotide and amino acid sequences are set forth in SEQ ID NOs: 3 and 4, respectively, and the β chain nucleotide and amino acid sequences are set forth in SEQ ID NOs: 5 and 6, respectively. Analyzing these sequences using the resources available through the website of THE INTERNATIONAL IMMUNOGENETICS INFORMATION SYSTEM® (www<<dot>>imgt<<dot>>org; hereinafter referred to as "IMGT") showed that IRS-2A had an alpha chain comprising a V-J region having an amino acid sequence that corresponds to amino acids 20-131 of SEQ ID NO: 4, which corresponds to a TRAV9D-4*04 V region and a TRAJ45*01 J region. IRS-2A has a TRAC*01 constant region. The beta chain comprises a V-D-J region having an amino acid sequence that corresponds to amino acids 20-133 of SEQ ID NO: 6, which corresponds to a TRBV14*01 V region, a TRBD1*01 D region, and a TRBJ2-7*01 J region. The beta chain has a TRBC2*03 constant region. Further analysis demonstrated that IRS-2A is characterized by an alpha chain comprising a CDR1 region comprising YSGTPY (amino acids 46-51 of SEQ ID NO: 4), a CDR2 region comprising YYSGDPVV (amino acids 69-76 of SEQ ID NO: 4), and a CDR3 region comprising AVSEGADRLT (amino acids 111-120 of SEQ ID NO: 4); and a beta chain comprising a CDR1 region comprising SGHDT (amino acids 46-50 of SEQ ID NO: 6), a CDR2 region comprising FRDEAV (amino acids 68-73 of SEQ ID NO: 6), and a CDR3 region comprising ASSLLDSSYEQY (amino acids 112-123 of SEQ ID NO: 6).

For IRS-2B, the α chain nucleotide and amino acid sequences are set forth in SEQ ID NOs: 7 and 8, respectively, and the β chain nucleotide and amino acid sequences are set forth in SEQ ID NOs: 9 and 10, respectively. Analyzing these sequences using the IMGT resources showed that IRS-2B had an alpha chain comprising a V-J region having an amino acid sequence that corresponds to amino acids 20-132 of SEQ ID NO: 7, which corresponds to a TRAV9D-4*04 V region and a TRAJ44*01 J region. IRS-2B has a TRAC*01 constant region. The beta chain comprises a V-D-J region having an amino acid sequence that corresponds to amino acids 19-131 of SEQ ID NO: 10, which corresponds to a TRBV13-3*01 V region, a TRBD1*01 D region, and a TRBJ2-1*01 J region. The beta chain has a TRBC2*03 constant region. Further analysis demonstrated that IRS-2A is characterized by an alpha chain comprising a CDR1 region comprising YSGTPY (amino acids 46-50 of SEQ ID NO: 8), a CDR2 region comprising YYSGDPVV (amino acids 69-76 of SEQ ID NO: 8), and a CDR3 region comprising AVSAGSGGKLT (amino acids 111-122 of SEQ ID NO: 8); and a beta chain comprising a CDR1 region comprising NNHDY (amino acids 45-49 of SEQ ID NO: 10), a CDR2 region comprising SYVADS (amino acids 67-72 of SEQ ID NO: 10), and a CDR3 region comprising ASSDRDNYAEQF (amino acids 110-122 of SEQ ID NO: 10).

It is understood that the IRS-2A and IRS-2B TCRs disclosed herein are exemplary only, and that other TCRs, TCR-like molecules, and portions thereof based on the sequence and subsequences of the IRS-2A and IRS-2B TCRs are also encompassed by the presently disclosed subject matter II.B. Phosphopeptides Based on CDC25b Gene Products In some embodiments, a phosphopeptide target is a fragment of a CDC25b gene product. As used herein, "CDC25b" refers to the cell division cycle 25B locus and its corresponding gene products. The family of CDC25 dual-specificity phosphatases regulates the activity of cyclin-dependent kinases by dephosphorylation of Tyr and Thr residues in their active sites (Kiyokawa & Ray, 2008). CDC25b overexpression in multiple malignancies is correlated with poor prognosis (Kiyokawa & Ray, 2008). However, as with IRS-2, the immunological display of the HLA-A2 restricted pCDC25b$_{38-46}$ phosphopeptide on different cancer cells has not been evaluated. Exemplary CDC25b gene products include the human IRS-2 gene products present in the GENBANK® biosequence database under accession numbers NM_021873.3 (cDNA nucleotide sequence) and NP_068659.1 (amino acid sequence encoded thereby; SEQ ID NO: 11). CDC25b is a phosphatase that is required for entry into mitosis. It has been reported to have oncogenic properties, although the precise role it plays in tumorigenesis and/or carcinogenesis is unknown.

In a particular embodiment, a phosphopeptide target that is derived from the human CDC25b protein comprises the amino acid sequence GLLGSPVRA (SEQ ID NO: 11; see also amino acids 38-46 of GENBANK® Accession No. NP_068659.1; SEQ ID NO: 11), wherein the serine at position 5 of this sequence is phosphorylated (referred to herein as "the GLLGpSPVRA phosphopeptide" or the "CDC25b phosphopeptide").

A TCR that binds to the CDC25b phosphopeptide, referred to herein as "the CDC25b TCR", was isolated as described herein. The nucleotide sequence of the α and β chains and the amino acid sequences encoded thereby for the CDC25b TCR were determined. The α chain nucleotide and amino acid sequences are set forth in SEQ ID NOs: 13 and 14, respectively, β chain nucleotide and amino acid sequences are set forth in SEQ ID NOs: 15 and 16, respectively.

Analyzing these sequences using the IMGT resources showed that the CDC25b TCR had an alpha chain comprising a V-J region having an amino acid sequence that corresponds to amino acids 22-132 of SEQ ID NO: 14, which corresponds to a TRAV3-3*02 V region and a TRAJ12*01 J region. The CDC25b TCR has a TRAC*01 constant region. The beta chain comprises a V-D-J region having an amino acid sequence that corresponds to amino acids 30-138 of SEQ ID NO: 16, which corresponds to a TRBV13-2*01 V region, a TRBD2*01 D region, and a TRBJ2-5*01 J region. The beta chain has a TRBC2*03 constant region. Further analysis demonstrated that the CDC25b TCR is characterized by an alpha chain comprising a CDR1 region comprising DPNSYY (amino acids 48-53 of SEQ ID NO: 14), a CDR2 region comprising VFSSTEI (amino acids 71-77 of SEQ ID NO: 14), and a CDR3 region comprising AVKPGGYKVV (amino acids 112-121 of SEQ ID NO: 14); and a beta chain comprising a CDR1 region comprising NNHNN (amino acids 56-60 of SEQ ID NO: 16), a CDR2 region comprising SYGAGS (amino acids 78-83 of SEQ ID NO: 16), and a CDR3 region comprising ASGGDTQY (amino acids 121-129 of SEQ ID NO: 16). It is understood that the CDC25b TCR disclosed herein is exemplary only, and that other TCRs, TCR-like molecules, and portions thereof based on the sequence and subsequences of the CDC25b TCR are also encompassed by the presently disclosed subject matter.

II.C. Phosphopeptides Based on Desmuslin Gene Products

In some embodiments, a phosphopeptide target is a fragment of a desmuslin gene product. As used herein, "desmuslin" refers to the desmuslin locus and its corresponding gene products. Desmuslin is also referred to "synemin", of which there are multiple isoforms in humans. Exemplary desmuslin gene products include the human gene products present in the GENBANK® biosequence database under accession numbers NM_145728.2 (synemin isoform A cDNA nucleotide sequence) and NP_663780.2 (amino acid sequence encoded thereby; SEQ ID NO: 17) and NM_015286.5 (synemin isoform B cDNA nucleotide sequence) and NP_056101.5 (amino acid sequence encoded thereby; SEQ ID NO: 18).

Desmuslin/synemin proteins are cytoskeletal intermediate filament (IF) proteins that are involved in providing mechanical stress resistance.

In a particular embodiment, a phosphopeptide target that is derived from the human desmuslin/synemin protein comprises the amino acid sequence RTFSPTYGL (SEQ ID NO: 19; see also, for example, amino acids 426-434 of GENBANK® Accession No. NP_663780.2; SEQ ID NO: 17), wherein the serine at position 4 of this sequence is phosphorylated (referred to herein as "the desmuslin phosphopeptide").

Two TCRs that bind to the desmuslin phosphopeptide, referred to herein as "DESA" and "DESB", were isolated as described herein. The nucleotide sequences of the α and β chains and the amino acid sequences encoded thereby for these two desmuslin phosphopeptide-specific TCRs were determined.

For DESA, the α chain nucleotide and amino acid sequences are set forth in SEQ ID NOs: 20 and 21, respectively, and the β chain nucleotide and amino acid sequences are set forth in SEQ ID NOs: 22 and 23, respectively. Analyzing these sequences using the IMGT resources showed that DESA had an alpha chain comprising a V-J region having an amino acid sequence that corresponds to amino acids 20-131 of SEQ ID NO: 21, which corresponds to a TRAV9D-4*02 V region and a TRAJ31*01 J region. DESA has a TRAC*01 constant region. The beta chain comprises a V-D-J region having an amino acid sequence that corresponds to amino acids 30-140 of SEQ ID NO: 23, which corresponds to a TRBV12-1*01 V region, a TRBD1*01 D region, and a TRBJ1-1*01/J1-1*02 J region. The beta chain has a TRBC1*01 constant region. Further analysis demonstrated that DESA is characterized by an alpha chain comprising a CDR1 region comprising YSGTPY (amino acids 46-51 of SEQ ID NO: 21), a CDR2 region comprising YYSGDPVV (amino acids 69-76 of SEQ ID NO: 21), and a CDR3 region comprising VLSYSNNRIF (amino acids 111-120 of SEQ ID NO: 21); and a beta chain comprising a CDR1 region comprising SGHSN (amino acids 56-60 of SEQ ID NO: 23), a CDR2 region comprising HYEKVE (amino acids 78-83 of SEQ ID NO: 23), and a CDR3 region comprising ASSLGGGEVF (amino acids 121-130 of SEQ ID NO: 23).

For DESB, the α chain nucleotide and amino acid sequences are set forth in SEQ ID NOs: 24 and 25, respectively, and the β chain nucleotide and amino acid sequences are set forth in SEQ ID NOs: 26 and 27, respectively. Analyzing these sequences using the IMGT resources showed that DESB had an alpha chain comprising a V-J region having an amino acid sequence that corresponds to amino acids 20-132 of SEQ ID NO: 25, which corresponds to a TRAV9D-4*02 V region and a TRAJ56*01 J region. DESB has a TRAC*01 constant region. The beta chain comprises a V-D-J region having an amino acid sequence that corresponds to amino acids 19-128 of SEQ ID NO: 27, which corresponds to a TRBV13-3*01 V region, a TRBD1*01 D region, and a TRBJ2-5*01 J region. The beta chain has a TRBC2*03 constant region. Further analysis demonstrated that DESB is characterized by an alpha chain comprising a CDR1 region comprising YSGTPY (amino acids 46-51 of SEQ ID NO: 25), a CDR2 region comprising YYSGDPVV (amino acids 69-76 of SEQ ID NO: 25), and a CDR3 region comprising VLRYGGNNKLT (amino acids 111-121 of SEQ ID NO: 25), and a beta chain comprising a CDR1 region comprising NNHDY (amino acids 45-49 of SEQ ID NO: 27), a CDR2 region comprising SYVADS (amino acids 67-72 of SEQ ID NO: 27), and a CDR3 region comprising ASRYRDTQY (amino acids 110-118 of SEQ ID NO: 27).

It is understood that the DESA and DESB TCRs disclosed herein are exemplary only, and that other TCRs, TCR-like molecules, and portions thereof based on the sequence and subsequences of the DESA and DESB TCRs are also encompassed by the presently disclosed subject matter.

II.D. Phosphopeptides Based on β-catenin Gene Products

In some embodiments, a phosphopeptide target is a fragment of a β-catenin gene product. As used herein, "β-catenin" refers to the CTNNB1 locus and its corresponding gene products. Exemplary β-catenin gene products include the human gene products present in the GENBANK® biosequence database under accession numbers NM_001904.3 (cDNA nucleotide sequence) and NP_001895.1 (amino acid sequence encoded thereby; SEQ ID NO: 28).

β-catenin proteins are dual function proteins that are involved in regulating the coordination of cell-cell adhesion and gene transcription. Mutations and overexpression of β-catenin have been associated with hepatocellular carcinoma, colorectal carcinoma, lung cancer, malignant breast tumors, ovarian cancer, and endometrial cancer (Morin, 1999). β-catenin is regulated by the β-catenin destruction complex, and in particular by the adenomatous polyposis coli (APC) protein, encoded by the tumor-suppressing APC gene. Genetic mutation of the APC gene is also strongly linked to cancers, and in particular colorectal cancer resulting from familial adenomatous polyposis (FAP).

In particular embodiments, phosphopeptide targets that are derived from the human β-catenin protein comprise the amino acid sequences YLDSGIHSGV (SEQ ID NO: 29; see also, for example, amino acids 30-39 of GENBANK® Accession No. NP_001895.1 (SEQ ID NO: 28), wherein the alanine at position 39 of GENBANK® Accession No. NP_001895.1 is replaced by a valine), wherein the serine at position 4 of this sequence is phosphorylated (referred to herein as "the β-catenin phosphopeptide A"); and YLDSGIHSGA (SEQ ID NO: 30; see also, for example, amino acids 30-39 of GENBANK® Accession No. NP_001895.1; SEQ ID NO: 28), wherein the serine at position 4 of this sequence is phosphorylated (referred to herein as "the β-catenin phosphopeptide B").

TCRs that bind to the β-catenin phosphopeptides A and B, referred to herein as "βCATA" and "βCATB", respectively, were isolated as described herein. The nucleotide sequences of the α and β chains and the amino acid sequences encoded thereby for these two β-catenin phosphopeptide-specific TCRs were determined.

For βCATA, the α chain nucleotide and amino acid sequences are set forth in SEQ ID NOs: 31 and 32, respectively, and the β chain nucleotide and amino acid sequences are set forth in SEQ ID NOs: 33 and 34, respectively. Analyzing these sequences using the IMGT resources showed that βCATA had an alpha chain comprising a V-J region having an amino acid sequence that corresponds to amino acids 21-129 of SEQ ID NO: 32, which corresponds to a TRAV13*02 V region and a TRAJ58*01 J region. βCATA has a TRAC*01 constant region. The beta chain comprises a V-D-J region having an amino acid sequence that corresponds to amino acids 20-128 of SEQ ID NO: 34, which corresponds to a TRBV5*01 V region, a TRBD1*01 D region, and a TRBJ2-7*01 J region. The beta chain has a TRBC2*03 constant region. Further analysis demonstrated that βCATA is characterized by an alpha chain comprising a CDR1 region comprising STATR (amino acids 47-51 of SEQ ID NO: 32), a CDR2 region comprising NPSGT (amino acids 69-73 of SEQ ID NO: 32), and a CDR3 region comprising AIPPGTGSKLS (amino acids 108-118 of SEQ ID NO: 32), and a beta chain comprising a CDR1 region comprising LGHNA (amino acids 45-49 of SEQ ID NO: 34), a CDR2 region comprising YNLKQL (amino acids 67-72 of SEQ ID NO: 34), and a CDR3 region comprising ASSQGQKGY (amino acids 110-118 of SEQ ID NO: 34).

For βCATB, the α chain nucleotide and amino acid sequences are set forth in SEQ ID NOs: 35 and 36, respectively, and the β chain nucleotide and amino acid sequences are set forth in SEQ ID NOs: 37 and 38, respectively. Analyzing these sequences using the IMGT resources showed that βCATB had an alpha chain comprising a V-J region having an amino acid sequence that corresponds to amino acids 21-130 of SEQ ID NO: 36, which corresponds to a TRAV8D-2*02 V region and a TRAJ34*02 J region. βCATB has a TRAC*01 constant region. The beta chain comprises a V-D-J region having an amino acid sequence that corresponds to amino acids 20-129 of SEQ ID NO: 38, which corresponds to a TRBV5*01 V region, a TRBD2*01 D region, and a TRBJ2-1*01 J region. The beta chain has a TRBC2*03 constant region. Further analysis demonstrated that βCATB is characterized by an alpha chain comprising a CDR1 region comprising TYTTV (amino acids 47-51 of SEQ ID NO: 36), a CDR2 region comprising IRSNERE (amino acids 69-75 of SEQ ID NO: 36), and a CDR3 region comprising ATGPNTKVV (amino acids 110-119 of SEQ ID NO: 36), and a beta chain comprising a CDR1 region comprising LGHKA (amino acids 45-49 of SEQ ID NO: 38), a CDR2 region comprising YNLKQL (amino acids 67-72 of SEQ ID NO: 38), and a CDR3 region comprising ASSQGGAEQF (amino acids 110-119 of SEQ ID NO: 38).

It is understood that the βCATA and βCATB TCRs disclosed herein are exemplary only, and that other TCRs, TCR-like molecules, and portions thereof based on the sequence and subsequences of the βCATA and βCATB TCRs are also encompassed by the presently disclosed subject matter.

II.E. Modifications to TCR Sequences to Generate Soluble TCRs, TCR-Like Molecules, and Portions Thereof In some embodiments, the TCRs, TCR-like molecules, and portions thereof of the presently disclosed subject matter are modified to generate soluble TCRs, TCR-like molecules, and portions thereof. Exemplary methods for generating soluble TCRs are disclosed, for example, in PCT International Patent Application Publication No. WO 1998/39482; U.S. Patent Application Publication No. 2005/0214284, and U.S. Patent Application Publication No. 2011/0070191.

By way of example and not limitation, a TCR, TCR-like molecule, or portion thereof of the presently disclosed subject matter can be modified to generate a soluble derivative thereof by deleting or otherwise mutating some or all of the amino acids of the transmembrane region and/or the cytoplasmic tail. In some embodiments, at least one of and in some embodiments in both of the α and β chain sequences are mutated and/or deleted. For the TCRs, TCR-like molecules, and portions thereof of the presently disclosed subject matter referred to herein above in Sections II.A.-II.D., a soluble TCR, TCR-like molecule, or a portion thereof comprises in some embodiments CDR1, CDR2, CDR3, or any combination thereof of any of the polypeptides of SEQ ID NOs: 4, 6, 8, 10, 14, 16, 21, 23, 25, 27, 32, 34, 36, or 38. In some embodiments, CDRs are as set forth in Table 1 below.

TABLE 1

CDR Sequences

| SEQ ID NO. | CDR1 (amino acids) | CDR2 (amino acids) | CDR3 (amino acids) |
|---|---|---|---|
| 4 | YSGTPY (46-51) | YYSGDPVV (69-76) | AVSEGADRLT (111-120) |
| 6 | SGHDT (46-50) | FRDEAV (68-73) | ASSLLDSSYEQY (112-123) |
| 8 | YSGTPY (46-50) | YYSGDPVV (69-76) | AVSAGSGGKLT (111-122) |
| 10 | NNHDY (45-49) | SYVADS (67-72) | ASSDRDNYAEQF (110-122) |
| 14 | DPNSYY (48-53) | VFSSTEI (71-77) | AVKPGGYKVV (112-121) |
| 16 | NNHNN (56-60) | SYGAGS (78-83) | ASGGDTQY (121-129) |
| 21 | YSGTPY (46-51) | YYSGDPVV (69-76) | VLSYSNNRIF (111-120) |
| 23 | SGHSN (56-60) | HYEKVE (78-83) | ASSLGGGEVF (121-130) |
| 25 | YSGTPY (46-51) | YYSGDPVV (69-76) | VLRYGGNNKLT (111-121) |
| 27 | NNHDY (45-49) | SYVADS (67-72) | ASRYRDTQY (110-118) |
| 32 | STATR (47-51) | NPSGT (69-73) | AIPPGTGSKLS (108-118) |
| 34 | LGHNA (45-49) | YNLKQL (67-72) | ASSQGQKGY (110-118) |
| 36 | TYTTV (47-51) | IRSNERE (69-75) | ATGPNTKVV (110-119) |
| 38 | LGHKA (45-49) | YNLKQL (67-72) | ASS QGGAEQF (110-119) |

In some embodiments, single-chain ("sc") constructs such as those disclosed in U.S. patent application Ser. Nos. 08/813,781 and 08/943,086 can be employed. Briefly, a single-chain ("sc") TCR molecule includes V-α and V-β chains that are covalently linked through a suitable linker sequence. For example, the V-α chain can be covalently linked to the V-β chain through a linker sequence (optionally a peptide linker sequence) fused to the C-terminus of the V-α chain and the N-terminus of the V-β chain. The V-α and V-β chains of the sc-TCR fusion protein are in some embodiments about 200 to 400 amino acids in length, in some embodiments about 300 to 350 amino acids in length, and in some embodiments can be at least 90%, 95%, 97%, 98%, 99%, or 100% identical to the V-α and V-β chains of the presently disclosed TCRs, TCR-like molecules, and portions thereof.

As disclosed in U.S. patent application Ser. No. 08/943, 086 application, the V-α chain of a sc-TCR molecule can in some embodiments further include a C-β chain or fragment thereof fused to the C-terminus of the V-β chain. Further, the V-α chain can in some embodiments include a C-α chain or fragment thereof fused to the C-terminus of the V-α chain and the N-terminus of the linker sequence.

As further disclosed in U.S. patent application Ser. No. 08/943,086, additional sc-TCR proteins of the presently disclosed subject matter include for example two peptide linker sequences, where the first peptide linker sequence is fused between the C-terminus of the V-α chain and the N-terminus of the V-β chain. The C-terminus of the V-β chain can be fused to the N-terminus of a C-β chain fragment. The second peptide linker is then fused to the C-terminus of the V-β chain or C-β chain fragment. In some embodiments, sc-TCR proteins can be made by fusing the V-β chain to the V-α chain through a suitable peptide linker in which the C-terminus of the V-β chain or C-β chain fragment thereof and the N-terminus of the V-α chain are covalently linked.

Thus, in some embodiments the TCRs, TCR-like molecules, and portions thereof of the presently disclosed subject matter are soluble TCR cytoplasmic domains, TCR-like cycloplasmic domains, and portions thereof that are stable at low concentrations and which can recognize MHC-peptide complexes. See e.g., U.S. Patent Application Publication No. 2002/0119149, which is incorporated by reference.

II.F. Conjugates of TCRs, TCR-Like Molecules, and Portions Thereof

In some embodiments, the TCRs, TCR-like molecules, and portions thereof of the presently disclosed subject matter (optionally wherein the TCRs, TCR-like molecules, and portions thereof are soluble TCRs, TCR-like molecules, and portions thereof) can be conjugated to one or more active agents. As used herein, the phrase "active agent" refers to any molecule that imparts to a TCR, TCR-like molecule, or portion thereof an activity of interest (including but not limited to a biological activity) that the TCR, TCR-like molecule, or portion thereof would not have absent the active agent. Exemplary active agents include immunostimulatory peptides and/or proteins, detectable labels, other TCRs, other TCR-like molecules, and/or portions thereof etc.

II.F.1. Immunostimulatory Peptides and Proteins

In some embodiments, the active agents comprise immunostimulatory peptides and/or proteins, and/or moieties such as but not limited to CD3 agonists (e.g., anti-CD3 antibodies). The CD3 antigen is present on mature human T cells, thymocytes, and a subset of natural killer cells. It is associated with the TCR and is involved in signal transduction of the TCR. Antibodies specific for the human CD3 antigen are well known. One such antibody is the murine monoclonal antibody OKT3 which was the first monoclonal antibody approved by the FDA. OKT3 is reported to be a potent T cell mitogen (Van Wauwe, 1980; U.S. Pat. No. 4,361,539) and a potent T cell killer (Wong et al., 1990). Other antibodies specific for the CD3 antigen have also been reported (see PCT International Patent Application Publication No. WO 2004/106380; U.S. Patent Application Publication No. 2004/0202657; U.S. Pat. Nos. 6,750,325; 6,706,265; Great Britain Patent Publication GB 2249310A; Clark et al., 1989; U.S. Pat. No. 5,968,509; U.S. Patent Application Publication No. 2009/0117102) Immune mobilising mTCR Against Cancer (ImmTAC; Immunocore Limited, Milton Park, Abington, Oxon, United Kingdom) are bifunctional proteins that combine affinity monoclonal T cell receptor (mTCR) targeting with a therapeutic mechanism of action (i.e., an anti-CD3 scFv).

II.F.2. Detectable Labels

Other suitable tags for detectably-labeling the TCRs, TCR-like molecules, and/or portions thereof include biotin, streptavidin, a cell toxin of, e.g., plant or bacterial origin such as, e.g., diphtheria toxin (DT), shiga toxin, abrin, cholera toxin, ricin, saporin, pseudomonas exotoxin (PE), pokeweed antiviral protein, or gelonin. Biologically active fragments of such toxins are well known in the art and include, e.g., DT A chain and ricin A chain. Additionally, the toxin can be an agent active at the cell surface such as, e.g., phospholipase enzymes (e.g., phospholipase C). See e.g., Moskaug et al., 1989; Pastan et al., 1986; Pastan et al., 1992; Olsnes & Pihl, 1981; PCT International Patent Application Publication No. WO 1994/29350; PCT International Patent Application Publication No. WO 1994/04689; and U.S. Pat. No. 5,620,939 for disclosure relating to making and using proteins comprising effectors or tags. An example of a tag that performs a biotin acceptor function is a BirA tag, as described in Beckett et al., 1999. As further described in Examples below, a BirA tag sequence can be included in a TCR, TCR-like molecule, and/or a portion thereof to promote biotinylation of the protein. Further, a tag can be a chemotherapeutic drug such as, e.g., vindesine, vincristine, vinblastin, methotrexate, adriamycin, bleomycin, or cisplatin.

Additionally, a tag can be a radionuclide or chelate, suitable for diagnostic or imaging studies such as iodine-131, yttrium-90, rhenium-188, iodine-123, indium-111, technetium-99m, gallium-67, thallium-201, or bismuth-212. Among the radionuclides used, gamma-emitters, positron-emitters, x-ray emitters and fluorescence-emitters are suitable for localization, while beta-emitters and alpha-emitters may also be used. Other suitable radioisotopes for the methods of the present invention include but are not limited to, cadmium-109, actinium-225, actinium-227, astatine-211, iodine-125, iodine-126, iodine-133, dysprosium-165, dysprosium-166, bismuth-212, bismuth-213, bromine-77, indium-113m, gallium-67, gallium-68, ruthenium-95, ruthenium-97, ruthenium-101, ruthenium-103, ruthenium-105, mercury-107, mercury-203, rhenium-186, rhenium-188, tellurium-99m, tellurium-121m, tellurium-122m, tellurium-125m, thulium-165, thulium-167, thulium-168, fluorine-18, silver-11, platinum-197, palladium-109, copper-67, phosphorus-32, phosphorus-33, yttrium-90, scandium-47, samarium-153, lutetium-177, rhodium-105, praseodymium-142, praseodymium-143, promethium-149, terbium-161, holmium-166, gold-198, gold-199, cobalt-57, cobalt-58, chromium-51, iron-59, selenium-75, and ytterbium-169. Preferably the radioisotope will emit in the 10-5,000 key range, more preferably 50-1,500 key, most preferably 50-500 key.

Suitable positron emitters and other useful radionuclides include, but are not limited to, $^{11}C$, $^{13}N$, $^{15}O$, $^{18}F$, $^{51}Mn$, $^{52}Fe$, $^{55}Co$, $^{60}Cu$, $^{61}Cu$, $^{62}Cu$, $^{64}Cu$, $^{62}Zn$, $^{63}Zn$, $^{70}As$, $^{71}As$, $^{72}As$, $^{76}Br$, $^{82}Rb$, $^{86}Y$, $^{89}Zr$, $^{94m}Tc$, $^{110}In$, $^{120}I$, $^{124}I$, $^{122}Xe$, $^{128}Ba$, $^{131}Ba$, $^{7}Be$, $^{204}Bi$, $^{205}Bi$, $^{206}Bi$, $^{14}C$, $^{36}Cl$, $^{48}Cr$, $^{51}Cr$, $^{155}Eu$, $^{153}Gd$, $^{66}Ga$, $^{72}Ga$, $^{3}H$, $^{115m}In$, $^{189}Ir$, $^{191m}Ir$, $^{192}Ir$, $^{194}Ir$, $^{55}Fe$, $^{119m}Os$, $^{42}K$, $^{226}Ra$, $^{186}Re$, $^{188}Re$, $^{82m}Rb$, $^{46}Sc$, $^{47}Sc$, $^{72}Se$, $^{105}Ag$, $^{22}Na$, $^{24}Na$, $^{89}Sr$, $^{35}S$, $^{38}S$, $^{177}Ta$, $^{96}Tc$, $^{201}Tl$, $^{202}Tl$, $^{113}Sn$, $^{117m}Sn$, $^{121}Sn$, $^{166}Yb$, $^{174}Yb$, $^{88}Y$, $^{90}Y$, $^{62}Zn$, and $^{65}Zn$.

Suitable chelates include, but are not limited to, diethylenetriamine pentaacetic acid (DTPA), 1,4,7,10-tetraazacyclotetradecane-1,4,7,10-tetraacetic acid (DOTA), 1-substituted 1,4,7-tricarboxymethyl-1,4,7,10 teraazacyclododecane triacetic acid (DO3A), ethylenediaminetetraacetic acid (EDTA), and 1,4,8,11-tetraazacyclotetradecane-1,4,8,11-tetraacetic acid (TETA). Additional chelating ligands are ethylenebis-(2-hydroxy-phenylglycine) (EHPG), and derivatives thereof, including 5-Cl-EHPG, 5Br-EHPG, 5-Me-EHPG, 5t-Bu-EHPG, and 5 sec-Bu-EHPG; benzodiethylenetriamine pentaacetic acid (benzo-DTPA)

and derivatives thereof, including dibenzo-DTPA, phenyl-DTPA, diphenyl-DTPA, benzyl-DTPA, and dibenzyl DTPA; bis-2 (hydroxybenzyl)-ethylenediaminediacetic acid (HBED) and derivatives thereof; the class of macrocyclic compounds which contain at least 3 carbon atoms, more preferably at least 6, and at least two heteroatoms (O and/or N), which macrocyclic compounds can consist of one ring, or two or three rings joined together at the hetero ring elements, e.g., benzo-DOTA, dibenzo-DOTA, and benzo-NOTA, where NOTA is 1,4,7-triazacyclononane N,N',N''-triacetic acid, benzo-TETA, benzo-DOTMA, where DOTMA is 1,4,7,10tetraazacyclotetradecane-1,4,7,10-tetra (methyl tetraacetic acid), and benzo-TETMA, where TETMA is 1,4,8,11-tetraazacyclotetradecane-1,4,8,11-(methyl tetraacetic acid); derivatives of 1,3-propylenedi-aminetetraacetic acid (PDTA) and triethylenetetraamine-hexaacetic acid (TTHA); derivatives of 1,5,10-N,N,N''-tris (2,3-dihydroxybenzoyl)-tricatecholate (LICAM) and 1,3,5-N,N',N''-tris(2,3-dihydroxybenzoyl)aminomethylbenzene (MECAM).

Other suitable tags include polyhistidine, fluorescent label, chemiluminescent label, nuclear magnetic resonance active label, chromophore label, positron emitting isotope detectable by a positron emission tomography ("PET") scanner, enzymatic markers such as beta-galactosidase and peroxidase including horse radish peroxidase, a nanoparticle, a paramagnetic metal ion, a contrast agent or an antigenic tag.

A suitable fluorescent label could include, but is not limited to, a $^{152}$Eu label, a fluorescein label, an isothiocyanate label, a rhodamine label, a phycoerythrin label, a phycocyanin label, an allophycocyanin label, an o-phthaldehyde label, a Texas Red label, a fluorescamine label, a lanthanide phosphor label, a fluorescent protein label, for example a green fluorescent protein (GFP) label, or a quantum dot label. Examples of chemiluminescent labels include a luminal label, an isoluminal label, an aromatic acridinium ester label, an imidazole label, an acridinium salt label, an oxalate ester label, a luciferin label, a luciferase label, an aequorin label, etc.

Suitable paramagnetic metal ions include, but are not limited to, $Mn^{2+}$, $Cu^{2+}$, $Fe^{2+}$, $Co^{2+}$, $Ni^{2+}$, $Gd^{3+}$, $Eu^{3+}$, $Dy^{3+}$, $Pr^{3+}$, $Cr^{3+}$, $Co^{3+}$, $Fe^{3+}$, $Ti^{3+}$, $Tb^{3+}$, $Nd^{3+}$, $Sm^{3+}$, $Ho^{3+}$, $Er^{3+}$, $Pa^{4+}$, and $Eu^{2+}$.

Enzyme markers that may be used include any readily detectable enzyme activity or enzyme substrate. Such enzymes include malate dehydrogenase, staphylococcal nuclease, delta-5-steroid isomerase, alcohol dehydrogenase, glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, acetylcholine esterase, luciferase, and DNA polymerase.

II.F.3. Conjugates with Other TCRs, TCR-Like Molecules, and Portions Thereof: Multivalent and Multimeric TCRs, TCR-Like Molecules, and Portions Thereof The soluble TCRs, TCR-like molecules, and portions thereof of the presently disclosed subject matter include monomeric and multimeric TCRs, TCR-like molecules, and portions thereof. Multimeric TCRs, TCR-like molecules, and portions thereof include those in which the TCR, TCR-like molecule, or portion thereof is fused to polypeptide domains or tags that facilitate multimerization. Such domains include immunoglobulin, leucine zipper, helix-turn-helix, and barrel-barrel motifs that facilitate protein dimerization. Such tags include antibody-binding epitopes, streptavidin-binding peptides, 6×His motif, biotin ligase target motif, and the like. Multimeric TCRs, TCR-like molecules, or portions thereof also include those generated through chemically crosslinking reactive amino acids or polysaccharides. Such amino acids (or polysaccharides) can be inherent in the structure of the TCRs, TCR-like molecules, and portions thereof, or can be added through genetic modification. Multimeric TCRs, TCR-like molecules, and portions thereof also include those generated through attachment to another molecule (or molecules) that may or may not include a detectable label as described herein. Such attachment molecules include streptavidin, biotin, antibodies, protein A or scaffolds that include protein-, lipid- and polysaccharide-coated or uncoated beads, nanoparticles, solid-phase surfaces, arrays, matrices, as described. For example, in various embodiments in which the detectable label is biotin, the method further comprises combining the TCR, TCR-like molecule, and/or portion thereof with streptavidin to multimerize the TCR, TCR-like molecule, and/or portion thereof.

It will be appreciated that any one of the tags disclosed herein can be used to detectably label the TCRs of the presently disclosed subject matter, particularly to detect cells and/or tissues such as, but not limited to tumor and/or cancer cells and tissues, expressing a phosphopeptide target of interest.

II.G. Substantially Identical TCRs, TCR-Like Molecules, and Portions Thereof

In some embodiments, a TCR, TCR-like molecule, or portion thereof of the presently disclosed subject matter comprises a nucleotide or amino acid sequence that is substantially identical to any of SEQ ID NOs: 3-10, 13-16, 20-27, and 31-38.

The term "substantially identical", as used herein to describe a degree of similarity between nucleotide or amino acid sequences, refers to two or more sequences that have in some embodiments at least about least 60%, in some embodiments at least about 70%, in some embodiments at least about 80%, in some embodiments at least about 90%, in some embodiments at least about 95%, in some embodiments at least about 96%, in some embodiments at least about 97%, in some embodiments at least about 98%, and in some embodiments at least about 99% nucleotide or amino acid identity, when compared and aligned for maximum correspondence, as measured using a sequence comparison algorithm as set forth herein below or by visual inspection. The substantial identity exists in nucleotide or amino acid sequences of in some embodiments at least about 25 residues, in some embodiments at least about 50 residues, in some embodiments at least about 100 residues, in some embodiments at least about 150 residues, in some embodiments at least about 200 residues, in some embodiments at least about 500 residues, in some embodiments at least about 1000 residues, and in some embodiments in nucleotide or amino acid sequences comprising a full length of any of SEQ ID NOs: 3-10, 13-16, 20-27, and 31-38. The term "full length", as used herein refers to the complete nucleotide or amino acid sequence of any of these particular SEQ ID NOs.

Thus, the terms "identical" or percent "identity" in the context of two or more nucleotide or amino acid sequences refer to two or more sequences or subsequences that are the same or have a specified percentage of nucleotides or amino acid residues that are the same, when compared and aligned for maximum correspondence, as measured using one of the sequence comparison algorithms disclosed herein or by visual inspection.

For sequence comparison, typically one sequence acts as a reference sequence to which test sequences are compared. When using a sequence comparison algorithm, test and reference sequences are entered into a computer program, subsequence coordinates are designated if necessary, and sequence algorithm program parameters are selected. The sequence comparison algorithm then calculates the percent sequence identity for the designated test sequence(s) relative to the reference sequence, based on the selected program parameters.

Optimal alignment of sequences for comparison can be conducted, e.g., by the local homology algorithm of Smith & Waterman, 1981, by the homology alignment algorithm of Needleman & Wunsch, 1970, by the search for similarity method of Pearson & Lipman, 1988, by computerized implementations of these algorithms (GAP, BESTFIT, FASTA, and TFASTA in the Wisconsin Genetics Software Package, Genetics Computer Group, Madison, Wis.), or by visual inspection. See generally, Ausubel et al., 1995.

A preferred algorithm for determining percent sequence identity and sequence similarity is the BLAST algorithm, which is described by Altschul et al., 1990. Software for performing BLAST analyses is publicly available through the National Center for Biotechnology Information (www<<dot>>ncbi<<dot>>nlm<<dot>>nih<<dot>>gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength W=11, an expectation E=10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See Henikoff & Henikoff, 1992.

In addition to calculating percent sequence identity, the BLAST algorithm also performs a statistical analysis of the similarity between two sequences. See e.g., Karlin & Altschul, 1993. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

III. Nucleic Acids

III.A. Nucleic Acids Encoding the Presently Disclosed TCRs, TCR-Like Molecules, and Portions Thereof In some embodiments, the presently disclosed subject matter provides nucleic acids that encode the presently disclosed TCRs, TCR-like molecules, and portions thereof. Exemplary nucleic acids that encode the disclosed TCRs, TCR-like molecules, and portions thereof include SEQ ID NOs: 3-10, 13-16, 20-27, and 31-38 as well as subsequences thereof.

As used herein, the phrases "nucleic acid", "polynucleotide", "oligonucleotide", and "nucleic acid molecule" are used interchangeably to refer to a polymer of DNA and/or RNA, which can be single-stranded, double-stranded, or multi-stranded, synthesized or obtained (e.g., isolated and/or purified) from natural sources, which can contain natural, non-natural, and/or altered nucleotides, and which can contain natural, non-natural, and/or altered internucleotide linkages including, but not limited to phosphoroamidate linkages and/or phosphorothioate linkages instead of the phosphodiester found between the nucleotides of an unmodified oligonucleotide.

In some embodiments, the nucleic acids of the presently disclosed subject matter comprise a nucleotide sequence as set forth in any of SEQ ID NOs: 3-10, 13-16, 20-27, and 31-38 as well as subsequences thereof. In some embodiments, the nucleotide sequence does not comprise any insertions, deletions, inversions, and/or substitutions relative to SEQ ID NOs: 3-10, 13-16, 20-27, and 31-38, although contiguous subsequences of any of these SEQ ID NOs. is encompassed within the presently disclosed subject matter. In some embodiments, however, a nucleotide sequence can comprise one or more insertions, deletions, inversions, and/ or substitutions relative to SEQ ID NOs: 3-10, 13-16, 20-27, and 31-38.

In some embodiments, the nucleic acids of the presently disclosed subject matter are recombinant. As used herein, the term "recombinant" refers to (i) molecules that are constructed outside living cells by joining natural or synthetic nucleic acid segments to nucleic acid molecules that can replicate in a living cell; or (ii) molecules that result from the replication of those described in (i) above. For purposes herein, the replication can be in vitro replication or in vivo replication.

The nucleic acids can be constructed based on chemical synthesis and/or enzymatic ligation reactions using procedures known in the art (see e.g., Sambrook & and Russell, 2001; and Ausubel et al., 1989). For example, a nucleic acid can be chemically synthesized using naturally occurring nucleotides and/or variously modified nucleotides designed to increase the biological stability of the molecules and/or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, β-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively or in addition, one or more of the nucleic acids of the presently disclosed subject matter can be purchased from a commercial source such as, but not limited to Macromolecular Resources of Fort Collins, Colo. and Synthegen of Houston, Tex.

The nucleic acid can comprise any nucleotide sequence that encodes any of the modified TCRs, TCR-like molecules, portions thereof, polypeptides, proteins, or functional portions or functional variants thereof of the presently disclosed subject matter. For example, in some embodiments the nucleic acid can comprise a nucleotide sequence comprising SEQ ID NOs: 3, 5, 7, 9, 13, 15, 20, 22, 24, 26, 31, 33, 35, or 37, and/or can encode a polypeptide having an amino acid sequence as set forth in SEQ ID NOs: 4, 6, 8, 10, 14, 16, 21, 23, 25, 27, 32, 34, 36, or 38, or a portion thereof. The nucleotide sequence can in some embodiments comprise a nucleotide sequence which is degenerate to any of these sequences or a combination of degenerate sequences.

The presently disclosed subject matter also provides an isolated or purified nucleic acid comprising a nucleotide sequence that is complementary to the nucleotide sequence of any of the nucleic acids described herein or a nucleotide sequence that hybridizes under stringent conditions to the nucleotide sequence of any of the nucleic acids described herein. In some embodiments, the nucleotide sequence that hybridizes under stringent conditions hybridizes under high stringency conditions. As used herein, the phrase "high stringency conditions" refers to a set of hybridization condition wherein a nucleotide sequence specifically hybridizes to a target sequence (e.g., a nucleotide sequence of any of the nucleic acids described herein) in an amount that is detectably stronger than non-specific hybridization. High stringency conditions include conditions that would distinguish a polynucleotide with an exact complementary sequence, or one containing only a few scattered mismatches, from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between a nucleotide sequence and a target, and are particularly suitable for detecting expression of any of the TCRs, TCR-like molecules, or portions thereof described herein. It is generally appreciated that conditions can be rendered more stringent by the addition of increasing amounts of formamide. An exemplary high stringency hybridization condition employs 0.015 M sodium chloride/0.0015 M sodium citrate/0.1% sodium dodecyl sulfate (SDS) at 50° C. (0.1×SSC/0.1% SDS). Denaturing agents, such as formamide, can also be employed. Exemplary high stringency hybridization conditions employing formamide include 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50-100 µg/ml), 0.1% SDS, and 10% dextran sulfate at 42° C., with washes at 42° C. in 0.2×SSC (sodium chloride/sodium citrate) and 50% formamide at 55° C. followed by a high-stringency wash consisting of 0.1×SSC containing EDTA at 55° C.

III.B. Vectors for Recombinant Expression of the Presently Disclosed TCRs, TCR-Like Molecules, and Portions Thereof The nucleic acids of the presently disclosed subject matter can in some embodiments be incorporated into a vector, optionally an expression vector, further optionally a recombinant expression vector. The presently disclosed subject matter thus provides in some embodiments recombinant expression vectors comprising any of the nucleic acids disclosed herein. As sued herein, the phrases "expression vector" and "recombinant expression vector" refer to genetically-modified oligonucleotide and/or polynucleotide constructs that permit the expression of an mRNA, protein, polypeptide, and/or peptide by a host cell, when the construct comprises a nucleotide sequence encoding the mRNA, protein, polypeptide, and/or peptide, and the vector is contacted with the cell under conditions sufficient to have the mRNA, protein, polypeptide, and/or peptide expressed within the cell. The vectors of the presently disclosed subject matter are in some embodiments not naturally-occurring as a whole. However, parts of the vectors can be naturally-occurring. Expression vectors can comprise any type of nucleotides, including, but not limited to DNA and RNA, which can be single-stranded or double-stranded, synthesized or obtained in part from natural sources, and which can contain natural, non-natural, and/or altered nucleotides. The expression vectors can comprise naturally-occurring and/or non-naturally-occurring internucleotide linkages. In some embodiments, non-naturally occurring or altered nucleotides or internucleotide linkages do not hinder the transcription or replication of the vector.

The expression vectors of the presently disclosed subject matter can be any suitable expression vector, and can be used to transform or transfect any suitable host. Suitable vectors include those designed for propagation and expansion or for expression or both, such as plasmids and viruses. In some embodiments, the vector can be selected from the group consisting of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λG10, λGT11, λZapII (Stratagene), λEMBL4, and λNM1149, also can be used. Examples of plant expression vectors include pBI01, pBI101.2, pBI101.3, pBI121, and pBIN19 (Clontech). Examples of animal expression vectors include pEUK-C1, pMAM, and pMAMneo (Clontech).

In some embodiments, the recombinant expression vector is a viral vector, including but not limited both integrating and non-integrating viral vectors. Exemplary viral vectors include, but are not limited to adenoviral vectors, lentiviral vectors, retroviral vectors, episomal vectors, and non-episomal vectors. Exemplary viral vectors are disclosed in, for example, U.S. Pat. Nos. 8,119,772 and 8,552,150, both to Yang et al.; U.S. Pat. Nos. 6,277,633 and 6,521,457, both to Olsen; and U.S. Patent Application Publication No. 2012/0135034 of Dropulic and U.S. Patent Application Publication No. 2008/0254008 of Dropulic et al. (both assigned to Lentigen Corporation of Gaithersburg, Md., United States of America). Lentiviral vector systems are also commercially available from Cell Biolabs, Inc. of San Diego, Calif., United States of America and OriGene Technologies, Inc. of Rockville, Md., United States of America. In some embodiments, a vector is a viral episomal vector, optionally based on adenovirus and/or adeno-associated virus (AAV). An exemplary minimal adenovirus-based episomal vector is described in PCT International Patent Application Publication No. WO 2002/085287 of Balague et al. A non-viral episomal vector is disclosed in WO 1998/007876 of Antoniou et al.

The expression vectors of the presently disclosed subject matter can be prepared using standard recombinant DNA techniques described in, for example, Sambrook & Russell, 2001; Ausubel et al., 1989. Constructs of expression vectors, which can be circular or linear, can be prepared to contain a replication system functional in a prokaryotic or eukaryotic host cell. Replication systems can be derived, e.g., from ColE1, 2μ plasmid, λ, SV40, bovine papilloma virus, and the like.

In some embodiments, an expression vector comprises regulatory sequences, including but not limited to transcription, translation, initiation, and termination codons, which are specific to the type of host (e.g., bacterium, fungus, plant, or animal) into which the vector is to be introduced, as appropriate and taking into consideration whether the vector is DNA- or RNA-based.

An expression vector of the presently disclosed subject matter can also include one or more marker genes, which allow for selection of transformed or transfected hosts. Marker genes can include biocide resistance, e.g., resistance to antibiotics, heavy metals, etc., complementation in an auxotrophic host to provide prototrophy, and the like. Suitable marker genes for an expression vectors can include, for example, neomycin/G418 resistance genes, hygromycin resistance genes, histidinol resistance genes, tetracycline resistance genes, and ampicillin resistance genes.

An expression vector can comprise a native or non-native promoter operably linked to the nucleotide sequence encoding the modified TCR, TCR-like molecule, portion thereof, polypeptide, or protein (including functional portions and functional variants thereof), or to the nucleotide sequence that is complementary to or that hybridizes to a nucleotide sequence encoding the modified TCR, TCR-like molecule, portion thereof, polypeptide, or protein disclosed herein. The selection of promoters, in some embodiments strong, weak, inducible, tissue-specific, and/or developmental-specific, is within the ordinary skill of the artisan. Similarly, the combining of a nucleotide sequence with a promoter is also within the skill of the artisan. The promoter can be in some embodiments a non-viral promoter or a viral promoter including, but not limited to a cytomegalovirus (CMV) promoter, an SV40 promoter, an RSV promoter, a promoter found in the long-terminal repeat of a retrovirus, etc.

An expression vector can in some embodiments be designed for transient expression, stable expression, or both transient and stable expression. Also, an expression vector can be made for constitutive expression or for inducible expression.

Further, expression vectors can in some embodiments be made to include a suicide gene. As used herein, the phrase "suicide gene" refers to a nucleotide sequence that causes a cell expressing the nucleotide sequence to die. A suicide gene can in some embodiments be a nucleotide sequence that confers sensitivity upon a cell expressing the nucleotide sequence as a transcription product and/or as a translation product to an agent (such as but not limited to a drug) such that when the cell is contacted with and/or exposed to the agent, the agent directly or indirectly causes the cell to die. Suicide genes are known in the art and include, for example, the Herpes Simplex Virus (HSV) thymidine kinase (TK) gene, cytosine daminase, purine nucleoside phosphorylase, and nitroreductase (see e.g., Springer, 2004).

IV. Host Cells for Production and/or Expression of TCRs, TCR-Like Molecules, and Portions Thereof In some embodiments, the presently disclosed subject matter also provides host comprising the disclosed isolated and/or soluble TCR, TCR-like molecule, or portion thereof, and/or an isolated nucleic acid disclosed herein. In some embodiments, the host cells are employed for the product and/or expression of a disclosed isolated and/or soluble TCR, TCR-like molecule, or portion thereof.

V. Isolation of Soluble TCRs, TCR-Like Molecules, and Portions Thereof

In some embodiments, the TCRs, TCR-like molecules, and the portions thereof are soluble. As used herein, the term "soluble" refers to the fact that a TCR, TCR-like molecule, or a portion thereof is not anchored to a cell membrane via a transmembrane region as is typical for full length TCRs. Methods for producing and isolating soluble TCRs, TCR-like molecules, and portions thereof are exemplified in Molloy et al., 2005; Fremont et al., 1996; Pecorari et al., 1999; and U.S. Patent Application Publication No. 2005/0214284 of Price-Schiavi et al.

In some embodiments, soluble TCRs, TCR-like molecules, and portions thereof are produced by screening a phage library. An exemplary method for screening a phage library for soluble TCRs, TCR-like molecules, and portions thereof is presented in PCT International Patent Application Publication No. WO 2001/062908.

VI. Adoptive T Cell Therapy Utilizing the Presently Disclosed TCRs, TCR-Like Molecules, and Portions Thereof In some embodiments, the TCRs, TCR-like molecules, portions thereof of the presently disclosed subject matter, and T cells comprising the same, can be employed for use in adoptive T cell therapy. Generally, adoptive T cell therapy relies on the in vitro expansion of endogenous, cancer-reactive T cells. These T cells can be harvested from cancer patients, manipulated, and then reintroduced into the same or a different patient as a mechanism for generating productive tumor immunity. Adoptive T cell therapy has had promising early clinical results and has been associated with clinical responses.

CD8+ cytotoxic T lymphocytes are the primary effector cells in adoptive T cell therapy. However, CD4+ T cells might also play an important role in maintaining CD8+ cytotoxic function and transplantation of tumor reactive CD4+ T cells has been associated with some efficacy in metastatic melanoma. T cells used in adoptive therapy can be harvested from a variety of sites, including peripheral blood, malignant effusions, resected lymph nodes, and tumor biopsies. Although T cells harvested from the peripheral blood are easier to obtain technically, tumor-infiltrating lymphocytes (TILs) obtained from biopsies might contain a higher frequency of tumor-reactive cells.

Once harvested, T cells can be expanded either through polyclonal stimulation with activating antibodies or through exposure to specific tumor antigens. This second approach requires the identification of relevant targets, however.

Given the frequency of antigen loss variants in current clinical trials, the selection of appropriate targets could be challenging, potentially making polyclonal stimulation a more attractive approach. In some embodiments, a relevant target comprises an antigenic fragment of an IRS2 polypeptide (i.e., SEQ ID NO: 2), a CDC25b polypeptide (i.e., SEQ ID NO: 11), a desmuslin//synemin polypeptide (i.e., SEQ ID NOs: 17 and 18), and/or a β-catenin polypeptide (i.e., SEQ ID NO: 28). In some embodiments, the antigenic fragment comprises an amino acid sequence as set forth in SEQ ID NOs: 2, 12, 19, 29, or 30.

Several strategies, including the enforced expression of costimulatory proteins and telomerase, have been used to extend the life span of cultured T cells. IL-15 has also been considered as a possible additive to cultures in order to enhance the production of cytotoxic cells. Engraftment of adoptively transferred T cells appears to be enhanced in lymphodepleted hosts, and strategies to combine pretreatment with lymphodepleting chemotherapy and adoptive T cell transplantation appear to increase treatment efficacy significantly.

Two alternative approaches attempt to circumvent low levels of endogenous antitumor reactivity in the peripheral blood by directly supplying T cells with the ability to recognize tumors. T cells harvested from the peripheral blood can be engineered to express TCRs, TCR-like molecules, and/or portions thereof that have been selected for tumor recognition. This approach has been tested in metastatic melanoma. However, because TCR recognition of an antigen is MHC restricted, each engineered TCR can typically only be used in patients with the required MHC allele. MHC restriction can be bypassed by engineering T cells to express novel chimeric fusion proteins that link the antigen-binding domain of the B cell receptor with the signaling component of the TCR complex. These "T-bodies" can directly bind tumor antigens, leading to T cell activation, but can be used to target only cell surface overexpressed proteins while in some embodiments TCRs, TCR-like molecules, and portions thereof recognize peptides derived from proteins in all cell compartments. In some embodiments, the presently disclosed subject matter employs a T cell that has been modified to express a TCR, a TCR-like molecule, and/or a portion thereof as defined herein.

VII. Other Methods

VII.A. Methods of Treatment Using Conjugates Comprising TCRs, TCR-Like Molecules, and/or Portions Thereof In some embodiments, the conjugates of the TCRs, TCR-like molecules, or portions thereof with active agents are used to treat a condition in a subject in need thereof. In some embodiments, the Exemplary soluble fusion proteins for use with the presently disclosed subject matter are in some embodiments fully functional and soluble. By the term "fully functional" or similar term is meant that the fusion protein specifically binds ligand. Assays for detecting such specific binding include, but are not limited to standard immunoblot techniques such as Western blotting. Functional fragments of such soluble TCRs and TCR-like molecules are able to bind antigen with in some embodiments at least 70% of the affinity of the corresponding full-length TCR or TCR-like molecule, in some embodiments at least about 80% of the affinity of the corresponding full-length TCR or TCR-like molecule, in some embodiments at least about 90% of the affinity of the corresponding full-length TCR or TCR-like molecule, in some embodiments at least about 95% of the affinity of the corresponding full-length TCR or TCR-like molecule, and in some embodiments greater than 95% of the affinity of the corresponding full-length TCR or TCR-like molecule as determined by Western blot or Surface Plasma Resonance analysis.

VII.B. Methods of Using the Disclosed TCRs, TCR-Like Molecules, and Portions Thereof as Diagnostic Agents In some embodiments, the presently disclosed TCRs, TCR-like molecules, and portions thereof can be employed as diagnostic agents. By way of example and not limitation, the presently disclosed TCRs, TCR-like molecules, and portions thereof can be employed in a detection and/or diagnostic assay such as but not limited to immunohistochemistry to localize their cognate phosphopeptides in samples from subjects. For example, a tumor biopsy could be contacted with a TCR, TCR-like molecule, and/or a portion thereof that has been conjugated with a detectable label under conditions sufficient for the presently disclosed TCRs, TCR-like molecules, and portions thereof to bind to its cognate phosphopeptide, and this binding can be detected using standard techniques. Such an approach can be used, for example, for assaying tumor biopsies to determine whether the cells present in the biopsy express a given phosphopeptide and, in some embodiments, to what extent the phosphopeptide is expressed in the tumor cells. For those phosphopeptides that are expressed specifically by tumor cells, such an approach can also be used to assess tumor margins by determining whether or not the cells at the periphery of a tumor biopsy express or do not express a given phosphopeptide.

VII.C. Methods of Modifying the Disclosed TCRs, TCR-Like Molecules, and Portions Thereof to Increase Binding Affinity Methods of testing a TCR, TCR-like molecule, or a portion thereof of the presently disclosed subject matter for an ability to recognize a target and/or a cell and for antigen specificity are known in the art. For example, Clay et al., 1999, teaches methods of measuring the release of cytokines (e.g., interferon-γ (IFNγ), granulocyte/monocyte colony stimulating factor (GM-CSF), tumor necrosis factor α (TNF-α), or interleukin 2 (IL-2)). In addition, TCR function can be evaluated by measurement of cellular cytotoxicity, as described, for example, in Zhao et al., 2005.

Additionally, once a TCR, TCR-like molecule, or portion thereof that binds to a peptide of interest has been identified, the amino acid sequence of the same (referred to herein as a "reference sequence") can be modified to increase its binding affinity for the peptide of interest. In some embodiments, a phage library can be constructed that includes a plurality of modified TCRs, TCR-like molecules, or portions thereof, wherein the modified TCRs, TCR-like molecules, or portions thereof comprise amino acid sequences that include one or more substitutions, deletions, or insertions of the amino acids of the reference sequence. In some embodiments, amino acid sequence modifications are produced in the CDR regions, optionally just the CDR3 region, but in some embodiments also including one or both of the CDR1 and CDR2 regions. An exemplary method for screening a phage library of modified TCRs, TCR-like molecules, or portions thereof is presented in PCT International Patent Application Publication No. WO 2001/062908.

EXAMPLES

The following Examples provide further illustrative embodiments. In light of the present disclosure and the general level of skill in the art, those of skill will appreciate that the following EXAMPLES are intended to be exemplary only and that numerous changes, modifications, and alterations can be employed without departing from the scope of the presently disclosed subject matter.

Materials and Methods for the EXAMPLES

Cell Line Care.

Breast cancer cell lines were maintained in D-MEM media containing 10% fetal bovine serum (FBS), 2 mM 1-glutamine, 15 mM Hepes, and Pen/Strep (complete). Melanoma, ovarian carcinoma, and colorectal cancer lines were maintained in complete RPMI (CELLGRO®, Mediatech, Inc. A Corning Subsidiary, Manassas, Va., United States of America; see Zarling et al., 2006). Transfectants of the B lymphoblastoid cell line C1R expressing either HLA-A2 (C1R-A2) or a chimeric MHC class I molecule consisting of α1 and α2 domains of HLA-A2 and α3 domain of H-2D$^d$ (C1R-AAD) were maintained in complete RPMI with 300 μg/ml Hygromycin B (CELLGRO®) or G418 (CELLGRO®), respectively (see Zarling et al., 2006).

Human CD8 T-Cell Culture and IFN-γ ELISpot.

Magnetic bead-enriched (Miltenyi Biotec Inc., Auburn, Calif., United States of America; Catalogue No. 130-096-495) human CD8 T-cells were co-cultured with irradiated, peptide-pulsed matured DC for 7 days in individual 96-well microcultures at a 15:1 T-cell:DC ratio (see Tsai et al., 1998). For experiments evaluating memory responses, enriched CD8 T-cells were further magnetic bead-enriched for CD45RO$^+$ cells (Miltenyi Biotec Inc., Auburn, Calif., United States of America; Catalogue No. 130-046-001). An indirect ELISpot was performed as described in Slingluff et al., 2009 using 25,000 cells/well with or without 75,000 peptide-pulsed (10 μg/ml) T2 targets. All human protocols were approved by the Institutional Review Board for Health Sciences Research of the University of Virginia, Charlottesville, Va., United States of America.

Generation of Murine Phosphopeptide-Specific T-Cells.

Murine CD8 T-cells specific for the pIRS-2$_{1097-1105}$ (RVApSPTSGV; SEQ ID NO: 2), pCDC25b$_{38-46}$ (GLLGpSPVRA; SEQ ID NO: 12), desmuslin (RTFpSPTYGL; SEQ ID NO: 19), and pβ-catenin$_{30-39}$ (YLDpSGIHSGV; SEQ ID NO: 29 and YLDpSGIHSGA; SEQ ID NO: 30) phosphopeptides were generated in AAD transgenic mice as described (see Zarling et al., 2000; Zarling et al., 2006). Yellow Fever NS4B$_{214-222}$ (LLWNGPMAV; SEQ ID NO: 54), and M1$_{58-66}$ Flu (GILGFVFTL; SEQ ID NO: 55) peptides were used as controls. Peptides were synthesized by GenScript USA Inc. (Piscataway, N.J. United States of America) or Bio-Synthesis Inc. (Lewisville, Tex., United States of America). All protocols were approved by the Institutional Animal Care and Use Committee (IACUC) of the University of Virginia, Charlottesville, Va., United States of America.

Cloning of Phosphopeptide-Specific Murine TCR α and β Chains.

pIRS-2$_{1097-1105}$-specific, pCDC25b$_{38-46}$-specific, pDesmuslin$_{426-435}$-specific, and pβ-catenin$_{30-39}$-specific murine CD8 T-cell lines were magnetically enriched for CD8a (Miltenyi Biotec Inc., Auburn, Calif., United States of America; Catalogue No. 130-049-401) and total RNA isolated using PURELINK™ MICRO-TO-MIDI™ Total RNA isolation kit (INVITROGEN™ Corporation, Carlsbad, Calif., United States of America). cDNA was synthesized from total RNA (3 μg) using the GENERACER™ Kit (INVITROGEN™ Corporation, Carlsbad, Calif., United States of America) as described (see Santomasso et al., 2007). 5'-RACE PCR was performed using the GENERACER™ 5' primer and one of three 3' gene-specific primers:

TCR-CαRev (5'-ACTGGACCACAGCCTCAGCGTCAT-3'; SEQ ID NO: 39);

TCR-Cβ1Rev (5'-TGAATTCTTTCTTTTGACCATAGCCAT-3'; SEQ ID NO: 40);

or

TCR-Cβ2Rev (5'-GGAATTTTTTTTCTTGACCATGGCCAT-3'; SEQ ID NO: 41).

RACE PCR products of correct size (~900 bp) were cloned into the pCR®4-TOPO® vector (INVITROGEN™ Corporation, Carlsbad, Calif., United States of America). TCR sequences were confirmed in both directions and matched to the IMGT database available on the World Wide Web at www<<dot>>imgt<<dot>>org.

Electroporation of IVT RNA Encoding Phosphopeptide-Specific TCR Chains.

IVT RNA of the TCR 43 chains and transfection of OKT3-activated human CD8 T-cells were performed as described in Johnson et al., 2006 and Zhao et al., 2005. The 5' primers included sequences for T7 RNA polymerase binding and transcription, followed by a Kozak sequence, a start codon and the next 16-17 bp of Vα or Vβ region for each TCR gene while the 3' primers included 66 T residues (T$_{66}$) and 16-25 bp of the relevant α or β constant region sequence.

A first pIRS-2$_{1097-1105}$-specific TCR α chain cDNA (SEQ ID NO: 3) was amplified using the 5' primer (5'-TAATACGACTCACTATAGGGAGAGCCACC ATGCTCCTGGCACTCCTCCC-3'; SEQ ID NO: 42), and the 3' primer (5'-(T$_{66}$)AA CTGGACCACAGCCTCAGCGTC-3'; SEQ ID NO: 43). A first pIRS-2$_{1097-1105}$-specific TCR β chain cDNA (SEQ ID NO: 5) was amplified using the 5' primer (5'-T AATACGACTCACTATAGGGAGAGCCAC-CATGGGCACCAGGCTTCTTGG-3'; SEQ ID NO: 44) and the 3' primer (5'-(T$_{66}$)A GGAATTTTTTTTCTTGACCATG-GCC-3'; SEQ ID NO: 45). A second pIRS-2$_{1097-1105}$-specific TCR α chain cDNA (SEQ ID NO: 7) was amplified using the 5' primer (5'-TAATACGACTCACTATAGGGAGAGC-CACCATGCTCCTGGCACTC CTCCC-3'; SEQ ID NO: 42), and the 3' primer (5'-(T$_{66}$)AA CTGGACCACAGC-CTCAGCGTC-3'; SEQ ID NO: 43). A second pIRS-2$_{1097-1105}$-specific TCR β chain cDNA (SEQ ID NO: 9) was amplified using the 5' primer (5'-T AATACGACTCAC-TATAGGGAGAGCCACCATGGGCTCCAGACTCT-TCTTT-3'; SEQ ID NO: 48) and the 3' primer (5'-(T$_{66}$) AGGAATTTTTTTTCTTGACCATGGCC-3'; SEQ ID NO: 45).

A pCDC25b$_{38-46}$-specific TCR α chain cDNA (SEQ ID NO: 13) was amplified using the 5' primer (5'-TAATAC-GACTCACTATAGGGAGAGCCACC ATGAAGACAGT-GACTGGACC-3'; SEQ ID NO: 46) and the 3' primer (5'-(T$_{66}$) AACT GGACCACAGCCTCAGCGTC-3'; SEQ ID NO: 43). A pCDC25b$_{38-46}$-specific TCR β chain cDNA (SEQ ID NO: 15) was amplified using the 5' primer (5'-TAATACGACTCACTATAGGGAGAGCCACCATGTCT AACACTGCCTTCCCT-3'; SEQ ID NO: 47) and the 3' primer (5'-(T$_{66}$)A GGAATTTTTTTTCTTGACCATGGCC SEQ ID NO: 45).

A first pDesmuslin$_{426-435}$-specific TCR α chain cDNA (SEQ ID NO: 20) was amplified using the 5' primer (5'-TAATACGACTCACTATAGGGAGAG CCACCATGCTC-CTGGCACTCCTCCC-3'; SEQ ID NO: 42), and the 3' primer (5'-(T$_{66}$)AACTGGACCACAGCCTCAGCGTC-3'; SEQ ID NO: 43). A first pDesmuslin$_{426-435}$-specific TCR β chain cDNA (SEQ ID NO: 22) was amplified using the 5' primer (5'-TAATACGACTCACTATAGGGAGAGCCAC-CATGT CTAACACTGTCCTCGCT-3'; SEQ ID NO: 49) and the 3' primer (5'-(T$_{66}$)CTA TGAATTCTTTCTTTT-GACCATAGCCATCAC-3'; SEQ ID NO: 50). A second pDesmuslin$_{426-435}$-specific TCR α chain cDNA (SEQ ID NO: 24) was amplified using the 5' primer (5'-TAATAC-GACTCACTATAGGGAGAGCCACCATGCTCCTGG CACTCCTCCC-3'; SEQ ID NO: 42), and the 3' primer (5'-(T$_{66}$) AACTGGACCACAGCCTCAGCGTC-3'; SEQ ID NO: 43). A second pDesmuslin$_{426-435}$-specific TCR β chain cDNA (SEQ ID NO: 26) was amplified using the 5' primer (5'-TAATACGACTCACTATAGGGAGAGCCAC-CATGGGCTCC AGACTCTTCTTT-3'; SEQ ID NO: 48) and the 3' primer (5'-(T$_{66}$)A GGAATTTTTTTTCTTGAC-CATGGCC-3'; SEQ ID NO: 45).

A first pβcatenin$_{30-39}$-specific TCR α chain cDNA (SEQ ID NO: 31) was amplified using the 5' primer (5'-TAATAC-GACTCACTATAGGGAGAGCCACC ATGAAGAGGCT-GCTGTGTTCT-3'; SEQ ID NO: 51), and the 3' primer (5'-(T$_{66}$)A ACTGGACCACAGCCTCAGCGTC-3'; SEQ ID NO: 43). A first pβcatenin$_{30-39}$-specific TCR β chain cDNA (SEQ ID NO: 33) was amplified using the 5' primer (5'-TAATA CGACTCACTATAGGGAGAGCCACCA TGAGCTGCAGGCTTCTC-3'; SEQ ID NO: 52) and the 3' primer (5'-(T$_{66}$)A GGAATTTTTTTTCTTGACCATGGCC-3'; SEQ ID NO: 45). A second pβcatenin$_{30-39}$-specific TCR α chain cDNA (SEQ ID NO: 35) was amplified using the 5' primer (5'-TAATACGACTCACTATAGGGAGAGCCAC-CATGAACAGATTCCTGG GAATATC-3'; SEQ ID NO: 53), and the 3' primer (5'-(T$_{66}$)AAC TGGACCACAGC-CTCAGCGTC-3'; SEQ ID NO: 43). A second pβcatenin$_{30-39}$-specific TCR β chain cDNA (SEQ ID NO: 37) was amplified using the 5' primer (5'-TAATAC GACT-CACTATAGGGAGAGCCACCATGAGCTGCAGGCT-TCTC-3'; SEQ ID NO: 52) and the 3' primer (5'-(T$_{66}$) AGGAATTTTTTTT CTTGACCATGGCC-3'; SEQ ID NO: 45).

Prior to electroporation, donor T-cells were washed three times in serum-free OPTI-MEM® media (Life Technologies Corporation, Gaithersburg, Md., United States of America) and were suspended at 25×10$^6$/ml. Cells were mixed with 2 μg IVT RNA of each TCR α and β chain per 10$^6$ cells and transferred to pre-chilled BTX 2 mm gap cuvettes. Using the BTX T820 electroporation system (BTX Instrument Division, Harvard Apparatus, Inc. Holliston, Mass., United States of America), cells were pulsed at 500V for 0.3 msec. Transfected cells were placed in AIM-V® brand serum-free medium (Life Technologies Corporation, Gaithersburg, Md., United States of America) with 5% AB$^+$ serum (GEM-CELL™; Gemini Bio-Products, West Sacramento, Calif., United States of America) for 8-24 hours and evaluated for TCR expression and functionality.

Functional Analysis of Phosphopeptide-Specific Murine TCR-Expressing Human CD8 T-Cells.

14-16 hours post-electroporation, phosphopeptide-specific murine TCR-transfected human CD8 T-cells were co-cultured in AIM-V (Life Technologies Corporation, Gaithersburg, Md., United States of America) supplemented with 5% human AB$^+$ serum (GEMCELL™; Gemini Bio-Products, West Sacramento, Calif., United States of America) with peptide-pulsed or unpulsed C1R-AAD, C1R-A2, or cancer cells endogenously expressing the pIRS-2$_{1097-1105}$ or the pCDC25b$_{38-46}$ phosphopeptide. Cell surface expression of mouse TCRβ, human CD3, and human CD8 molecules on human CD8 T-cells were assessed using antibodies from either Becton Dickinson Bioscience (San Jose, Calif., United States of America) or eBioScience Inc. (San Diego, Calif., United States of America). During a 5 hour co-culture of stimulator cells with phosphopeptide-specific murine TCR-transfected human CD8-T cells at 37° C., anti-human CD107a-Alexa 647 antibody (eBioScience Inc., San Diego, Calif., United States of America) was added in the presence of 5 μg/ml Brefeldin A (SIGMA-AL-DRICH® Co. LLC, St. Louis, Mo., United States of America), 5 μg/ml Monensin (eBioScience Inc., San Diego, Calif., United States of America) and 300 IU/ml human IL-2 (Chiron Corporation, Emeryville, Calif., United States of America). Cells were then stained for surface molecule expression, fixed and permeabilized using CYTOFIX/CY-TOPERM™ (Becton Dickinson Bioscience (San Jose, Calif., United States of America) and stained for intracellular cytokine (anti-IFN-γ and anti-TNF-α, eBioScience Inc., San Diego, Calif., United States of America). Immunofluoresence was analyzed using the Becton Dickinson FAC-SCANTO™ I or FACSCANTO™II flow cytometer and analyzed using FlowJo software (Tree Star, Inc., Ashland, Oreg., United States of America).

In Vitro Cytotoxicity Assay.

Phosphopeptide-specific murine TCR-expressing human CD8 T-cells were co-cultured for 5 hours with a 1:1 mix of C1R-A2 cells pulsed with 1 μM phosphopeptide and stained with 1 μM carboxyfluorescein succinimidyl ester (CFSE; Life Technologies) and unpulsed C1R-A2 cells stained with 0.1 μM CFSE. Specific killing was assessed by evaluating percent loss of the peptide-pulsed population relative to the unpulsed population.

Western Analysis.

Lysates were generated as described in Zarling et al., 2006 or using the THERMO SCIENTIFIC™ NE-PER™ protein extraction kit (Thermo Fisher Scientific Inc., Waltham, Mass., United States of America). Protein was loaded and separated on 8-16% gradient gel (ISC BioExpress, Kaysville, Utah, United States of America, or THERMO SCI-ENTIFIC™, Thermo Fisher Scientific Inc., Waltham, Mass., United States of America) by SDS/PAGE. Lysate created in HEK293T cells (NBL1-08995; Novus Biologicals, LLC, Littleton, Colo., United States of America) was used as a positive control for CDC25b (loaded 1 μg of protein in order to not over-expose blot). Proteins were transferred to Immobilon FL PVDF (EMD Millipore Corporation, Billerica, Mass., United States of America) and membranes blocked and probed with pSer$^{1100}$-IRS-specific Ab and GAPDH-specific Ab (Santa Cruz, SC-25778) as previously described (Zarling et al., 2006). The blots were then stripped with Restore Plus (Thermo Scientific) and reprobed with anti-IRS-2 specific antibodies (Santa Cruz, H-205). For CDC25b, total CDC25b protein was detected with CDC25b Antibody (C-20, Santa Cruz) after first blocking with 5% clarified milk with 0.1% Tween® 20 brand nonionic detergent. Pixel density for the staining of pSer$^{1100}$-IRS-2 or total CDC25b was determined using ALPHAEASEFC™ software.

Immunohistochemistry.

Formalin-fixed paraffin-embedded cell line pellets and tissue microarrays of metastatic melanoma samples (Biorepository and Tissue Research Facility of the University of Virginia, Charlottesville, Va., United States of America)

were deparaffinized, rehydrated, counterstained with hematoxylin, incubated with anti-Ser$^{1100}$-pIRS-2 for 3 hours at 4° C. after antigen retrieval, and specific antibody staining was detected using IMMPACT™ AEC (3-amino-9-ethylcarbazole; Vector Laboratories, Inc., Burlingame, Calif., United States of America). Antibodies were removed with ethanol and acidified potassium permanganate and then reprobed with anti-IRS-2 (Santa Cruz Biotechnology, Inc., Dallas, Tex., United States of America). A comparison of mean specific staining densities/unit area was performed for each metastatic melanoma and the adjacent uninvolved tissue using the Aperio "Positive Pixel count" (PPC) algorithm on an Aperio Scanner. To calculate specific staining, the PPC of representative sections from peptide-blocked slides was subtracted from the PPC of corresponding representative sections stained with the anti-Ser$^{1100}$-pIRS-2 antibody without blocking peptide.

Tumor Control.

Seven to 8 week old male NOD/SCID/IL-ORγc$^{-/-}$ mice (The Jackson Laboratory, Bar Harbor, Me., United States of America) were inoculated subcutaneously with $1.4 \times 10^6$ AAD$^+$ SLM2 melanoma cells. $3 \times 10^6$ human CD8 T-cells expressing either pIRS-2- or pCDC25b-specific TCR, or $1.5 \times 10^6$ of both populations, were adoptively transferred 3 days later. An additional $1.5 \times 10^6$ T-cells were given 4 days later. All mice received 1500 CU of IL-2 (R&D Systems, Inc., Minneapolis, Minn., United States of America) imp. every other day for 10 days. Tumor size was measured every 2-3 days with a digital caliper, and calculated as L×W (mm$^2$). Tumor free survival is equal to the measurement day when the tumor size was >30 mm$^2$.

Statistical Analysis.

Log-rank (Mantel Cox Test) analysis, Cox proportional hazard modeling, and parametric modeling were performed to determine statistical significance where indicated. p values less than 0.05 were considered significant.

Example 1

Immunogenicity of Phosphopeptides for Human Donors In Vitro

Figure 1B:
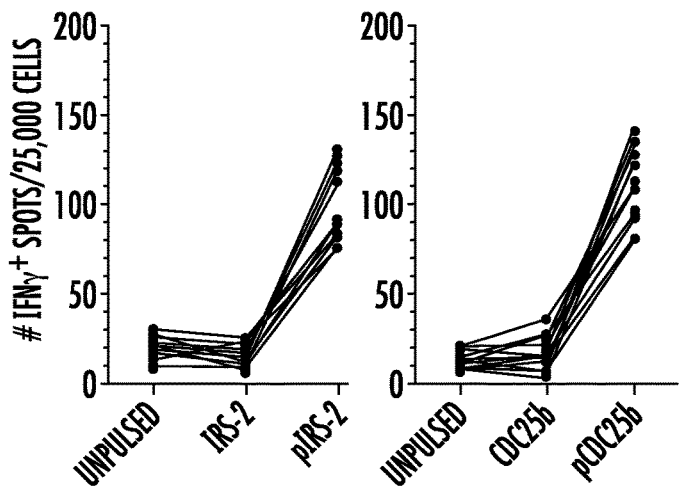

The pIRS-2$_{1097-1105}$ and pCDC25b$_{38-46}$ phosphopeptides were initially identified on two melanomas and an ovarian carcinoma (Zarling et al., 2006), but their abilities to induce T-cell responses in humans was not evaluated. Thus, T-cells from normal human donors were cultured in replicate microwells with autologous mature dendritic cells (DC) pulsed with either pIRS-2$_{1097-1105}$ or pCDC25b$_{38-46}$. After 7 days, T-cells in these cultures produced IFN-☐ when restimulated with phosphopeptide-pulsed HLA-A2$^+$ targets (see FIGS. 1A and 1B; "p" refers to the phosphorylated form). They did not recognize targets pulsed with the unphosphorylated (IRS-2$_{1097-1105}$ or CDC25b$_{38-46}$) homologous peptide (see FIG. 1B). The magnitude of these responses was surprisingly high. Donor 44's phosphopeptide-specific responses were significantly greater than that to a yellow fever virus peptide (LLWNGPMAV; SEQ ID NO: 54), to which this donor had not been previously exposed. Donor 54 had been immunized with yellow fever vaccine and this individual's phosphopeptide specific responses were somewhat lower than the yellow fever response although still strong (see FIG. 1A).

Figure 1C:
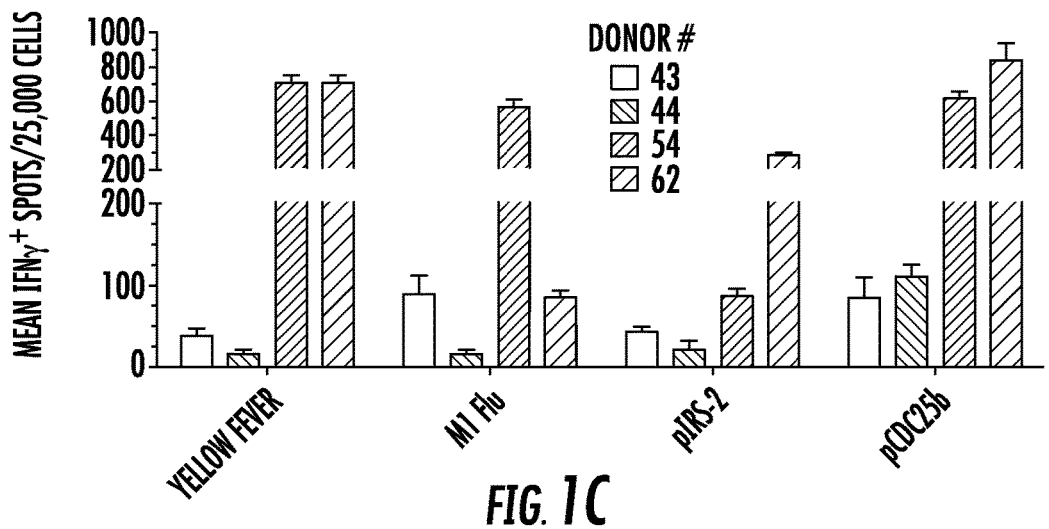
Figure 1D:
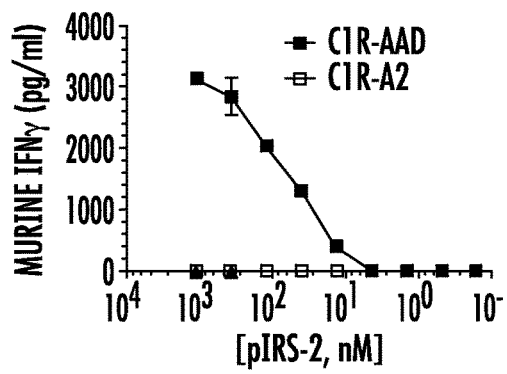
Figure 1D:
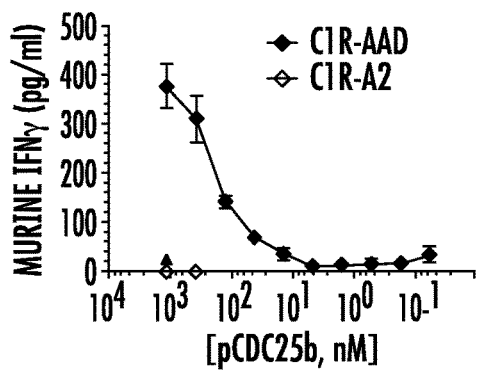

It has recently been established that immunity to some leukemia-associated phosphopeptides in normal individuals resides in the central memory compartment (Cobbold et al., 2013). Thus, CD45RO$^+$ CD8 T-cells were isolated from four (4) different donors using magnetic beads and stimulated them with autologous DC pulsed with either pIRS-2$_{1097-1105}$ or pCDC25b$_{38-46}$ for 7 days. Using a cutoff of >50 spots/25,000 cells, all four donors showed moderate to strong pre-existing memory responses to the pCDC25b$_{38-46}$ peptide, and 2/4 donors responded to pIRS-2$_{1097-1105}$ (see FIG. 1C). In all cases, the T-cells were specific to the phosphorylated peptide and did not recognize the unphosphorylated homolog. The magnitude of these memory responses was quite variable among peptides and donors, but was in some cases equivalent to or greater than memory responses to influenza or yellow fever epitopes (Note: donors 54 and 62 had been immunized with a yellow fever vaccine and had a strong yellow fever peptide-specific memory T cell response. Donors 43 and 44 were yellow fever naïve). This was inconsistent with the development of self-tolerance to these phosphopeptides. Combined, the strength of the responses in FIG. 1 was consistent with the possibility that these three normal human donors had been previously exposed to both phosphopeptides. However, none of these donors had indications of autoimmune disease, consistent with the possibility that these phosphopeptides were not displayed on normal tissue.

Example 2

Functional Activity of Phosphopeptide-Specific Murine TCR Upon Expression in Human CD8 T-Cells Recent reports have shown that adoptive transfer of human T-cells transfected with cloned high affinity tumor-reactive TCR can lead to positive clinical responses in cancer patients (Cohen et al., 2006; Morgan et al., 2006; Johnson et al., 2009; Park et al., 2011). These high avidity TCR also enable the expression of endogenously processed and presented TAA on cancers of multiple types to be determined.

Figure 2A:
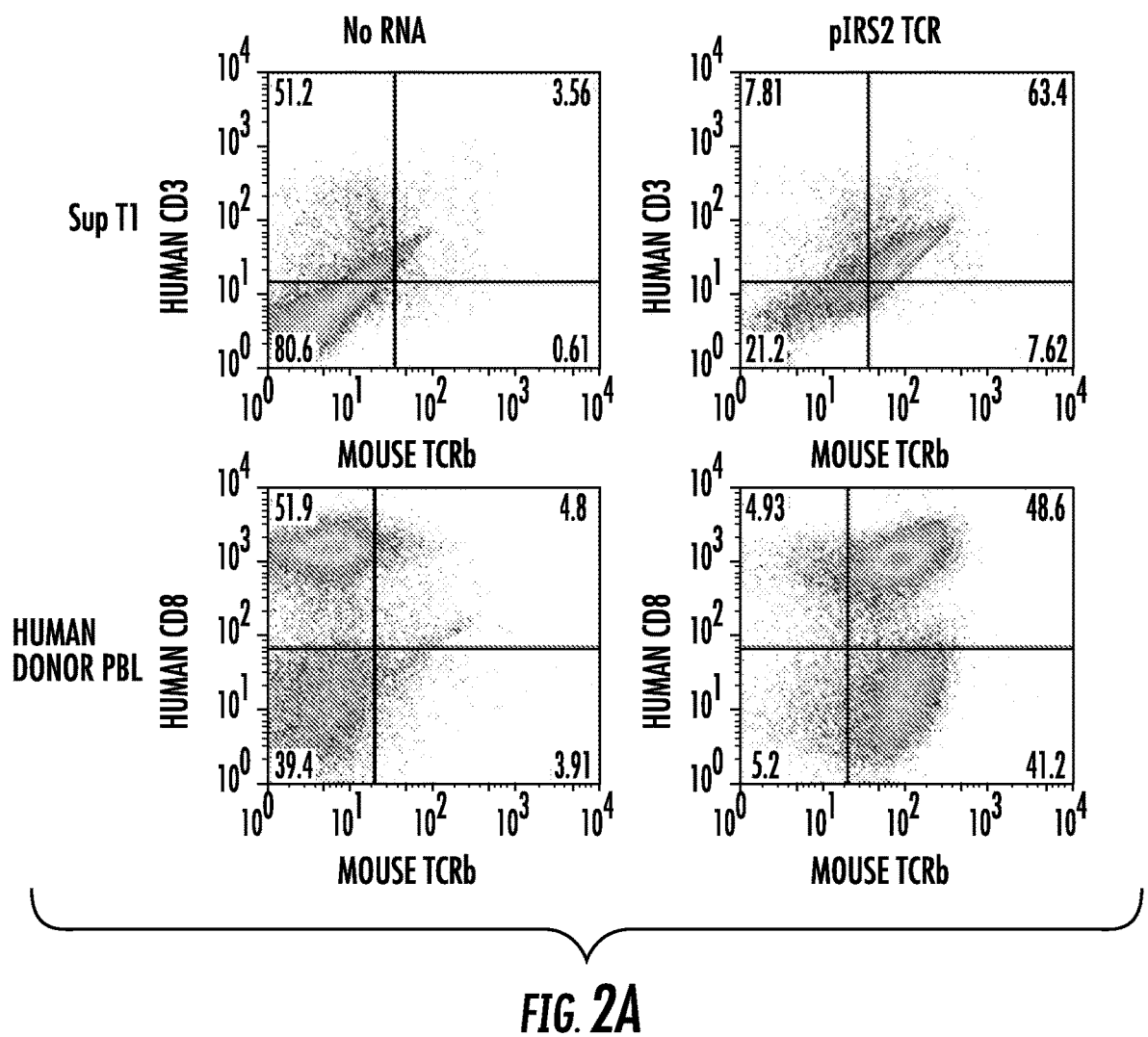
FIGS. 2A-2C are a series of plots showing that electroporation of in vitro-transcribed (IVT) RNA encoding murine TCR chains resulted in functional cell surface expression of phosphopeptide-specific TCR. Detection of murine TCR on the surface of TCR-deficient SupT1 (FIG. 2A) or human T lymphocytes (FIGS. 2A-2C) following electroporation of IVT RNA encoding the pIRS-$2_{1097-1105}$ TCR alpha and beta chains of SEQ ID NOs: 4 and 6. Note that expression of TCR chains resulted in cell surface expression of CD3 on SupT1 cells.
Figure 2B:
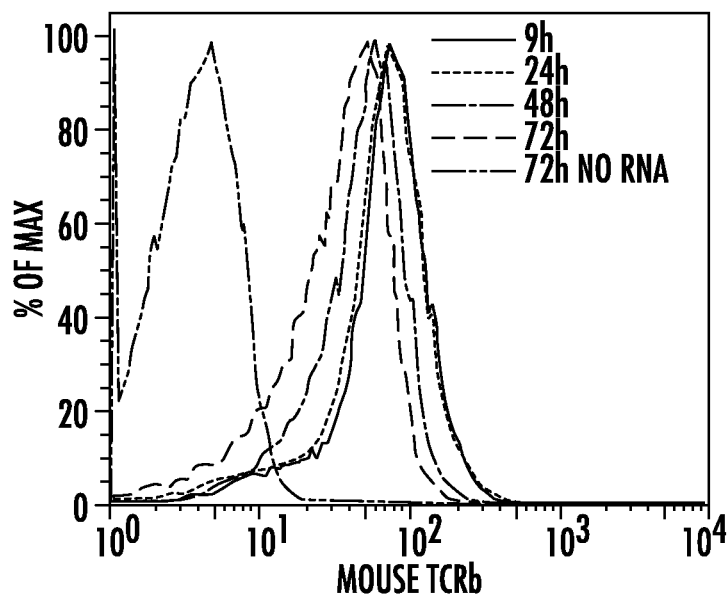
Figure 2C:
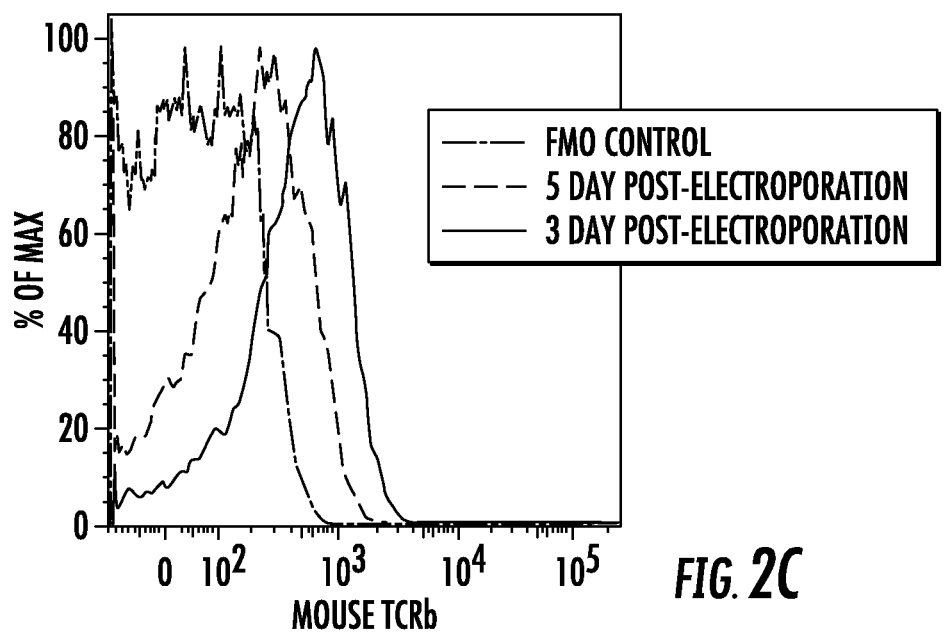

In order to bypass potential limitations in self-tolerance and the generation of unintended cross-reactivities, HLA transgenic mice were employed to elicit phosphopeptide-specific murine T-cells from which TCR chains were cloned. AAD mice, expressing a class I MHC molecule that contains the α1 and α2 domains from HLA-A2, and the α3, transmembrane, and cytoplasmic domains from H-2D$^d$, were immunized with autologous DC pulsed with either pIRS-2$_{1097-1105}$ or pCDC25b$_{38-46}$. CD8 T-cell lines derived from these animals secreted IFN-γ when cultured with AAD$^+$ targets pulsed with the phosphorylated forms of these epitopes but not their non-phosphorylated counterparts (see FIG. 1D; non-phosphorylated homolog indicated by triangles). However, they failed to recognize phosphopeptide-pulsed targets expressing fully human HLA-A2, most likely due to the low affinity of murine CD8 for the human α3 domain (see Cohen et al., 2006; Jorritsma et al., 2007).

cDNAs encoding the TCR α and β chains from pIRS-2$_{1097-1105}$-specific (SEQ ID NOs: 3 and 5 and 4 and 6, respectively) or pCDC25b$_{38-46}$-specific (SEQ ID NOs: 13 and 15, respectively) T-cell lines were molecularly cloned and utilized as templates to produce in vitro transcribed (IVT) RNA (Zhao et al., 2006; Santomasso et al., 2007). Electroporation of IVT RNA into either TCR-deficient SupT1 cells or human CD8 and CD4 T-cells resulted in surface expression as detected by staining for mouse TCRβ (FIGS. 2A and 2B). TCR expression was detected at high levels at 9 hours (FIG. 2B) with some TCR still detectable out to 5 days post-electroporation (FIG. 2C).

Human CD8 T-cells electroporated with IVT RNA encoding either TCR produced IFN-γ and/or upregulated CD107a, a marker of cytotoxic activity, in a dose-dependent manner after co-culture with phosphopeptide-pulsed AAD$^+$ targets (see FIGS. 3A and 3B). Both TCR conferred half-maximal recognition at a peptide dose of ~400-800 pM. In contrast to the murine T-cells expressing these TCR (FIG. 1D), the human CD8 T-cells recognized phosphopeptide-pulsed targets expressing HLA-A2 at least as well as those expressing AAD (FIGS. 3A and 3B). Neither cell produced IFN-γ or upregulated CD107a in response to HLA-A2$^+$ targets pulsed with high levels of the non-phosphorylated peptide. Human CD8 T-cells expressing the pIRS-2-specific murine TCR also killed pIRS-2$_{1097-1105}$-pulsed, but not pCDC25b$_{38-46}$-pulsed, targets in vitro (FIG. 3A), while those expressing the pCDC25b-specific TCR killed pCDC25b$_{38-46}$-pulsed but not pIRS-2$_{1097-1105}$ or pβ-catenin$_{30-39}$-pulsed targets (FIG. 3B). Thus, the expression of these murine TCR in human CD8 T-cells imparted phosphopeptide-specific, high-avidity recognition and both cytotoxic and cytokine-secreting effector activities.

Figure 3C:
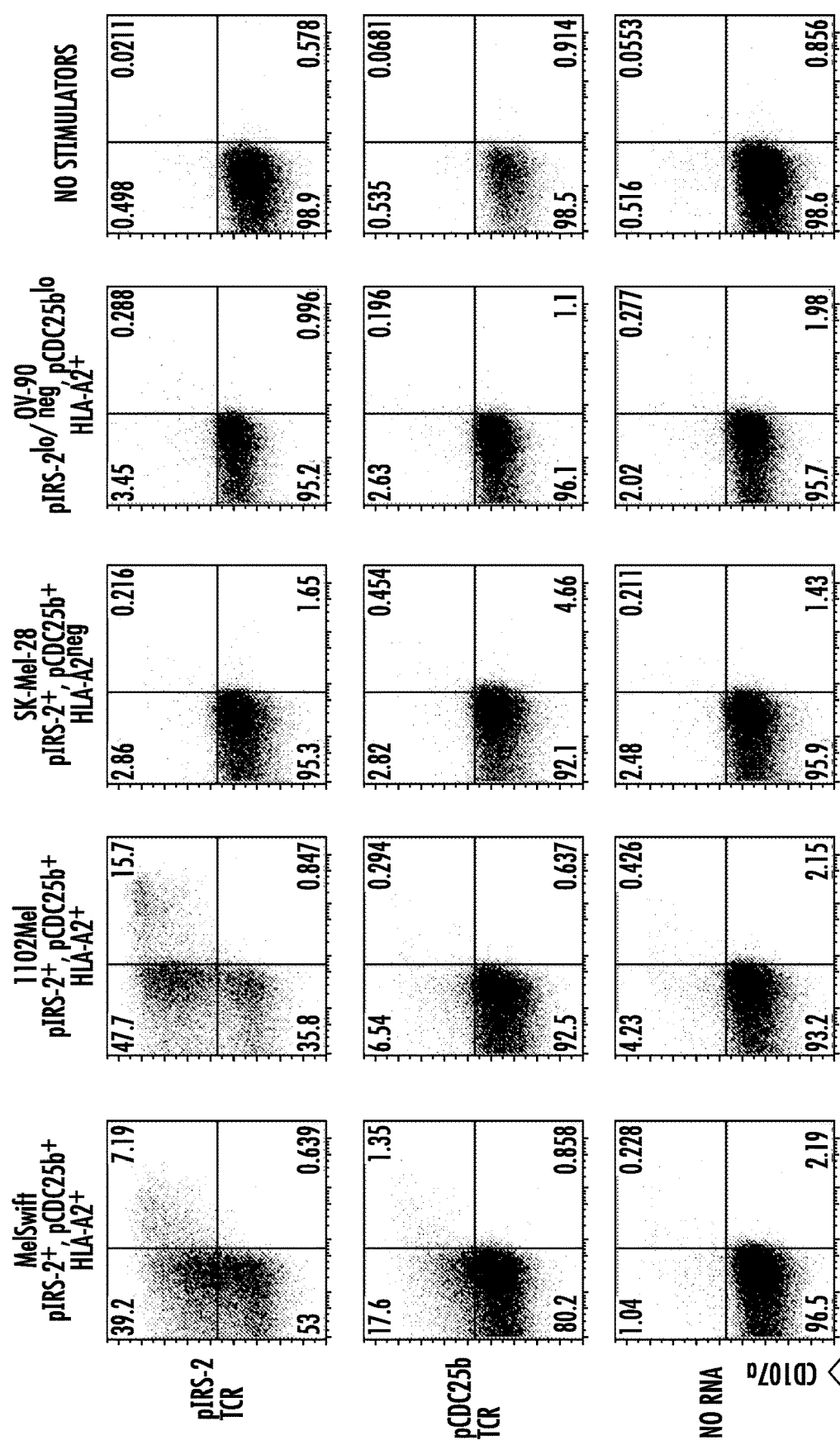

Example 3 pIRS-2$_{1097-1105}$ and pCDC25b$_{38-46}$ Phosphopeptides are Broadly Expressed on Cancer Cells Whether these transfected human CD8 T-cells could recognize endogenously processed and presented pIRS-2$_{1097-1105}$ or pCDC25b$_{38-46}$ phosphopeptide on HLA-A2$^+$ cancer cell lines was investigated. To correlate pIRS-2$_{1097-1105}$-specific T-cell recognition with phosphopeptide expression, an antibody specific for the Ser$^{1100}$-phosphorylated IRS-2 protein (pSer$^{1100}$-IRS-2) as well as an antibody that recognizes total IRS-2 protein (Zarling et al., 2006) were employed. A substantial fraction of pIRS-2$_{1097-1105}$-specific T-cells upregulated CD107a, and a subset of these also produced IFN-γ upon co-culture with two HLA-A2$^+$ melanoma cell lines, MelSwift and 1102Mel (FIG. 3C). These two cell lines also expressed high levels of pSer$^{1100}$-IRS-2 (FIG. 4). However, no recognition was evident upon co-culture with an HLA-A2$^{neg}$ pSer$^{1100}$-IRS-2$^+$ melanoma, SK-Mel-28, or an HLA-A2$^+$, low to negative pSer$^{1100}$-IRS-2 ovarian carcinoma, OV-90. There is no specific antibody for Ser$^{42}$-phosphorylated CDC25b. However, human CD8 T-cells transfected to express the pCDC25b$_{38-46}$-specific TCR recognized two HLA-A2$^+$ melanomas that expressed high levels of total CDC25b (MelSwift and 1102Mel), and failed to recognize either an HLA-A2$^{neg}$ CDC25b$^+$ melanoma, SK-Mel-28, or an HLA-A2$^+$ CDC25$^{lo}$ ovarian carcinoma, OV-90 (FIGS. 3C and 5).

These T-cells were then employed to evaluate expression of pIRS-2$_{4097-1105}$ and pCDC25b$_{38-46}$ on HLA-A2$^+$ cancer cell lines of different histological origins. For the HLA-A2$^+$ cancer cells, Western blots were loaded based on cell equivalents so it would be possible to correlate Ser$^{1100}$-phosphorylated IRS-2 directly with T-cell recognition. Although the amount varied, Ser$^{1100}$-phosphorylated IRS-2 was detected by Western blot in the majority of melanoma, ovarian cancer, colorectal adenocarcinoma, breast cancer, bladder cancer, and non-small cell lung cancer (NSCLC) lines evaluated, but was poorly expressed in prostate cancer cells (see FIGS. 4A and 4C). None of the bladder, prostate, or NSCLC cancer cells were HLA-A2$^+$ and their recognition by pIRS-2$_{1097-1105}$-specific T-cells could not be tested.

Figure 4A:
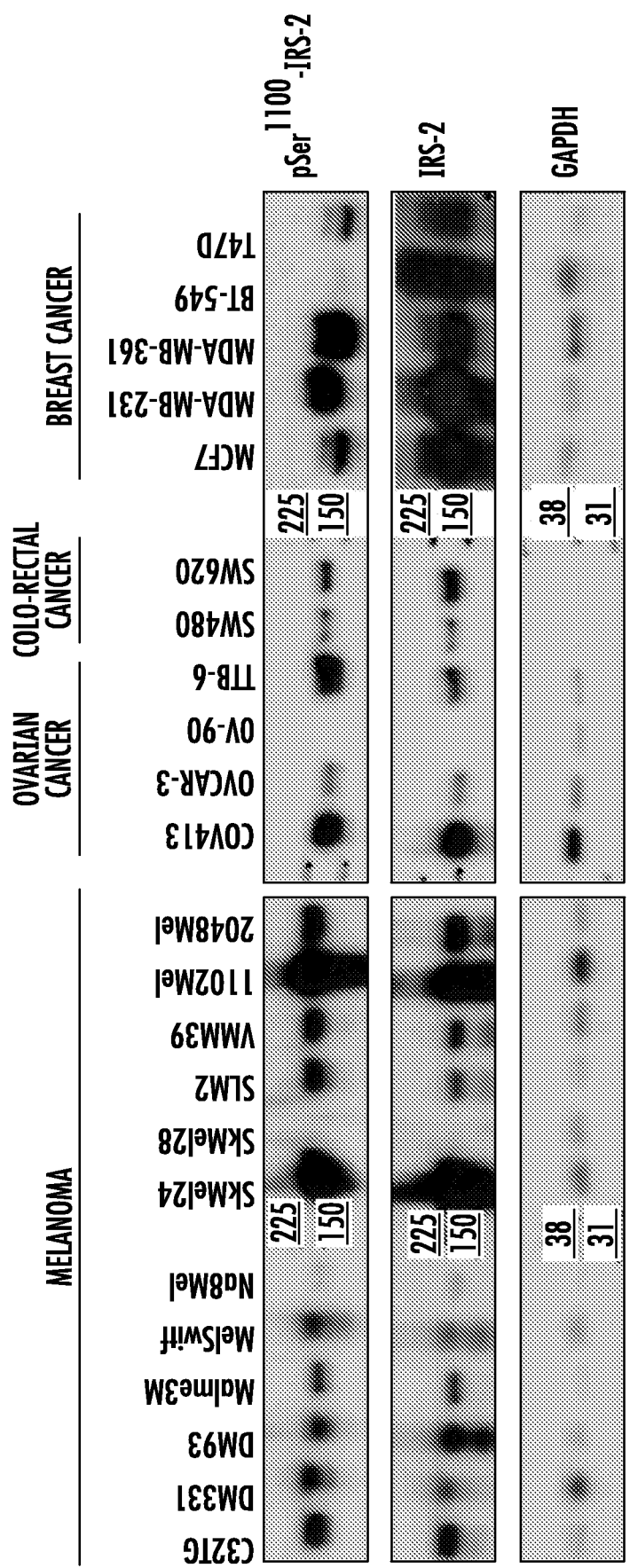
FIGS. 4A-4D depict the results of experiments showing that pIRS-$2_{1097-1105}$ was endogenously processed and presented by cancer cells of multiple histological types.
Figure 4B:
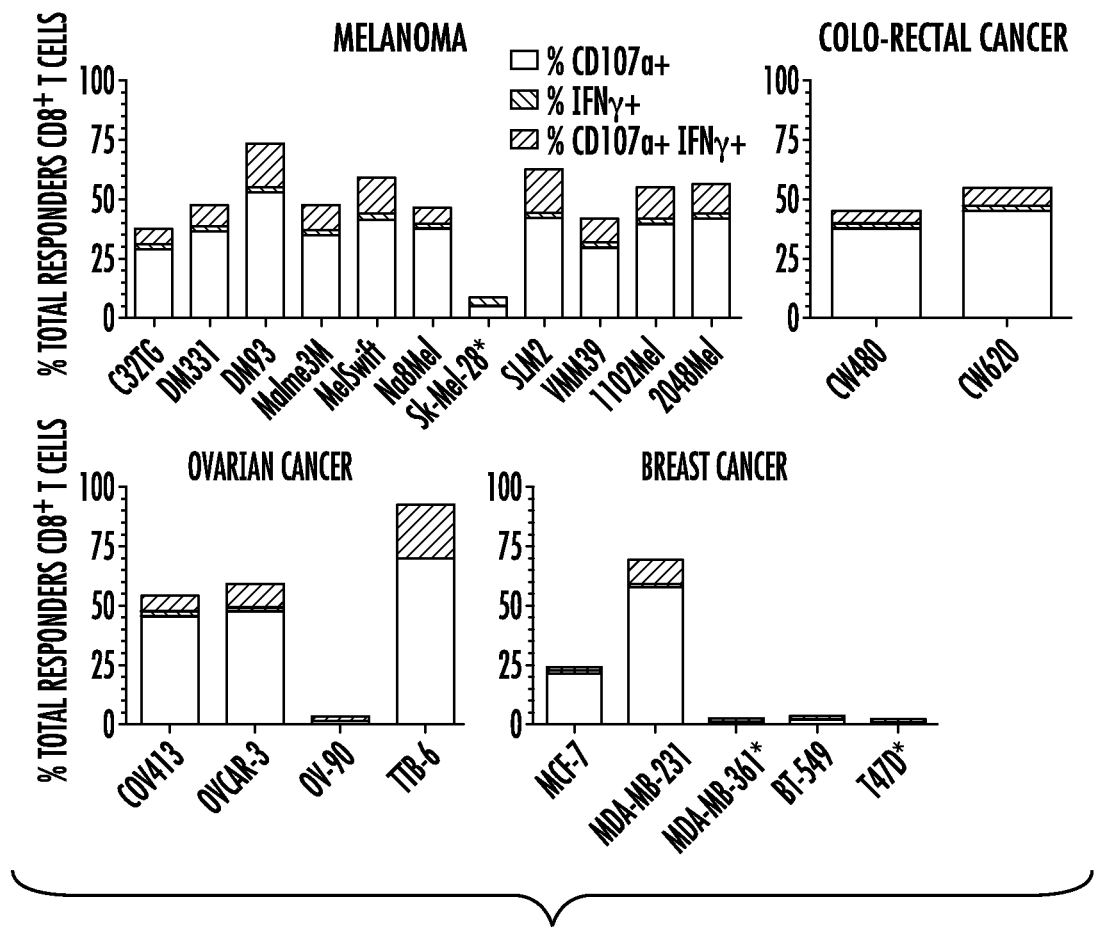
Figure 4C:
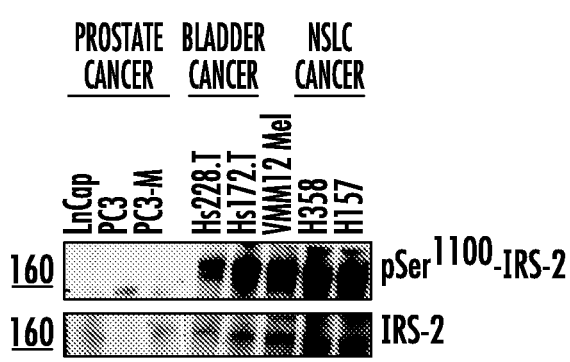
Figure 4D:
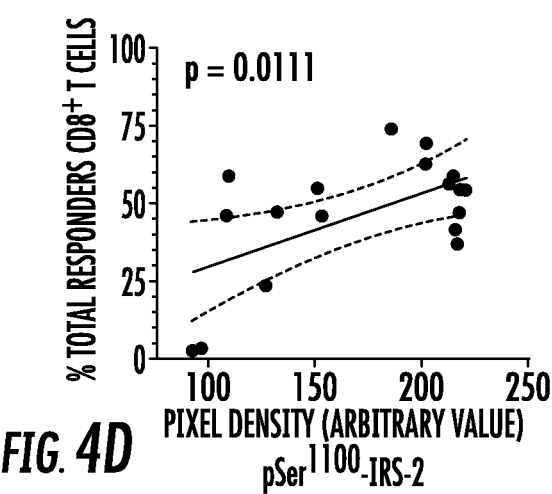
Figure 5A:
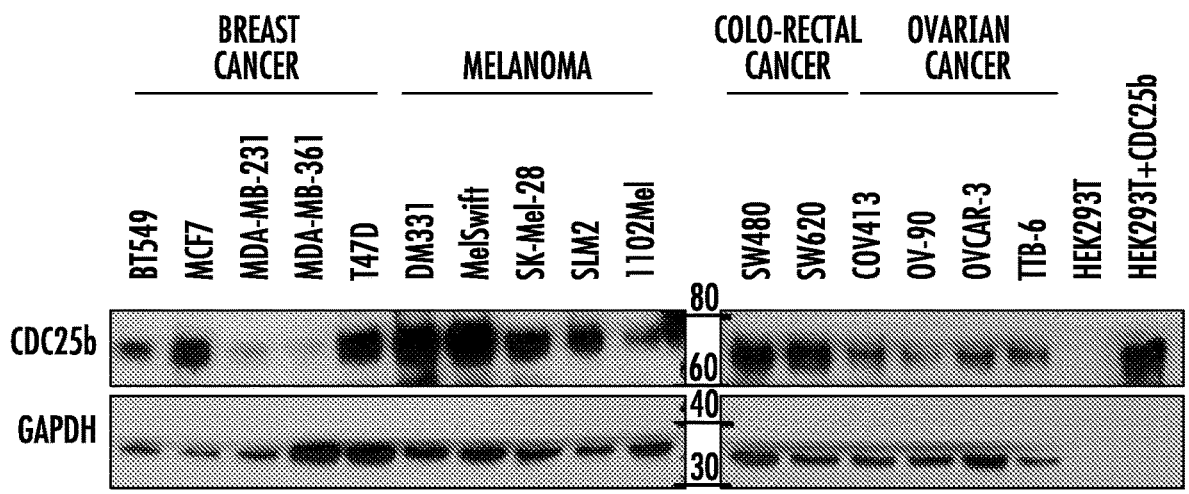
FIGS. 5A-5C show the results of experiments showing pCDC25b$_{38-46}$-specific TCR-expressing human CD8 T-cells recognized endogenously processed and presented phosphopeptide on human melanoma and breast cancer cells.
Figure 5B:
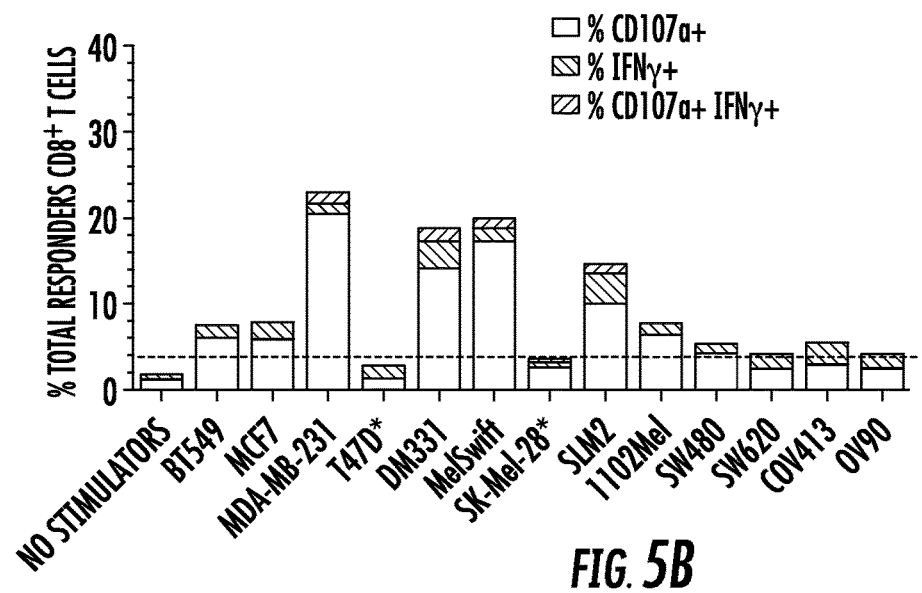

However, of the HLA-A2$^+$ cell lines evaluated, pIRS-2$_{1097-1105}$ was presented by 10/10 melanomas evaluated, 3/4 ovarian carcinomas, 2/2 colorectal carcinomas, and 2/3 breast carcinomas (see FIG. 4B). Cancer cells that were better recognized by pIRS-2$_{1097-1105}$-specific T-cells also expressed higher amounts of pSer$^{1100}$-IRS-2 detected by Western blot (FIG. 4D). pCDC25b$_{38-46}$-specific T-cells also did not recognize the HLA-A2$^{neg}$ cancer cells T47D and SK-Mel-28 (FIGS. 3C and 5B). They did recognize 3/4 HLA-A2$^+$ melanomas, 3/3 breast cancer lines (FIGS. 3C and 5B), and the HLA-A2$^+$ EBV-transformed lymphoblastoid cell line JY.

However, although pCDC25b-specific T-cells showed high avidity and high-level recognition of peptide-pulsed targets (see FIG. 3B), their recognition of these cancer cells was relatively low (see FIG. 5B). They also did not recognize the two colorectal adenocarcinomas and four ovarian cancer cell lines evaluated.

Figure 5C:
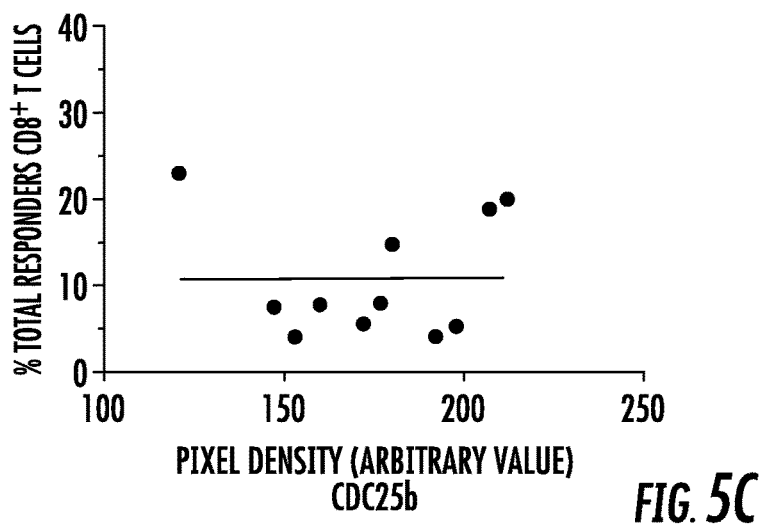

Good pCDC25b$_{38-46}$-specific T-cell recognition was associated with high level expression of the CDC25b source protein in some cells but low level expression in others, with no correlation between level of source protein and pCDC25b$_{38-46}$-specific T-cell recognition (FIG. 5C). This suggested that there were differences in the level or the turnover of pSer$^{42}$-CDC25b in relation to the total CDC25b protein in different cancer cells. In sum, pIRS-2$_{1097-1105}$ phosphopeptide was endogenously processed and presented in a large number of cancers of different histological origin, and this display elicited strong effector responses from pIRS-2-specific TCR-expressing human CD8 T-cells. In contrast, while pCDC25b$_{38-46}$ phosphopeptide was presented by melanoma, breast cancer, and EBV-transformed lymphoblastoid cell lines, its overall expression was more limited.

Example 4

Mitotically Active Melanoma Cells Express High Levels of pSer$^{1100}$-IRS-2 Protein The expression of pSer$^{1100}$-IRS-2 in human melanoma explants and normal tissues was evaluated. Sections from cell blocks containing the positive pSer$_{1100}$-IRS-2 SLM2 melanoma, the low to negative pSer-IRS-2 OV-90 ovarian carcinoma, and a melanoma metastasis to the lung, each of which had been stained in the presence or absence of blocking pIRS-2$_{4097-1105}$ phosphopeptide, were compared. The results are presented in FIG. 6.

Figures 6A, 6B, 6C:
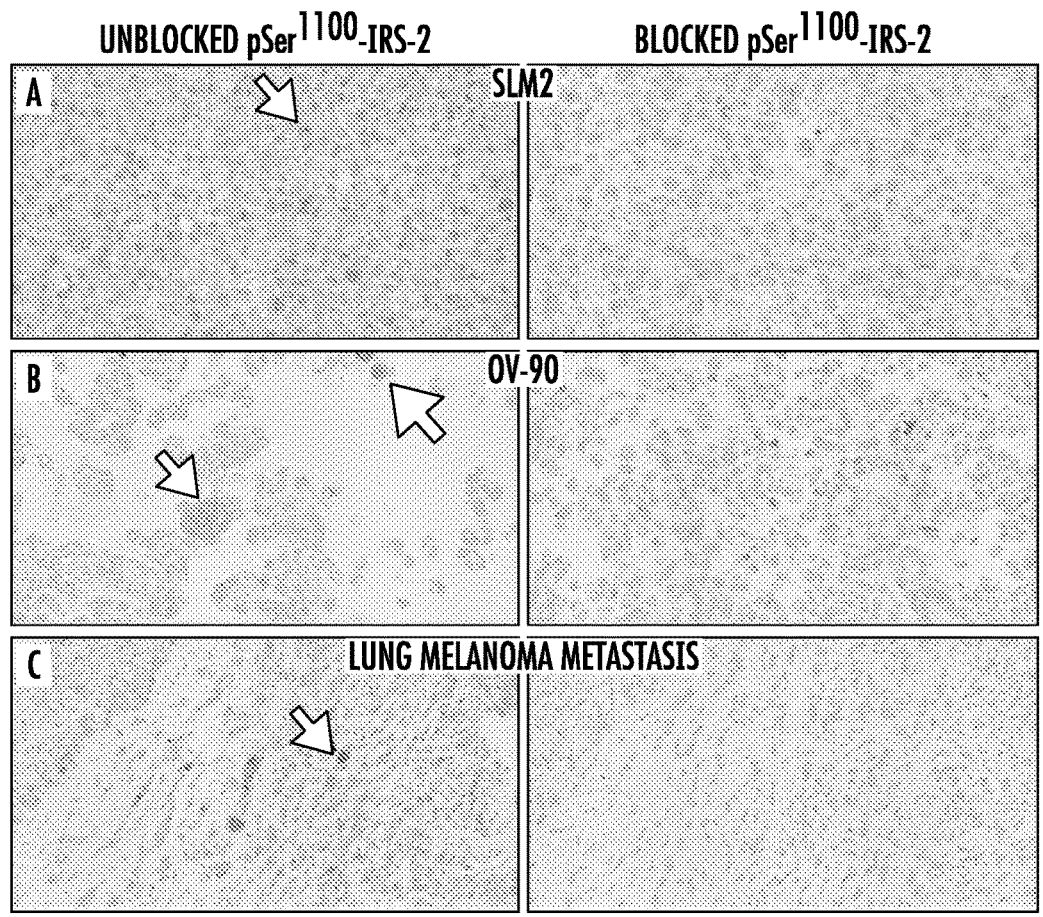
FIGS. 6A-6C are a series of immunohistochemistry photos showing that pSer$^{1100}$-IRS-2 staining was highest in mitotic cancer cells. pSer$^{1100}$-IRS-2 stained tissue sections from the melanoma cell line SLM2 (FIG. 6A), ovarian carcinoma OV-90 (FIG. 6B), and a lung melanoma metastasis (FIG. 6C) without (left panels) or with (right panels) blocking peptide added to antibody during staining. 100× magnification is shown. Arrows indicate mitotic cells.

As shown therein, addition of the blocking peptide largely eliminated staining for all samples. Strong cytoplasmic staining for pSer$^{1100}$-IRS-2 was evident in the SLM2 melanoma, with the highest staining in cells with condensed chromosomes and undergoing mitosis (FIG. 6A). Staining of mitotic cells was also evident in the OV-90 ovarian carcinoma, but these cells were a significantly lower fraction of the total cell number, and staining of non-mitotic cells was very weak (FIG. 6B). This was consistent with the very weak pSer$^{1100}$-IRS-2 Western blot staining (FIG. 4A) and lack of T-cell recognition by pIRS-2$_{1097-1105}$-specific T-cells (FIGS. 3C and 4B). Strong staining was also evident in the human melanoma lung metastasis specimen, again with the highest level in mitotic cells (FIG. 6C).

Figure 7:
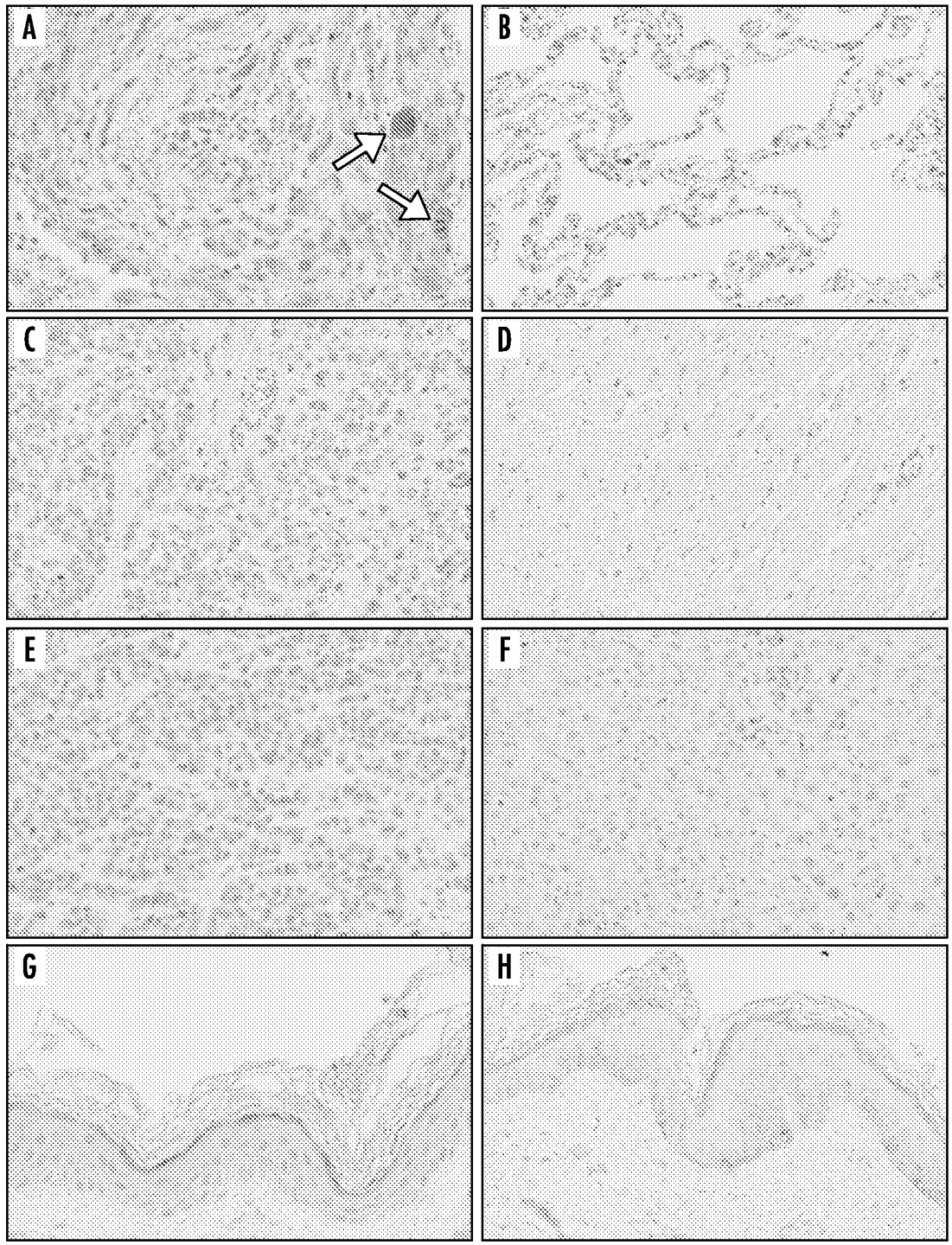
FIGS. 7A-7H are a series of immunohistochemistry photos showing Ser$^{100}$-phosphorylated IRS-2 expression in metastatic melanoma sections involving vital organs. pSer$^{1100}$-IRS-2 stained sections (100× magnification) from melanoma metastases in lung, heart and liver (FIGS. 7A, 7C, and 7E, respectively), together with the adjacent uninvolved tissues (FIGS. 7B, 7D, and 7F, respectively). Arrows in FIG. 7A indicate mitotic cells with intense staining; the strongest staining occurs in the large malignant cells with mitotic figures with the remainder being a mixture of non-mitotic melanoma cells and peritumoral stroma. Similar increased staining of mitotically active cells was observed in all melanoma metastases examined Normal skin specimens stained with pSer$^{1100}$-IRS-2 are shown in FIGS. 7G and 7H. Mild diffuse epidermal staining for pSer$^{1100}$-IRS-2 is present in FIG. 7G, and only partially diminished in the presence of blocking peptide (FIG. 7H).
Figure 8:
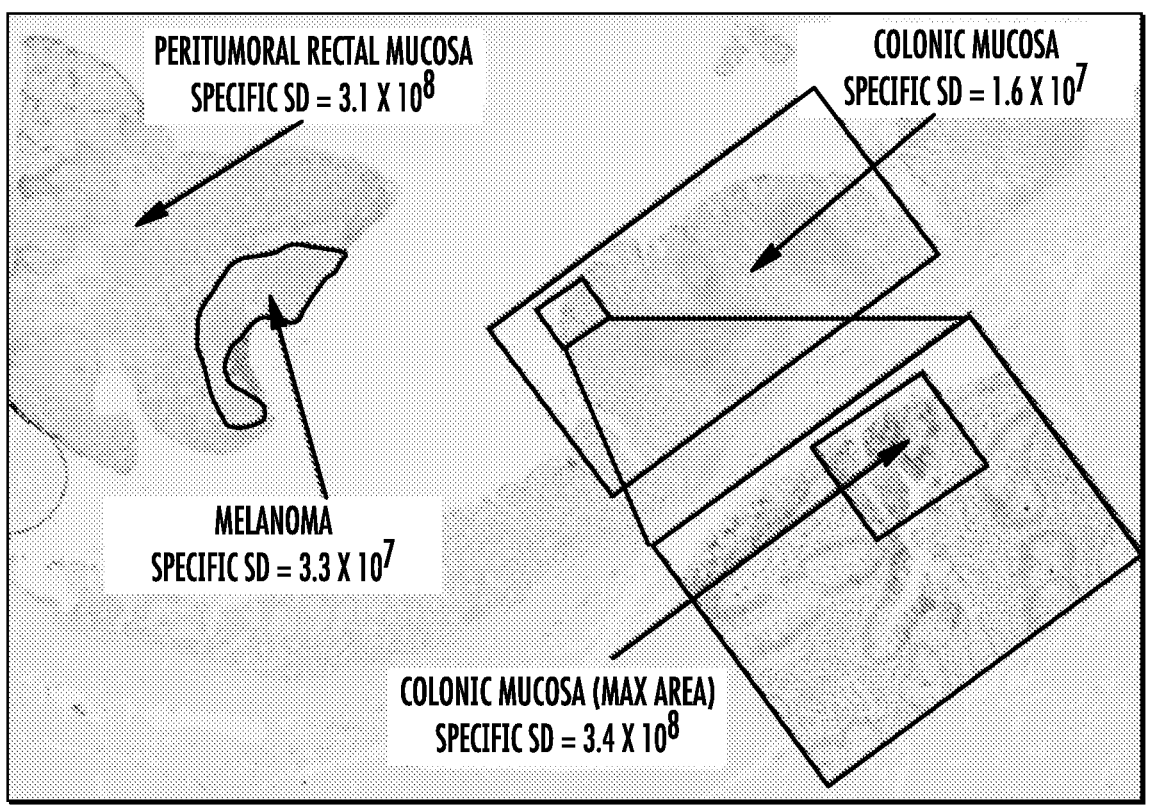
FIG. 8 is an immunohistochemistry photo showing pSer1100-IRS-2 staining of colon melanoma metastasis. pSer1100-IRS-2 staining of colorectal cancer containing a melanoma metastasis. Specific staining densities are identified for the melanoma ($3.3 \times 10^7$), peritumoral rectal mucosa ($3.1 \times 10^8$), and neighboring colonic mucosa ($1.6 \times 10^7$ or $3.4 \times 10^8$).

Tissue blocks of metastatic melanoma that included adjacent non-neoplastic tissue were also evaluated. The non-neoplastic tissues evaluated were heart (n=1), liver (n=1), lung (n=3), and colon (n=1). Addition of the blocking peptide almost completely inhibited staining for all of these samples. The melanoma metastases varied widely in their level of pSer$^{1100}$-IRS-2 (see FIGS. 7A, 7C, and 7E, and Table 2). Increased staining was observed in mitotically active melanoma cells and also in peritumoral stroma (FIGS. 7A and 8). When quantified as total staining intensity per unit area of tissue section, pSer-IRS-2 staining varied among normal tissues, but was not convincingly different than that in tumors (see Table 2 below). However, there were few mitotic cells and thus few intensely staining cells in most normal tissues (FIGS. 7B, 7D, and 7F). High staining intensities were observed in colonic mucosal epithelial cells adjacent to a melanoma metastasis (FIG. 8), and in normal colon biopsies. This might have been indicative of the high mitotic activity of colonic epithelial cells. The high staining of mucosal epithelial cells was mainly limited to those at the epithelial surface; whereas staining of deeper portions of the mucosa and submucosa was lower than that of the rectal melanoma shown (FIG. 8).

It was also notable that rectal mucosa and stroma immediately adjacent to the rectal melanoma had focally high staining intensity. To explore whether high staining intensity in normal superficial mucosal epithelial cells in the colon might signal a more global high expression in surface epithelium generally, normal skin was also stained. There was low staining in the epidermis, much of which persisted despite peptide blocking, indicating that the staining of normal epidermis was largely non-specific (see FIGS. 7G and 7H).

TABLE 2

Specific Anti-Ser1100-pIRS-2 Staining Density (Positive Pixel Count × $10^7/\mu^2$) for Melanoma Metastases and Surrounding Tissues

| Tissue specimen | Melanoma Metastasis | Adjacent Normal Tissue | Pseudostratified Respiratory Epithelium within Normal Tissue | Peritumoral Stroma |
|---|---|---|---|---|
| Heart muscle with melanoma metastasis | 2.2 | 0.4 | ND | ND |
| Liver with melanoma metastasis | 1.5 | 4.3 | ND | ND |
| Lung with melanoma metastasis A | 6.1 | 1.7 | 5.5 | 2.8 |
| Lung with melanoma metastasis B | 7.1 | 9.8 | 21 | 14 |
| Lung with melanoma metastasis C | 9.4 | 2.5 | ND | ND |
| Colon with melanoma metastasis | 3.3 | 1.6-34 | | |
| Normal skin A | ND | 0.42 | | |
| Normal skin B | ND | 2.4 | | |
| Mean in mitotic cells (lung with melanoma metastasis B)** | 27 | ND | ND | ND |
| Mean in mitotic cells (SLM2 melanoma)* | 419.5 | | | |

Specific staining with anti-Ser1100-pIRS-2 was determined by subtracting the positive pixel count (PPC) for representative sections from peptide-blocked slides from the PPC from corresponding representative sections without blocking peptide.
ND = not done.
**mean for mitotic cells (n = 5) in Lung B melanoma metastasis.
*mean for mitotic cells (n = 5) in SLM2 melanoma cells in vitro.

Overall, these data suggested that successful immune targeting of pSer$^{1100}$-IRS-2: 1) might selectively target dividing malignant cells; and 2) also might target peritumoral stroma. Each of these could support tumor control. The data also raised the possibility that immune targeting of pSer$^{1100}$-IRS-2 could carry some risk of adverse effects on colonic epithelium but not other normal tissues evaluated.

Example 5

Phosphopeptide-Specific TCR-Expressing T-Cells can Slow Tumor Outgrowth

Whether these two phosphopeptides could serve as immunotherapeutic targets for treatment of cancer was also tested. NOD/SCID/IL-2Rγc$^{-/-}$ mice were inoculated subcutaneously with SLM2 melanoma cells, and 3 days later were injected with human CD8 T-cells expressing either the pIRS-2-specific or pCDC25b-specific TCR, or both populations, together with IL-2. A second infusion of transfected CD8 T-cells was given 4 days later. Outgrowth of tumor was evident past day 25 in all groups (see FIG. 9), most likely due to gradual loss of expression of the phosphopeptide-specific murine TCR (FIG. 2C), or loss of the T-cells.

Figure 9A:
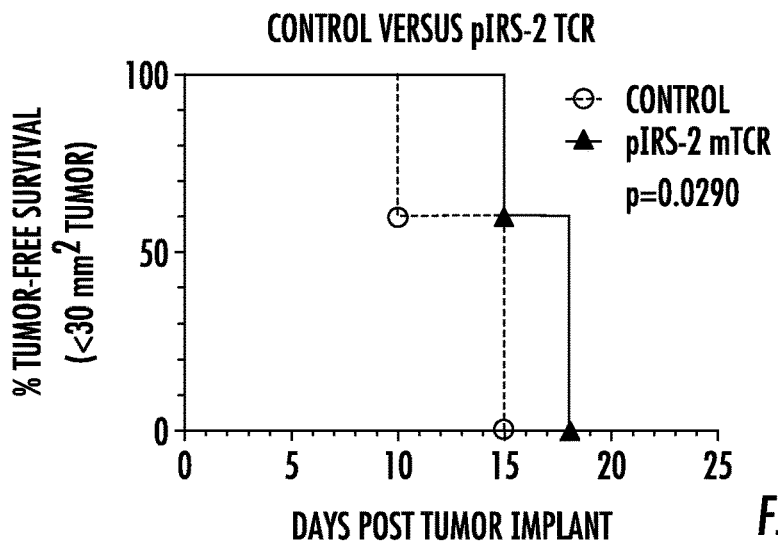
FIGS. 9A-9C are a series of plots showing enhanced tumor-free survival following adoptive transfer of phosphopeptide-specific TCR-expressing human CD8 T-cells. SLM2AAD melanoma tumor-bearing NOD/SCID/IL-2Rγc$^{-/-}$ mice were injected with phosphopeptide-specific TCR-expressing human CD8 T-cells on days 3 and 7, together with 1500 CU/ml IL-2 every other day for 10 days. Control animals (open circles) only received IL-2.
Figure 9B:
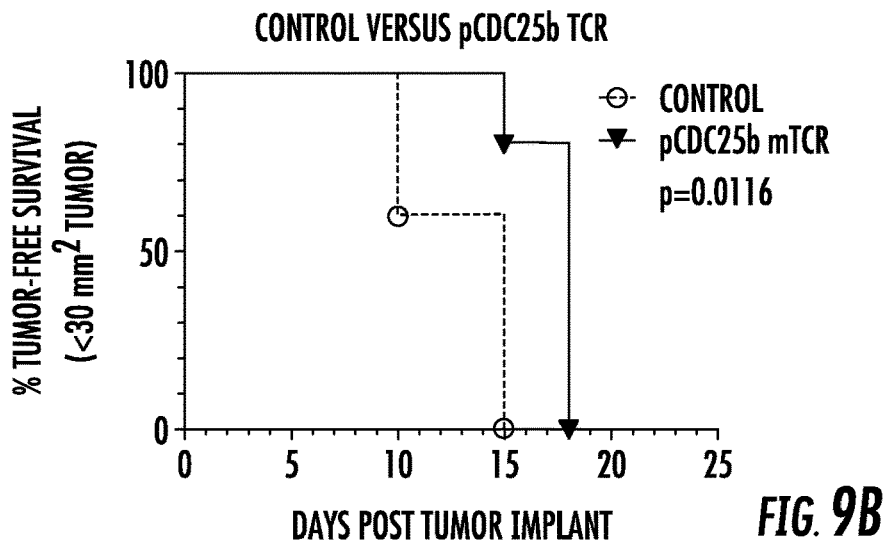
Figure 9C:
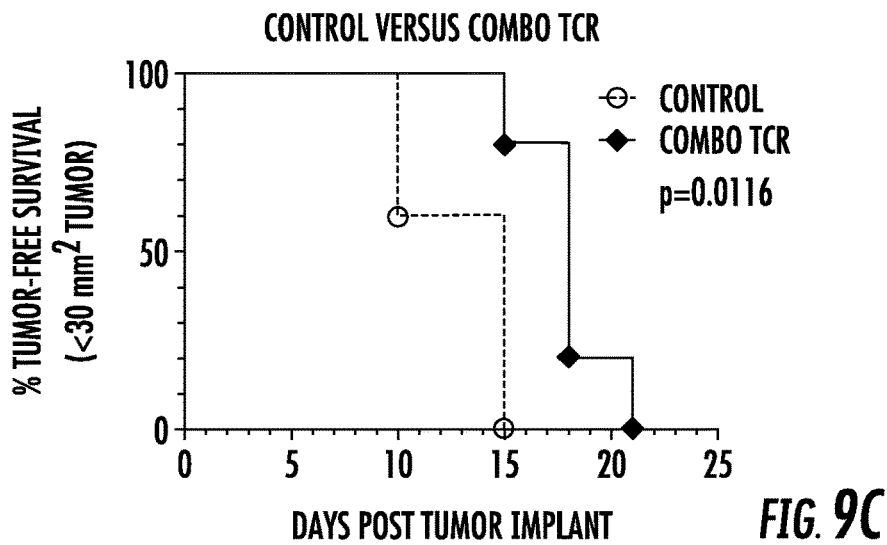
Figure 10A:
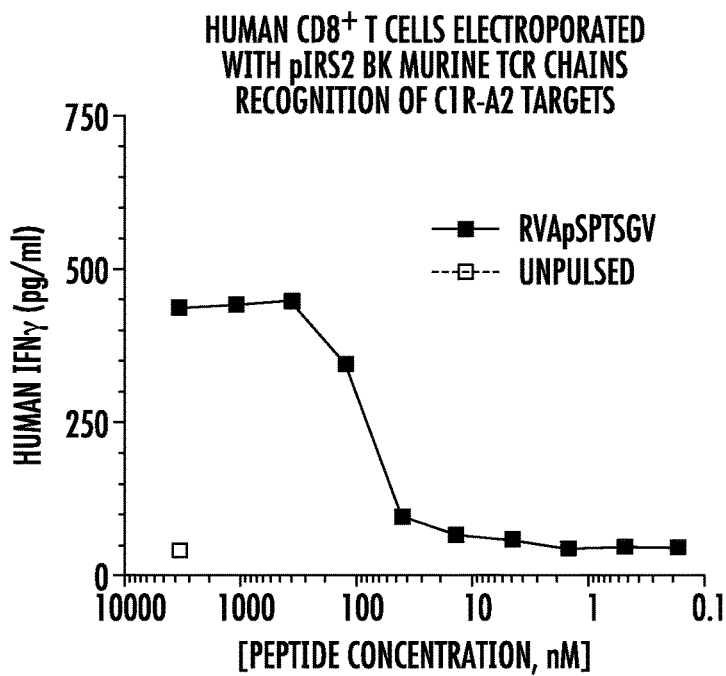
FIGS. 10A-10B depict the results of experiments showing expression of phosphopeptide-specific murine TCR in human CD8 T-cells conferred recognition of HLA-A2+ targets and effector function. Human CD8 T-cells were electroporated with IVT RNA encoding murine TCR αβ chains specific for pIRS-2 (pIRS2 BK TCR.
Figure 10B:
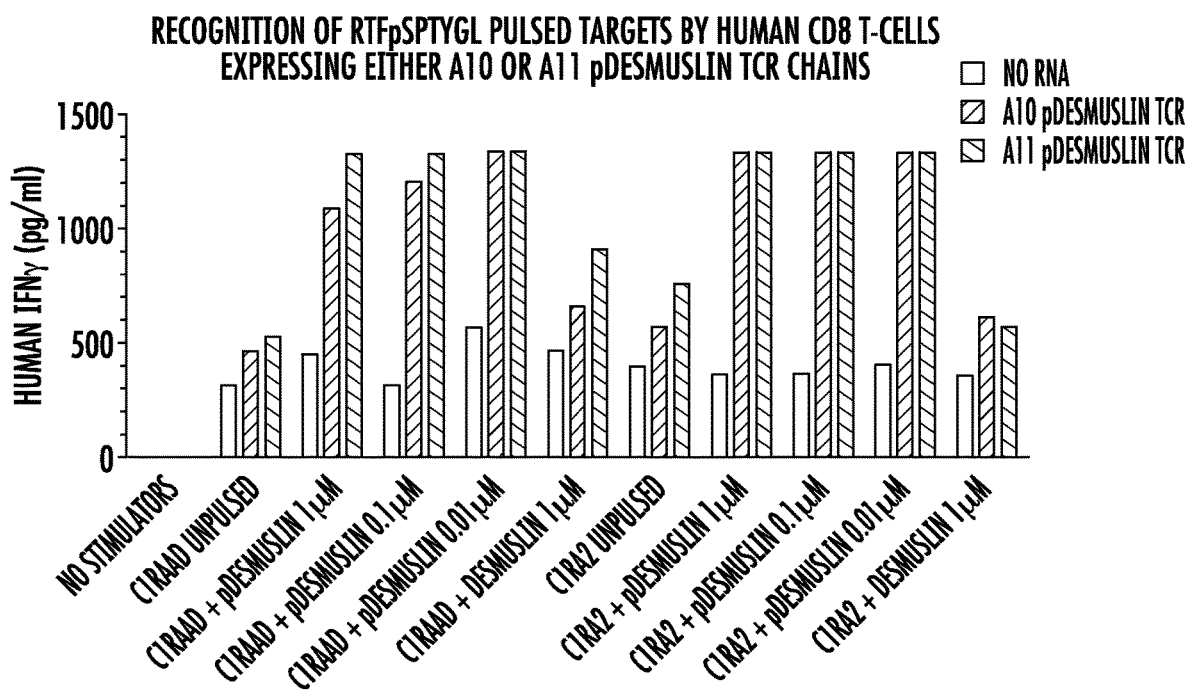
Figure 11A:
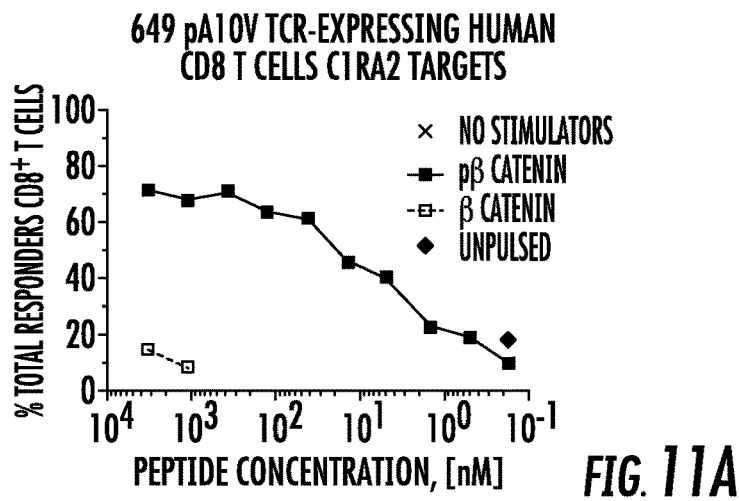
FIGS. 11A-11C depict the results of experiments showing expression of pβcatenin-specific murine TCR in human CD8 T-cells conferred recognition of HLA-A2+ targets and effector function. Human CD8 T-cells were electroporated with IVT RNA encoding phosphopeptide-specific murine TCR αβ chains (FIG. 11A: 649 pA10V βcatenin TCR; B: 653 pβcatenin TCR, and assayed 12-14 hours later.
Figure 11B:
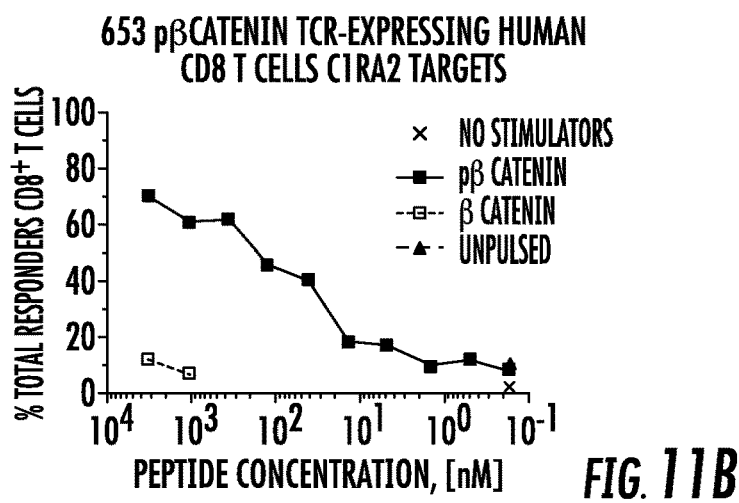
Figure 11C:
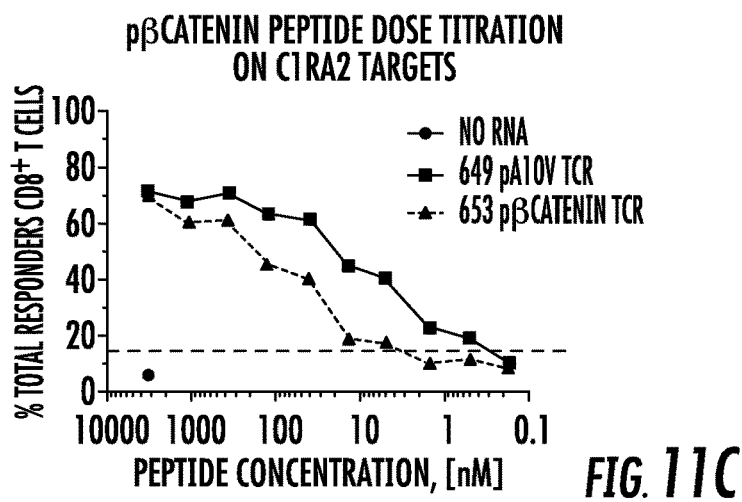

However, animals that had received phosphopeptide-specific TCR-expressing cells remained tumor-free (tumor size less than 30 mm$^2$) for significantly longer than control animals that only received IL-2 (see FIG. 9). Indeed, infusion of either pIRS-2$_{1097-1105}$-specific or pCDC25b$_{38-46}$-specific CD8 T-cells or both populations resulted in delayed outgrowth in comparison to the control animals. Overall, this demonstrated that the endogenous levels of pIRS-2$_{1097-1105}$ and pCDC25b$_{38-46}$ phosphopeptide on melanoma were sufficient for T-cell recognition and allowed some delay in tumor growth in vivo.

Discussion of the Examples

Disclosed herein are the characterizations of two new phosphopeptide TAAs, pIRS-2$_{1097-1105}$ and pCDC25b$_{38-46}$, which are endogenously processed and presented on multiple HLA-A2$^+$ cancers. Both phosphopeptides were strongly immunogenic in vitro for human T-cells and in vivo for HLA-A2 transgenic mice, lending credence to their effectiveness as vaccines. Indeed, memory responses in four normal healthy donors to the pCDC25b$_{38-46}$ phosphopeptide and 2/4 normal donors to the pIRS-2$_{1097-1105}$ phosphopeptide were observed. This suggested that these healthy individuals had been previously exposed to a stimulus that has established immunological memory to these two phosphorylated TAAs.

Immunological responses to cancer-testes antigens is usually only seen in cancer patients, not normal individuals, and is associated with poor prognosis (Scanlan et al., 2002). Tolerance is also believed to limit much of the immune response to the tissue-associated differentiation antigens (Colella et al., 2000; Touloukian et al., 2003). Memory responses to the pIRS-2$_{1097-1105}$ and pCDC25b$_{38-46}$ phosphopeptide in normal individuals are evidence of previous encounters with nascent tumors that have disregulated phosphorylation cascades.

To explore the display of endogenously processed and presented phosphopeptide on cancer cells, the TCRs from murine CD8 T-cell lines specific for each phosphopeptide were isolated and transfected into human CD8 T-cells. A phosphosite-specific antibody was also employed to determine whether patient tumor samples and cancers of different histological origins expressed the phosphorylated IRS-2 source protein. pIRS-2$_{4097-1105}$-specific murine TCR-modified human CD8 T-cells recognized endogenously processed and presented phosphopeptide on multiple HLA-A2+ melanomas and breast, ovarian, and colorectal carcinomas, and this recognition correlated with the level of expression of $Ser_{1100}$-phosphorylated IRS-2 source protein. Mitotically active cells also had the strongest staining for $Ser^{1100}$-phosphorylated IRS-2 protein, in both tumors and surrounding peritumoral areas.

pCDC25b$_{38-46}$-specific TCR-modified human CD8 T-cells recognized endogenously processed and presented phosphopeptide on several HLA-A2+ melanoma, breast cancer, and lymphoblastoid cell lines. Thus, disclosed herein are new reagents that can be utilized to evaluate and treat cancer patients: murine TCR chains specific for either pIRS-$2_{1097-1105}$- or pCDC25b$_{38-46}$-peptides that can be utilized as immunotherapeutic agents to target patient's immune responses against these post-translationally modified epitopes. In addition, the pIRS-$2_{1097-1105}$-specific TCR therapy can be combined with $Ser^{1100}$-IRS-2 phospho-specific antibody to determine whether patient tumor samples express $pSer^{1100}$-IRS-2 protein.

One approach currently showing some promise for the treatment of cancer patients involves the adoptive transfer of tumor-specific CD8 T-cells, generated through vaccination and/or by genetic modification via expression of TCR chains specific for an appropriate TAA (Rosenberg, 2008). Most of the TCR chains currently cloned and studied in human clinical trials for melanoma have been specific for melanocyte differentiation proteins (Rosenberg et al., 2004; Rosenberg, 2008; Park et al., 2011). Although of importance for melanoma, extending this form of immunotherapy to antigens that are broadly expressed on other types of cancers, such as disclosed herein for the pIRS-$2_{1097-1105}$ and pCDC25b$_{38-46}$ phosphopeptides, can facilitate the broadening of adoptive cell therapy to multiple cancer patients.

In sum, pIRS-$2_{1097-1105}$ phosphopeptide was presented by a large number of cancers of different histological origin, and this display elicited strong effector responses from pIRS-2-specific TCR-expressing human CD8 T-cells. Similarly, while pCDC25b$_{38-46}$ phosphopeptide was presented by melanoma, breast cancer, and EBV-transformed lymphoblastoid cell lines, its overall expression was more limited.

REFERENCES

All references listed in the instant disclosure, including but not limited to all patents, patent applications and publications thereof, scientific journal articles, and database entries (including but not limited to GENBANK® database entries and including all annotations available therein) are incorporated herein by reference in their entireties to the extent that they supplement, explain, provide a background for, and/or teach methodology, techniques, and/or compositions employed herein. The discussion of the references is intended merely to summarize the assertions made by their authors. No admission is made that any reference (or a portion of any reference) is relevant prior art. Applicants reserve the right to challenge the accuracy and pertinence of any cited reference.

Altschul et al. (1990) *J Mol Biol* 215:403-410
Ausubel et al. (1989), *Current Protocols in Molecular Biology*, John Wiley & Sons, New York.
Ausubel et al. (1995) *Short Protocols in Molecular Biology*, 3rd ed. John Wiley & Sons, New York, N.Y., United States of America.
Beckett et al. (1999) *Protein Sci* 8:921-929.
Boissan et al. (2005) *Am J Pathol* 167:869-877.
Boon et al. (1994) *Annu Rev Immunol* 12:337-365.
Chan & Lee (2008) *J Mammary Gland Biol Neoplasia* 13:415-422.
Clark et al. (1989) *Eur J Immunol* 19:381-388.
Clay et al. (1999) *J Immunol* 163:507-513.
Cobbold et al. (2013) *Sci Transl Med* 5:203ra125-203ra125.
Cohen et al. (2006) *Cancer Res* 66:8878-8886.
Colella et al. (2000) *J Exp Med* 191:1221-1231.
Dearth et al. (2006) *Mol Cell Biol* 26:9302-9314.
Dearth et al. (2007) *Cell Cycle* 6:705-713.
Dunn et al. (2004) *Annu Rev Immunol* 22:329-360.
Fremont et al. (1996) *Curr Opin Immunol* 8:93-100.
Great Britain Patent Publication GB 2249310A.
GENBANK® Biosequence Database Accession Nos. NM_001904.3; NM_021873.3; NM_145728.2; NP_001895.1; NP_003740.2; NP_056101.5; NP_068658.1; NP_663780.2.
Henikoff & Henikoff (1992) *Proc Natl Acad Sci USA* 89:10915-10919
Hirohashi et al. (2009) *Cancer Sci* 100:798-806.
Hiugano et al. (2009) *Cancer* 115:3670-3679.
Hogan et al. (1998) *Cancer Res* 58:5144-5150.
Jackson et al. (2001) *Oncogene* 20:7318-7325.
Jacob et al. (1997) *Int J Cancer* 71:325-332.
Johnson et al. (2006) *J Immunol* 177:6548-6559.
Johnson et al. (2009) *Blood* 114:535-546.
Jorritsma et al. (2007) *Blood* 110:3564-3572.
Karlin & Altschul (1993) *Proc Natl Acad Sci USA* 90:5873-5877.
Kim et al. (2004) *Oncogene* 23:130-141.
Knobbe & Reifenberger (2003) *Brain Pathol* 13:507-518.
Molloy et al. (2005) *Curr Opin Pharmacol* 5:438-443.
Morgan et al. (2006) *Science* 314:126-129.
Morin (1999) *Bioessays* 21:1021-1030.
Moskaug, et al. *J Biol Chem* 264:15709-15713.
Mosquera et al. (2005) *J Immunol* 174:4381-4388.
Nagle et al. (2004) *Mol Cell Biol* 24:9726-9735.
Needleman & Wunsch (1970) *J Mol Biol* 48:443-453.
Olsnes & Pihl (1981) *Pharmacol Ther* 15:355-381.
Park et al. (2011) *Trends Biotechnol* 29:550-557.
Parmiani et al. (2002) *J Natl Cancer Inst* 94:805-818.
Parsons et al. (2005) *Nature* 436:792-.
Pastan et al. (1986) *Cell* 47:641.
Pastan et al. (1992) *Ann Rev Biochem* 61:331-354.
PCT International Patent Application Publication Nos. WO 1994/04689; WO 1994/29350; WO 1996/013593; WO 1998/007876; WO 1998/39482; WO 1999/018129; WO 2001/062908; WO 2002/085287; WO 2004/056845; WO 2004/106380; WO 2004/202657; WO 2009/117102; WO 2013/057586.
Pearson & Lipman (1988) *Proc Natl Acad Sci USA* 85:2444-2448.
Pecorari et al. (1999) *J Mol Biol* 285:1831-1843.
Peiper et al. (1997) *Eur Immunol* 27:1115-1123.
Peoples et al. (1993) *Surgery* 114:227-234.
Richman & Kranz (2007) *Biomol Eng* 24:361-373,
Rock & Goldberg (1999) *Annu Rev Immunol* 17:739-779.
Rosenberg et al. (2004) *Nat Med* 10:909-915.
Rosenberg (2008) *Proc Natl Acad Sci USA* 105:12643-12644.
Sambrook & and Russell (2001) *Molecular Cloning: A Laboratory Manual, Third Edition*, Cold Spring Harbor Laboratory Press, Cold Spring Harbor, N.Y., United States of America.
Santomasso et al. (2007) *Proc Natl Acad Sci USA* 104:19073-19078.
Scanlan et al. (2002) *Immunol Rev* 188:22-32.

Schendel et al. (1993) *J Immunol* 151:4209-4220.
Schwartzentruber et al. (2011) *New Eng J Med* 364:2119-2127.
Simpson et al. (2005) *Nat Rev Cancer* 5:615-625.
Slingluff et al. (1994) *Cancer Res* 54:2731-2737.
Slingluff et al. (2004) *J Clin Oncol* 22:4474-4485.
Slingluff et al. (2009) *Clin Cancer Res* 15:7036-7044.
Slovin et al. (1986) *J Immunol* 137:3042-3048.
Smith & Waterman (1981) *Adv Appl Math* 2:482-489
Springer (2004) *Suicide Gene Therapy: Methods and Reviews* (Methods in Molecular Medicine), Humana Press, New York, N.Y., United States of America.
Touloukian et al. (2003) *J Immunol* 170:1579-1585.
U.S. Patent Application Publication Nos. 2002/0119149; 2005/0214284; 2008/0015139; 2009/0117102; 2011/0070191; 2012/0252742.
U.S. patent application Ser. Nos. 08/813,781; 08/943,086.
U.S. Pat. Nos. 4,361,539; 5,620,939; 5,968,509; 6,277,633; 6,521,457; 6,706,265; 6,750,325; 7,569,664; 8,119,772; 8,552,150.
Van Wauwe (1980) *J Immunol* 124:2708-2718.
Watts (1997) *Annu Rev Immunol* 15: 821-850.
Watts (1997) *Annu Rev Immunol* 15:821-850.
Weber (2002) *Cancer Invest* 20:208-221.
Williamson et al. (2006) *Proc Natl Acad Sci USA* 103: 14649-14650.
Wong et al. (1990) *Transplantation* 50:683-689.
Yasumura et al. (1993) *Cancer Res* 53:1461-1468.
Yoshino et al. (1994) *Cancer Res* 54:3387-3390.
Zarling et al. (2000) *J Exp Med* 192:1755-1762.
Zarling et al. (2006) *Proc Natl Acad Sci USA* 103:14889-14894.
Zarling et al. (2014) *Cancer Res* 74:6784-6795.
Zhao et al. (2005) *J Immunol* 174:4415-4423.

It will be understood that various details of the presently disclosed subject matter may be changed without departing from the scope of the presently disclosed subject matter. Furthermore, the foregoing description is for the purpose of illustration only, and not for the purpose of limitation.

---

What is claimed is:

1. An isolated T cell receptor (TCR), or portion thereof, that specifically binds to a phosphopeptide-HLA-A2 complex, wherein the phosphopeptide has the amino acid sequence set forth in SEQ ID NO: 12, and the isolated TCR, or portion thereof, comprises:
an alpha chain variable domain comprising a CDR1 region sequence comprising amino acids 48-53 of SEQ ID NO: 14, a CDR2 region sequence comprising amino acids 71-77 of SEQ ID NO: 14, and a CDR3 region sequence comprising amino acids 112-121 of SEQ ID NO: 14; and
a beta chain variable domain comprising a CDR1 region sequence comprising amino acids 56-60 of SEQ ID NO: 16, a CDR2 region sequence comprising amino acids 78-83 of SEQ ID NO: 16, and a CDR3 region sequence comprising amino acids 121-129 of SEQ ID NO: 16.

2. The isolated TCR, or portion thereof, of claim 1, wherein the alpha chain variable domain comprises an amino acid sequence at least 95% identical to amino acids 22-132 of SEQ ID NO: 14.

3. The isolated TCR, or portion thereof, of claim 1, wherein the beta chain variable domain comprises an amino acid sequence at least 95% identical to amino acids 30-138 of SEQ ID NO: 16.

4. The isolated TCR, or portion thereof, of claim 1, wherein the alpha chain variable domain comprises an amino acid sequence at least 95% identical to amino acids 22-132 of SEQ ID NO: 14, and wherein the beta chain variable domain comprises an amino acid sequence at least 95% identical to amino acids 30-138 of SEQ ID NO: 16.

5. The isolated TCR, or portion thereof, of claim 1, wherein the alpha chain variable domain comprises the amino acid sequence of amino acids 22-132 of SEQ ID NO: 14, and wherein the beta chain variable domain comprises the amino acid sequence of amino acids 30-138 of SEQ ID NO: 16.

6. An isolated TCR alpha chain, or portion thereof, comprising an alpha chain variable domain comprising a CDR1 region sequence comprising amino acids 48-53 of SEQ ID NO: 14, a CDR2 region sequence comprising amino acids 71-77 of SEQ ID NO: 14, and a CDR3 region sequence comprising amino acids 112-121 of SEQ ID NO: 14.

7. The isolated TCR alpha chain, or portion thereof, of claim 6, wherein the alpha chain variable domain comprises an amino acid sequence at least 95% identical to amino acids 22-132 of SEQ ID NO: 14.

8. The isolated TCR alpha chain, or portion thereof, of claim 6, wherein the alpha chain variable domain comprises the amino acid sequence of amino acids 22-132 of SEQ ID NO: 14.

9. An isolated TCR beta chain, or portion thereof, comprising a beta chain variable domain comprising a CDR1 region sequence comprising amino acids 56-60 of SEQ ID NO: 16, a CDR2 region sequence comprising amino acids 78-83 of SEQ ID NO: 16, and a CDR3 region sequence comprising amino acids 121-129 of SEQ ID NO: 16.

10. The isolated TCR beta chain, or portion thereof, of claim 9, wherein the beta chain variable domain comprises an amino acid sequence at least 95% identical to amino acids 30-138 of SEQ ID NO: 16.

11. The isolated TCR beta chain, or portion thereof, of claim 9, wherein the beta chain variable domain comprises the amino acid sequence of amino acids 30-138 of SEQ ID NO: 16.

12. The isolated TCR, or portion thereof, of claim 1, wherein the isolated TCR, or portion thereof, is conjugated to an active agent.

13. The isolated TCR, or portion thereof, of claim 12, wherein the active agent is a detectable label selected from the group consisting of biotin, streptavidin, an enzyme or catalytically active fragment thereof, a radionuclide, a nanoparticle, a paramagnetic metal ion, and a fluorescent, phosphorescent, or chemiluminescent molecule.

14. The isolated TCR, or portion thereof, of claim 12, wherein the active agent is an immunostimulatory molecule.

15. The isolated TCR, or portion thereof, of claim 14, wherein the immunostimulatory molecule is a CD3 agonist wherein said CD3 agonist is an anti-CD3 antibody.

16. The isolated TCR, or portion thereof, of claim 12, wherein the active agent is a therapeutic agent selected from the group consisting of an alkylating agent, an antimetabolite, a natural product having pharmacological activity, a mitotic inhibitor, an antibiotic, a cytotoxic agent, and a chemotherapeutic agent.

17. The isolated TCR, or portion thereof, of claim 1, wherein the isolated TCR, or portion thereof, is humanized, comprises a human constant domain, or both.

18. A pharmaceutical composition comprising the isolated TCR, or portion thereof, of claim 1.

19. The pharmaceutical composition of claim 18, wherein the pharmaceutical composition further comprises an adjuvant selected from the group consisting of montanide ISA-51, QS-21, tetanus helper peptides, GM-CSF, cyclophosamide, bacillus Calmette-Guerin (BCG), corynbacterium parvum, levamisole, azimezone, isoprinisone, dinitrochlorobenezene (DNCB), keyhole limpet hemocyanins (KLH), Freund's adjuvant (complete and incomplete), mineral gels, aluminum hydroxide (Alum), lysolecithin, pluronic polyols, polyanions, peptides, oil emulsions, dinitrophenol, diphtheria toxin (DT).

20. A kit comprising:
 (i) a cytokine and/or an adjuvant; and
 (ii) a composition comprising the isolated TCR, or portion thereof, of claim 1.

* * * * *

SEQUENCE LISTING

```
<160> NUMBER OF SEQ ID NOS: 55

<210> SEQ ID NO 1
<211> LENGTH: 1338
<212> TYPE: PRT
<213> ORGANISM: Homo sapiens

<400> SEQUENCE: 1

Met Ala Ser Pro Pro Arg His Gly Pro Pro Gly Pro Ala Ser Gly Asp
1               5                   10                  15

Gly Pro Asn Leu Asn Asn Asn Asn Asn Asn Asn His Ser Val Arg
            20                  25                  30

Lys Cys Gly Tyr Leu Arg Lys Gln Lys His Gly His Lys Arg Phe Phe
        35                  40                  45

Val Leu Arg Gly Pro Gly Ala Gly Gly Asp Glu Ala Thr Ala Gly Gly
    50                  55                  60

Gly Ser Ala Pro Gln Pro Pro Arg Leu Glu Tyr Tyr Glu Ser Glu Lys
65                  70                  75                  80

Lys Trp Arg Ser Lys Ala Gly Ala Pro Lys Arg Val Ile Ala Leu Asp
                85                  90                  95

Cys Cys Leu Asn Ile Asn Lys Arg Ala Asp Ala Lys His Lys Tyr Leu
            100                 105                 110

Ile Ala Leu Tyr Thr Lys Asp Glu Tyr Phe Ala Val Ala Ala Glu Asn
        115                 120                 125

Glu Gln Glu Gln Glu Gly Trp Tyr Arg Ala Leu Thr Asp Leu Val Ser
    130                 135                 140

Glu Gly Arg Ala Ala Ala Gly Asp Ala Pro Pro Ala Ala Pro Ala
145                 150                 155                 160

Ala Ser Cys Ser Ala Ser Leu Pro Gly Ala Leu Gly Gly Ser Ala Gly
                165                 170                 175

Ala Ala Gly Ala Glu Asp Ser Tyr Gly Leu Val Ala Pro Ala Thr Ala
            180                 185                 190

Ala Tyr Arg Glu Val Trp Gln Val Asn Leu Lys Pro Lys Gly Leu Gly
        195                 200                 205

Gln Ser Lys Asn Leu Thr Gly Val Tyr Arg Leu Cys Leu Ser Ala Arg
    210                 215                 220

Thr Ile Gly Phe Val Lys Leu Asn Cys Glu Gln Pro Ser Val Thr Leu
```

```
            225                 230                 235                 240
        Gln Leu Met Asn Ile Arg Arg Cys Gly His Ser Asp Ser Phe Phe Phe
                        245                 250                 255
        Ile Glu Val Gly Arg Ser Ala Val Thr Gly Pro Gly Glu Leu Trp Met
                        260                 265                 270
        Gln Ala Asp Asp Ser Val Val Ala Gln Asn Ile His Glu Thr Ile Leu
                        275                 280                 285
        Glu Ala Met Lys Ala Leu Lys Glu Leu Phe Glu Phe Arg Pro Arg Ser
                        290                 295                 300
        Lys Ser Gln Ser Ser Gly Ser Ser Ala Thr His Pro Ile Ser Val Pro
        305                 310                 315                 320
        Gly Ala Arg Arg His His His Leu Val Asn Leu Pro Pro Ser Gln Thr
                        325                 330                 335
        Gly Leu Val Arg Arg Ser Arg Thr Asp Ser Leu Ala Ala Thr Pro Pro
                        340                 345                 350
        Ala Ala Lys Cys Ser Ser Cys Arg Val Arg Thr Ala Ser Glu Gly Asp
                        355                 360                 365
        Gly Gly Ala Ala Ala Gly Ala Ala Ala Gly Ala Arg Pro Val Ser
                        370                 375                 380
        Val Ala Gly Ser Pro Leu Ser Pro Gly Pro Val Arg Ala Pro Leu Ser
        385                 390                 395                 400
        Arg Ser His Thr Leu Ser Gly Gly Cys Gly Gly Arg Gly Ser Lys Val
                        405                 410                 415
        Ala Leu Leu Pro Ala Gly Gly Ala Leu Gln His Ser Arg Ser Met Ser
                        420                 425                 430
        Met Pro Val Ala His Ser Pro Pro Ala Ala Thr Ser Pro Gly Ser Leu
                        435                 440                 445
        Ser Ser Ser Ser Gly His Gly Ser Gly Ser Tyr Pro Pro Pro Pro Gly
                        450                 455                 460
        Pro His Pro Pro Leu Pro His Pro Leu His His Gly Pro Gly Gln Arg
        465                 470                 475                 480
        Pro Ser Ser Gly Ser Ala Ser Ala Ser Gly Ser Pro Ser Asp Pro Gly
                        485                 490                 495
        Phe Met Ser Leu Asp Glu Tyr Gly Ser Ser Pro Gly Asp Leu Arg Ala
                        500                 505                 510
        Phe Cys Ser His Arg Ser Asn Thr Pro Glu Ser Ile Ala Glu Thr Pro
                        515                 520                 525
        Pro Ala Arg Asp Gly Gly Gly Gly Glu Phe Tyr Gly Tyr Met Thr
        530                 535                 540
        Met Asp Arg Pro Leu Ser His Cys Gly Arg Ser Tyr Arg Arg Val Ser
        545                 550                 555                 560
        Gly Asp Ala Ala Gln Asp Leu Asp Arg Gly Leu Arg Lys Arg Thr Tyr
                        565                 570                 575
        Ser Leu Thr Thr Pro Ala Arg Gln Arg Pro Val Pro Gln Pro Ser Ser
                        580                 585                 590
        Ala Ser Leu Asp Glu Tyr Thr Leu Met Arg Ala Thr Phe Ser Gly Ser
                        595                 600                 605
        Ala Gly Arg Leu Cys Pro Ser Cys Pro Ala Ser Ser Pro Lys Val Ala
                        610                 615                 620
        Tyr His Pro Tyr Pro Glu Asp Tyr Gly Asp Ile Glu Ile Gly Ser His
        625                 630                 635                 640
        Arg Ser Ser Ser Ser Asn Leu Gly Ala Asp Asp Gly Tyr Met Pro Met
                        645                 650                 655
```

-continued

```
Thr Pro Gly Ala Ala Leu Ala Gly Ser Gly Ser Gly Cys Arg Ser
            660                 665                 670

Asp Asp Tyr Met Pro Met Ser Pro Ala Ser Val Ser Ala Pro Lys Gln
        675                 680                 685

Ile Leu Gln Pro Arg Ala Ala Ala Ala Ala Ala Val Pro Ser
    690                 695                 700

Ala Gly Pro Ala Gly Pro Ala Pro Thr Ser Ala Ala Gly Arg Thr Phe
705                 710                 715                 720

Pro Ala Ser Gly Gly Gly Tyr Lys Ala Ser Pro Ala Glu Ser Ser
                725                 730                 735

Pro Glu Asp Ser Gly Tyr Met Arg Met Trp Cys Gly Ser Lys Leu Ser
            740                 745                 750

Met Glu His Ala Asp Gly Lys Leu Leu Pro Asn Gly Asp Tyr Leu Asn
        755                 760                 765

Val Ser Pro Ser Asp Ala Val Thr Thr Gly Thr Pro Pro Asp Phe Phe
    770                 775                 780

Ser Ala Ala Leu His Pro Gly Gly Glu Pro Leu Arg Gly Val Pro Gly
785                 790                 795                 800

Cys Cys Tyr Ser Ser Leu Pro Arg Ser Tyr Lys Ala Pro Tyr Thr Cys
                805                 810                 815

Gly Gly Asp Ser Asp Gln Tyr Val Leu Met Ser Ser Pro Val Gly Arg
            820                 825                 830

Ile Leu Glu Glu Glu Arg Leu Glu Pro Gln Ala Thr Pro Gly Pro Ser
        835                 840                 845

Gln Ala Ala Ser Ala Phe Gly Ala Gly Pro Thr Gln Pro Pro His Pro
    850                 855                 860

Val Val Pro Ser Pro Val Arg Pro Ser Gly Gly Arg Pro Glu Gly Phe
865                 870                 875                 880

Leu Gly Gln Arg Gly Arg Ala Val Arg Pro Thr Arg Leu Ser Leu Glu
                885                 890                 895

Gly Leu Pro Ser Leu Pro Ser Met His Glu Tyr Pro Leu Pro Pro Glu
            900                 905                 910

Pro Lys Ser Pro Gly Glu Tyr Ile Asn Ile Asp Phe Gly Glu Pro Gly
        915                 920                 925

Ala Arg Leu Ser Pro Pro Ala Pro Pro Leu Leu Ala Ser Ala Ala Ser
    930                 935                 940

Ser Ser Ser Leu Leu Ser Ala Ser Ser Pro Ala Ser Ser Leu Gly Ser
945                 950                 955                 960

Gly Thr Pro Gly Thr Ser Ser Asp Ser Arg Gln Arg Ser Pro Leu Ser
                965                 970                 975

Asp Tyr Met Asn Leu Asp Phe Ser Ser Pro Lys Ser Pro Lys Pro Gly
            980                 985                 990

Ala Pro Ser Gly His Pro Val Gly Ser Leu Asp Gly Leu Leu Ser Pro
        995                 1000                 1005

Glu Ala Ser Ser Pro Tyr Pro Pro Leu Pro Pro Arg Pro Ser Ala
    1010                 1015                 1020

Ser Pro Ser Ser Ser Leu Gln Pro Pro Pro Pro Pro Ala Pro
    1025                 1030                 1035

Gly Glu Leu Tyr Arg Leu Pro Pro Ala Ser Ala Val Ala Thr Ala
    1040                 1045                 1050

Gln Gly Pro Gly Ala Ala Ser Ser Leu Ser Ser Asp Thr Gly Asp
    1055                 1060                 1065
```

```
Asn Gly Asp Tyr Thr Glu Met Ala Phe Gly Val Ala Ala Thr Pro
    1070            1075                1080

Pro Gln Pro Ile Ala Ala Pro Pro Lys Pro Glu Ala Ala Arg Val
    1085            1090                1095

Ala Ser Pro Thr Ser Gly Val Lys Arg Leu Ser Leu Met Glu Gln
    1100            1105                1110

Val Ser Gly Val Glu Ala Phe Leu Gln Ala Ser Gln Pro Pro Asp
    1115            1120                1125

Pro His Arg Gly Ala Lys Val Ile Arg Ala Asp Pro Gln Gly Gly
    1130            1135                1140

Arg Arg Arg His Ser Ser Glu Thr Phe Ser Ser Thr Thr Thr Val
    1145            1150                1155

Thr Pro Val Ser Pro Ser Phe Ala His Asn Pro Lys Arg His Asn
    1160            1165                1170

Ser Ala Ser Val Glu Asn Val Ser Leu Arg Lys Ser Ser Glu Gly
    1175            1180                1185

Gly Val Gly Val Gly Pro Gly Gly Asp Glu Pro Pro Thr Ser
    1190            1195                1200

Pro Arg Gln Leu Gln Pro Ala Pro Pro Leu Ala Pro Gln Gly Arg
    1205            1210                1215

Pro Trp Thr Pro Gly Gln Pro Gly Gly Leu Val Gly Cys Pro Gly
    1220            1225                1230

Ser Gly Gly Ser Pro Met Arg Arg Glu Thr Ser Ala Gly Phe Gln
    1235            1240                1245

Asn Gly Leu Asn Tyr Ile Ala Ile Asp Val Arg Glu Glu Pro Gly
    1250            1255                1260

Leu Pro Pro Gln Pro Gln Pro Pro Pro Pro Leu Pro Gln Pro
    1265            1270                1275

Gly Asp Lys Ser Ser Trp Gly Arg Thr Arg Ser Leu Gly Gly Leu
    1280            1285                1290

Ile Ser Ala Val Gly Val Gly Ser Thr Gly Gly Gly Cys Gly Gly
    1295            1300                1305

Pro Gly Pro Gly Ala Leu Pro Pro Ala Asn Thr Tyr Ala Ser Ile
    1310            1315                1320

Asp Phe Leu Ser His His Leu Lys Glu Ala Thr Ile Val Lys Glu
    1325            1330                1335

<210> SEQ ID NO 2
<211> LENGTH: 9
<212> TYPE: PRT
<213> ORGANISM: Homo sapiens

<400> SEQUENCE: 2

Arg Val Ala Ser Pro Thr Ser Gly Val
1               5

<210> SEQ ID NO 3
<211> LENGTH: 807
<212> TYPE: DNA
<213> ORGANISM: Mus musculus
<220> FEATURE:
<221> NAME/KEY: CDS
<222> LOCATION: (1)..(807)

<400> SEQUENCE: 3 atg ctc ctg gca ctc ctc cca gtg ctg ggg ata cac ttt gtc ctg aga     48
Met Leu Leu Ala Leu Leu Pro Val Leu Gly Ile His Phe Val Leu Arg
1               5                   10                  15
```

```
gat gcc caa gct cag tca gtg aca cag ccc gat gct cgc gtc act gtc      96
Asp Ala Gln Ala Gln Ser Val Thr Gln Pro Asp Ala Arg Val Thr Val
             20                  25                  30 tct gaa gga gcc tct ctg cag ctg aga tgc aag tat tcc tac tct ggg     144
Ser Glu Gly Ala Ser Leu Gln Leu Arg Cys Lys Tyr Ser Tyr Ser Gly
         35                  40                  45 acg cct tat ctg ttc tgg tat gtc cag tac ccg cgg cag ggg ctg cag    192
Thr Pro Tyr Leu Phe Trp Tyr Val Gln Tyr Pro Arg Gln Gly Leu Gln
     50                  55                  60 ctg ctc ctc aag tac tat tcc gga gac cca gtg gtt caa gga gtg aat    240
Leu Leu Leu Lys Tyr Tyr Ser Gly Asp Pro Val Val Gln Gly Val Asn
65                  70                  75                  80 ggc ttt gag gct gag ttc atc aag agt aac tct tcc ttc cac ctg cgg    288
Gly Phe Glu Ala Glu Phe Ile Lys Ser Asn Ser Ser Phe His Leu Arg
                 85                  90                  95 aaa gcc tct gtg cac tgg agc gac tcg gct gtg tac ttc tgt gct gtg    336
Lys Ala Ser Val His Trp Ser Asp Ser Ala Val Tyr Phe Cys Ala Val
            100                 105                 110 agc gaa ggt gca gat aga ctc acc ttt ggg aaa gga act cag ctg atc    384
Ser Glu Gly Ala Asp Arg Leu Thr Phe Gly Lys Gly Thr Gln Leu Ile
        115                 120                 125 atc cag ccc tac atc cag aac cca gaa cct gct gtg tac cag tta aaa    432
Ile Gln Pro Tyr Ile Gln Asn Pro Glu Pro Ala Val Tyr Gln Leu Lys
    130                 135                 140 gat cct cgg tct cag gac agc acc ctc tgc ctg ttc acc gac ttt gac    480
Asp Pro Arg Ser Gln Asp Ser Thr Leu Cys Leu Phe Thr Asp Phe Asp
145                 150                 155                 160 tcc caa atc aat gtg ccg aaa acc atg gaa tct gga acg ctc atc act    528
Ser Gln Ile Asn Val Pro Lys Thr Met Glu Ser Gly Thr Leu Ile Thr
                165                 170                 175 gac aaa act gtg ctg gac atg aaa gct atg gat tcc aag agc aat ggg    576
Asp Lys Thr Val Leu Asp Met Lys Ala Met Asp Ser Lys Ser Asn Gly
            180                 185                 190 gcc att gcc tgg agc aac cag aca agc ttc acc tgc caa gat atc ttc    624
Ala Ile Ala Trp Ser Asn Gln Thr Ser Phe Thr Cys Gln Asp Ile Phe
        195                 200                 205 aaa gag acc aac gcc acc tac ccc agt tca gac gtt ccc tgt gat gcc    672
Lys Glu Thr Asn Ala Thr Tyr Pro Ser Ser Asp Val Pro Cys Asp Ala
    210                 215                 220 acg ttg act gag aaa agc ttt gaa aca gat atg aac cta aac ttt caa    720
Thr Leu Thr Glu Lys Ser Phe Glu Thr Asp Met Asn Leu Asn Phe Gln
225                 230                 235                 240 aac ctg tca gtt atg gga ctc cga atc ctc ctg aaa gta gcc gga       768
Asn Leu Ser Val Met Gly Leu Arg Ile Leu Leu Lys Val Ala Gly
                245                 250                 255 ttt aac ctg ctc atg acg ctg agg ctg tgg tcc agt taa              807
Phe Asn Leu Leu Met Thr Leu Arg Leu Trp Ser Ser
            260                 265

<210> SEQ ID NO 4
<211> LENGTH: 268
<212> TYPE: PRT
<213> ORGANISM: Mus musculus

<400> SEQUENCE: 4

Met Leu Leu Ala Leu Leu Pro Val Leu Gly Ile His Phe Val Leu Arg
1               5                   10                  15

Asp Ala Gln Ala Gln Ser Val Thr Gln Pro Asp Ala Arg Val Thr Val
            20                  25                  30
```

```
Ser Glu Gly Ala Ser Leu Gln Leu Arg Cys Lys Tyr Ser Tyr Ser Gly
         35                  40                  45

Thr Pro Tyr Leu Phe Trp Tyr Val Gln Tyr Pro Arg Gln Gly Leu Gln
     50                  55                  60

Leu Leu Leu Lys Tyr Tyr Ser Gly Asp Pro Val Val Gln Gly Val Asn
 65                  70                  75                  80

Gly Phe Glu Ala Glu Phe Ile Lys Ser Asn Ser Ser Phe His Leu Arg
                 85                  90                  95

Lys Ala Ser Val His Trp Ser Asp Ser Ala Val Tyr Phe Cys Ala Val
                100                 105                 110

Ser Glu Gly Ala Asp Arg Leu Thr Phe Gly Lys Gly Thr Gln Leu Ile
            115                 120                 125

Ile Gln Pro Tyr Ile Gln Asn Pro Glu Pro Ala Val Tyr Gln Leu Lys
        130                 135                 140

Asp Pro Arg Ser Gln Asp Ser Thr Leu Cys Leu Phe Thr Asp Phe Asp
145                 150                 155                 160

Ser Gln Ile Asn Val Pro Lys Thr Met Glu Ser Gly Thr Leu Ile Thr
                165                 170                 175

Asp Lys Thr Val Leu Asp Met Lys Ala Met Asp Ser Lys Ser Asn Gly
            180                 185                 190

Ala Ile Ala Trp Ser Asn Gln Thr Ser Phe Thr Cys Gln Asp Ile Phe
        195                 200                 205

Lys Glu Thr Asn Ala Thr Tyr Pro Ser Ser Asp Val Pro Cys Asp Ala
    210                 215                 220

Thr Leu Thr Glu Lys Ser Phe Glu Thr Asp Met Asn Leu Asn Phe Gln
225                 230                 235                 240

Asn Leu Ser Val Met Gly Leu Arg Ile Leu Leu Leu Lys Val Ala Gly
                245                 250                 255

Phe Asn Leu Leu Met Thr Leu Arg Leu Trp Ser Ser
                260                 265

<210> SEQ ID NO 5
<211> LENGTH: 921
<212> TYPE: DNA
<213> ORGANISM: Mus musculus
<220> FEATURE:
<221> NAME/KEY: CDS
<222> LOCATION: (1)..(921)

<400> SEQUENCE: 5 atg ggc acc agg ctt ctt ggc tgg gca gtg ttc tgt ctc ctt gac aca     48
Met Gly Thr Arg Leu Leu Gly Trp Ala Val Phe Cys Leu Leu Asp Thr
 1               5                  10                  15 gta ctg tct gaa gct gga gtc acc cag tct ccc aga tat gca gtc cta     96
Val Leu Ser Glu Ala Gly Val Thr Gln Ser Pro Arg Tyr Ala Val Leu
                 20                  25                  30 cag gaa ggg caa gct gtt tcc ttt tgg tgt gac cct att tct gga cat    144
Gln Glu Gly Gln Ala Val Ser Phe Trp Cys Asp Pro Ile Ser Gly His
             35                  40                  45 gat acc ctt tac tgg tat cag cag ccc aga gac cag ggg ccc cag ctt    192
Asp Thr Leu Tyr Trp Tyr Gln Gln Pro Arg Asp Gln Gly Pro Gln Leu
         50                  55                  60 cta gtt tac ttt cgg gat gag gct gtt ata gat aat tca cag ttg ccc    240
Leu Val Tyr Phe Arg Asp Glu Ala Val Ile Asp Asn Ser Gln Leu Pro
 65                  70                  75                  80 tcg gat cga ttt tct gct gtg agg cct aaa gga act aac tcc act ctc    288
Ser Asp Arg Phe Ser Ala Val Arg Pro Lys Gly Thr Asn Ser Thr Leu
                 85                  90                  95
```

```
aag atc cag tct gca aag cag ggc gac aca gcc acc tat ctc tgt gcc    336
Lys Ile Gln Ser Ala Lys Gln Gly Asp Thr Ala Thr Tyr Leu Cys Ala
            100                 105                 110 agc agt tta ttg gac agc tcc tat gaa cag tac ttc ggt ccc ggc acc    384
Ser Ser Leu Leu Asp Ser Ser Tyr Glu Gln Tyr Phe Gly Pro Gly Thr
        115                 120                 125 agg ctc acg gtt tta gag gat ctg aga aat gtg act cca ccc aag gtc    432
Arg Leu Thr Val Leu Glu Asp Leu Arg Asn Val Thr Pro Pro Lys Val
130                 135                 140 tcc ttg ttt gag cca tca aaa gca gag att gca aac aaa caa aag gct    480
Ser Leu Phe Glu Pro Ser Lys Ala Glu Ile Ala Asn Lys Gln Lys Ala
145                 150                 155                 160 acc ctc gtg tgc ttg gcc agg ggc ttc ttc cct gac cac gtg gag ctg    528
Thr Leu Val Cys Leu Ala Arg Gly Phe Phe Pro Asp His Val Glu Leu
                165                 170                 175 agc tgg tgg gtg aat ggc aag gag gtc cac agt ggg gtc agc acg gac    576
Ser Trp Trp Val Asn Gly Lys Glu Val His Ser Gly Val Ser Thr Asp
            180                 185                 190 cct cag gcc tac aag gag agc aat tat agc tac tgc ctg agc agc cgc    624
Pro Gln Ala Tyr Lys Glu Ser Asn Tyr Ser Tyr Cys Leu Ser Ser Arg
        195                 200                 205 ctg agg gtc tct gct acc ttc tgg cac aat cct cga aac cac ttc cgc    672
Leu Arg Val Ser Ala Thr Phe Trp His Asn Pro Arg Asn His Phe Arg
210                 215                 220 tgc caa gtg cag ttc cat ggg ctt tca gag gag gac aag tgg cca gag    720
Cys Gln Val Gln Phe His Gly Leu Ser Glu Glu Asp Lys Trp Pro Glu
225                 230                 235                 240 ggc tca ccc aaa cct gtc aca cag aac atc agt gca gag gcc tgg ggc    768
Gly Ser Pro Lys Pro Val Thr Gln Asn Ile Ser Ala Glu Ala Trp Gly
                245                 250                 255 cga gca gac tgt gga atc act tca gca tcc tat cat cag ggg gtt ctg    816
Arg Ala Asp Cys Gly Ile Thr Ser Ala Ser Tyr His Gln Gly Val Leu
            260                 265                 270 tct gca acc atc ctc tat gag atc cta ctg ggg aag gcc acc cta tat    864
Ser Ala Thr Ile Leu Tyr Glu Ile Leu Leu Gly Lys Ala Thr Leu Tyr
        275                 280                 285 gct gtg ctg gtc agt ggc ctg gtg ctg atg gcc atg gtc aag aaa aaa    912
Ala Val Leu Val Ser Gly Leu Val Leu Met Ala Met Val Lys Lys Lys
290                 295                 300 aat tcc tag                                                        921
Asn Ser
305

<210> SEQ ID NO 6
<211> LENGTH: 306
<212> TYPE: PRT
<213> ORGANISM: Mus musculus

<400> SEQUENCE: 6

Met Gly Thr Arg Leu Leu Gly Trp Ala Val Phe Cys Leu Leu Asp Thr
1               5                   10                  15

Val Leu Ser Glu Ala Gly Val Thr Gln Ser Pro Arg Tyr Ala Val Leu
            20                  25                  30

Gln Glu Gly Gln Ala Val Ser Phe Trp Cys Asp Pro Ile Ser Gly His
        35                  40                  45

Asp Thr Leu Tyr Trp Tyr Gln Gln Pro Arg Asp Gln Gly Pro Gln Leu
    50                  55                  60

Leu Val Tyr Phe Arg Asp Glu Ala Val Ile Asp Asn Ser Gln Leu Pro
65                  70                  75                  80
```

-continued

```
Ser Asp Arg Phe Ser Ala Val Arg Pro Lys Gly Thr Asn Ser Thr Leu
                85                  90                  95

Lys Ile Gln Ser Ala Lys Gln Gly Asp Thr Ala Thr Tyr Leu Cys Ala
            100                 105                 110

Ser Ser Leu Leu Asp Ser Ser Tyr Glu Gln Tyr Phe Gly Pro Gly Thr
        115                 120                 125

Arg Leu Thr Val Leu Glu Asp Leu Arg Asn Val Thr Pro Pro Lys Val
    130                 135                 140

Ser Leu Phe Glu Pro Ser Lys Ala Glu Ile Ala Asn Lys Gln Lys Ala
145                 150                 155                 160

Thr Leu Val Cys Leu Ala Arg Gly Phe Phe Pro Asp His Val Glu Leu
                165                 170                 175

Ser Trp Trp Val Asn Gly Lys Glu Val His Ser Gly Val Ser Thr Asp
            180                 185                 190

Pro Gln Ala Tyr Lys Glu Ser Asn Tyr Ser Tyr Cys Leu Ser Ser Arg
        195                 200                 205

Leu Arg Val Ser Ala Thr Phe Trp His Asn Pro Arg Asn His Phe Arg
    210                 215                 220

Cys Gln Val Gln Phe His Gly Leu Ser Glu Glu Asp Lys Trp Pro Glu
225                 230                 235                 240

Gly Ser Pro Lys Pro Val Thr Gln Asn Ile Ser Ala Glu Ala Trp Gly
                245                 250                 255

Arg Ala Asp Cys Gly Ile Thr Ser Ala Ser Tyr His Gln Gly Val Leu
            260                 265                 270

Ser Ala Thr Ile Leu Tyr Glu Ile Leu Leu Gly Lys Ala Thr Leu Tyr
        275                 280                 285

Ala Val Leu Val Ser Gly Leu Val Leu Met Ala Met Val Lys Lys Lys
    290                 295                 300

Asn Ser
305
```

<210> SEQ ID NO 7
<211> LENGTH: 810
<212> TYPE: DNA
<213> ORGANISM: Mus musculus
<220> FEATURE:
<221> NAME/KEY: CDS
<222> LOCATION: (1)..(810)

<400> SEQUENCE: 7

```
atg ctc ctg gca ctc ctc cca gtg ctg ggg ata cac ttt gtc ctg aga        48
Met Leu Leu Ala Leu Leu Pro Val Leu Gly Ile His Phe Val Leu Arg
1               5                   10                  15 gat gcc caa gct cag tca gtg aca cag ccc gat gct cgc gtc act gtc       96
Asp Ala Gln Ala Gln Ser Val Thr Gln Pro Asp Ala Arg Val Thr Val
            20                  25                  30 tct gaa gga gcc tct ctg cag ctg aga tgc aag tat tcc tac tct ggg      144
Ser Glu Gly Ala Ser Leu Gln Leu Arg Cys Lys Tyr Ser Tyr Ser Gly
        35                  40                  45 acg cct tat ctg ttc tgg tat gtc cag tac ccg cgg cag ggg ctg cag      192
Thr Pro Tyr Leu Phe Trp Tyr Val Gln Tyr Pro Arg Gln Gly Leu Gln
    50                  55                  60 ctg ctc ctc aag tac tat tcc gga gac cca gtg gtt caa gga gtg aat      240
Leu Leu Leu Lys Tyr Tyr Ser Gly Asp Pro Val Val Gln Gly Val Asn
65                  70                  75                  80 ggc ttt gag gct gag ttc atc aag agt aac tct tcc ttc cac ctg cgg      288
Gly Phe Glu Ala Glu Phe Ile Lys Ser Asn Ser Ser Phe His Leu Arg
```

```
aaa gcc tct gtg cac tgg agc gac tcg gct gtg tac ttc tgt gct gtg      336
Lys Ala Ser Val His Trp Ser Asp Ser Ala Val Tyr Phe Cys Ala Val
                100                 105                 110 agc gct ggc agt ggt gga aaa ctc act ttg ggg gct gga aca aga ctt      384
Ser Ala Gly Ser Gly Gly Lys Leu Thr Leu Gly Ala Gly Thr Arg Leu
            115                 120                 125 cag gtc aac ctt gac atc cag aac cca gaa cct gct gtg tac cag tta      432
Gln Val Asn Leu Asp Ile Gln Asn Pro Glu Pro Ala Val Tyr Gln Leu
130                 135                 140 aaa gat cct cgg tct cag gac agc acc ctc tgc ctg ttc acc gac ttt      480
Lys Asp Pro Arg Ser Gln Asp Ser Thr Leu Cys Leu Phe Thr Asp Phe
145                 150                 155                 160 gac tcc caa gtc aat gtg ccg aaa acc atg gaa tct gga acg ttc atc      528
Asp Ser Gln Val Asn Val Pro Lys Thr Met Glu Ser Gly Thr Phe Ile
                165                 170                 175 gct gac aaa act gtg ctg gac atg aaa gct atg gat tcc aag agc aat      576
Ala Asp Lys Thr Val Leu Asp Met Lys Ala Met Asp Ser Lys Ser Asn
            180                 185                 190 ggg gcc att gcc tgg agc aac cag aca agc ttc acc tgc caa gat atc      624
Gly Ala Ile Ala Trp Ser Asn Gln Thr Ser Phe Thr Cys Gln Asp Ile
        195                 200                 205 ttc aaa gag acc aac gcc acc tac ccc agt tca gac gtt ccc tgt gat      672
Phe Lys Glu Thr Asn Ala Thr Tyr Pro Ser Ser Asp Val Pro Cys Asp
210                 215                 220 gcc acg ttg act gag aaa agc ttt gaa aca gat atg aac cta aac ttt      720
Ala Thr Leu Thr Glu Lys Ser Phe Glu Thr Asp Met Asn Leu Asn Phe
225                 230                 235                 240 caa aac ctg tca gtt atg gga ctc cga atc ctc ctg aaa gta gcc           768
Gln Asn Leu Ser Val Met Gly Leu Arg Ile Leu Leu Leu Lys Val Ala
                245                 250                 255 gga ttt aac ctg ctc atg acg ctg agg ctg tgg tcc agt taa               810
Gly Phe Asn Leu Leu Met Thr Leu Arg Leu Trp Ser Ser
            260                 265
```

<210> SEQ ID NO 8
<211> LENGTH: 269
<212> TYPE: PRT
<213> ORGANISM: Mus musculus

<400> SEQUENCE: 8

```
Met Leu Leu Ala Leu Leu Pro Val Leu Gly Ile His Phe Val Leu Arg
1               5                   10                  15

Asp Ala Gln Ala Gln Ser Val Thr Gln Pro Asp Ala Arg Val Thr Val
            20                  25                  30

Ser Glu Gly Ala Ser Leu Gln Leu Arg Cys Lys Tyr Ser Tyr Ser Gly
        35                  40                  45

Thr Pro Tyr Leu Phe Trp Tyr Val Gln Tyr Pro Arg Gln Gly Leu Gln
    50                  55                  60

Leu Leu Leu Lys Tyr Tyr Ser Gly Asp Pro Val Val Gln Gly Val Asn
65                  70                  75                  80

Gly Phe Glu Ala Glu Phe Ile Lys Ser Asn Ser Ser Phe His Leu Arg
                85                  90                  95

Lys Ala Ser Val His Trp Ser Asp Ser Ala Val Tyr Phe Cys Ala Val
            100                 105                 110

Ser Ala Gly Ser Gly Gly Lys Leu Thr Leu Gly Ala Gly Thr Arg Leu
        115                 120                 125

Gln Val Asn Leu Asp Ile Gln Asn Pro Glu Pro Ala Val Tyr Gln Leu
```

```
                130               135               140
Lys Asp Pro Arg Ser Gln Asp Ser Thr Leu Cys Leu Phe Thr Asp Phe
145                 150                 155                 160

Asp Ser Gln Val Asn Val Pro Lys Thr Met Glu Ser Gly Thr Phe Ile
                165                 170                 175

Ala Asp Lys Thr Val Leu Asp Met Lys Ala Met Asp Ser Lys Ser Asn
            180                 185                 190

Gly Ala Ile Ala Trp Ser Asn Gln Thr Ser Phe Thr Cys Gln Asp Ile
                195                 200                 205

Phe Lys Glu Thr Asn Ala Thr Tyr Pro Ser Ser Asp Val Pro Cys Asp
        210                 215                 220

Ala Thr Leu Thr Glu Lys Ser Phe Glu Thr Asp Met Asn Leu Asn Phe
225                 230                 235                 240

Gln Asn Leu Ser Val Met Gly Leu Arg Ile Leu Leu Leu Lys Val Ala
                245                 250                 255

Gly Phe Asn Leu Leu Met Thr Leu Arg Leu Trp Ser Ser
                260                 265
```

<210> SEQ ID NO 9
<211> LENGTH: 915
<212> TYPE: DNA
<213> ORGANISM: Mus musculus
<220> FEATURE:
<221> NAME/KEY: CDS
<222> LOCATION: (1)..(915)

<400> SEQUENCE: 9

```
atg ggc tcc aga ctc ttc ttt gtg gtt ttg att ctc ctg tgt gca aaa      48
Met Gly Ser Arg Leu Phe Phe Val Val Leu Ile Leu Leu Cys Ala Lys
1               5                   10                  15 cac atg gag gct gca gtc acc caa agt cca aga agc aag gtg gca gta      96
His Met Glu Ala Ala Val Thr Gln Ser Pro Arg Ser Lys Val Ala Val
            20                  25                  30 aca gga gga aag gtg aca ttg agc tgt cac cag gct aat aac cat gac     144
Thr Gly Gly Lys Val Thr Leu Ser Cys His Gln Ala Asn Asn His Asp
        35                  40                  45 tat atg tac tgg tat cgg cag gac acg ggg cat ggg ctg agg ctg atc     192
Tyr Met Tyr Trp Tyr Arg Gln Asp Thr Gly His Gly Leu Arg Leu Ile
    50                  55                  60 cat tac tca tat gtc gct gac agc acg gag aaa gga gat atc cct gat     240
His Tyr Ser Tyr Val Ala Asp Ser Thr Glu Lys Gly Asp Ile Pro Asp
65                  70                  75                  80 ggg tac aag gcc tcc aga cca agc caa gag aat ttc tct ctc att ctg     288
Gly Tyr Lys Ala Ser Arg Pro Ser Gln Glu Asn Phe Ser Leu Ile Leu
                85                  90                  95 gag ttg gct tcc ctt tct cag aca gct gta tat ttc tgt gcc agc agt     336
Glu Leu Ala Ser Leu Ser Gln Thr Ala Val Tyr Phe Cys Ala Ser Ser
            100                 105                 110 gat agg gac aac tat gct gag cag ttc ttc gga cca ggg aca cga ctc     384
Asp Arg Asp Asn Tyr Ala Glu Gln Phe Phe Gly Pro Gly Thr Arg Leu
        115                 120                 125 acc gtc cta gag gat ctg aga aat gtg act cca ccc aag gtc tcc ttg     432
Thr Val Leu Glu Asp Leu Arg Asn Val Thr Pro Pro Lys Val Ser Leu
    130                 135                 140 ttt gag cca tca aaa gca gag att gca aac aaa caa aag gct acc ctc     480
Phe Glu Pro Ser Lys Ala Glu Ile Ala Asn Lys Gln Lys Ala Thr Leu
145                 150                 155                 160 gtg tgc ttg gcc agg ggc ttc ttc cct gac cac gtg gag ctg agc tgg     528
Val Cys Leu Ala Arg Gly Phe Phe Pro Asp His Val Glu Leu Ser Trp
```

```
                        165                 170                 175
tgg gtg aat ggc aag gag gtc cgc agt ggg gtc agc acg gac cct cag     576
Trp Val Asn Gly Lys Glu Val Arg Ser Gly Val Ser Thr Asp Pro Gln
            180                 185                 190 gcc tac aag gag agc aat tat agc tac tgc ctg agc agc cgc ctg agg     624
Ala Tyr Lys Glu Ser Asn Tyr Ser Tyr Cys Leu Ser Ser Arg Leu Arg
                195                 200                 205 gtc tct gct acc ttc tgg cac aat cct cga aac cac ttc cgc tgc caa     672
Val Ser Ala Thr Phe Trp His Asn Pro Arg Asn His Phe Arg Cys Gln
210                 215                 220 gtg cag ttc cat ggg ctt tca gag gag gac aag tgg cca gag ggc tca     720
Val Gln Phe His Gly Leu Ser Glu Glu Asp Lys Trp Pro Glu Gly Ser
225                 230                 235                 240 ccc aaa cct gtc aca cag aac atc agt gca gag gcc tgg ggc cga gca     768
Pro Lys Pro Val Thr Gln Asn Ile Ser Ala Glu Ala Trp Gly Arg Ala
                245                 250                 255 gac tgt gga atc act tca gca tcc tat cat cag ggg gtt ctg tct gca     816
Asp Cys Gly Ile Thr Ser Ala Ser Tyr His Gln Gly Val Leu Ser Ala
                260                 265                 270 acc atc ctc tat gag atc cta ctg ggg aag gcc acc cta tac gct gtg     864
Thr Ile Leu Tyr Glu Ile Leu Leu Gly Lys Ala Thr Leu Tyr Ala Val
                275                 280                 285 ctg gtc agt ggc ctg gtg ctg atg gcc atg gtc aag aaa aaa aat tcc     912
Leu Val Ser Gly Leu Val Leu Met Ala Met Val Lys Lys Lys Asn Ser
290                 295                 300 taa                                                                 915

<210> SEQ ID NO 10
<211> LENGTH: 304
<212> TYPE: PRT
<213> ORGANISM: Mus musculus

<400> SEQUENCE: 10

Met Gly Ser Arg Leu Phe Phe Val Val Leu Ile Leu Leu Cys Ala Lys
1               5                   10                  15

His Met Glu Ala Ala Val Thr Gln Ser Pro Arg Ser Lys Val Ala Val
                20                  25                  30

Thr Gly Gly Lys Val Thr Leu Ser Cys His Gln Ala Asn Asn His Asp
            35                  40                  45

Tyr Met Tyr Trp Tyr Arg Gln Asp Thr Gly His Gly Leu Arg Leu Ile
    50                  55                  60

His Tyr Ser Tyr Val Ala Asp Ser Thr Glu Lys Gly Asp Ile Pro Asp
65                  70                  75                  80

Gly Tyr Lys Ala Ser Arg Pro Ser Gln Glu Asn Phe Ser Leu Ile Leu
                85                  90                  95

Glu Leu Ala Ser Leu Ser Gln Thr Ala Val Tyr Phe Cys Ala Ser Ser
            100                 105                 110

Asp Arg Asp Asn Tyr Ala Glu Gln Phe Phe Gly Pro Gly Thr Arg Leu
        115                 120                 125

Thr Val Leu Glu Asp Leu Arg Asn Val Thr Pro Pro Lys Val Ser Leu
    130                 135                 140

Phe Glu Pro Ser Lys Ala Glu Ile Ala Asn Lys Gln Lys Ala Thr Leu
145                 150                 155                 160

Val Cys Leu Ala Arg Gly Phe Phe Pro Asp His Val Glu Leu Ser Trp
                165                 170                 175

Trp Val Asn Gly Lys Glu Val Arg Ser Gly Val Ser Thr Asp Pro Gln
            180                 185                 190
```

```
Ala Tyr Lys Glu Ser Asn Tyr Ser Tyr Cys Leu Ser Ser Arg Leu Arg
            195                 200                 205

Val Ser Ala Thr Phe Trp His Asn Pro Arg Asn His Phe Arg Cys Gln
210                 215                 220

Val Gln Phe His Gly Leu Ser Glu Glu Asp Lys Trp Pro Glu Gly Ser
225                 230                 235                 240

Pro Lys Pro Val Thr Gln Asn Ile Ser Ala Glu Ala Trp Gly Arg Ala
                245                 250                 255

Asp Cys Gly Ile Thr Ser Ala Ser Tyr His Gln Gly Val Leu Ser Ala
                260                 265                 270

Thr Ile Leu Tyr Glu Ile Leu Leu Gly Lys Ala Thr Leu Tyr Ala Val
            275                 280                 285

Leu Val Ser Gly Leu Val Leu Met Ala Met Val Lys Lys Asn Ser
            290                 295                 300

<210> SEQ ID NO 11
<211> LENGTH: 580
<212> TYPE: PRT
<213> ORGANISM: Homo sapiens

<400> SEQUENCE: 11

Met Glu Val Pro Gln Pro Glu Pro Ala Pro Gly Ser Ala Leu Ser Pro
1               5                   10                  15

Ala Gly Val Cys Gly Gly Ala Gln Arg Pro Gly His Leu Pro Gly Leu
            20                  25                  30

Leu Leu Gly Ser His Gly Leu Leu Gly Ser Pro Val Arg Ala Ala Ala
            35                  40                  45

Ser Ser Pro Val Thr Thr Leu Thr Gln Thr Met His Asp Leu Ala Gly
    50                  55                  60

Leu Gly Ser Glu Thr Pro Lys Ser Gln Val Gly Thr Leu Leu Phe Arg
65                  70                  75                  80

Ser Arg Ser Arg Leu Thr His Leu Ser Leu Ser Arg Arg Ala Ser Glu
                85                  90                  95

Ser Ser Leu Ser Ser Glu Ser Ser Glu Ser Ser Asp Ala Gly Leu Cys
            100                 105                 110

Met Asp Ser Pro Ser Pro Met Asp Pro His Met Ala Glu Gln Thr Phe
        115                 120                 125

Glu Gln Ala Ile Gln Ala Ala Ser Arg Ile Ile Arg Asn Glu Gln Phe
    130                 135                 140

Ala Ile Arg Arg Phe Gln Ser Met Pro Val Arg Leu Leu Gly His Ser
145                 150                 155                 160

Pro Val Leu Arg Asn Ile Thr Asn Ser Gln Ala Pro Asp Gly Arg Arg
                165                 170                 175

Lys Ser Glu Ala Gly Ser Gly Ala Ala Ser Ser Gly Glu Asp Lys
            180                 185                 190

Glu Asn Asp Gly Phe Val Phe Lys Met Pro Trp Lys Pro Thr His Pro
        195                 200                 205

Ser Ser Thr His Ala Leu Ala Glu Trp Ala Ser Arg Arg Glu Ala Phe
    210                 215                 220

Ala Gln Arg Pro Ser Ser Ala Pro Asp Leu Met Cys Leu Ser Pro Asp
225                 230                 235                 240

Arg Lys Met Glu Val Glu Glu Leu Ser Pro Leu Ala Leu Gly Arg Phe
                245                 250                 255

Ser Leu Thr Pro Ala Glu Gly Asp Thr Glu Glu Asp Asp Gly Phe Val
            260                 265                 270
```

Asp Ile Leu Glu Ser Asp Leu Lys Asp Asp Ala Val Pro Pro Gly
        275                 280                 285

Met Glu Ser Leu Ile Ser Ala Pro Leu Val Lys Thr Leu Glu Lys Glu
290                 295                 300

Glu Glu Lys Asp Leu Val Met Tyr Ser Lys Cys Gln Arg Leu Phe Arg
305                 310                 315                 320

Ser Pro Ser Met Pro Cys Ser Val Ile Arg Pro Ile Leu Lys Arg Leu
                325                 330                 335

Glu Arg Pro Gln Asp Arg Asp Thr Pro Val Gln Asn Lys Arg Arg Arg
                340                 345                 350

Ser Val Thr Pro Pro Glu Glu Gln Gln Glu Ala Glu Glu Pro Lys Ala
                355                 360                 365

Arg Val Leu Arg Ser Lys Ser Leu Cys His Asp Glu Ile Glu Asn Leu
370                 375                 380

Leu Asp Ser Asp His Arg Glu Leu Ile Gly Asp Tyr Ser Lys Ala Phe
385                 390                 395                 400

Leu Leu Gln Thr Val Asp Gly Lys His Gln Asp Leu Lys Tyr Ile Ser
                405                 410                 415

Pro Glu Thr Met Val Ala Leu Leu Thr Gly Lys Phe Ser Asn Ile Val
                420                 425                 430

Asp Lys Phe Val Ile Val Asp Cys Arg Tyr Pro Tyr Glu Tyr Glu Gly
                435                 440                 445

Gly His Ile Lys Thr Ala Val Asn Leu Pro Leu Glu Arg Asp Ala Glu
                450                 455                 460

Ser Phe Leu Leu Lys Ser Pro Ile Ala Pro Cys Ser Leu Asp Lys Arg
465                 470                 475                 480

Val Ile Leu Ile Phe His Cys Glu Phe Ser Ser Glu Arg Gly Pro Arg
                485                 490                 495

Met Cys Arg Phe Ile Arg Glu Arg Asp Arg Ala Val Asn Asp Tyr Pro
                500                 505                 510

Ser Leu Tyr Tyr Pro Glu Met Tyr Ile Leu Lys Gly Gly Tyr Lys Glu
                515                 520                 525

Phe Phe Pro Gln His Pro Asn Phe Cys Glu Pro Gln Asp Tyr Arg Pro
                530                 535                 540

Met Asn His Glu Ala Phe Lys Asp Glu Leu Lys Thr Phe Arg Leu Lys
545                 550                 555                 560

Thr Arg Ser Trp Ala Gly Glu Arg Ser Arg Glu Leu Cys Ser Arg
                565                 570                 575

Leu Gln Asp Gln
        580

<210> SEQ ID NO 12
<211> LENGTH: 9
<212> TYPE: PRT
<213> ORGANISM: Homo sapiens

<400> SEQUENCE: 12

Gly Leu Leu Gly Ser Pro Val Arg Ala
1               5

<210> SEQ ID NO 13
<211> LENGTH: 810
<212> TYPE: DNA
<213> ORGANISM: Mus musculus
<220> FEATURE:
<221> NAME/KEY: CDS

<222> LOCATION: (1)..(810)

<400> SEQUENCE: 13

```
atg aag aca gtg act gga cct ttg ttc ctg tgc ttc tgg ctg cag ctg      48
Met Lys Thr Val Thr Gly Pro Leu Phe Leu Cys Phe Trp Leu Gln Leu
 1               5                  10                  15 aac tgt gtg agc aga ggc gag cag gtg gag cag cgc cct cct cac ctg      96
Asn Cys Val Ser Arg Gly Glu Gln Val Glu Gln Arg Pro Pro His Leu
             20                  25                  30 agt gtc cgg gag gga gac agt gcc gtt atc atc tgc acc tac aca gac     144
Ser Val Arg Glu Gly Asp Ser Ala Val Ile Ile Cys Thr Tyr Thr Asp
         35                  40                  45 cct aac agt tat tac ttc ttc tgg tac aag caa gag ccg ggg gca ggt     192
Pro Asn Ser Tyr Tyr Phe Phe Trp Tyr Lys Gln Glu Pro Gly Ala Gly
     50                  55                  60 ctt cag ttg ctt atg aag gtt ttc tca agt acg gaa ata aac gaa ggg     240
Leu Gln Leu Leu Met Lys Val Phe Ser Ser Thr Glu Ile Asn Glu Gly
 65                  70                  75                  80 caa gga ttc act gtc cta ctg aac aag aaa gac caa caa ctc tct ctg     288
Gln Gly Phe Thr Val Leu Leu Asn Lys Lys Asp Gln Gln Leu Ser Leu
                 85                  90                  95 aac ctc aca gct gcc cat cct ggg gac tca gcc gtg tac ttc tgc gca     336
Asn Leu Thr Ala Ala His Pro Gly Asp Ser Ala Val Tyr Phe Cys Ala
            100                 105                 110 gtc aaa cct gga ggc tat aaa gtg gtc ttt gga agt ggg act cga ttg     384
Val Lys Pro Gly Gly Tyr Lys Val Val Phe Gly Ser Gly Thr Arg Leu
        115                 120                 125 ctg gta agc cct gac atc cag aac cca gaa cct gct gtg tac cag tta     432
Leu Val Ser Pro Asp Ile Gln Asn Pro Glu Pro Ala Val Tyr Gln Leu
    130                 135                 140 aaa gat cct cgg tct cag gac agc acc ctc tgc ctg ttc acc gac ttt     480
Lys Asp Pro Arg Ser Gln Asp Ser Thr Leu Cys Leu Phe Thr Asp Phe
145                 150                 155                 160 gac tcc caa atc aat gtg ccg aaa acc atg gaa tct gga acg ttc atc     528
Asp Ser Gln Ile Asn Val Pro Lys Thr Met Glu Ser Gly Thr Phe Ile
                165                 170                 175 act gac aaa act gtg ctg gac atg aaa gct atg gat tcc aag agc aat     576
Thr Asp Lys Thr Val Leu Asp Met Lys Ala Met Asp Ser Lys Ser Asn
            180                 185                 190 ggg gcc att gcc tgg agc aac cag aca agc ttc acc tgc caa gat atc     624
Gly Ala Ile Ala Trp Ser Asn Gln Thr Ser Phe Thr Cys Gln Asp Ile
        195                 200                 205 ttc aaa gag acc aac gcc acc tac ccc agt tca gac gtt ccc tgt gat     672
Phe Lys Glu Thr Asn Ala Thr Tyr Pro Ser Ser Asp Val Pro Cys Asp
    210                 215                 220 gcc acg ttg aca gag aaa agc ttt gaa aca gat atg aac cta aac ttt     720
Ala Thr Leu Thr Glu Lys Ser Phe Glu Thr Asp Met Asn Leu Asn Phe
225                 230                 235                 240 caa aac ctg tca gtt atg gga ctc cga atc ctc ctg ctg aaa gta gcc     768
Gln Asn Leu Ser Val Met Gly Leu Arg Ile Leu Leu Leu Lys Val Ala
                245                 250                 255 gga ttt aac ctg ctc atg acg ctg agg ctg tgg tcc agt taa             810
Gly Phe Asn Leu Leu Met Thr Leu Arg Leu Trp Ser Ser
            260                 265
```

<210> SEQ ID NO 14
<211> LENGTH: 269
<212> TYPE: PRT
<213> ORGANISM: Mus musculus

<400> SEQUENCE: 14

```
Met Lys Thr Val Thr Gly Pro Leu Phe Leu Cys Phe Trp Leu Gln Leu
1               5                   10                  15

Asn Cys Val Ser Arg Gly Glu Gln Val Glu Gln Arg Pro Pro His Leu
            20                  25                  30

Ser Val Arg Glu Gly Asp Ser Ala Val Ile Ile Cys Thr Tyr Thr Asp
        35                  40                  45

Pro Asn Ser Tyr Tyr Phe Phe Trp Tyr Lys Gln Glu Pro Gly Ala Gly
    50                  55                  60

Leu Gln Leu Leu Met Lys Val Phe Ser Ser Thr Glu Ile Asn Glu Gly
65              70                  75                  80

Gln Gly Phe Thr Val Leu Leu Asn Lys Lys Asp Gln Gln Leu Ser Leu
            85                  90                  95

Asn Leu Thr Ala Ala His Pro Gly Asp Ser Ala Val Tyr Phe Cys Ala
        100                 105                 110

Val Lys Pro Gly Gly Tyr Lys Val Val Phe Gly Ser Gly Thr Arg Leu
    115                 120                 125

Leu Val Ser Pro Asp Ile Gln Asn Pro Glu Pro Ala Val Tyr Gln Leu
130                 135                 140

Lys Asp Pro Arg Ser Gln Asp Ser Thr Leu Cys Leu Phe Thr Asp Phe
145                 150                 155                 160

Asp Ser Gln Ile Asn Val Pro Lys Thr Met Glu Ser Gly Thr Phe Ile
            165                 170                 175

Thr Asp Lys Thr Val Leu Asp Met Lys Ala Met Asp Ser Lys Ser Asn
        180                 185                 190

Gly Ala Ile Ala Trp Ser Asn Gln Thr Ser Phe Thr Cys Gln Asp Ile
    195                 200                 205

Phe Lys Glu Thr Asn Ala Thr Tyr Pro Ser Ser Asp Val Pro Cys Asp
210                 215                 220

Ala Thr Leu Thr Glu Lys Ser Phe Glu Thr Asp Met Asn Leu Asn Phe
225                 230                 235                 240

Gln Asn Leu Ser Val Met Gly Leu Arg Ile Leu Leu Leu Lys Val Ala
            245                 250                 255

Gly Phe Asn Leu Leu Met Thr Leu Arg Leu Trp Ser Ser
    260                 265

<210> SEQ ID NO 15
<211> LENGTH: 936
<212> TYPE: DNA
<213> ORGANISM: Mus musculus
<220> FEATURE:
<221> NAME/KEY: CDS
<222> LOCATION: (1)..(936)

<400> SEQUENCE: 15 atg tct aac act gcc ttc cct gac ccc gcc tgg aac acc acc ctg cta         48
Met Ser Asn Thr Ala Phe Pro Asp Pro Ala Trp Asn Thr Thr Leu Leu
1               5                   10                  15 tct tgg gtt gct ctc ttt ctc ctg gga aca aaa cac atg gag gct gca         96
Ser Trp Val Ala Leu Phe Leu Leu Gly Thr Lys His Met Glu Ala Ala
            20                  25                  30 gtc acc caa agc cca aga aac aag gtg gca gta aca gga gga aag gtg        144
Val Thr Gln Ser Pro Arg Asn Lys Val Ala Val Thr Gly Gly Lys Val
        35                  40                  45 aca ttg agc tgt aat cag act aat aac cac aac aac atg tac tgg tat        192
Thr Leu Ser Cys Asn Gln Thr Asn Asn His Asn Asn Met Tyr Trp Tyr
    50                  55                  60
```

```
cgg cag gac acg ggg cat ggg ctg agg ctg atc cat tat tca tat ggt    240
Arg Gln Asp Thr Gly His Gly Leu Arg Leu Ile His Tyr Ser Tyr Gly
 65                  70                  75                  80 gct ggc agc act gag aaa gga gat atc cct gat gga tac aag gcc tcc    288
Ala Gly Ser Thr Glu Lys Gly Asp Ile Pro Asp Gly Tyr Lys Ala Ser
                 85                  90                  95 aga cca agc caa gag aac ttc tcc ctc att ctg gag ttg gct acc ccc    336
Arg Pro Ser Gln Glu Asn Phe Ser Leu Ile Leu Glu Leu Ala Thr Pro
            100                 105                 110 tct cag aca tca gtg tac ttc tgt gcc agc ggt ggc gac acc cag tac    384
Ser Gln Thr Ser Val Tyr Phe Cys Ala Ser Gly Gly Asp Thr Gln Tyr
        115                 120                 125 ttt ggg cca ggc act cgg ctc ctc gtg tta gag gat ctg aga aat gtg    432
Phe Gly Pro Gly Thr Arg Leu Leu Val Leu Glu Asp Leu Arg Asn Val
    130                 135                 140 act cca ccc aag gtc tcc ttg ttt gag cca tca aaa gca gag att gca    480
Thr Pro Pro Lys Val Ser Leu Phe Glu Pro Ser Lys Ala Glu Ile Ala
145                 150                 155                 160 aac aaa caa aag gct acc ctc gtg tgc ttg gcc agg ggc ttc ttc cct    528
Asn Lys Gln Lys Ala Thr Leu Val Cys Leu Ala Arg Gly Phe Phe Pro
                165                 170                 175 gac cac gtg gag ctg agc tgg tgg gtg aat ggc aag gag gtc cac agt    576
Asp His Val Glu Leu Ser Trp Trp Val Asn Gly Lys Glu Val His Ser
            180                 185                 190 ggg gtc agc acg gac cct cag gcc tac aag gag cgc aat tat agc tac    624
Gly Val Ser Thr Asp Pro Gln Ala Tyr Lys Glu Arg Asn Tyr Ser Tyr
        195                 200                 205 tgc ctg agc agc cgc ctg agg gtc tct gct acc ttc tgg cac aat cct    672
Cys Leu Ser Ser Arg Leu Arg Val Ser Ala Thr Phe Trp His Asn Pro
    210                 215                 220 cga aac cac ttc cgc tgc caa gtg cag ttc cat ggg ctt tca gag gag    720
Arg Asn His Phe Arg Cys Gln Val Gln Phe His Gly Leu Ser Glu Glu
225                 230                 235                 240 gac aag tgg cca gag ggc tca ccc aaa cct gtc aca cag aac atc agt    768
Asp Lys Trp Pro Glu Gly Ser Pro Lys Pro Val Thr Gln Asn Ile Ser
                245                 250                 255 gca gag gcc tgg ggc cga gca gac tgt gga atc act tca gca tcc tat    816
Ala Glu Ala Trp Gly Arg Ala Asp Cys Gly Ile Thr Ser Ala Ser Tyr
            260                 265                 270 cat cag ggg gtt ctg tct gca acc atc ctc tat gag atc cta ctg ggg    864
His Gln Gly Val Leu Ser Ala Thr Ile Leu Tyr Glu Ile Leu Leu Gly
        275                 280                 285 aag gcc acc cta tat gct gtg ctg gtc agt ggc ctg gtg ctg atg gcc    912
Lys Ala Thr Leu Tyr Ala Val Leu Val Ser Gly Leu Val Leu Met Ala
    290                 295                 300 atg gtc aag aaa aaa aat tcc taa                                    936
Met Val Lys Lys Lys Asn Ser
305                 310

<210> SEQ ID NO 16
<211> LENGTH: 311
<212> TYPE: PRT
<213> ORGANISM: Mus musculus

<400> SEQUENCE: 16

Met Ser Asn Thr Ala Phe Pro Asp Pro Ala Trp Asn Thr Thr Leu Leu
1               5                   10                  15

Ser Trp Val Ala Leu Phe Leu Leu Gly Thr Lys His Met Glu Ala Ala
            20                  25                  30

Val Thr Gln Ser Pro Arg Asn Lys Val Ala Val Thr Gly Gly Lys Val
```

```
            35                  40                  45
Thr Leu Ser Cys Asn Gln Thr Asn Asn His Asn Asn Met Tyr Trp Tyr
 50                  55                  60

Arg Gln Asp Thr Gly His Gly Leu Arg Leu Ile His Tyr Ser Tyr Gly
 65                  70                  75                  80

Ala Gly Ser Thr Glu Lys Gly Asp Ile Pro Asp Gly Tyr Lys Ala Ser
                 85                  90                  95

Arg Pro Ser Gln Glu Asn Phe Ser Leu Ile Leu Glu Leu Ala Thr Pro
            100                 105                 110

Ser Gln Thr Ser Val Tyr Phe Cys Ala Ser Gly Gly Asp Thr Gln Tyr
        115                 120                 125

Phe Gly Pro Gly Thr Arg Leu Leu Val Leu Glu Asp Leu Arg Asn Val
    130                 135                 140

Thr Pro Pro Lys Val Ser Leu Phe Glu Pro Ser Lys Ala Glu Ile Ala
145                 150                 155                 160

Asn Lys Gln Lys Ala Thr Leu Val Cys Leu Ala Arg Gly Phe Phe Pro
                165                 170                 175

Asp His Val Glu Leu Ser Trp Trp Val Asn Gly Lys Glu Val His Ser
            180                 185                 190

Gly Val Ser Thr Asp Pro Gln Ala Tyr Lys Glu Arg Asn Tyr Ser Tyr
        195                 200                 205

Cys Leu Ser Ser Arg Leu Arg Val Ser Ala Thr Phe Trp His Asn Pro
    210                 215                 220

Arg Asn His Phe Arg Cys Gln Val Gln Phe His Gly Leu Ser Glu Glu
225                 230                 235                 240

Asp Lys Trp Pro Glu Gly Ser Pro Lys Pro Val Thr Gln Asn Ile Ser
                245                 250                 255

Ala Glu Ala Trp Gly Arg Ala Asp Cys Gly Ile Thr Ser Ala Ser Tyr
            260                 265                 270

His Gln Gly Val Leu Ser Ala Thr Ile Leu Tyr Glu Ile Leu Leu Gly
        275                 280                 285

Lys Ala Thr Leu Tyr Ala Val Leu Val Ser Gly Leu Val Leu Met Ala
    290                 295                 300

Met Val Lys Lys Lys Asn Ser
305                 310

<210> SEQ ID NO 17
<211> LENGTH: 1565
<212> TYPE: PRT
<213> ORGANISM: Homo sapiens

<400> SEQUENCE: 17

Met Leu Ser Trp Arg Leu Gln Thr Gly Pro Glu Lys Ala Glu Leu Gln
 1               5                  10                  15

Glu Leu Asn Ala Arg Leu Tyr Asp Tyr Val Cys Arg Val Arg Glu Leu
                 20                  25                  30

Glu Arg Glu Asn Leu Leu Leu Glu Glu Leu Arg Gly Arg Arg Gly
            35                  40                  45

Arg Glu Gly Leu Trp Ala Glu Gly Gln Ala Arg Cys Ala Glu Glu Ala
        50                  55                  60

Arg Ser Leu Arg Gln Gln Leu Asp Glu Leu Ser Trp Ala Thr Ala Leu
 65                  70                  75                  80

Ala Glu Gly Glu Arg Asp Ala Leu Arg Arg Glu Leu Arg Glu Leu Gln
                 85                  90                  95
```

Arg Leu Asp Ala Glu Glu Arg Ala Ala Arg Gly Arg Leu Asp Ala Glu
                100                 105                 110

Leu Gly Ala Gln Gln Arg Glu Leu Gln Glu Ala Leu Gly Ala Arg Ala
            115                 120                 125

Ala Leu Glu Ala Leu Leu Gly Arg Leu Gln Ala Glu Arg Arg Gly Leu
        130                 135                 140

Asp Ala Ala His Glu Arg Asp Val Arg Glu Leu Arg Ala Arg Ala Ala
145                 150                 155                 160

Ser Leu Thr Met His Phe Arg Ala Arg Ala Thr Gly Pro Ala Ala Pro
                165                 170                 175

Pro Pro Arg Leu Arg Glu Val His Asp Ser Tyr Ala Leu Leu Val Ala
            180                 185                 190

Glu Ser Trp Arg Glu Thr Val Gln Leu Tyr Glu Asp Glu Val Arg Glu
        195                 200                 205

Leu Glu Glu Ala Leu Arg Arg Gly Gln Glu Ser Arg Leu Gln Ala Glu
210                 215                 220

Glu Glu Thr Arg Leu Cys Ala Gln Glu Ala Glu Ala Leu Arg Arg Glu
225                 230                 235                 240

Ala Leu Gly Leu Glu Gln Leu Arg Ala Arg Leu Glu Asp Ala Leu Leu
                245                 250                 255

Arg Met Arg Glu Glu Tyr Gly Ile Gln Ala Glu Glu Arg Gln Arg Val
            260                 265                 270

Ile Asp Cys Leu Glu Asp Glu Lys Ala Thr Leu Thr Leu Ala Met Ala
        275                 280                 285

Asp Trp Leu Arg Asp Tyr Gln Asp Leu Leu Gln Val Lys Thr Gly Leu
            290                 295                 300

Ser Leu Glu Val Ala Thr Tyr Arg Ala Leu Leu Glu Gly Glu Ser Asn
305                 310                 315                 320

Pro Glu Ile Val Ile Trp Ala Glu His Val Glu Asn Met Pro Ser Glu
                325                 330                 335

Phe Arg Asn Lys Ser Tyr His Tyr Thr Asp Ser Leu Leu Gln Arg Glu
            340                 345                 350

Asn Glu Arg Asn Leu Phe Ser Arg Gln Lys Ala Pro Leu Ala Ser Phe
        355                 360                 365

Asn His Ser Ser Ala Leu Tyr Ser Asn Leu Ser Gly His Arg Gly Ser
    370                 375                 380

Gln Thr Gly Thr Ser Ile Gly Gly Asp Ala Arg Arg Gly Phe Leu Gly
385                 390                 395                 400

Ser Gly Tyr Ser Ser Ala Thr Thr Gln Gln Glu Asn Ser Tyr Gly
                405                 410                 415

Lys Ala Val Ser Ser Gln Thr Asn Val Arg Thr Phe Ser Pro Thr Tyr
            420                 425                 430

Gly Leu Leu Arg Asn Thr Glu Ala Gln Val Lys Thr Phe Pro Asp Arg
        435                 440                 445

Pro Lys Ala Gly Asp Thr Arg Glu Val Pro Val Tyr Ile Gly Glu Asp
    450                 455                 460

Ser Thr Ile Ala Arg Glu Ser Tyr Arg Asp Arg Asp Lys Val Ala
465                 470                 475                 480

Ala Gly Ala Ser Glu Ser Thr Arg Ser Asn Glu Arg Thr Val Ile Leu
                485                 490                 495

Gly Lys Lys Thr Glu Val Lys Ala Thr Arg Glu Gln Glu Arg Asn Arg
            500                 505                 510

Pro Glu Thr Ile Arg Thr Lys Pro Glu Glu Lys Met Phe Asp Ser Lys

-continued

```
                515                 520                 525
Glu Lys Ala Ser Glu Glu Arg Asn Leu Arg Trp Glu Leu Thr Lys
        530                 535                 540
Leu Asp Lys Glu Ala Arg Gln Arg Glu Ser Gln Gln Met Lys Glu Lys
545                 550                 555                 560
Ala Lys Glu Lys Asp Ser Pro Lys Glu Lys Ser Val Arg Glu Arg Glu
                565                 570                 575
Val Pro Ile Ser Leu Glu Val Ser Gln Asp Arg Arg Ala Glu Val Ser
            580                 585                 590
Pro Lys Gly Leu Gln Thr Pro Val Lys Asp Ala Gly Gly Thr Gly
        595                 600                 605
Arg Glu Ala Glu Ala Arg Glu Leu Arg Phe Arg Leu Gly Thr Ser Asp
        610                 615                 620
Ala Thr Gly Ser Leu Gln Gly Asp Ser Met Thr Glu Thr Val Ala Glu
625                 630                 635                 640
Asn Ile Val Thr Ser Ile Leu Lys Gln Phe Thr Gln Ser Pro Glu Thr
                645                 650                 655
Glu Ala Ser Ala Asp Ser Phe Pro Asp Thr Lys Val Thr Tyr Val Asp
            660                 665                 670
Arg Lys Glu Leu Pro Gly Glu Arg Lys Thr Lys Thr Glu Ile Val Val
        675                 680                 685
Glu Ser Lys Leu Thr Glu Asp Val Asp Val Ser Asp Glu Ala Gly Leu
        690                 695                 700
Asp Tyr Leu Leu Ser Lys Asp Ile Lys Glu Val Gly Leu Lys Gly Lys
705                 710                 715                 720
Ser Ala Glu Gln Met Ile Gly Asp Ile Ile Asn Leu Gly Leu Lys Gly
                725                 730                 735
Arg Glu Gly Arg Ala Lys Val Val Asn Val Glu Ile Val Glu Glu Pro
            740                 745                 750
Val Ser Tyr Val Ser Gly Glu Lys Pro Glu Glu Phe Ser Val Pro Phe
        755                 760                 765
Lys Val Glu Glu Val Glu Asp Val Ser Pro Gly Pro Trp Gly Leu Val
        770                 775                 780
Lys Glu Glu Glu Gly Tyr Gly Glu Ser Asp Val Thr Phe Ser Val Asn
785                 790                 795                 800
Gln His Arg Arg Thr Lys Gln Pro Gln Glu Asn Thr Thr His Val Glu
                805                 810                 815
Glu Val Thr Glu Ala Gly Asp Ser Glu Gly Glu Gln Ser Tyr Phe Val
            820                 825                 830
Ser Thr Pro Asp Glu His Pro Gly Gly His Asp Arg Asp Asp Gly Ser
        835                 840                 845
Val Tyr Gly Gln Ile His Ile Glu Glu Ser Thr Ile Arg Tyr Ser
        850                 855                 860
Trp Gln Asp Glu Ile Val Gln Gly Thr Arg Arg Thr Gln Lys Asp
865                 870                 875                 880
Gly Ala Val Gly Glu Lys Val Val Lys Pro Leu Asp Val Pro Ala Pro
                885                 890                 895
Ser Leu Glu Gly Asp Leu Gly Ser Thr His Trp Lys Gln Ala Arg
            900                 905                 910
Ser Gly Glu Phe His Ala Glu Pro Thr Val Ile Glu Lys Glu Ile Lys
        915                 920                 925
Ile Pro His Glu Phe His Thr Ser Met Lys Gly Ile Ser Ser Lys Glu
        930                 935                 940
```

-continued

```
Pro Arg Gln Gln Leu Val Glu Val Ile Gly Gln Leu Glu Glu Thr Leu
945                 950                 955                 960

Pro Glu Arg Met Arg Glu Glu Leu Ser Ala Leu Thr Arg Glu Gly Gln
                965                 970                 975

Gly Gly Pro Gly Ser Val Ser Val Asp Val Lys Lys Val Gln Gly Ala
            980                 985                 990

Gly Gly Ser Ser Val Thr Leu Val Ala Glu Val Asn Val Ser Gln Thr
        995                 1000                1005

Val Asp Ala Asp Arg Leu Asp Leu Glu Glu Leu Ser Lys Asp Glu
    1010                1015                1020

Ala Ser Glu Met Glu Lys Ala Val Glu Ser Val Val Arg Glu Ser
    1025                1030                1035

Leu Ser Arg Gln Arg Ser Pro Ala Pro Gly Ser Pro Asp Glu Glu
    1040                1045                1050

Gly Gly Ala Glu Ala Pro Ala Ala Gly Ile Arg Phe Arg Arg Trp
    1055                1060                1065

Ala Thr Arg Glu Leu Tyr Ile Pro Ser Gly Glu Ser Glu Val Ala
    1070                1075                1080

Gly Gly Ala Ser His Ser Ser Gly Gln Arg Thr Pro Gln Gly Pro
    1085                1090                1095

Val Ser Ala Thr Val Glu Val Ser Ser Pro Thr Gly Phe Ala Gln
    1100                1105                1110

Ser Gln Val Leu Glu Asp Val Ser Gln Ala Ala Arg His Ile Lys
    1115                1120                1125

Leu Gly Pro Ser Glu Val Trp Arg Thr Glu Arg Met Ser Tyr Glu
    1130                1135                1140

Gly Pro Thr Ala Glu Val Val Glu Val Ser Ala Gly Gly Asp Leu
    1145                1150                1155

Ser Gln Ala Ala Ser Pro Thr Gly Ala Ser Arg Ser Val Arg His
    1160                1165                1170

Val Thr Leu Gly Pro Gly Gln Ser Pro Leu Ser Arg Glu Val Ile
    1175                1180                1185

Phe Leu Gly Pro Ala Pro Ala Cys Pro Glu Ala Trp Gly Ser Pro
    1190                1195                1200

Glu Pro Gly Pro Ala Glu Ser Ser Ala Asp Met Asp Gly Ser Gly
    1205                1210                1215

Arg His Ser Thr Phe Gly Cys Arg Gln Phe His Ala Glu Lys Glu
    1220                1225                1230

Ile Ile Phe Gln Gly Pro Ile Ser Ala Ala Gly Lys Val Gly Asp
    1235                1240                1245

Tyr Phe Ala Thr Glu Glu Ser Val Gly Thr Gln Thr Ser Val Arg
    1250                1255                1260

Gln Leu Gln Leu Gly Pro Lys Glu Gly Phe Ser Gly Gln Ile Gln
    1265                1270                1275

Phe Thr Ala Pro Leu Ser Asp Lys Val Glu Leu Gly Val Ile Gly
    1280                1285                1290

Asp Ser Val His Met Glu Gly Leu Pro Gly Ser Ser Thr Ser Ile
    1295                1300                1305

Arg His Ile Ser Ile Gly Pro Gln Arg His Gln Thr Thr Gln Gln
    1310                1315                1320

Ile Val Tyr His Gly Leu Val Pro Gln Leu Gly Glu Ser Gly Asp
    1325                1330                1335
```

-continued

```
Ser Glu Ser Thr Val His Gly Glu Gly Ser Ala Asp Val His Gln
    1340                1345                1350

Ala Thr His Ser His Thr Ser Gly Arg Gln Thr Val Met Thr Glu
    1355                1360                1365

Lys Ser Thr Phe Gln Ser Val Val Ser Glu Ser Pro Gln Glu Asp
    1370                1375                1380

Ser Ala Glu Asp Thr Ser Gly Ala Glu Met Thr Ser Gly Val Ser
    1385                1390                1395

Arg Ser Phe Arg His Ile Arg Leu Gly Pro Thr Glu Thr Glu Thr
    1400                1405                1410

Ser Glu His Ile Ala Ile Arg Gly Pro Val Ser Arg Thr Phe Val
    1415                1420                1425

Leu Ala Gly Ser Ala Asp Ser Pro Glu Leu Gly Lys Leu Ala Asp
    1430                1435                1440

Ser Ser Arg Thr Leu Arg His Ile Ala Pro Gly Pro Lys Glu Thr
    1445                1450                1455

Ser Phe Thr Phe Gln Met Asp Val Ser Asn Val Glu Ala Ile Arg
    1460                1465                1470

Ser Arg Thr Gln Glu Ala Gly Ala Leu Gly Val Ser Asp Arg Gly
    1475                1480                1485

Ser Trp Arg Asp Ala Asp Ser Arg Asn Asp Gln Ala Val Gly Val
    1490                1495                1500

Ser Phe Lys Ala Ser Ala Gly Glu Gly Asp Gln Ala His Arg Glu
    1505                1510                1515

Gln Gly Lys Glu Gln Ala Met Phe Asp Lys Lys Val Gln Leu Gln
    1520                1525                1530

Arg Met Val Asp Gln Arg Ser Val Ile Ser Asp Glu Lys Lys Val
    1535                1540                1545

Ala Leu Leu Tyr Leu Asp Asn Glu Glu Glu Asn Asp Gly His
    1550                1555                1560

Trp Phe
    1565

<210> SEQ ID NO 18
<211> LENGTH: 1253
<212> TYPE: PRT
<213> ORGANISM: Homo sapiens

<400> SEQUENCE: 18

Met Leu Ser Trp Arg Leu Gln Thr Gly Pro Glu Lys Ala Glu Leu Gln
1               5                   10                  15

Glu Leu Asn Ala Arg Leu Tyr Asp Tyr Val Cys Arg Val Arg Glu Leu
                20                  25                  30

Glu Arg Glu Asn Leu Leu Leu Glu Glu Leu Arg Gly Arg Arg Gly
            35                  40                  45

Arg Glu Gly Leu Trp Ala Glu Gly Gln Ala Arg Cys Ala Glu Glu Ala
        50                  55                  60

Arg Ser Leu Arg Gln Gln Leu Asp Glu Leu Ser Trp Ala Thr Ala Leu
65                  70                  75                  80

Ala Glu Gly Glu Arg Asp Ala Leu Arg Arg Glu Leu Arg Glu Leu Gln
                85                  90                  95

Arg Leu Asp Ala Glu Glu Arg Ala Ala Arg Gly Arg Leu Asp Ala Glu
            100                 105                 110

Leu Gly Ala Gln Gln Arg Glu Leu Gln Glu Ala Leu Gly Ala Arg Ala
        115                 120                 125
```

```
Ala Leu Glu Ala Leu Leu Gly Arg Leu Gln Ala Glu Arg Arg Gly Leu
130                 135                 140

Asp Ala Ala His Glu Arg Asp Val Arg Glu Leu Arg Ala Arg Ala Ala
145                 150                 155                 160

Ser Leu Thr Met His Phe Arg Ala Arg Ala Thr Gly Pro Ala Ala Pro
            165                 170                 175

Pro Pro Arg Leu Arg Glu Val His Asp Ser Tyr Ala Leu Leu Val Ala
            180                 185                 190

Glu Ser Trp Arg Glu Thr Val Gln Leu Tyr Glu Asp Glu Val Arg Glu
        195                 200                 205

Leu Glu Glu Ala Leu Arg Arg Gly Gln Glu Ser Arg Leu Gln Ala Glu
210                 215                 220

Glu Glu Thr Arg Leu Cys Ala Gln Glu Ala Glu Ala Leu Arg Arg Glu
225                 230                 235                 240

Ala Leu Gly Leu Glu Gln Leu Arg Ala Arg Leu Glu Asp Ala Leu Leu
            245                 250                 255

Arg Met Arg Glu Glu Tyr Gly Ile Gln Ala Glu Glu Arg Gln Arg Val
            260                 265                 270

Ile Asp Cys Leu Glu Asp Glu Lys Ala Thr Leu Thr Leu Ala Met Ala
275                 280                 285

Asp Trp Leu Arg Asp Tyr Gln Asp Leu Leu Gln Val Lys Thr Gly Leu
290                 295                 300

Ser Leu Glu Val Ala Thr Tyr Arg Ala Leu Leu Glu Gly Glu Ser Asn
305                 310                 315                 320

Pro Glu Ile Val Ile Trp Ala Glu His Val Glu Asn Met Pro Ser Glu
            325                 330                 335

Phe Arg Asn Lys Ser Tyr His Tyr Thr Asp Ser Leu Leu Gln Arg Glu
            340                 345                 350

Asn Glu Arg Asn Leu Phe Ser Arg Gln Lys Ala Pro Leu Ala Ser Phe
        355                 360                 365

Asn His Ser Ser Ala Leu Tyr Ser Asn Leu Ser Gly His Arg Gly Ser
370                 375                 380

Gln Thr Gly Thr Ser Ile Gly Gly Asp Ala Arg Arg Gly Phe Leu Gly
385                 390                 395                 400

Ser Gly Tyr Ser Ser Ala Thr Thr Gln Gln Glu Asn Ser Tyr Gly
            405                 410                 415

Lys Ala Val Ser Ser Gln Thr Asn Val Arg Thr Phe Ser Pro Thr Tyr
            420                 425                 430

Gly Leu Leu Arg Asn Thr Glu Ala Gln Val Lys Thr Phe Pro Asp Arg
        435                 440                 445

Pro Lys Ala Gly Asp Thr Arg Glu Val Pro Val Tyr Ile Gly Glu Asp
    450                 455                 460

Ser Thr Ile Ala Arg Glu Ser Tyr Arg Asp Arg Asp Lys Val Ala
465                 470                 475                 480

Ala Gly Ala Ser Glu Ser Thr Arg Ser Asn Glu Arg Thr Val Ile Leu
            485                 490                 495

Gly Lys Lys Thr Glu Val Lys Ala Thr Arg Glu Gln Glu Arg Asn Arg
            500                 505                 510

Pro Glu Thr Ile Arg Thr Lys Pro Glu Glu Lys Met Phe Asp Ser Lys
        515                 520                 525

Glu Lys Ala Ser Glu Glu Arg Asn Leu Arg Trp Glu Glu Leu Thr Lys
530                 535                 540
```

```
Leu Asp Lys Glu Ala Arg Gln Arg Glu Ser Gln Met Lys Glu Lys
545                 550                 555                 560

Ala Lys Glu Lys Asp Ser Pro Lys Glu Lys Ser Val Arg Glu Arg
            565                 570                 575

Val Pro Ile Ser Leu Glu Val Ser Gln Asp Arg Arg Ala Glu Val Ser
                580                 585                 590

Pro Lys Gly Leu Gln Thr Pro Val Lys Asp Ala Gly Gly Thr Gly
        595                 600                 605

Arg Glu Ala Glu Ala Arg Glu Leu Arg Phe Arg Leu Gly Thr Ser Asp
610                 615                 620

Ala Thr Gly Ser Leu Gln Gly Asp Ser Met Thr Glu Thr Val Ala Glu
625                 630                 635                 640

Asn Ile Val Thr Ser Ile Leu Lys Gln Phe Thr Gln Ser Pro Glu Thr
                645                 650                 655

Glu Ala Ser Ala Asp Ser Phe Pro Asp Thr Lys Val Thr Tyr Val Asp
            660                 665                 670

Arg Lys Glu Leu Pro Gly Glu Arg Lys Thr Lys Thr Glu Ile Val Val
675                 680                 685

Glu Ser Lys Leu Thr Glu Asp Val Asp Val Ser Asp Glu Ala Gly Leu
690                 695                 700

Asp Tyr Leu Leu Ser Lys Asp Ile Lys Glu Val Gly Leu Lys Gly Lys
705                 710                 715                 720

Ser Ala Glu Gln Met Ile Gly Asp Ile Ile Asn Leu Gly Leu Lys Gly
                725                 730                 735

Arg Glu Gly Arg Ala Lys Val Val Asn Val Glu Ile Val Glu Glu Pro
            740                 745                 750

Val Ser Tyr Val Ser Gly Glu Lys Pro Glu Glu Phe Ser Val Pro Phe
        755                 760                 765

Lys Val Glu Glu Val Glu Asp Val Ser Pro Gly Pro Trp Gly Leu Val
770                 775                 780

Lys Glu Glu Glu Gly Tyr Gly Glu Ser Asp Val Thr Phe Ser Val Asn
785                 790                 795                 800

Gln His Arg Arg Thr Lys Gln Pro Gln Glu Asn Thr Thr His Val Glu
                805                 810                 815

Glu Val Thr Glu Ala Gly Asp Ser Glu Gly Glu Gln Ser Tyr Phe Val
            820                 825                 830

Ser Thr Pro Asp Glu His Pro Gly Gly His Asp Arg Asp Asp Gly Ser
        835                 840                 845

Val Tyr Gly Gln Ile His Ile Glu Glu Glu Ser Thr Ile Arg Tyr Ser
850                 855                 860

Trp Gln Asp Glu Ile Val Gln Gly Thr Arg Arg Arg Thr Gln Lys Asp
865                 870                 875                 880

Gly Ala Val Gly Glu Lys Val Val Lys Pro Leu Asp Val Pro Ala Pro
                885                 890                 895

Ser Leu Glu Gly Asp Leu Gly Ser Thr His Trp Lys Glu Gln Ala Arg
            900                 905                 910

Ser Gly Glu Phe His Ala Glu Pro Thr Val Ile Glu Lys Glu Ile Lys
        915                 920                 925

Ile Pro His Glu Phe His Thr Ser Met Lys Gly Ile Ser Ser Lys Glu
        930                 935                 940

Pro Arg Gln Gln Leu Val Glu Val Ile Gly Gln Leu Glu Glu Thr Leu
945                 950                 955                 960

Pro Glu Arg Met Arg Glu Glu Leu Ser Ala Leu Thr Arg Glu Gly Gln
```

```
                  965                 970                 975
Gly Gly Pro Gly Ser Val Ser Val Asp Val Lys Lys Val Gln Gly Ala
            980                 985                 990
Gly Gly Ser Ser Val Thr Leu Val Ala Glu Val Asn Val Ser Gln Thr
        995                 1000                1005
Val Asp Ala Asp Arg Leu Asp Leu Glu Glu Leu Ser Lys Asp Glu
    1010                1015                1020
Ala Ser Glu Met Glu Lys Ala Val Glu Ser Val Val Arg Glu Ser
    1025                1030                1035
Leu Ser Arg Gln Arg Ser Pro Ala Pro Gly Ser Pro Asp Glu Glu
    1040                1045                1050
Gly Gly Ala Glu Ala Pro Ala Ala Gly Ile Arg Phe Arg Arg Trp
    1055                1060                1065
Ala Thr Arg Glu Leu Tyr Ile Pro Ser Gly Glu Ser Glu Val Ala
    1070                1075                1080
Gly Gly Ala Ser His Ser Ser Gly Gln Arg Thr Pro Gln Gly Pro
    1085                1090                1095
Val Ser Ala Thr Val Glu Val Ser Ser Pro Thr Gly Phe Ala Gln
    1100                1105                1110
Ser Gln Val Leu Glu Asp Val Ser Gln Ala Ala Arg His Ile Lys
    1115                1120                1125
Leu Gly Pro Ser Glu Val Trp Arg Thr Glu Arg Met Ser Tyr Glu
    1130                1135                1140
Gly Pro Thr Ala Glu Val Val Glu Met Asp Val Ser Asn Val Glu
    1145                1150                1155
Ala Ile Arg Ser Arg Thr Gln Glu Ala Gly Ala Leu Gly Val Ser
    1160                1165                1170
Asp Arg Gly Ser Trp Arg Asp Ala Asp Ser Arg Asn Asp Gln Ala
    1175                1180                1185
Val Gly Val Ser Phe Lys Ala Ser Ala Gly Glu Gly Asp Gln Ala
    1190                1195                1200
His Arg Glu Gln Gly Lys Glu Gln Ala Met Phe Asp Lys Lys Val
    1205                1210                1215
Gln Leu Gln Arg Met Val Asp Gln Arg Ser Val Ile Ser Asp Glu
    1220                1225                1230
Lys Lys Val Ala Leu Leu Tyr Leu Asp Asn Glu Glu Glu Glu Asn
    1235                1240                1245
Asp Gly His Trp Phe
    1250

<210> SEQ ID NO 19
<211> LENGTH: 9
<212> TYPE: PRT
<213> ORGANISM: Homo sapiens

<400> SEQUENCE: 19

Arg Thr Phe Ser Pro Thr Tyr Gly Leu
1               5

<210> SEQ ID NO 20
<211> LENGTH: 807
<212> TYPE: DNA
<213> ORGANISM: Mus musculus
<220> FEATURE:
<221> NAME/KEY: CDS
<222> LOCATION: (1)..(807)
```

```
<400> SEQUENCE: 20 atg ctc ctg gcg ctc ctc cca gtg ctg ggg ata cac ttt gtc ctg aga      48
Met Leu Leu Ala Leu Leu Pro Val Leu Gly Ile His Phe Val Leu Arg
1               5                   10                  15 gat gcc caa gct cag tca gtg acg cag ccc gat gct cgc gcc act gtc      96
Asp Ala Gln Ala Gln Ser Val Thr Gln Pro Asp Ala Arg Ala Thr Val
            20                  25                  30 tct gaa gga gcc tct ctg cgg ctg aga tgc aag tat tcc tac tct ggg     144
Ser Glu Gly Ala Ser Leu Arg Leu Arg Cys Lys Tyr Ser Tyr Ser Gly
        35                  40                  45 aca cct tat ctg ttc tgg tat gtc cag tac ccg cgg cag ggg ctg cag     192
Thr Pro Tyr Leu Phe Trp Tyr Val Gln Tyr Pro Arg Gln Gly Leu Gln
    50                  55                  60 ctg ctc ctc aag tac tat tca gga gac cca gtg gtt caa gga gtg aat     240
Leu Leu Leu Lys Tyr Tyr Ser Gly Asp Pro Val Val Gln Gly Val Asn
65                  70                  75                  80 ggc ttc gag gct gag ttc agc aag agt aac tct tcc ttc cac ctg cgg     288
Gly Phe Glu Ala Glu Phe Ser Lys Ser Asn Ser Ser Phe His Leu Arg
                85                  90                  95 aaa gcc tct gtg cac tgg agc gac tct gct gtg tac ttc tgt gtt ttg     336
Lys Ala Ser Val His Trp Ser Asp Ser Ala Val Tyr Phe Cys Val Leu
            100                 105                 110 agc tat agc aat aac aga atc ttc ttt ggt gat ggg acg cag ctg gtg     384
Ser Tyr Ser Asn Asn Arg Ile Phe Phe Gly Asp Gly Thr Gln Leu Val
        115                 120                 125 atg aag ccc aac atc cag aac cca gaa cct gct gtg tac cag tta aaa     432
Met Lys Pro Asn Ile Gln Asn Pro Glu Pro Ala Val Tyr Gln Leu Lys
    130                 135                 140 gat cct cgg tct cag gac agc acc ctc tgc ctg ttc acc gac ttt gac     480
Asp Pro Arg Ser Gln Asp Ser Thr Leu Cys Leu Phe Thr Asp Phe Asp
145                 150                 155                 160 tcc caa atc aat gtg ccg aaa acc atg gaa tct gga acg ttc atc act     528
Ser Gln Ile Asn Val Pro Lys Thr Met Glu Ser Gly Thr Phe Ile Thr
                165                 170                 175 gac aaa act gtg ctg gac atg aaa gct atg gat tcc aag agc aat ggg     576
Asp Lys Thr Val Leu Asp Met Lys Ala Met Asp Ser Lys Ser Asn Gly
            180                 185                 190 gcc att gcc tgg agc aac cag aca agc ttc acc tgc caa gat atc ttc     624
Ala Ile Ala Trp Ser Asn Gln Thr Ser Phe Thr Cys Gln Asp Ile Phe
        195                 200                 205 aaa gag acc aac gcc acc tac ccc agt tca gac gtt ccc tgt gat gcc     672
Lys Glu Thr Asn Ala Thr Tyr Pro Ser Ser Asp Val Pro Cys Asp Ala
    210                 215                 220 acg ttg act gag aaa agc ttt gaa aca gat atg aac cta aac ttt caa     720
Thr Leu Thr Glu Lys Ser Phe Glu Thr Asp Met Asn Leu Asn Phe Gln
225                 230                 235                 240 aac ctg tca gtt atg gga ctc cga atc ctc ctg aaa gta gcc gga         768
Asn Leu Ser Val Met Gly Leu Arg Ile Leu Leu Lys Val Ala Gly
                245                 250                 255 ttt aac ctg ctc atg acg ctg agg ctg tgg tcc agt taa                 807
Phe Asn Leu Leu Met Thr Leu Arg Leu Trp Ser Ser
            260                 265

<210> SEQ ID NO 21
<211> LENGTH: 268
<212> TYPE: PRT
<213> ORGANISM: Mus musculus

<400> SEQUENCE: 21

Met Leu Leu Ala Leu Leu Pro Val Leu Gly Ile His Phe Val Leu Arg
```

```
  1               5                  10                 15
Asp Ala Gln Ala Gln Ser Val Thr Gln Pro Asp Ala Arg Ala Thr Val
                20                 25                 30

Ser Glu Gly Ala Ser Leu Arg Leu Arg Cys Lys Tyr Ser Tyr Ser Gly
                35                 40                 45

Thr Pro Tyr Leu Phe Trp Tyr Val Gln Tyr Pro Arg Gln Gly Leu Gln
 50                 55                 60

Leu Leu Leu Lys Tyr Tyr Ser Gly Asp Pro Val Val Gln Gly Val Asn
 65                 70                 75                 80

Gly Phe Glu Ala Glu Phe Ser Lys Ser Asn Ser Ser Phe His Leu Arg
                85                 90                 95

Lys Ala Ser Val His Trp Ser Asp Ser Ala Val Tyr Phe Cys Val Leu
                100                105                110

Ser Tyr Ser Asn Asn Arg Ile Phe Phe Gly Asp Gly Thr Gln Leu Val
                115                120                125

Met Lys Pro Asn Ile Gln Asn Pro Glu Pro Ala Val Tyr Gln Leu Lys
 130                135                140

Asp Pro Arg Ser Gln Asp Ser Thr Leu Cys Leu Phe Thr Asp Phe Asp
145                 150                155                160

Ser Gln Ile Asn Val Pro Lys Thr Met Glu Ser Gly Thr Phe Ile Thr
                165                170                175

Asp Lys Thr Val Leu Asp Met Lys Ala Met Asp Ser Lys Ser Asn Gly
                180                185                190

Ala Ile Ala Trp Ser Asn Gln Thr Ser Phe Thr Cys Gln Asp Ile Phe
                195                200                205

Lys Glu Thr Asn Ala Thr Tyr Pro Ser Ser Asp Val Pro Cys Asp Ala
 210                215                220

Thr Leu Thr Glu Lys Ser Phe Glu Thr Asp Met Asn Leu Asn Phe Gln
225                 230                235                240

Asn Leu Ser Val Met Gly Leu Arg Ile Leu Leu Leu Lys Val Ala Gly
                245                250                255

Phe Asn Leu Leu Met Thr Leu Arg Leu Trp Ser Ser
                260                265

<210> SEQ ID NO 22
<211> LENGTH: 942
<212> TYPE: DNA
<213> ORGANISM: Mus musculus
<220> FEATURE:
<221> NAME/KEY: CDS
<222> LOCATION: (1)..(942)
<220> FEATURE:
<221> NAME/KEY: misc_feature
<222> LOCATION: (582)..(583)
<223> OTHER INFORMATION: n is a, c, g, or t

<400> SEQUENCE: 22 atg tct aac act gtc ctc gct gat tct gcc tgg ggc atc acc ctg cta    48
Met Ser Asn Thr Val Leu Ala Asp Ser Ala Trp Gly Ile Thr Leu Leu
 1               5                  10                 15 tct tgg gtt act gtc ttt ctc ttg gga aca agt tca gca gat tct ggg    96
Ser Trp Val Thr Val Phe Leu Leu Gly Thr Ser Ser Ala Asp Ser Gly
                20                 25                 30 gtt gtc cag tct cca aga cac ata atc aaa gaa aag gga gga agg tcc   144
Val Val Gln Ser Pro Arg His Ile Ile Lys Glu Lys Gly Gly Arg Ser
                35                 40                 45 gtt ctg acg tgt att ccc atc tct gga cat agc aat gtg gtc tgg tac   192
Val Leu Thr Cys Ile Pro Ile Ser Gly His Ser Asn Val Val Trp Tyr
```

```
                50                     55                      60
cag cag act ctg ggg aag gaa tta aag ttc ctt att cag cat tat gaa       240
Gln Gln Thr Leu Gly Lys Glu Leu Lys Phe Leu Ile Gln His Tyr Glu
 65              70                      75                  80 aag gtg gag aga gac aaa gga ttc cta ccc agc aga ttc tca gtc caa       288
Lys Val Glu Arg Asp Lys Gly Phe Leu Pro Ser Arg Phe Ser Val Gln
                 85                      90                  95 cag ttt gat gac tat cac tct gaa atg aac atg agt gcc ttg gaa ctg       336
Gln Phe Asp Asp Tyr His Ser Glu Met Asn Met Ser Ala Leu Glu Leu
                 100                     105                 110 gag gac tct gct atg tac ttc tgt gcc agc tct ctg ggg ggt gga gaa       384
Glu Asp Ser Ala Met Tyr Phe Cys Ala Ser Ser Leu Gly Gly Gly Glu
             115                     120                 125 gtc ttc ttt ggt aaa gga acc aga ctc aca gtt gta gag gat ctg aga       432
Val Phe Phe Gly Lys Gly Thr Arg Leu Thr Val Val Glu Asp Leu Arg
         130                     135                 140 aat gtg act cca ccc aag gtc tcc ttg ttt gag cca tca aaa gca gag       480
Asn Val Thr Pro Pro Lys Val Ser Leu Phe Glu Pro Ser Lys Ala Glu
145                     150                     155             160 att gca aac aaa caa aag gct acc ctc gtg tgc ttg gcc agg ggc ttc       528
Ile Ala Asn Lys Gln Lys Ala Thr Leu Val Cys Leu Ala Arg Gly Phe
                 165                     170                 175 ttc cct gac cac gtg gag ctg agc tgg tgg gtg aat ggc aag gag gtc       576
Phe Pro Asp His Val Glu Leu Ser Trp Trp Val Asn Gly Lys Glu Val
                 180                     185                 190 cac agn ngg gtc agc acg gac cct cag gcc tac aag gag agc aat tat       624
His Xaa Xaa Val Ser Thr Asp Pro Gln Ala Tyr Lys Glu Ser Asn Tyr
             195                     200                 205 agc tac tgc ctg agc agc cgc ctg agg gtc tct gct acc ttc tgg cac       672
Ser Tyr Cys Leu Ser Ser Arg Leu Arg Val Ser Ala Thr Phe Trp His
         210                     215                 220 aat cct cgc aac cac ttc cgc tgc caa gtg cag ttc cat ggg ctt tca       720
Asn Pro Arg Asn His Phe Arg Cys Gln Val Gln Phe His Gly Leu Ser
225                     230                     235             240 gag gag gac aag tgg cca gag ggc tca ccc aaa cct gtc aca cag aac       768
Glu Glu Asp Lys Trp Pro Glu Gly Ser Pro Lys Pro Val Thr Gln Asn
                 245                     250                 255 atc agt gca gag gcc tgg ggc cga gca gac tgt ggg att acc tca gca       816
Ile Ser Ala Glu Ala Trp Gly Arg Ala Asp Cys Gly Ile Thr Ser Ala
                 260                     265                 270 tcc tat caa caa ggg gtc ttg tct gcc acc atc ctc tat gag atc ctg       864
Ser Tyr Gln Gln Gly Val Leu Ser Ala Thr Ile Leu Tyr Glu Ile Leu
             275                     280                 285 cta ggg aaa gcc acc ctg tat gct gtg ctt gtc agt aca ctg gtg gtg       912
Leu Gly Lys Ala Thr Leu Tyr Ala Val Leu Val Ser Thr Leu Val Val
         290                     295                 300 atg gct atg gtc aaa aaa aag aat tcc taa                               942
Met Ala Met Val Lys Lys Lys Asn Ser
305                     310

<210> SEQ ID NO 23
<211> LENGTH: 313
<212> TYPE: PRT
<213> ORGANISM: Mus musculus
<220> FEATURE:
<221> NAME/KEY: misc_feature
<222> LOCATION: (194)..(194)
<223> OTHER INFORMATION: The 'Xaa' at location 194 stands for Arg, or
      Ser.
<220> FEATURE:
<221> NAME/KEY: misc_feature
<222> LOCATION: (195)..(195)
```

<223> OTHER INFORMATION: The 'Xaa' at location 195 stands for Arg, Gly, or Trp.

<400> SEQUENCE: 23

```
Met Ser Asn Thr Val Leu Ala Asp Ser Ala Trp Gly Ile Thr Leu Leu
1               5                   10                  15

Ser Trp Val Thr Val Phe Leu Leu Gly Thr Ser Ser Ala Asp Ser Gly
            20                  25                  30

Val Val Gln Ser Pro Arg His Ile Ile Lys Glu Lys Gly Gly Arg Ser
        35                  40                  45

Val Leu Thr Cys Ile Pro Ile Ser Gly His Ser Asn Val Val Trp Tyr
    50                  55                  60

Gln Gln Thr Leu Gly Lys Glu Leu Lys Phe Leu Ile Gln His Tyr Glu
65                  70                  75                  80

Lys Val Glu Arg Asp Lys Gly Phe Leu Pro Ser Arg Phe Ser Val Gln
                85                  90                  95

Gln Phe Asp Asp Tyr His Ser Glu Met Asn Met Ser Ala Leu Glu Leu
            100                 105                 110

Glu Asp Ser Ala Met Tyr Phe Cys Ala Ser Ser Leu Gly Gly Gly Glu
        115                 120                 125

Val Phe Phe Gly Lys Gly Thr Arg Leu Thr Val Val Glu Asp Leu Arg
    130                 135                 140

Asn Val Thr Pro Pro Lys Val Ser Leu Phe Glu Pro Ser Lys Ala Glu
145                 150                 155                 160

Ile Ala Asn Lys Gln Lys Ala Thr Leu Val Cys Leu Ala Arg Gly Phe
                165                 170                 175

Phe Pro Asp His Val Glu Leu Ser Trp Trp Val Asn Gly Lys Glu Val
            180                 185                 190

His Xaa Xaa Val Ser Thr Asp Pro Gln Ala Tyr Lys Ser Asn Tyr
        195                 200                 205

Ser Tyr Cys Leu Ser Ser Arg Leu Arg Val Ser Ala Thr Phe Trp His
    210                 215                 220

Asn Pro Arg Asn His Phe Arg Cys Gln Val Gln Phe His Gly Leu Ser
225                 230                 235                 240

Glu Glu Asp Lys Trp Pro Glu Gly Ser Pro Lys Pro Val Thr Gln Asn
                245                 250                 255

Ile Ser Ala Glu Ala Trp Gly Arg Ala Asp Cys Gly Ile Thr Ser Ala
            260                 265                 270

Ser Tyr Gln Gln Gly Val Leu Ser Ala Thr Ile Leu Tyr Glu Ile Leu
    275                 280                 285

Leu Gly Lys Ala Thr Leu Tyr Ala Val Leu Val Ser Thr Leu Val Val
    290                 295                 300

Met Ala Met Val Lys Lys Lys Asn Ser
305                 310
```

<210> SEQ ID NO 24
<211> LENGTH: 810
<212> TYPE: DNA
<213> ORGANISM: Mus musculus
<220> FEATURE:
<221> NAME/KEY: CDS
<222> LOCATION: (1)..(810)

<400> SEQUENCE: 24

```
atg ctc ctg gcg ctc ctc cca gtg ctg ggg ata cac ttt gtc ctg aga      48
Met Leu Leu Ala Leu Leu Pro Val Leu Gly Ile His Phe Val Leu Arg
1               5                   10                  15
```

```
gat gcc caa gct cag tca gtg acg cag ccc gat gct cgc gtc act gtc      96
Asp Ala Gln Ala Gln Ser Val Thr Gln Pro Asp Ala Arg Val Thr Val
         20                  25                  30 tct gaa gga gcc tct ctg cag ctg aga tgc aag tat tcc tac tct ggg     144
Ser Glu Gly Ala Ser Leu Gln Leu Arg Cys Lys Tyr Ser Tyr Ser Gly
     35                  40                  45 aca cct tat ctg ttc tgg tat gcc cag tac ccg cgg cag ggg ctg cag     192
Thr Pro Tyr Leu Phe Trp Tyr Ala Gln Tyr Pro Arg Gln Gly Leu Gln
 50                  55                  60 ctg ctc ctc aag tac tat tca gga gac cca gtg gtt caa gga gtg aat     240
Leu Leu Leu Lys Tyr Tyr Ser Gly Asp Pro Val Val Gln Gly Val Asn
 65                  70                  75                  80 ggc ttc gag gct gag ttc agc aag agt aac tct tcc ttc cac ctg cgg     288
Gly Phe Glu Ala Glu Phe Ser Lys Ser Asn Ser Ser Phe His Leu Arg
                 85                  90                  95 aaa gcc tct gtg cac tgg agc gac tct gct gtg tac ttc tgt gtt ttg     336
Lys Ala Ser Val His Trp Ser Asp Ser Ala Val Tyr Phe Cys Val Leu
            100                 105                 110 agg tac gga ggc aat aat aag ctg act ttt ggt caa gga acc gtt ctg     384
Arg Tyr Gly Gly Asn Asn Lys Leu Thr Phe Gly Gln Gly Thr Val Leu
        115                 120                 125 agt gtt ata cca gac atc cag aac cca gaa cct gct gtg tac cag tta     432
Ser Val Ile Pro Asp Ile Gln Asn Pro Glu Pro Ala Val Tyr Gln Leu
130                 135                 140 aaa gat cct cgg tct cag gac agc acc ctc tgc ctg ttc acc gac ttt     480
Lys Asp Pro Arg Ser Gln Asp Ser Thr Leu Cys Leu Phe Thr Asp Phe
145                 150                 155                 160 gac tcc caa atc aat gtg ccg aaa acc atg gaa tct gga acg ttc atc     528
Asp Ser Gln Ile Asn Val Pro Lys Thr Met Glu Ser Gly Thr Phe Ile
                165                 170                 175 act gac aaa act gtg ctg gac atg aaa gct atg gat tcc aag agc aat     576
Thr Asp Lys Thr Val Leu Asp Met Lys Ala Met Asp Ser Lys Ser Asn
            180                 185                 190 ggg gcc att gcc tgg agc aac cag aca agc ttc acc tgc caa gat atc     624
Gly Ala Ile Ala Trp Ser Asn Gln Thr Ser Phe Thr Cys Gln Asp Ile
        195                 200                 205 ttc aaa gag acc aac gcc acc tac ccc agt tca gac gtt ccc tgt gat     672
Phe Lys Glu Thr Asn Ala Thr Tyr Pro Ser Ser Asp Val Pro Cys Asp
    210                 215                 220 gcc acg ttg act gag aaa agc ttt gaa aca gat atg aac cta aac ttt     720
Ala Thr Leu Thr Glu Lys Ser Phe Glu Thr Asp Met Asn Leu Asn Phe
225                 230                 235                 240 cag aac ctg tca gtt atg gga ctc cga atc ctc ctg ctg aaa gta gcc     768
Gln Asn Leu Ser Val Met Gly Leu Arg Ile Leu Leu Leu Lys Val Ala
                245                 250                 255 gga ttt aac ctg ctc atg acg ctg agg ctg tgg tcc agt tga             810
Gly Phe Asn Leu Leu Met Thr Leu Arg Leu Trp Ser Ser
            260                 265
```

<210> SEQ ID NO 25
<211> LENGTH: 269
<212> TYPE: PRT
<213> ORGANISM: Mus musculus

<400> SEQUENCE: 25

```
Met Leu Leu Ala Leu Leu Pro Val Leu Gly Ile His Phe Val Leu Arg
 1               5                  10                  15

Asp Ala Gln Ala Gln Ser Val Thr Gln Pro Asp Ala Arg Val Thr Val
             20                  25                  30
```

-continued

```
Ser Glu Gly Ala Ser Leu Gln Leu Arg Cys Lys Tyr Ser Tyr Ser Gly
         35                  40                  45

Thr Pro Tyr Leu Phe Trp Tyr Ala Gln Tyr Pro Arg Gln Gly Leu Gln
 50                  55                  60

Leu Leu Leu Lys Tyr Tyr Ser Gly Asp Pro Val Val Gln Gly Val Asn
65                  70                  75                  80

Gly Phe Glu Ala Glu Phe Ser Lys Ser Asn Ser Ser Phe His Leu Arg
                 85                  90                  95

Lys Ala Ser Val His Trp Ser Asp Ser Ala Val Tyr Phe Cys Val Leu
            100                 105                 110

Arg Tyr Gly Gly Asn Asn Lys Leu Thr Phe Gly Gln Gly Thr Val Leu
        115                 120                 125

Ser Val Ile Pro Asp Ile Gln Asn Pro Glu Pro Ala Val Tyr Gln Leu
    130                 135                 140

Lys Asp Pro Arg Ser Gln Asp Ser Thr Leu Cys Leu Phe Thr Asp Phe
145                 150                 155                 160

Asp Ser Gln Ile Asn Val Pro Lys Thr Met Glu Ser Gly Thr Phe Ile
                165                 170                 175

Thr Asp Lys Thr Val Leu Asp Met Lys Ala Met Asp Ser Lys Ser Asn
            180                 185                 190

Gly Ala Ile Ala Trp Ser Asn Gln Thr Ser Phe Thr Cys Gln Asp Ile
        195                 200                 205

Phe Lys Glu Thr Asn Ala Thr Tyr Pro Ser Ser Asp Val Pro Cys Asp
    210                 215                 220

Ala Thr Leu Thr Glu Lys Ser Phe Glu Thr Asp Met Asn Leu Asn Phe
225                 230                 235                 240

Gln Asn Leu Ser Val Met Gly Leu Arg Ile Leu Leu Leu Lys Val Ala
                245                 250                 255

Gly Phe Asn Leu Leu Met Thr Leu Arg Leu Trp Ser Ser
            260                 265

<210> SEQ ID NO 26
<211> LENGTH: 906
<212> TYPE: DNA
<213> ORGANISM: Mus musculus
<220> FEATURE:
<221> NAME/KEY: CDS
<222> LOCATION: (1)..(906)

<400> SEQUENCE: 26 atg ggc tcc aga ctc ttc ttt gtg gtt ttg att ctc ctg tgt gca aaa      48
Met Gly Ser Arg Leu Phe Phe Val Val Leu Ile Leu Leu Cys Ala Lys
1               5                   10                  15 cac atg gag gct gca gtc acc caa agt cca aga agc aag gtg gcg gta      96
His Met Glu Ala Ala Val Thr Gln Ser Pro Arg Ser Lys Val Ala Val
            20                  25                  30 aca gga gga aag gtg aca ttg agc tgt cac cag act aat aac cat gac     144
Thr Gly Gly Lys Val Thr Leu Ser Cys His Gln Thr Asn Asn His Asp
        35                  40                  45 tat atg tac tgg tat cgg cag gac acg ggg cat ggg ctg agg ctg atc     192
Tyr Met Tyr Trp Tyr Arg Gln Asp Thr Gly His Gly Leu Arg Leu Ile
    50                  55                  60 cat tac tca tat gtc gct gac agc acg gag aaa gga gat atc cct gat     240
His Tyr Ser Tyr Val Ala Asp Ser Thr Glu Lys Gly Asp Ile Pro Asp
65                  70                  75                  80 ggg tac aag gcc tcc aga cca agc caa gag aat ttc tct ctc att ctg     288
Gly Tyr Lys Ala Ser Arg Pro Ser Gln Glu Asn Phe Ser Leu Ile Leu
                85                  90                  95
```

| | | | | | | | | | | | | | | | |
|---|---|---|---|---|---|---|---|---|---|---|---|---|---|---|---|
|gag|ttg|gct|tcc|ctt|tct|cag|aca|gct|gta|tat|ttc|tgt|gcc|agc|agg|
|Glu|Leu|Ala|Ser|Leu|Ser|Gln|Thr|Ala|Val|Tyr|Phe|Cys|Ala|Ser|Arg|
| | |  |100| | | |105| | | |  |110| | | |

336 tac agg gac acc cag tac ttt ggg cca ggc act cgg ctc ctc gtg tta    384
Tyr Arg Asp Thr Gln Tyr Phe Gly Pro Gly Thr Arg Leu Leu Val Leu
            115                 120                 125 gag gat ctg aga aat gtg act cca ccc aag gtc tcc ttg ttt gag cca    432
Glu Asp Leu Arg Asn Val Thr Pro Pro Lys Val Ser Leu Phe Glu Pro
        130                 135                 140 tca aaa gca gag att gca aac aag caa aag gct acc ctc gtg tgc ttg    480
Ser Lys Ala Glu Ile Ala Asn Lys Gln Lys Ala Thr Leu Val Cys Leu
145                 150                 155                 160 gcc agg ggc ttc ttc cct gac cac gtg gag ctg agc tgg tgg gtg aat    528
Ala Arg Gly Phe Phe Pro Asp His Val Glu Leu Ser Trp Trp Val Asn
                165                 170                 175 ggc aag gag gtc cac agt ggg gtc agc acg gac cct cag gcc tac aag    576
Gly Lys Glu Val His Ser Gly Val Ser Thr Asp Pro Gln Ala Tyr Lys
            180                 185                 190 gag agc aat tat agc tac tgc ctg agc agc cgc ctg agg gtc tct gct    624
Glu Ser Asn Tyr Ser Tyr Cys Leu Ser Ser Arg Leu Arg Val Ser Ala
        195                 200                 205 acc ttc tgg cac aat cct cga aac cac ttc cgc tgc caa gtg cag ttc    672
Thr Phe Trp His Asn Pro Arg Asn His Phe Arg Cys Gln Val Gln Phe
    210                 215                 220 cat ggg ctt tca gag gag gac aag tgg cca gag ggc tca ccc aaa cct    720
His Gly Leu Ser Glu Glu Asp Lys Trp Pro Glu Gly Ser Pro Lys Pro
225                 230                 235                 240 gtc aca cag aac atc agt gca gag gcc tgg ggc cga gca gac tgt gga    768
Val Thr Gln Asn Ile Ser Ala Glu Ala Trp Gly Arg Ala Asp Cys Gly
                245                 250                 255 atc act tca gca tcc tat cat cag ggg gtt ctg tct gca acc atc ctc    816
Ile Thr Ser Ala Ser Tyr His Gln Gly Val Leu Ser Ala Thr Ile Leu
            260                 265                 270 tat gag atc cta ctg ggg aag gcc acc tta tat gct gtg ctg gtc agt    864
Tyr Glu Ile Leu Leu Gly Lys Ala Thr Leu Tyr Ala Val Leu Val Ser
        275                 280                 285 ggc ctg gtg ctg atg gcc atg gtc aag aaa aaa aat tcc tag            906
Gly Leu Val Leu Met Ala Met Val Lys Lys Lys Asn Ser
    290                 295                 300

<210> SEQ ID NO 27
<211> LENGTH: 301
<212> TYPE: PRT
<213> ORGANISM: Mus musculus

<400> SEQUENCE: 27

Met Gly Ser Arg Leu Phe Phe Val Val Leu Ile Leu Leu Cys Ala Lys
1               5                   10                  15

His Met Glu Ala Ala Val Thr Gln Ser Pro Arg Ser Lys Val Ala Val
                20                  25                  30

Thr Gly Gly Lys Val Thr Leu Ser Cys His Gln Thr Asn Asn His Asp
            35                  40                  45

Tyr Met Tyr Trp Tyr Arg Gln Asp Thr Gly His Gly Leu Arg Leu Ile
        50                  55                  60

His Tyr Ser Tyr Val Ala Asp Ser Thr Glu Lys Gly Asp Ile Pro Asp
65                  70                  75                  80

Gly Tyr Lys Ala Ser Arg Pro Ser Gln Glu Asn Phe Ser Leu Ile Leu
                85                  90                  95

-continued

```
Glu Leu Ala Ser Leu Ser Gln Thr Ala Val Tyr Phe Cys Ala Ser Arg
                100                 105                 110

Tyr Arg Asp Thr Gln Tyr Phe Gly Pro Gly Thr Arg Leu Leu Val Leu
            115                 120                 125

Glu Asp Leu Arg Asn Val Thr Pro Pro Lys Val Ser Leu Phe Glu Pro
        130                 135                 140

Ser Lys Ala Glu Ile Ala Asn Lys Gln Lys Ala Thr Leu Val Cys Leu
145                 150                 155                 160

Ala Arg Gly Phe Phe Pro Asp His Val Glu Leu Ser Trp Trp Val Asn
                165                 170                 175

Gly Lys Glu Val His Ser Gly Val Ser Thr Asp Pro Gln Ala Tyr Lys
            180                 185                 190

Glu Ser Asn Tyr Ser Tyr Cys Leu Ser Ser Arg Leu Arg Val Ser Ala
        195                 200                 205

Thr Phe Trp His Asn Pro Arg Asn His Phe Arg Cys Gln Val Gln Phe
210                 215                 220

His Gly Leu Ser Glu Glu Asp Lys Trp Pro Glu Gly Ser Pro Lys Pro
225                 230                 235                 240

Val Thr Gln Asn Ile Ser Ala Glu Ala Trp Gly Arg Ala Asp Cys Gly
                245                 250                 255

Ile Thr Ser Ala Ser Tyr His Gln Gly Val Leu Ser Ala Thr Ile Leu
            260                 265                 270

Tyr Glu Ile Leu Leu Gly Lys Ala Thr Leu Tyr Ala Val Leu Val Ser
        275                 280                 285

Gly Leu Val Leu Met Ala Met Val Lys Lys Lys Asn Ser
290                 295                 300

<210> SEQ ID NO 28
<211> LENGTH: 781
<212> TYPE: PRT
<213> ORGANISM: Homo sapiens

<400> SEQUENCE: 28

Met Ala Thr Gln Ala Asp Leu Met Glu Leu Asp Met Ala Met Glu Pro
1               5                   10                  15

Asp Arg Lys Ala Ala Val Ser His Trp Gln Gln Gln Ser Tyr Leu Asp
            20                  25                  30

Ser Gly Ile His Ser Gly Ala Thr Thr Thr Ala Pro Ser Leu Ser Gly
        35                  40                  45

Lys Gly Asn Pro Glu Glu Glu Asp Val Asp Thr Ser Gln Val Leu Tyr
    50                  55                  60

Glu Trp Glu Gln Gly Phe Ser Gln Ser Phe Thr Gln Glu Gln Val Ala
65                  70                  75                  80

Asp Ile Asp Gly Gln Tyr Ala Met Thr Arg Ala Gln Arg Val Arg Ala
                85                  90                  95

Ala Met Phe Pro Glu Thr Leu Asp Glu Gly Met Gln Ile Pro Ser Thr
            100                 105                 110

Gln Phe Asp Ala Ala His Pro Thr Asn Val Gln Arg Leu Ala Glu Pro
        115                 120                 125

Ser Gln Met Leu Lys His Ala Val Val Asn Leu Ile Asn Tyr Gln Asp
    130                 135                 140

Asp Ala Glu Leu Ala Thr Arg Ala Ile Pro Glu Leu Thr Lys Leu Leu
145                 150                 155                 160

Asn Asp Glu Asp Gln Val Val Val Asn Lys Ala Ala Val Met Val His
                165                 170                 175
```

```
Gln Leu Ser Lys Lys Glu Ala Ser Arg His Ala Ile Met Arg Ser Pro
            180                 185                 190

Gln Met Val Ser Ala Ile Val Arg Thr Met Gln Asn Thr Asn Asp Val
            195                 200                 205

Glu Thr Ala Arg Cys Thr Ala Gly Thr Leu His Asn Leu Ser His His
210                 215                 220

Arg Glu Gly Leu Leu Ala Ile Phe Lys Ser Gly Ile Pro Ala Leu
225                 230                 235                 240

Val Lys Met Leu Gly Ser Pro Val Asp Ser Val Leu Phe Tyr Ala Ile
                245                 250                 255

Thr Thr Leu His Asn Leu Leu His Gln Glu Gly Ala Lys Met Ala
            260                 265                 270

Val Arg Leu Ala Gly Gly Leu Gln Lys Met Val Ala Leu Leu Asn Lys
            275                 280                 285

Thr Asn Val Lys Phe Leu Ala Ile Thr Thr Asp Cys Leu Gln Ile Leu
290                 295                 300

Ala Tyr Gly Asn Gln Glu Ser Lys Leu Ile Ile Leu Ala Ser Gly Gly
305                 310                 315                 320

Pro Gln Ala Leu Val Asn Ile Met Arg Thr Tyr Thr Tyr Glu Lys Leu
                325                 330                 335

Leu Trp Thr Thr Ser Arg Val Leu Lys Val Leu Ser Val Cys Ser Ser
            340                 345                 350

Asn Lys Pro Ala Ile Val Glu Ala Gly Gly Met Gln Ala Leu Gly Leu
            355                 360                 365

His Leu Thr Asp Pro Ser Gln Arg Leu Val Gln Asn Cys Leu Trp Thr
370                 375                 380

Leu Arg Asn Leu Ser Asp Ala Ala Thr Lys Gln Glu Gly Met Glu Gly
385                 390                 395                 400

Leu Leu Gly Thr Leu Val Gln Leu Leu Gly Ser Asp Asp Ile Asn Val
                405                 410                 415

Val Thr Cys Ala Ala Gly Ile Leu Ser Asn Leu Thr Cys Asn Asn Tyr
            420                 425                 430

Lys Asn Lys Met Met Val Cys Gln Val Gly Gly Ile Glu Ala Leu Val
            435                 440                 445

Arg Thr Val Leu Arg Ala Gly Asp Arg Glu Asp Ile Thr Glu Pro Ala
450                 455                 460

Ile Cys Ala Leu Arg His Leu Thr Ser Arg His Gln Glu Ala Glu Met
465                 470                 475                 480

Ala Gln Asn Ala Val Arg Leu His Tyr Gly Leu Pro Val Val Val Lys
                485                 490                 495

Leu Leu His Pro Pro Ser His Trp Pro Leu Ile Lys Ala Thr Val Gly
            500                 505                 510

Leu Ile Arg Asn Leu Ala Leu Cys Pro Ala Asn His Ala Pro Leu Arg
            515                 520                 525

Glu Gln Gly Ala Ile Pro Arg Leu Val Gln Leu Leu Val Arg Ala His
530                 535                 540

Gln Asp Thr Gln Arg Arg Thr Ser Met Gly Gly Thr Gln Gln Gln Phe
545                 550                 555                 560

Val Glu Gly Val Arg Met Glu Glu Ile Val Glu Gly Cys Thr Gly Ala
                565                 570                 575

Leu His Ile Leu Ala Arg Asp Val His Asn Arg Ile Val Ile Arg Gly
            580                 585                 590
```

-continued

```
Leu Asn Thr Ile Pro Leu Phe Val Gln Leu Leu Tyr Ser Pro Ile Glu
            595                 600                 605

Asn Ile Gln Arg Val Ala Ala Gly Val Leu Cys Glu Leu Ala Gln Asp
        610                 615                 620

Lys Glu Ala Ala Glu Ala Ile Glu Ala Glu Gly Ala Thr Ala Pro Leu
625                 630                 635                 640

Thr Glu Leu Leu His Ser Arg Asn Glu Gly Val Ala Thr Tyr Ala Ala
                645                 650                 655

Ala Val Leu Phe Arg Met Ser Glu Asp Lys Pro Gln Asp Tyr Lys Lys
                660                 665                 670

Arg Leu Ser Val Glu Leu Thr Ser Ser Leu Phe Arg Thr Glu Pro Met
            675                 680                 685

Ala Trp Asn Glu Thr Ala Asp Leu Gly Leu Asp Ile Gly Ala Gln Gly
        690                 695                 700

Glu Pro Leu Gly Tyr Arg Gln Asp Asp Pro Ser Tyr Arg Ser Phe His
705                 710                 715                 720

Ser Gly Gly Tyr Gly Gln Asp Ala Leu Gly Met Asp Pro Met Met Glu
                725                 730                 735

His Glu Met Gly Gly His His Pro Gly Ala Asp Tyr Pro Val Asp Gly
                740                 745                 750

Leu Pro Asp Leu Gly His Ala Gln Asp Leu Met Asp Gly Leu Pro Pro
            755                 760                 765

Gly Asp Ser Asn Gln Leu Ala Trp Phe Asp Thr Asp Leu
        770                 775                 780

<210> SEQ ID NO 29
<211> LENGTH: 10
<212> TYPE: PRT
<213> ORGANISM: Homo sapiens

<400> SEQUENCE: 29

Tyr Leu Asp Ser Gly Ile His Ser Gly Val
1               5                   10

<210> SEQ ID NO 30
<211> LENGTH: 10
<212> TYPE: PRT
<213> ORGANISM: Homo sapiens

<400> SEQUENCE: 30

Tyr Leu Asp Ser Gly Ile His Ser Gly Ala
1               5                   10

<210> SEQ ID NO 31
<211> LENGTH: 801
<212> TYPE: DNA
<213> ORGANISM: Mus musculus
<220> FEATURE:
<221> NAME/KEY: CDS
<222> LOCATION: (1)..(801)

<400> SEQUENCE: 31 atg aag agg ctg ctg tgt tct ctg ctg ggg ctt ctg tgc acc cag gtt     48
Met Lys Arg Leu Leu Cys Ser Leu Leu Gly Leu Leu Cys Thr Gln Val
1               5                   10                  15 tgc tgg gtg aaa gga cag caa gtg cag cag agt ccc gca tcc ttg gtt     96
Cys Trp Val Lys Gly Gln Gln Val Gln Gln Ser Pro Ala Ser Leu Val
            20                  25                  30 ctg cag gag ggg gag aac gca gag ctg cag tgt aac ttt tcc tcc aca    144
Leu Gln Glu Gly Glu Asn Ala Glu Leu Gln Cys Asn Phe Ser Ser Thr
```

-continued

```
                35                  40                  45
gca acc cgg ctg cag tgg ttt tac caa cat cct ggg gga aga ctc gtc    192
Ala Thr Arg Leu Gln Trp Phe Tyr Gln His Pro Gly Gly Arg Leu Val
 50                  55                  60 agc ctg ttc tac aat cct tct ggg aca aag cac act gga aga ctg aca    240
Ser Leu Phe Tyr Asn Pro Ser Gly Thr Lys His Thr Gly Arg Leu Thr
 65                  70                  75                  80 tcc acc aca gtc act aac gaa cgt cgc agc tct ttg cac att tcc tcc    288
Ser Thr Thr Val Thr Asn Glu Arg Arg Ser Ser Leu His Ile Ser Ser
                 85                  90                  95 tcc cag aca aca gac tca ggc act tat ttc tgt gct atc ccc cca ggc    336
Ser Gln Thr Thr Asp Ser Gly Thr Tyr Phe Cys Ala Ile Pro Pro Gly
            100                 105                 110 act ggg tct aag ctg tca ttt ggg aag ggg gca aag ctc aca gtg agt    384
Thr Gly Ser Lys Leu Ser Phe Gly Lys Gly Ala Lys Leu Thr Val Ser
        115                 120                 125 cca gac atc cag aac cca gaa cct gct gtg tac cag tta aaa gat cct    432
Pro Asp Ile Gln Asn Pro Glu Pro Ala Val Tyr Gln Leu Lys Asp Pro
130                 135                 140 cgg tct cag gac agc acc ctc tgc ctg ttc acc gac ttt gac tcc caa    480
Arg Ser Gln Asp Ser Thr Leu Cys Leu Phe Thr Asp Phe Asp Ser Gln
145                 150                 155                 160 atc aat gtg ccg aaa acc atg gaa tct gga acg ttc atc act gac aaa    528
Ile Asn Val Pro Lys Thr Met Glu Ser Gly Thr Phe Ile Thr Asp Lys
                165                 170                 175 act gtg ctg gac atg aaa gct atg gat tcc aag agc aat ggg gcc att    576
Thr Val Leu Asp Met Lys Ala Met Asp Ser Lys Ser Asn Gly Ala Ile
            180                 185                 190 gcc tgg agc aac cag aca agc ttc acc tgc caa gat atc ttc aaa gag    624
Ala Trp Ser Asn Gln Thr Ser Phe Thr Cys Gln Asp Ile Phe Lys Glu
        195                 200                 205 acc aac gcc acc tac ccc agt tca gac gtt ccc tgt gat gcc acg ttg    672
Thr Asn Ala Thr Tyr Pro Ser Ser Asp Val Pro Cys Asp Ala Thr Leu
    210                 215                 220 act gag aaa agc ttt gaa aca gat atg aac cta aac ttt caa aac ctg    720
Thr Glu Lys Ser Phe Glu Thr Asp Met Asn Leu Asn Phe Gln Asn Leu
225                 230                 235                 240 tca gtt atg gga ctc cga atc ctc ctg aaa gta gcc gga ttt aac        768
Ser Val Met Gly Leu Arg Ile Leu Leu Lys Val Ala Gly Phe Asn
                245                 250                 255 ctg ctc atg acg ctg agg ctg tgg tcc agt taa                        801
Leu Leu Met Thr Leu Arg Leu Trp Ser Ser
            260                 265

<210> SEQ ID NO 32
<211> LENGTH: 266
<212> TYPE: PRT
<213> ORGANISM: Mus musculus

<400> SEQUENCE: 32

Met Lys Arg Leu Leu Cys Ser Leu Leu Gly Leu Leu Cys Thr Gln Val
 1               5                  10                  15

Cys Trp Val Lys Gly Gln Gln Val Gln Gln Ser Pro Ala Ser Leu Val
             20                  25                  30

Leu Gln Glu Gly Glu Asn Ala Glu Leu Gln Cys Asn Phe Ser Ser Thr
         35                  40                  45

Ala Thr Arg Leu Gln Trp Phe Tyr Gln His Pro Gly Gly Arg Leu Val
     50                  55                  60

Ser Leu Phe Tyr Asn Pro Ser Gly Thr Lys His Thr Gly Arg Leu Thr
```

```
                65                  70                  75                  80
Ser Thr Thr Val Thr Asn Glu Arg Arg Ser Ser Leu His Ile Ser Ser
                        85                  90                  95

Ser Gln Thr Thr Asp Ser Gly Thr Tyr Phe Cys Ala Ile Pro Pro Gly
                100                 105                 110

Thr Gly Ser Lys Leu Ser Phe Lys Gly Ala Lys Leu Thr Val Ser
            115                 120                 125

Pro Asp Ile Gln Asn Pro Glu Pro Ala Val Tyr Gln Leu Lys Asp Pro
            130                 135                 140

Arg Ser Gln Asp Ser Thr Leu Cys Leu Phe Thr Asp Phe Asp Ser Gln
145                 150                 155                 160

Ile Asn Val Pro Lys Thr Met Glu Ser Gly Thr Phe Ile Thr Asp Lys
                165                 170                 175

Thr Val Leu Asp Met Lys Ala Met Asp Ser Lys Ser Asn Gly Ala Ile
                180                 185                 190

Ala Trp Ser Asn Gln Thr Ser Phe Thr Cys Gln Asp Ile Phe Lys Glu
            195                 200                 205

Thr Asn Ala Thr Tyr Pro Ser Ser Asp Val Pro Cys Asp Ala Thr Leu
            210                 215                 220

Thr Glu Lys Ser Phe Glu Thr Asp Met Asn Leu Asn Phe Gln Asn Leu
225                 230                 235                 240

Ser Val Met Gly Leu Arg Ile Leu Leu Lys Val Ala Gly Phe Asn
                245                 250                 255

Leu Leu Met Thr Leu Arg Leu Trp Ser Ser
                260                 265

<210> SEQ ID NO 33
<211> LENGTH: 906
<212> TYPE: DNA
<213> ORGANISM: Mus musculus
<220> FEATURE:
<221> NAME/KEY: CDS
<222> LOCATION: (1)..(906)

<400> SEQUENCE: 33 atg agc tgc agg ctt ctc ctc tat gtt tcc cta tgt ctt gtg gaa aca      48
Met Ser Cys Arg Leu Leu Leu Tyr Val Ser Leu Cys Leu Val Glu Thr
1               5                   10                  15 gca ctc atg aac act aaa att act cag tca cca aga tat cta atc ctg     96
Ala Leu Met Asn Thr Lys Ile Thr Gln Ser Pro Arg Tyr Leu Ile Leu
                20                  25                  30 gga aga gca aat aag tct ttg gaa tgt gag caa cat ctg gga cat aat    144
Gly Arg Ala Asn Lys Ser Leu Glu Cys Glu Gln His Leu Gly His Asn
            35                  40                  45 gct atg tac tgg tat aaa cag agc gct gag aag ccg cca gag ctc atg    192
Ala Met Tyr Trp Tyr Lys Gln Ser Ala Glu Lys Pro Pro Glu Leu Met
        50                  55                  60 ttt ctc tac aat ctt aaa cag ttg att cga aat gag acg gtg ccc agt    240
Phe Leu Tyr Asn Leu Lys Gln Leu Ile Arg Asn Glu Thr Val Pro Ser
65                  70                  75                  80 cgt ttt ata cct gaa tgc cca gac agc tcc aag cta ctt tta cat ata    288
Arg Phe Ile Pro Glu Cys Pro Asp Ser Ser Lys Leu Leu Leu His Ile
                85                  90                  95 tct gcc gtg gat cca gaa gac tca gct gtc tat ttt tgt gcc agc agc    336
Ser Ala Val Asp Pro Glu Asp Ser Ala Val Tyr Phe Cys Ala Ser Ser
                100                 105                 110 caa gga cag aaa cag tac ttc ggt ccc ggc acc agg ctc acg gtt tta    384
Gln Gly Gln Lys Gln Tyr Phe Gly Pro Gly Thr Arg Leu Thr Val Leu
```

```
                115                 120                 125
gag gat ctg aga aat gtg act cca ccc aag gtc tcc ttg ttt gag cca       432
Glu Asp Leu Arg Asn Val Thr Pro Pro Lys Val Ser Leu Phe Glu Pro
    130                 135                 140 tca aaa gca gag att gca aac aaa caa aag gct acc ctc gtg tgc ttg       480
Ser Lys Ala Glu Ile Ala Asn Lys Gln Lys Ala Thr Leu Val Cys Leu
145                 150                 155                 160 gcc agg ggc ttc ttc cct gac cac gtg gag ctg agc tgg tgg gtg aat       528
Ala Arg Gly Phe Phe Pro Asp His Val Glu Leu Ser Trp Trp Val Asn
                165                 170                 175 ggc aag gag gtc cac agt ggg gtc agc acg gac cct cag gcc tac aag       576
Gly Lys Glu Val His Ser Gly Val Ser Thr Asp Pro Gln Ala Tyr Lys
            180                 185                 190 gag agc aat tat agc tac tgc ctg agc agc cgc ctg agg gtc tct gct       624
Glu Ser Asn Tyr Ser Tyr Cys Leu Ser Ser Arg Leu Arg Val Ser Ala
        195                 200                 205 acc ttc tgg cac aat cct cga aac cac ttc cgc tgc caa gtg cag ttc       672
Thr Phe Trp His Asn Pro Arg Asn His Phe Arg Cys Gln Val Gln Phe
    210                 215                 220 cat ggg ctt tca gag gag gac aag tgg cca gag ggc tta ccc aaa cct       720
His Gly Leu Ser Glu Glu Asp Lys Trp Pro Glu Gly Leu Pro Lys Pro
225                 230                 235                 240 gtc aca cag aac atc agt gca gag gcc tgg ggc cga gca gac tgt gga       768
Val Thr Gln Asn Ile Ser Ala Glu Ala Trp Gly Arg Ala Asp Cys Gly
                245                 250                 255 atc act tca gca tcc tat cat cag ggg gtt ctg tct gca acc atc ctc       816
Ile Thr Ser Ala Ser Tyr His Gln Gly Val Leu Ser Ala Thr Ile Leu
            260                 265                 270 tat gag atc cta ctg ggg aag gcc acc cta tat gct gtg ctg gtc agt       864
Tyr Glu Ile Leu Leu Gly Lys Ala Thr Leu Tyr Ala Val Leu Val Ser
        275                 280                 285 ggc ctg gtg ctg atg gcc atg gtc aag aaa aaa aat tcc taa               906
Gly Leu Val Leu Met Ala Met Val Lys Lys Lys Asn Ser
    290                 295                 300

<210> SEQ ID NO 34
<211> LENGTH: 301
<212> TYPE: PRT
<213> ORGANISM: Mus musculus

<400> SEQUENCE: 34

Met Ser Cys Arg Leu Leu Tyr Val Ser Leu Cys Leu Val Glu Thr
1               5                   10                  15

Ala Leu Met Asn Thr Lys Ile Thr Gln Ser Pro Arg Tyr Leu Ile Leu
            20                  25                  30

Gly Arg Ala Asn Lys Ser Leu Glu Cys Glu Gln His Leu Gly His Asn
        35                  40                  45

Ala Met Tyr Trp Tyr Lys Gln Ser Ala Glu Lys Pro Pro Glu Leu Met
    50                  55                  60

Phe Leu Tyr Asn Leu Lys Gln Leu Ile Arg Asn Glu Thr Val Pro Ser
65                  70                  75                  80

Arg Phe Ile Pro Glu Cys Pro Asp Ser Ser Lys Leu Leu Leu His Ile
                85                  90                  95

Ser Ala Val Asp Pro Glu Asp Ser Ala Val Tyr Phe Cys Ala Ser Ser
            100                 105                 110

Gln Gly Gln Lys Gln Tyr Phe Gly Pro Gly Thr Arg Leu Thr Val Leu
        115                 120                 125

Glu Asp Leu Arg Asn Val Thr Pro Pro Lys Val Ser Leu Phe Glu Pro
```

```
                130                 135                 140
Ser Lys Ala Glu Ile Ala Asn Lys Gln Lys Ala Thr Leu Val Cys Leu
145                 150                 155                 160

Ala Arg Gly Phe Phe Pro Asp His Val Glu Leu Ser Trp Trp Val Asn
                165                 170                 175

Gly Lys Glu Val His Ser Gly Val Ser Thr Asp Pro Gln Ala Tyr Lys
                180                 185                 190

Glu Ser Asn Tyr Ser Tyr Cys Leu Ser Ser Arg Leu Arg Val Ser Ala
                195                 200                 205

Thr Phe Trp His Asn Pro Arg Asn His Phe Arg Cys Gln Val Gln Phe
                210                 215                 220

His Gly Leu Ser Glu Glu Asp Lys Trp Pro Glu Gly Leu Pro Lys Pro
225                 230                 235                 240

Val Thr Gln Asn Ile Ser Ala Glu Ala Trp Gly Arg Ala Asp Cys Gly
                245                 250                 255

Ile Thr Ser Ala Ser Tyr His Gln Gly Val Leu Ser Ala Thr Ile Leu
                260                 265                 270

Tyr Glu Ile Leu Leu Gly Lys Ala Thr Leu Tyr Ala Val Leu Val Ser
                275                 280                 285

Gly Leu Val Leu Met Ala Met Val Lys Lys Lys Asn Ser
                290                 295                 300

<210> SEQ ID NO 35
<211> LENGTH: 804
<212> TYPE: DNA
<213> ORGANISM: Mus musculus
<220> FEATURE:
<221> NAME/KEY: CDS
<222> LOCATION: (1)..(804)

<400> SEQUENCE: 35 atg aac aga ttc ctg gga ata tct ttg gtg act cta tgg ttt caa gtg     48
Met Asn Arg Phe Leu Gly Ile Ser Leu Val Thr Leu Trp Phe Gln Val
1               5                   10                  15 gcc tgg gca aag agc caa tgg gga gaa gag aat ctt cag gct ctg agc     96
Ala Trp Ala Lys Ser Gln Trp Gly Glu Glu Asn Leu Gln Ala Leu Ser
            20                  25                  30 atc cag gag ggt gaa gat gtc acc atg aac tgc agt tac aag act tac    144
Ile Gln Glu Gly Glu Asp Val Thr Met Asn Cys Ser Tyr Lys Thr Tyr
        35                  40                  45 aca act gtt gtt cag tgg tac aga cag aag tca ggc aaa ggc cct gcc    192
Thr Thr Val Val Gln Trp Tyr Arg Gln Lys Ser Gly Lys Gly Pro Ala
    50                  55                  60 cag cta atc tta ata cgt tca aat gag cga gag aag cgc agt gga aga    240
Gln Leu Ile Leu Ile Arg Ser Asn Glu Arg Glu Lys Arg Ser Gly Arg
65                  70                  75                  80 ctc aga gcc acc ctt gac act tcc agc cag agc agc tcc ctg tcc atc    288
Leu Arg Ala Thr Leu Asp Thr Ser Ser Gln Ser Ser Ser Leu Ser Ile
                85                  90                  95 act ggt act cta gct aca gac act gct gtg tac ttc tgt gct act ggg    336
Thr Gly Thr Leu Ala Thr Asp Thr Ala Val Tyr Phe Cys Ala Thr Gly
            100                 105                 110 ccc aat acc aac aaa gtc gtc ttt gga aca ggg acc aga tta caa gta    384
Pro Asn Thr Asn Lys Val Val Phe Gly Thr Gly Thr Arg Leu Gln Val
        115                 120                 125 tta cca aac atc cag aac cca gaa cct gct gtg tac cag tta aaa gat    432
Leu Pro Asn Ile Gln Asn Pro Glu Pro Ala Val Tyr Gln Leu Lys Asp
    130                 135                 140
```

| | | |
|---|---|---|
| cct cgg tct cag gac agc acc ctc tgc ctg ttc acc gac ttt gac tcc<br>Pro Arg Ser Gln Asp Ser Thr Leu Cys Leu Phe Thr Asp Phe Asp Ser<br>145                            150                            155                       160 | | 480 |
| caa atc aat gtg ccg aaa acc atg gaa tct gga acg ttc atc act gac<br>Gln Ile Asn Val Pro Lys Thr Met Glu Ser Gly Thr Phe Ile Thr Asp<br>                                    165                            170                            175 | | 528 |
| aaa act gtg ctg gac atg aaa gct atg gat tcc aag agc aat ggg gcc<br>Lys Thr Val Leu Asp Met Lys Ala Met Asp Ser Lys Ser Asn Gly Ala<br>                     180                            185                            190 | | 576 |
| att gcc tgg agc aac cag aca agc ttc acc tgc caa gat atc ttc aaa<br>Ile Ala Trp Ser Asn Gln Thr Ser Phe Thr Cys Gln Asp Ile Phe Lys<br>               195                            200 | | 624 |
| gag acc aac gcc acc tac ccc agt tca gac gtt ccc tgt gat gcc acg<br>Glu Thr Asn Ala Thr Tyr Pro Ser Ser Asp Val Pro Cys Asp Ala Thr<br>          210                        215 | | 672 |
| ttg act gag aaa agc ttt gaa aca gat atg aac cta aac ttt caa aac<br>Leu Thr Glu Lys Ser Phe Glu Thr Asp Met Asn Leu Asn Phe Gln Asn<br>225                            230 | | 720 |
| ctg tca gtt atg gga ctc cga atc ctc ctg aaa gta gcc gga ttt<br>Leu Ser Val Met Gly Leu Arg Ile Leu Leu Lys Val Ala Gly Phe<br>                   245                       250                        255 | | 768 |
| aac ctg ctc atg acg ctg agg ctg tgg tcc agt tga<br>Asn Leu Leu Met Thr Leu Arg Leu Trp Ser Ser<br>          260                        265 | | 804 |

<210> SEQ ID NO 36
<211> LENGTH: 267
<212> TYPE: PRT
<213> ORGANISM: Mus musculus

<400> SEQUENCE: 36

Met Asn Arg Phe Leu Gly Ile Ser Leu Val Thr Leu Trp Phe Gln Val
1                      5                            10                            15

Ala Trp Ala Lys Ser Gln Trp Gly Glu Glu Asn Leu Gln Ala Leu Ser
                    20                            25                            30

Ile Gln Glu Gly Glu Asp Val Thr Met Asn Cys Ser Tyr Lys Thr Tyr
                            35                            40                            45

Thr Thr Val Val Gln Trp Tyr Arg Gln Lys Ser Gly Lys Gly Pro Ala
    50                            55                            60

Gln Leu Ile Leu Ile Arg Ser Asn Glu Arg Glu Lys Arg Ser Gly Arg
65                      70                            75                            80

Leu Arg Ala Thr Leu Asp Thr Ser Ser Gln Ser Ser Ser Leu Ser Ile
                    85                            90                            95

Thr Gly Thr Leu Ala Thr Asp Thr Ala Val Tyr Phe Cys Ala Thr Gly
                  100                           105                        110

Pro Asn Thr Asn Lys Val Val Phe Gly Thr Gly Thr Arg Leu Gln Val
             115                            120                          125

Leu Pro Asn Ile Gln Asn Pro Glu Pro Ala Val Tyr Gln Leu Lys Asp
    130                          135                          140

Pro Arg Ser Gln Asp Ser Thr Leu Cys Leu Phe Thr Asp Phe Asp Ser
145                     150                            155                        160

Gln Ile Asn Val Pro Lys Thr Met Glu Ser Gly Thr Phe Ile Thr Asp
                  165                           170                        175

Lys Thr Val Leu Asp Met Lys Ala Met Asp Ser Lys Ser Asn Gly Ala
            180                            185                          190

Ile Ala Trp Ser Asn Gln Thr Ser Phe Thr Cys Gln Asp Ile Phe Lys
          195                          200                        205

```
Glu Thr Asn Ala Thr Tyr Pro Ser Ser Asp Val Pro Cys Asp Ala Thr
    210                 215                 220
Leu Thr Glu Lys Ser Phe Glu Thr Asp Met Asn Leu Asn Phe Gln Asn
225                 230                 235                 240
Leu Ser Val Met Gly Leu Arg Ile Leu Leu Lys Val Ala Gly Phe
            245                 250                 255
Asn Leu Leu Met Thr Leu Arg Leu Trp Ser Ser
            260                 265

<210> SEQ ID NO 37
<211> LENGTH: 909
<212> TYPE: DNA
<213> ORGANISM: Mus musculus
<220> FEATURE:
<221> NAME/KEY: CDS
<222> LOCATION: (1)..(909)

<400> SEQUENCE: 37
```

| | | | | | | | | | | | | | | | | |
|---|---|---|---|---|---|---|---|---|---|---|---|---|---|---|---|---|
| atg | agc | tgc | agg | ctt | ctc | ctc | tat | gtt | tcc | cta | tgt | ctt | gtg | gaa | aca | 48 |
| Met | Ser | Cys | Arg | Leu | Leu | Leu | Tyr | Val | Ser | Leu | Cys | Leu | Val | Glu | Thr | |
| 1 | | | | 5 | | | | | 10 | | | | | 15 | | |
| gca | ctc | atg | aac | act | aaa | att | act | cag | tca | cca | aga | tat | cta | atc | ctg | 96 |
| Ala | Leu | Met | Asn | Thr | Lys | Ile | Thr | Gln | Ser | Pro | Arg | Tyr | Leu | Ile | Leu | |
| | | | 20 | | | | | 25 | | | | | 30 | | | |
| gga | aga | gca | aat | aag | tct | ttg | gaa | tgt | gag | caa | cat | ctg | gga | cat | aat | 144 |
| Gly | Arg | Ala | Asn | Lys | Ser | Leu | Glu | Cys | Glu | Gln | His | Leu | Gly | His | Asn | |
| | | 35 | | | | | 40 | | | | | 45 | | | | |
| gct | atg | tac | tgg | tat | aaa | cag | agc | gct | gag | aag | ccg | cca | gag | ctc | atg | 192 |
| Ala | Met | Tyr | Trp | Tyr | Lys | Gln | Ser | Ala | Glu | Lys | Pro | Pro | Glu | Leu | Met | |
| | 50 | | | | | 55 | | | | | 60 | | | | | |
| ttt | ctc | tac | aat | ctt | aaa | cag | ttg | att | cga | aat | gag | acg | gtg | ccc | agt | 240 |
| Phe | Leu | Tyr | Asn | Leu | Lys | Gln | Leu | Ile | Arg | Asn | Glu | Thr | Val | Pro | Ser | |
| 65 | | | | | 70 | | | | | 75 | | | | | 80 | |
| cgt | ttt | ata | cct | gaa | tgc | cca | gac | agc | tcc | aag | cta | ctt | tta | cat | ata | 288 |
| Arg | Phe | Ile | Pro | Glu | Cys | Pro | Asp | Ser | Ser | Lys | Leu | Leu | Leu | His | Ile | |
| | | | | 85 | | | | | 90 | | | | | 95 | | |
| tct | gcc | gtg | gat | cca | gaa | gac | tca | gct | gtc | tat | ttt | tgt | gcc | agc | agc | 336 |
| Ser | Ala | Val | Asp | Pro | Glu | Asp | Ser | Ala | Val | Tyr | Phe | Cys | Ala | Ser | Ser | |
| | | | 100 | | | | | 105 | | | | | 110 | | | |
| caa | ggt | ggt | gct | gag | cag | ttc | ttc | gga | cca | ggg | aca | cga | ctc | acc | gtc | 384 |
| Gln | Gly | Gly | Ala | Glu | Gln | Phe | Phe | Gly | Pro | Gly | Thr | Arg | Leu | Thr | Val | |
| | | 115 | | | | | 120 | | | | | 125 | | | | |
| cta | gag | gat | ctg | aga | aat | gtg | act | cca | ccc | aag | gtc | tcc | ttg | ttt | gag | 432 |
| Leu | Glu | Asp | Leu | Arg | Asn | Val | Thr | Pro | Pro | Lys | Val | Ser | Leu | Phe | Glu | |
| | 130 | | | | | 135 | | | | | 140 | | | | | |
| cca | tca | aaa | gca | gag | att | gca | aac | aaa | caa | aag | gct | acc | ctc | gtg | tgc | 480 |
| Pro | Ser | Lys | Ala | Glu | Ile | Ala | Asn | Lys | Gln | Lys | Ala | Thr | Leu | Val | Cys | |
| 145 | | | | | 150 | | | | | 155 | | | | | 160 | |
| ttg | gcc | agg | ggc | ttc | ttc | cct | gac | cac | gtg | gag | ctg | agc | tgg | tgg | gtg | 528 |
| Leu | Ala | Arg | Gly | Phe | Phe | Pro | Asp | His | Val | Glu | Leu | Ser | Trp | Trp | Val | |
| | | | | 165 | | | | | 170 | | | | | 175 | | |
| aat | ggc | aag | gag | gtc | cac | agt | ggg | gtc | agc | acg | gac | cct | cag | gcc | tac | 576 |
| Asn | Gly | Lys | Glu | Val | His | Ser | Gly | Val | Ser | Thr | Asp | Pro | Gln | Ala | Tyr | |
| | | | 180 | | | | | 185 | | | | | 190 | | | |
| aag | gag | agc | aat | tat | agc | tac | tgc | ctg | agc | agc | cgc | ctg | agg | gtc | tct | 624 |
| Lys | Glu | Ser | Asn | Tyr | Ser | Tyr | Cys | Leu | Ser | Ser | Arg | Leu | Arg | Val | Ser | |
| | | 195 | | | | | 200 | | | | | 205 | | | | |
| gct | acc | ttc | tgg | cac | aat | cct | cga | aac | cac | ttc | cgc | tgc | caa | gtg | cag | 672 |
| Ala | Thr | Phe | Trp | His | Asn | Pro | Arg | Asn | His | Phe | Arg | Cys | Gln | Val | Gln | |
| | 210 | | | | | 215 | | | | | 220 | | | | | |

```
ttc cat ggg ctt tca gag gag gac aag tgg cca gag ggc tca ccc aaa         720
Phe His Gly Leu Ser Glu Glu Asp Lys Trp Pro Glu Gly Ser Pro Lys
225                 230                 235                 240 cct gtc aca cag aac atc agt gca gag gcc tgg ggc cga gca gac tgt         768
Pro Val Thr Gln Asn Ile Ser Ala Glu Ala Trp Gly Arg Ala Asp Cys
            245                 250                 255 gga atc act tca gca tcc tat cat cag ggg gtt ctg tct gca acc atc         816
Gly Ile Thr Ser Ala Ser Tyr His Gln Gly Val Leu Ser Ala Thr Ile
        260                 265                 270 ctc tat gag atc cta ctg ggg aag gcc acc cta tat gct gtg ctg gtc         864
Leu Tyr Glu Ile Leu Leu Gly Lys Ala Thr Leu Tyr Ala Val Leu Val
    275                 280                 285 agt ggc ctg gtg ctg atg gcc atg gtc aag aaa aaa aat tcc tag             909
Ser Gly Leu Val Leu Met Ala Met Val Lys Lys Lys Asn Ser
290                 295                 300
```

<210> SEQ ID NO 38
<211> LENGTH: 302
<212> TYPE: PRT
<213> ORGANISM: Mus musculus

<400> SEQUENCE: 38

```
Met Ser Cys Arg Leu Leu Leu Tyr Val Ser Leu Cys Leu Val Glu Thr
1               5                   10                  15

Ala Leu Met Asn Thr Lys Ile Thr Gln Ser Pro Arg Tyr Leu Ile Leu
            20                  25                  30

Gly Arg Ala Asn Lys Ser Leu Glu Cys Glu Gln His Leu Gly His Asn
        35                  40                  45

Ala Met Tyr Trp Tyr Lys Gln Ser Ala Glu Lys Pro Pro Glu Leu Met
    50                  55                  60

Phe Leu Tyr Asn Leu Lys Gln Leu Ile Arg Asn Glu Thr Val Pro Ser
65                  70                  75                  80

Arg Phe Ile Pro Glu Cys Pro Asp Ser Ser Lys Leu Leu Leu His Ile
                85                  90                  95

Ser Ala Val Asp Pro Glu Asp Ser Ala Val Tyr Phe Cys Ala Ser Ser
            100                 105                 110

Gln Gly Gly Ala Glu Gln Phe Phe Gly Pro Gly Thr Arg Leu Thr Val
        115                 120                 125

Leu Glu Asp Leu Arg Asn Val Thr Pro Pro Lys Val Ser Leu Phe Glu
    130                 135                 140

Pro Ser Lys Ala Glu Ile Ala Asn Lys Gln Lys Ala Thr Leu Val Cys
145                 150                 155                 160

Leu Ala Arg Gly Phe Phe Pro Asp His Val Glu Leu Ser Trp Trp Val
                165                 170                 175

Asn Gly Lys Glu Val His Ser Gly Val Ser Thr Asp Pro Gln Ala Tyr
            180                 185                 190

Lys Glu Ser Asn Tyr Ser Tyr Cys Leu Ser Ser Arg Leu Arg Val Ser
        195                 200                 205

Ala Thr Phe Trp His Asn Pro Arg Asn His Phe Arg Cys Gln Val Gln
    210                 215                 220

Phe His Gly Leu Ser Glu Glu Asp Lys Trp Pro Glu Gly Ser Pro Lys
225                 230                 235                 240

Pro Val Thr Gln Asn Ile Ser Ala Glu Ala Trp Gly Arg Ala Asp Cys
                245                 250                 255

Gly Ile Thr Ser Ala Ser Tyr His Gln Gly Val Leu Ser Ala Thr Ile
            260                 265                 270
```

```
Leu Tyr Glu Ile Leu Leu Gly Lys Ala Thr Leu Tyr Ala Val Leu Val
            275                 280                 285

Ser Gly Leu Val Leu Met Ala Met Val Lys Lys Asn Ser
    290                 295                 300
```

<210> SEQ ID NO 39
<211> LENGTH: 24
<212> TYPE: DNA
<213> ORGANISM: Artificial sequence
<220> FEATURE:
<223> OTHER INFORMATION: Artificially synthesized oligonucleotide primer

<400> SEQUENCE: 39
actggaccac agcctcagcg tcat       24

<210> SEQ ID NO 40
<211> LENGTH: 27
<212> TYPE: DNA
<213> ORGANISM: Artificial sequence
<220> FEATURE:
<223> OTHER INFORMATION: Artificially synthesized oligonucleotide primer

<400> SEQUENCE: 40
tgaattcttt cttttgacca tagccat       27

<210> SEQ ID NO 41
<211> LENGTH: 27
<212> TYPE: DNA
<213> ORGANISM: Artificial sequence
<220> FEATURE:
<223> OTHER INFORMATION: Artificially synthesized oligonucleotide primer

<400> SEQUENCE: 41 ggaattttttt ttcttgacca tggccat       27

<210> SEQ ID NO 42
<211> LENGTH: 49
<212> TYPE: DNA
<213> ORGANISM: Artificial sequence
<220> FEATURE:
<223> OTHER INFORMATION: Artificially synthesized oligonucleotide primer

<400> SEQUENCE: 42
taatacgact cactataggg agagccacca tgctcctggc actcctccc       49

<210> SEQ ID NO 43
<211> LENGTH: 89
<212> TYPE: DNA
<213> ORGANISM: Artificial sequence
<220> FEATURE:
<223> OTHER INFORMATION: Artificially synthesized oligonucleotide primer

<400> SEQUENCE: 43
tttttttttt tttttttttt tttttttttt tttttttttt tttttttttt tttttttttt       60 tttttttaact ggaccacagc ctcagcgtc       89

<210> SEQ ID NO 44
<211> LENGTH: 49
<212> TYPE: DNA
<213> ORGANISM: Artificial sequence
<220> FEATURE:
<223> OTHER INFORMATION: Artificially synthesized oligonucleotide primer

<400> SEQUENCE: 44
taatacgact cactataggg agagccacca tgggcaccag gcttcttgg       49

<210> SEQ ID NO 45
<211> LENGTH: 92
<212> TYPE: DNA
<213> ORGANISM: Artificial sequence
<220> FEATURE:
<223> OTHER INFORMATION: Artificially synthesized oligonucleotide primer

<400> SEQUENCE: 45
tttttttttt tttttttttt tttttttttt tttttttttt tttttttttt tttttttttt        60 tttttagga atttttttc ttgaccatgg cc                                          92

<210> SEQ ID NO 46
<211> LENGTH: 49
<212> TYPE: DNA
<213> ORGANISM: Artificial sequence
<220> FEATURE:
<223> OTHER INFORMATION: Artificially synthesized oligonucleotide primer

<400> SEQUENCE: 46
taatacgact cactataggg agagccacca tgaagacagt gactggacc                       49

<210> SEQ ID NO 47
<211> LENGTH: 50
<212> TYPE: DNA
<213> ORGANISM: Artificial sequence
<220> FEATURE:
<223> OTHER INFORMATION: Artificially synthesized oligonucleotide primer

<400> SEQUENCE: 47
taatacgact cactataggg agagccacca tgtctaacac tgccttccct                      50

<210> SEQ ID NO 48
<211> LENGTH: 50
<212> TYPE: DNA
<213> ORGANISM: Artificial Sequence
<220> FEATURE:
<223> OTHER INFORMATION: Artificially synthesized oligonucleotide primer

<400> SEQUENCE: 48
taatacgact cactataggg agagccacca tgggctccag actcttcttt                      50

<210> SEQ ID NO 49
<211> LENGTH: 50
<212> TYPE: DNA
<213> ORGANISM: Artificial Sequence
<220> FEATURE:
<223> OTHER INFORMATION: Artificially synthesized oligonucleotide primer

<400> SEQUENCE: 49
taatacgact cactataggg agagccacca tgtctaacac tgtcctcgct                      50

<210> SEQ ID NO 50
<211> LENGTH: 99
<212> TYPE: DNA
<213> ORGANISM: Artificial Sequence
<220> FEATURE:
<223> OTHER INFORMATION: Artificially synthesized oligonucleotide primer

<400> SEQUENCE: 50
tttttttttt tttttttttt tttttttttt tttttttttt tttttttttt tttttttttt        60 tttttctat gaattctttc ttttgaccat agccatcac                                   99

<210> SEQ ID NO 51

```
<211> LENGTH: 50
<212> TYPE: DNA
<213> ORGANISM: Artificial Sequence
<220> FEATURE:
<223> OTHER INFORMATION: Artificially synthesized oligonucleotide primer

<400> SEQUENCE: 51
taatacgact cactataggg agagccacca tgaagaggct gctgtgttct          50

<210> SEQ ID NO 52
<211> LENGTH: 47
<212> TYPE: DNA
<213> ORGANISM: Artificial Sequence
<220> FEATURE:
<223> OTHER INFORMATION: Artificially synthesized oligonucleotide primer

<400> SEQUENCE: 52
taatacgact cactataggg agagccacca tgagctgcag gcttctc             47

<210> SEQ ID NO 53
<211> LENGTH: 52
<212> TYPE: DNA
<213> ORGANISM: Artificial Sequence
<220> FEATURE:
<223> OTHER INFORMATION: Artificially synthesized oligonucleotide primer

<400> SEQUENCE: 53
taatacgact cactataggg agagccacca tgaacagatt cctgggaata tc       52

<210> SEQ ID NO 54
<211> LENGTH: 9
<212> TYPE: PRT
<213> ORGANISM: Artificial Sequence
<220> FEATURE:
<223> OTHER INFORMATION: Artifically synthesized peptide

<400> SEQUENCE: 54

Leu Leu Trp Asn Gly Pro Met Ala Val
1               5

<210> SEQ ID NO 55
<211> LENGTH: 9
<212> TYPE: PRT
<213> ORGANISM: Artificial Sequence
<220> FEATURE:
<223> OTHER INFORMATION: Artifically synthesized peptide

<400> SEQUENCE: 55

Gly Ile Leu Gly Phe Val Phe Thr Leu
1               5
```